US008735411B2

(12) United States Patent
Altenbach et al.

(10) Patent No.: US 8,735,411 B2
(45) Date of Patent: *May 27, 2014

(54) MACROCYCLIC BENZOFUSED PYRIMIDINE DERIVATIVES

(75) Inventors: Robert J. Altenbach, Chicago, IL (US); Huaqing Liu, Buffalo Grove, IL (US); Irene Drizin, Wadsworth, IL (US); Marlon D. Cowart, Round Lake Beach, IL (US); Neil Wishart, Jefferson, MA (US); David J. Babinski, Dallas, TX (US); Robert J. Gregg, Libertyville, IL (US); Arthur A. Hancock, Libertyville, IL (US); Kathryn J. Hancock, legal representative, Libertyville, IL (US); Timothy A. Esbenshade, Schaumburg, IL (US); Gin C. Hsieh, Long Grove, IL (US); Jorge D. Brioni, Vernon Hills, IL (US); Marie P. Honore, Evanston, IL (US); Lawrence A. Black, Libertyville, IL (US); Chen Zhao, Libertyville, IL (US); Brian D. Wakefield, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 1099 days.

This patent is subject to a terminal disclaimer.

(21) Appl. No.: 11/863,559

(22) Filed: Sep. 28, 2007

(65) Prior Publication Data

US 2008/0188452 A1     Aug. 7, 2008

Related U.S. Application Data

(60) Provisional application No. 60/849,027, filed on Oct. 2, 2006.

(51) Int. Cl.
*A61K 31/505*   (2006.01)
*C07D 239/70*   (2006.01)

(52) U.S. Cl.
USPC .......................................... 514/267; 544/249

(58) Field of Classification Search
None
See application file for complete search history.

(56) References Cited

U.S. PATENT DOCUMENTS

| 3,755,583 | A | 8/1973 | De Angelis et al. |
| 5,071,999 | A | 12/1991 | Schenke et al. |
| 2005/0101602 | A1 | 5/2005 | Basha et al. |
| 2006/0100194 | A1 | 5/2006 | Blackburn et al. |

FOREIGN PATENT DOCUMENTS

| JP | 02-221262 | * | 9/1990 |
| JP | 1994220059 | | 1/1993 |
| WO | 9507893 | | 3/1995 |
| WO | 2005037825 | | 4/2005 |
| WO | 2005042500 | | 5/2005 |
| WO | 2006041773 | | 4/2006 |
| WO | 2006050965 | | 5/2006 |
| WO | 2007090852 | | 8/2007 |

OTHER PUBLICATIONS

Hirota et al. Heterocycles, 1990, 31(1), 153-61.*
Jantzen and Robinson. Modern Pharmaceutics, 1996, p. 596.*
Sasaki et al. Journal of Heterocyclic Chemistry, 1990, 27(6), 1771-76.*
Nguyen, et al., Mol. Pharm., vol. 59, pp. 427-433 (2001).
Liu, et al., Journal of Pharm. and Exper. Ther., vol. 299, pp. 121-130 (2001).
Esbenshade, et al., Biochemical Pharmacology, vol. 68, pp. 933-945 (2004).
Krueger, et al., Journal of Pharm. and Exper. Ther., vol. 314, pp. 271-281 (2005).
Vogel, H., Drug Discovery and Evaluation, 2nd edition, editor Springer-Verlag, New York, pp. 702-706 (2002).
Smith, et al., Drug Develop. Research, vol. 54(3), pp. 140-153 (2001).
Kim, et al., Pain, vol. 50, pp. 355-363 (1992).
Bennett, et al., Pain, vol. 30, pp. 87-107 (1988).
Honore, et al., Behav. Brain Research, vol. 167, pp. 355-364 (2006).
Porreca, et al., Journal of Phar. and Exper. Ther., vol. 318, pp. 195-205 (2006).
Chaplan, et al., J. Neurosci. Meth., vol. 53, pp. 55-63 (1994).
Dixon, Annu. Rev. Pharm. Toxicol., vol. 20, pp. 441-462 (1980).
Coruzzi, Eur. Journal of Pharm., vol. 563, pp. 240-244 (2007).
Nargund, L., Revue Roumaine De Chimie, vol. 42, No. 11, pp. 1089-1091, XP009099310 (1997).
Nargund, L., Arzneimittel-Forschung, vol. 44, No. 2, pp. 156-158, XP001538224 (1994).
PCT International Search Report, PCT/US2007/080133, Mailing date May 9, 2008.
Parsons, et al., British Journal of Pharmacology vol. 147, pp. S127-S135 (2006).
Lazar-Molnar, et al., Biology and Medical Aspects, pp. 89-96 (2004).
Stark, Expert Opinion in Therapeutic Patents, vol. 13, pp. 851-865 (2003).
IUPAC 1974, Recommendations for Section E, Fundamentals Stereochemistry, in Pure Appl. Chem. vol. 45, pp. 13-30 (1976).
Furniss, et al., Vogel's Textbook of Practical Organic Chemistry, 5th edition, Longman Scientific & Technical, Essex CM20 2JE, England, Table of Contents (1989).
Liu, et al., Mol. Pharm, vol. 59, pp. 420-426 (2001).
De Esch, et al., Trends in Pharm. Sciences, vol. 26, pp. 462-469 (2005).
Oda, et al., Journal of the Pharm. Soc., vol. 98, pp. 319-322 (2005).
Zhu, et al., Mol. Pharm., vol. 59, pp. 434-441 (2001).

(Continued)

*Primary Examiner* — Noble Jarrell
(74) *Attorney, Agent, or Firm* — Lisa V. Mueller; Michael Best & Friedrich LLP

(57) ABSTRACT

Macrocyclic benzofused pyrimidine compounds, compositions comprising such compounds, methods for making the compounds, and methods of treating and preventing the progression of diseases, conditions and disorders using such compounds and compositions are described herein.

15 Claims, No Drawings

(56) References Cited

OTHER PUBLICATIONS

Gutzmer, et al., Journal of Immunology, vol. 174, pp. 5224-5232 (2005).
Coge, et al., Biochemical and Biophysical Research Comm., vol. 284, pp. 301-309 (2001).
Malinska, et al., 34th Meeting of the European Histamine Research Society in Bled, Slovenia, Poster No. 3 (2005).
Jablonowska, et al., 35th Meeting of the European Histamine Research Society in Delphi, Greece, Presentation O36 (May 10-13, 2006).
Ikawa, et al., Biol. Pharm. Bull. vol. 28(10), pp. 2016-2018 (2005).
Dunford, et al., The Journal of Immunology, vol. 176, pp. 7062-7070 (2006).
Akdis, et al., European Journal of Pharmacology, vol. 533, pp. 69-76 (2006).
Thurmond, et al., Journal of Pharm. and Exper. Ther., vol. 309, pp. 404-413 (2004).
Buckland, et al., British Journal of Pharm., vol. 140, pp. 1117-1127 (2003).
Cianchi, et al., Clinical Cancer Research, vol. 11(19), pp. 6807-6815 (2005).
Coruzzi, et al., 35th Meeting of the European Histamine Research Society in Delphi, Greece, Presentation O44 (May 10-13, 2006).
Varga, et al., Eur. Journal of Pharm., vol. 522, pp. 130-138 (2005).
Fogel, et al., 35th Meeting of the European Histamine Research Society in Delphi, Greece, Presentation P32 (May 10-13, 2006).
Bell, et al., British Journal of Pharm., vol. 142, pp. 374-380 (2004).
Dworkin, Clinical Journal of Pain, vol. 18(6), pp. 343-349 (2002).
Smith, et al., Drug Development Research, vol. 54(3), pp. 140-153 (2001).
Collins, et al., Expert Opinion on Emerging Drugs, vol. 10(1), pp. 95-108 (2005).
Vinik, et al., Medical Clinics of North America, vol. 88(4), pp. 947-999 (2004).
Dray, et al., Trends in Pharmacological Sciences, vol. 15(6), pp. 190-197 (1994).
Joshi, et al., Expert Opinion in Drug Disc., vol. 1, pp. 323-334 (2004).
Hartwig, et al., Ang. Chem. Int. Ed., vol. 37, pp. 2046-2067 (1998).
Wolfe, et al., Acc. Chem. Res., vol. 31, pp. 805-818 (1998).
Sugahara, et al., Chem. Pharm. Bull., vol. 45, pp. 719-721 (1997).
Wolfe, et al., J. of Organic Chem., vol. 65, pp. 1158-1174 (2000).
Kwong, et al., Org. Lett., vol. 4, pp. 581-584 (2002).
Klapars, et al., J. Amer. Chem. Soc., vol. 123, pp. 7727-7729 (2001).
Yang, et al., J. Organomet. Chem., vol. 576, pp. 125-146 (1999).
Kiyomori, et al., Tet. Lett., vol. 40, pp. 2657-2640 (1999).
Hartwig, J. Org. Chem., vol. 64(15), pp. 5575-5580 (1999).
Deshmukh, et al., J. Org. Chem., vol. 57(2), pp. 667-670 (1992).
Chan, et al., J. Med. Chem., vol. 48(13), pp. 4420-4431 (2005).
Caubere, et al., Bull. Soc. Chim. Fir., pp. 1415-1420 (1974).
Theis, et al., J. Org. Chem., vol. 42(2), pp. 280-281 (1977).
Sambaiah, et al., J. Org. Chem. vol. 64(10), pp. 3663-3670 (1999).
Rover, et al., J. Med. Chem., vol. 43(7), pp. 1329-1339 (2000).
Prescott, Ed., Methods in Cell Biology, vol. XIV, Academic Press, New York, N.Y., p. 33 et seq (1976).
Higuchi, et al., Pro-drugs as Novel Delivery Systems, vol. 14 of the A.C.S. Symposium Series (Table of Contents).
Roche, E., Bioreversible Carriers in Drug Design, American Pharmaceutical Association and Pergamon Press Table of Contents (1987).
Terzioglu, N. et al., "Synthesis and structure-activity relationships of indole and benzimidazole piperazines as histamine H4 receptor antagonists," Bioorg Med. Chem. Lett. (2004) 14(21):5251-5256.
Adami et al., "Antiinflammatory, Analgesic and Gastroprotective Effects of the Novel and Selective Histamine H4-Receptor Antagonist VUF5949," JNJ7777120 CHAT n gastroprotection by H4 EHRS Poster in Slovenia EHRS (May 2005).

* cited by examiner

MACROCYCLIC BENZOFUSED PYRIMIDINE DERIVATIVES

This application claims priority to provisional application Ser. No. 60/849,027 filed on Oct. 2, 2006.

BACKGROUND OF THE INVENTION

1. Technical Field

The invention relates to macrocyclic benzofused pyrimidine compounds, compositions comprising such compounds, methods for making the compounds, and methods of treating conditions and disorders using such compounds and compositions.

2. Description of Related Technology

Histamine modulates a number of physiological activities, acting through specific histamine receptors (reviewed in Parsons and Ganellin, British Journal of Pharmacology (2006) 147, S127-S135; Igaz and Hegyesi, in Histamine: Biology and Medical Aspects (2004), 89-96; Editor(s): A. Falus; Published S. Karger A G, Basel). Four histamine receptors have been identified as playing distinct physiological roles. These are the histamine $H_1$ receptor, the histamine $H_2$ receptor, the histamine $H_3$ receptor, and the histamine $H_4$ receptor. Compounds that modulate, or affect, the activity of these receptors may be used to treat diseases. For example, the well-known role of $H_1$ receptors in modulating allergic reaction has led to the clinical development of drugs that treat allergic rhinitis and other diseases by antagonizing the action of naturally-occurring, or endogenous, histamine in the body. Histamine $H_2$ receptor antagonists have been developed and proven clinically useful in treating diseases associated with excess stomach acidity. The histamine $H_3$ receptor is found predominantly on nerve terminals in the central nervous system (CNS) and the peripheral nervous system, i.e., periphery, and antagonists of this receptor have been documented in studies that benefit mammalian cognitive process, improve wakefulness, suppress symptoms of allergic rhinitis, and suppress weight gain. The histamine $H_4$ receptor is the most recently identified histamine receptor and has been characterized as a distinct histamine receptor. The histamine $H_4$ receptor has been found in a number of mammalian tissues and has been determined to modulate a number of physiological processes, including immunological function.

By use of histamine $H_4$ ligands in animal disease models as well as in in vitro and ex vivo studies, the histamine $H_4$ receptor has been demonstrated to play an important role in various physiological and pathophysiological processes. Separately, in experiments with histamine $H_4$ deficient (knock out) animals and cells and tissues from such histamine $H_4$ deficient animals, the histamine $H_4$ receptor has been demonstrated to play an important role in various physiological and pathophysiological processes. Examples of diseases and disorders where histamine $H_4$ receptors have been found to play an important role include, for example, asthma, allergy, rheumatoid arthritis, and inflammation.

The activity of histamine $H_4$ receptors can be modified or regulated by the administration of histamine $H_4$ receptor ligands. The ligands can demonstrate antagonist, inverse agonist, or partial agonist activity.

Histamine $H_4$ ligands in different structural classes have been reviewed in (Schwartz, Expert Opinion in Therapeutic Patents (2003) vol. 13, pp. 851-865). It would be beneficial to provide additional compounds demonstrating $H_4$ receptor-modulating activity that can be incorporated into pharmaceutical compositions useful for therapeutic methods.

SUMMARY OF THE INVENTION

The invention is directed to macrocyclic pyrimidine derivatives, particularly macrocyclic benzofused pyrimidine derivatives, as well as compositions comprising and methods of using the same. Compounds of the invention have the formula (I):

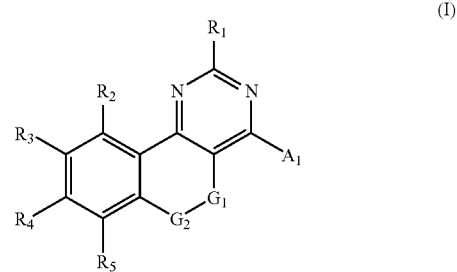

or a pharmaceutically acceptable salt, ester, amide, prodrug thereof, wherein $G_1$ is selected from oxygen, sulfur, S(O), S(O)$_2$, NR$_8$ and alkylene;

$G_2$ is selected from, oxygen, sulfur, S(O), S(O)$_2$, NR$_8$, and alkylene wherein each carbon of the alkylene groups of $G_1$ and $G_2$ may be optionally substituted with one or more groups selected from alkyl, fluoroalkyl, cyanoalkyl, cycloalkyl, fluorocycloalkyl, cycloalkoxyalkyl, alkylcycloalkyl, alkylfluorocycloalkyl, fluorine, acyl, acyloxy, alkenyl, alkoxy, alkoxyalkoxy, alkoxyalkyl, alkoxycarbonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, alkylthio, and oxo;

provided that when $G_1$ is oxygen, sulfur, S(O), S(O)$_2$ or NR$_8$, $G_2$ is alkylene;

provided that when $G_2$ is oxygen, sulfur, S(O), S(O)$_2$, or NR$_8$, $G_1$ is alkylene;

$R_1$ is selected from H, NH$_2$, —NH(acyl), —NH(alkyl), —N(alkyl)$_2$, —NH(C=O)aryl, —NH-alkylene(NR$_8$R$_9$), —NH(C=O)-alkylene(NR$_8$R$_9$), —NR$_8$(C=O)NR$_8$R$_9$, —NH-alkylene-heteroaryl, —NHOH, —NHOCH$_3$, —O-alkylene(NR$_8$R$_9$), alkyl, piperazine, fluoroalkyl, cyanoalkyl, cycloalkyl, fluorocycloalkyl, hydroxyalkyl, cyano, alkoxycarbonyl, carboxy, —(C=O)—(NR$_8$R$_9$), —(C=O)—NH-alkylene(NR$_8$R$_9$), and alkoxy;

$R_2$, $R_3$, $R_4$, $R_5$, are each independently selected from hydrogen, alkyl, fluoroalkyl, cyanoalkyl, cycloalkyl, fluorocycloalkyl, cycloalkoxyalkyl, alkylcycloalkyl, alkylfluorocycloalkyl, aryl, heteroaryl, heterocycle, O-aryl, O-heteroaryl, S-aryl, CONR$_8$R$_9$, NR$_8$COalkyl, —NR$_8$(C=O)Oalkyl, acyl, acyloxy, alkenyl, alkoxy, alkoxyalkoxy, alkoxyalkyl, alkoxycarbonyl, alkoxyimino, alkoxysulfonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, alkylthio, —NR$_8$R$_9$, -carbonyl (NR$_8$R$_9$), —SO$_2$(NR$_8$R$_9$), and N(R$_8$)SO$_2$(R$_9$); or $R_3$ and $R_4$ taken together with the carbon atoms to which each is attached form a ring, wherein $R_3$ and $R_4$ taken together are —CH$_2$CH$_2$CH$_2$—, —CH$_2$CH$_2$CH$_2$CH$_2$—, or —CH$_2$OCH$_2$—;

$R_6$ is selected from hydrogen, alkyl, fluoroalkyl, cyanoalkyl, hydroxyalkyl, alkoxyalkyl, cycloalkyl, fluorocycloalkyl, cycloalkoxyalkyl, alkylcycloalkyl, and alkylfluorocycloalkyl;

$R_7$ is selected from the group consisting of fluoroalkyl, hydroxyalkyl, alkoxyalkyl, fluorocycloalkyl, and alkylfluorocycloalkyl;

$R_8$ and $R_9$ are each independently selected from hydrogen, alkyl, fluoroalkyl, cycloalkyl, cyanoalkyl, fluorocycloalkyl, cycloalkoxyalkyl, alkylcycloalkyl, alkylfluorocycloalkyl, aryl, heteroaryl, heterocycle, acyl, alkoxyalkyl, alkoxycarbonyl, alkylcarbonyl, alkylsulfonyl, amido, formyl, hydroxy, and hydroxyalkyl;

$A_1$ is a group of structure $A_2$ or $A_3$.

wherein $A_2$ is

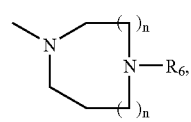  A

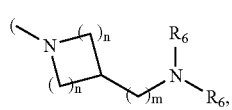  B

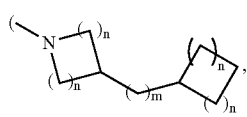  C

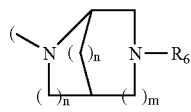  D

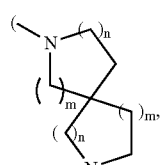  E

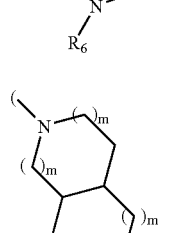  F

  G

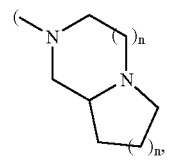

-continued

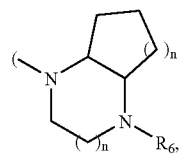  H

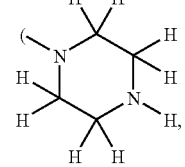  I

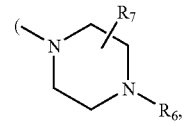  J

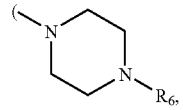  K

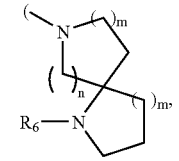  L

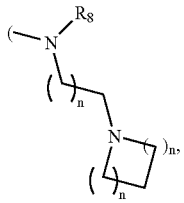  M

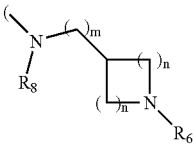  N

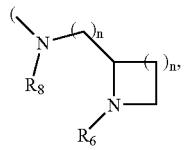  O

P

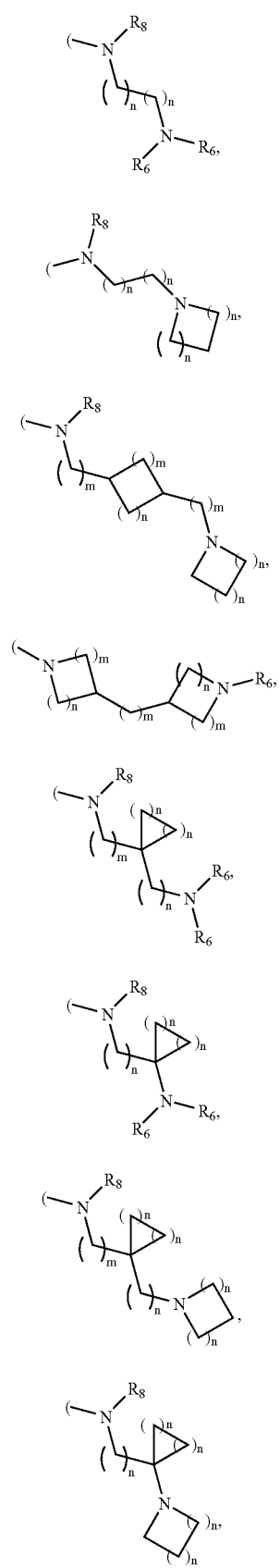
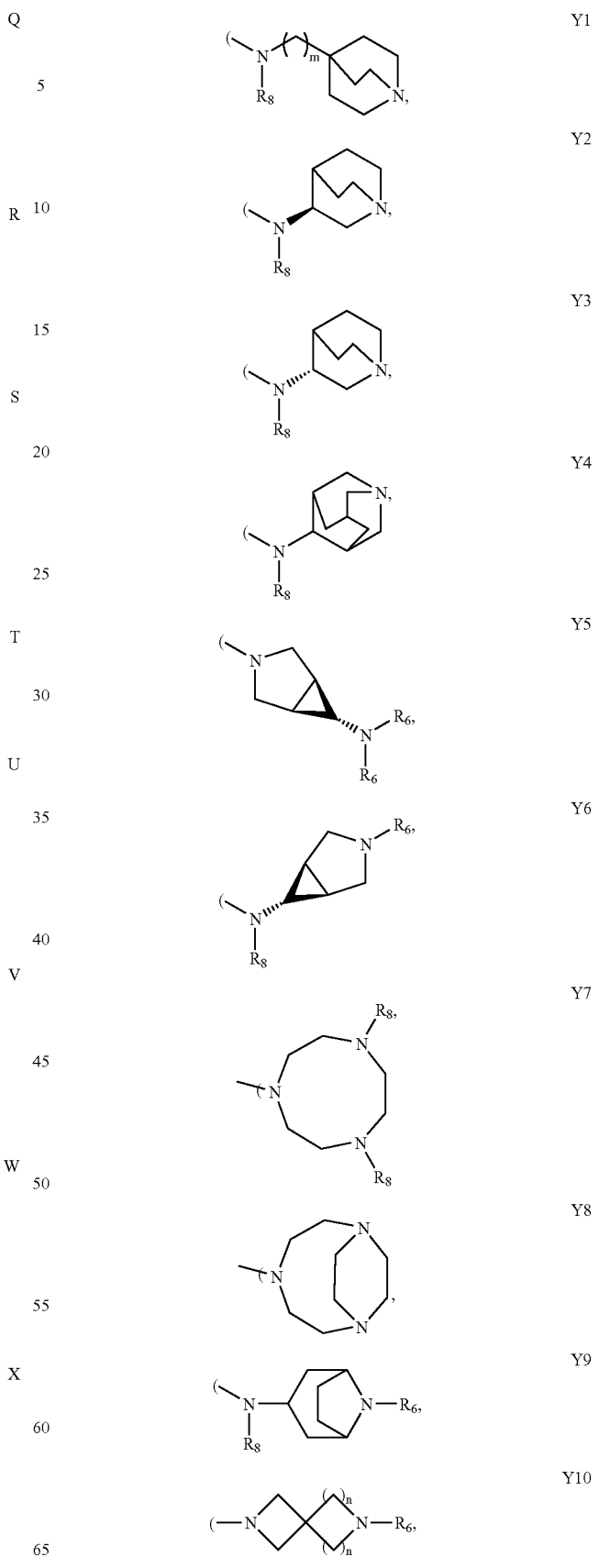

-continued
Y11 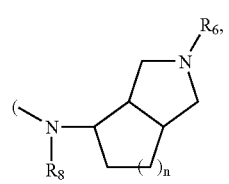
Y12 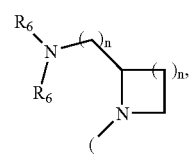
Y13 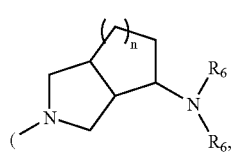
Y14 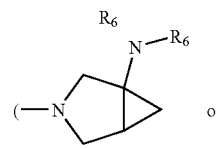
or
Y15 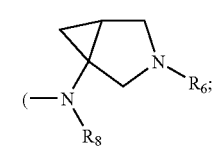
and $A_3$ is selected from
1M 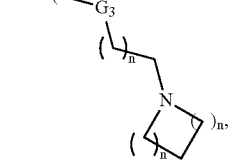
1N 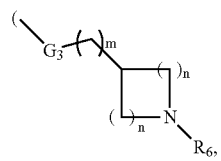
1O 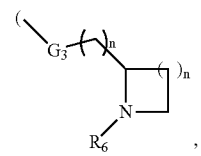
1P 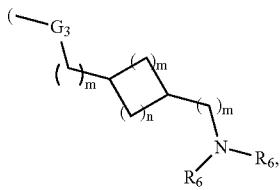
1Q 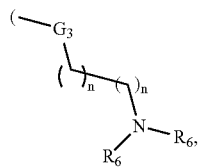
1R 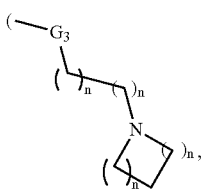
1S 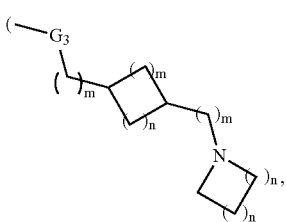
1U 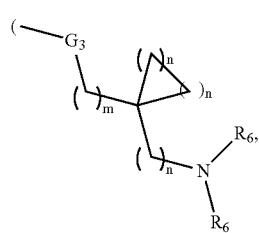
1V 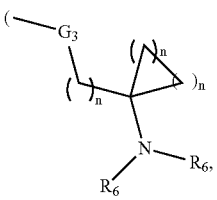
1W 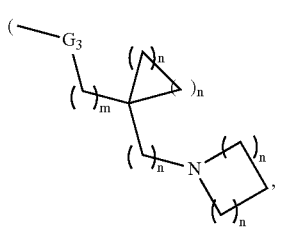
1X 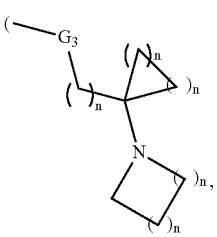

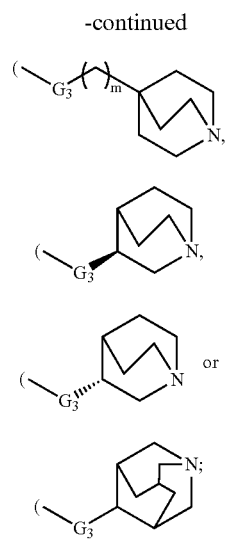

wherein $G_3$ is O, S, S(O), S(O)$_2$
n is 1, 2, or 3;
m is 0, 1, or 2;
wherein each carbon atom of groups $A_1$ may be optionally substituted with one or more groups selected from alkyl, fluoroalkyl, cyanoalkyl, cycloalkyl, fluorocycloalkyl, cycloalkoxyalkyl, alkylcycloalkyl, alkylfluorocycloalkyl, fluorine, acyl, acyloxy, alkenyl, alkoxy, alkoxyalkoxy, alkoxyalkyl, alkoxycarbonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, and alkylthio; provided that when $G_1$ is CH$_2$ and $G_2$ is selected from CH$_2$, CH$_2$CH$_2$, oxygen or sulfur and $R_1$ is selected from NH$_2$, NHalkyl, or alkyl, then $A_1$ is not a group of structure K; and further provided that when $G_1$ is CH$_2$CH$_2$ and $G_2$ is CH$_2$ and $R_1$ is selected from NH$_2$, NHalkyl, or alkyl, then $A_1$ is not a group of structure K.

Another aspect of the invention relates to pharmaceutical compositions comprising compounds of the invention. Such compositions can be administered in accordance with a method of the invention, typically as part of a therapeutic regimen for treatment or prevention of conditions and disorders related to histamine $H_4$ receptor activity.

In addition, compounds of the invention can have the formula (I) and also demonstrate an ability to modulate histamine $H_4$ receptor activity. In this aspect, the invention relates to a method of modulating histamine $H_4$ receptor activity. The method is useful for treating, or preventing conditions and disorders related to histamine $H_4$ receptor modulation in mammals. More particularly, the method is useful for treating or preventing conditions and disorders related to the immune system involving inflammatory processes, auto-immune disease, and also in nervous system activities involved in pain, such as inflammatory pain, and non-inflammatory pain, especially neuropathic pain. Accordingly, the compounds and compositions of the invention are useful as a medicament for treating or preventing histamine $H_4$ receptor modulated disease. Examples of such conditions and disorders include, but are not limited to, asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, osteoarthritis pain, post-surgical pain, non-inflammatory pain, neuropathic pain, subcategories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

Another aspect of the invention relates to the use of the compounds of the invention (compounds of formula (I)) in combination with histamine $H_1$ antagonists (such as loratidine), histamine $H_2$ antagonists (such as nizatidine), histamine $H_3$ antagonists (such as ABT-239), modulators of TNF-α (such as adalumamab), anti-inflammatory corticocosteroids (such as dexamethasone), 5-lipoxygenase inhibitors (such as zileuton), leukotriene antagonists (such as zafirlukast) or LTB4 antagonists, with NSAIDS (such as ibuprofen) including, COX-2 inhibitors (such as celecoxib), with β-adrenergic receptor agonists such as salmeterol, anti-nociceptive opiate agonists (such as morphine), anti-nociceptive alpha adrenergic agonists (such as dexmedetomidine), TRPV1 antagonists, nicotinic agonists such as ABT-418 or (1S,5S)-3-(5,6-dichloro-3-pyridinyl)-3,6-diazobicyclo [3.2.0]heptane, CB-1 agonists, CB-2 agonists, P2X7 antagonists, metabotropic glutamate receptor antagonists, an anticonvulsant such as gabapentin or pregabilin, and a tricyclic antidepressant such as amitriptyline. The compounds, compositions comprising the compounds, and methods for treating or preventing conditions and disorders by administering the compounds, are further described herein.

DETAILED DESCRIPTION OF THE INVENTION

Definition of Terms

Certain terms as used in the specification are intended to refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein means a straight or branched chain hydrocarbon containing from 2 to 10 carbons, and preferably 2, 3, 4, 5, or 6 carbons, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein means an alkoxy group, as defined herein, appended to the parent molecular moiety through a —C(=NH)— group, which also is defined as an imino group. Representative examples of alkoxyimino include, but are not limited to, imino(methoxy)methyl, ethoxy(imino)methyl and tert-butoxy(imino)methyl.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein means a straight or branched chain hydrocarbon containing from 1 to 10 carbon atoms, and preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylamino" as used herein means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylcycloalkyl" as used herein means an alkyl group, as defined herein, appended to the parent molecular moiety through a cycloalkyl group, as defined herein. Representative examples of alkylcycloalkyl include, but are not limited to, 4-ethylcyclohexyl, 3-methylcyclopentyl, 2-isopropylcyclopropyl and the like.

The term "alkylfluorocycloalkyl" as used herein means a fluorocycloalkyl group as defined herein, attached to an alkylene moiety, attached to the parent molecular moiety through the alkylene group. Representative examples of alkylfluorocycloalkyl include, but are not limited to, (4-fluorocyclohexyl)methyl, (2,2-difluorocyclobutyl)methyl and the like.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means an —NH$_2$ group.

The term "aryl," as used herein, means phenyl, a bicyclic aryl, or a tricyclic aryl. The bicyclic aryl is naphthyl, a phenyl fused to a cycloalkyl, or a phenyl fused to a cycloalkenyl. The bicyclic aryl of the invention must be attached to the parent molecular moiety through any available carbon atom contained within the phenyl ring. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, a bicyclic aryl fused to a cycloalkyl, a bicyclic aryl fused to a cycloalkenyl, or a bicyclic aryl fused to a phenyl. The tricyclic aryl is attached to the parent molecular moiety through any carbon atom contained within a phenyl ring. Representative examples of tricyclic aryl ring include, but are not limited to, azulenyl, dihydroanthracenyl, fluorenyl, and tetrahydrophenanthrenyl.

The carbon atoms of the aryl groups of this invention are substituted with hydrogen or are optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —NR$_8$R$_9$, (NR$_8$R$_9$)carbonyl, —SO$_2$NR$_8$R$_9$, —NR$_8$(C=O)NR$_8$R$_9$, —NR$_8$(C=O)Oalkyl, and N(R$_8$)SO$_2$(R$_9$). Where the aryl group is a phenyl group, the number of substituents is 0, 1, 2, 3, 4, or 5. Where the aryl group is a bicyclic aryl, the number of substituents is 0, 1, 2, 3, 4, 5, 6, or 7. Where the aryl group is a tricyclic aryl, the number of substituents is 0, 1, 2, 3, 4, 5, 6, 7, 8, or 9.

The term "arylalkyl" as used herein means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein means a —C(=O)— group.

The term "carboxy" as used herein means a —CO$_2$H group.

The term "cyano" as used herein means a —CN group, attached to the parent molecular moiety through the carbon.

The term "cyanoalkyl" as used herein means a —CN group attached to an alkylene, appended to the parent molecular moiety through the alkylene group. Representative examples of "cyanoalkyl" include, but are not limited to, 3-cyanopropyl, and 4-cyanobutyl.

The term "cyanophenyl" as used herein means a —CN group appended to the parent molecular moiety through a phenyl group, including, but not limited to, 4-cyanophenyl, 3-cyanophenyl, and 2-cyanophenyl.

The term "cycloalkyl" as used herein means a saturated cyclic hydrocarbon group containing from 3 to 10 carbons. Examples of cycloalkyl include cyclopropyl, cyclobutyl, cyclopentyl, cyclohexyl, cycloheptyl, and cyclooctyl. $C_3$-$C_5$ cycloalkyl in particular refers to a saturated cyclic hydrocarbon group containing from 3 to 5 carbons, for example, cyclopropyl, cyclobutyl, and cyclopentyl.

The term "cycloalkenyl" as used herein means a cyclic hydrocarbon group containing from 3 to 10 carbons, containing 1 or 2 carbon-carbon double bonds. Examples of cycloalkenyl include cyclopropenyl, cyclobutenyl, cyclopentenyl, cyclohexenyl, cycloheptentyl, and cyclooctenyl.

Each of the carbon atoms of the cycloalkyl or cycloalkenyl groups of the invention is substituted with 0, 1, or 2 substituents selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, oxo, nitro, alkylthio, —$NR_8R_9$, ($NR_8R_9$)carbonyl, —$SO_2N(R_8)$($R_9$), —$NR_8$(C=O)$NR_8R_9$, —$NR_8$(C=O)Oalkyl, and —N($R_8$)$SO_2$($R_9$), wherein, $R_8$ and $R_9$ are defined herein.

The term "cycloalkoxyalkyl" as used herein means a cycloalkyl group, as defined herein, appended to the parent molecular moiety through an —O-alkyl-group, wherein alkyl is as defined herein. Representative examples of cycloalkoxylalkyl include, but are not limited to, cyclobutoxymethyl, cyclopentyloxymethyl, 2-(cyclopentyloxy)ethyl and cyclohexyloxymethyl.

The term "cycloalkylcarbonyl" as used herein means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "cycloalkylalkyl" as used herein means a cycloalkyl group, as defined herein, appended to the parent molecular moiety through an alkyl group, as defined herein. Representative examples of cycloalkylalkyl include, but are not limited to, cyclopropylmethyl, cyclopentylmethyl, cyclohexylmethyl, and cycloheptylmethyl. ($C_3$-$C_5$ cycloalkyl)alkyl in particular refers to a saturated cyclic hydrocarbon group containing from 3 to 5 carbons, for example, cyclopropyl, cyclobutyl, and cyclopentyl, appended to the parent molecular moiety through a alkyl group.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" as used herein means —F.

The term "fluoroalkyl" as used herein means at least one fluoro group, appended to the parent molecular moiety through an alkyl group, as defined herein. Representative examples of fluoroalkyl include, but are not limited to, fluoromethyl, difluoromethyl, trifluoromethyl, pentafluoroethyl, and 2,2,2-trifluoroethyl.

The term "fluoroalkoxy" as used herein means at least one fluoro group, appended to the parent molecular moiety through an alkoxy group, as defined herein. Representative examples of fluoroalkoxy include, but are not limited to, fluoromethoxy, difluoromethoxy, trifluoromethoxy, pentafluoroethoxy, and 2,2,2-trifluoroethoxy.

The term "fluorocycloalkyl" as used herein means a fluoro as defined herein, attached to a cycloalkyl moiety, attached to the parent molecular moiety through the cycloalkyl group. Representative examples of fluorocycloalkyl include, but are not limited to, 4-fluorocyclohexyl, 2,2-difluorocyclobutyl and the like.

The term "formyl" as used herein means a —C(O)H group.

The term "halo" or "halogen" as used herein means Cl, Br, I, or F.

The term "haloalkoxy" as used herein means at least one halogen, as defined herein, appended to the parent molecular moiety through an alkoxy, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle", as used herein, refers to non-aromatic cyclic groups that contain at least one heteroatom. Non-aromatic heterocycles are non-aromatic cyclic groups that contain at least one heteroatom; examples of non-aromatic heterocyclic groups or non-aromatic heterocycles are further defined below. Heterocyclic rings are connected to the parent molecular moiety through a carbon atom, or alternatively in the case of heterocyclic rings that contain a bivalent nitrogen atom having a free site for attachment, the heterocyclic ring may be connected to the parent molecular moiety though a nitrogen atom. Additionally, the heterocycles may be present as tautomers.

The term "heteroaryl", as used herein, refers to an aromatic ring containing one or more heteroatoms independently selected from nitrogen, oxygen, and sulfur. Such rings can be monocyclic or bicyclic as further described herein.

The terms "monocyclic heteroaryl" or "5- or 6-membered heteroaryl ring", as used herein, refer to 5- or 6-membered aromatic rings containing at least one heteroatom independently selected from nitrogen, oxygen, and sulfur. The 5-membered ring contains two double bonds; such a ring may contain one, two, three or four nitrogen atoms, or may contain one or two nitrogen atoms and one oxygen atom, or may contain one or two nitrogen atoms and one sulfur atom, or may contain one oxygen atom, or may contain one sulfur atom. The 6-membered ring contains three double bonds, or alternatively, the 6-membered ring may contains 2 double bonds within the ring when the ring is substituted with an oxo group. Furthermore, the 6-membered ring may contain one, two, three or four nitrogen atoms, or may contain one or two nitrogen atoms and one oxygen atom, or may contain one or two nitrogen atoms and one sulfur atom, or may contain one or two nitrogen atoms and one sulfur atom, or may contain one or two nitrogen atoms and or one oxygen atom. The 5- or 6-membered heteroaryl is connected to the parent molecular moiety through any carbon atom or any nitrogen atom contained within the monocyclic heteroaryl ring. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, thiadiazolyl, thiadiazolonyl, thiadiazinonyl, oxadiazolyl, oxadiazolonyl, oxadiazinonyl, thiazolyl, thienyl, triazinyl, triazolyl, triazolyl, pyridazinonyl, pyridonyl, and pyrimidinonyl.

The term "bicyclic heteroaryl" or "8- to 12-membered bicyclic heteroaryl ring", as used herein, refers to an 8-, 9-, 10-, 11-, or 12-membered bicyclic aromatic ring wherein one or more of the atoms of the ring has been replaced with at least one heteroatom selected from oxygen, sulfur, and nitrogen. The bicyclic heteroaryl of the invention may be attached to the parent molecular moiety through any available carbon atom or nitrogen atom contained within the heteroaryl ring. Representative examples of bicyclic heteroaryl rings include indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, 1,5-dihydro-benzo[b][1,4]diazepin-2-on-yl, and pyrrolopyrimidinyl.

Heteroaryl groups of the invention, whether monocyclic or bicyclic, are substituted with hydrogen, or optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, oxo, $—NR^8R^9$, $(NR^8R^9)carbonyl$, $—SO_2N(R^8)(R^9)$, $—NR_8(C=O)NR_8R_9$, $—NR_8(C=O)Oalkyl$, and $—N(R^8)SO_2(R^9)$. Monocyclic heteroaryl or 5- or 6-membered heteroaryl rings are substituted with 0, 1, 2, 3, 4, or 5 substituents. Bicyclic heteroaryl or 8- to 12-membered bicyclic heteroaryl rings are substituted with 0, 1, 2, 3, 4, 5, 6, 7, 8, or 9 substituents. Heteroaryl groups of the invention may be present as tautomers.

The term "heterocycle" or "heterocyclic" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S. The 3- or 4-membered ring contains 1 heteroatom selected from the group consisting of O, N and S. The 5-membered ring contains zero or one double bond and one, two or three heteroatoms selected from the group consisting of O, N and S. The 6- or 7-membered ring may contain zero, one, or two double bonds provided that the ring, when taken together with a substituent, does not tautomerize with a substituent to form an aromatic ring. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, a monocyclic heterocycle fused to a cycloalkyl, a monocyclic heterocycle fused to a cycloalkenyl, or a monocyclic heterocycle fused to a monocyclic heterocycle. The bicyclic heterocycle is connected to the parent molecular moiety through any carbon atom or any nitrogen atom contained within the monocyclic heterocycle. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

The non-aromatic heterocycles of the invention substituted with hydrogen, or optionally substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, $—NR_8R_9$, $(NR_8R_9)carbonyl$, $—SO_2N(R_8)(R_9)$, $—NR_8(C=O)NR_8R_9$, $—NR_8(C=O)Oalkyl$, and $—N(R_8)SO_2(R_9)$.

The term "hydroxy" as used herein means an —OH group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyidiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, $CH_2I_2$, or a dihaloboronate ester, for example with methyl iodide, benzyl iodide, triethylsilyltriflate, acetyl chloride, benzyl chloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "mercapto" as used herein means a —SH group.

The term "$(NR_8R_9)$" as used herein means both an $R_8$ and $R_9$ group, wherein $R_8$ and $R_9$ are each as defined for compounds of formula (I), are appended to the parent molecular moiety through a nitrogen atom. The "$(NR_8R_9)$" is appended to the parent molecular moiety through the nitrogen.

The term "$(NR_8R_9)alkyl$" as used herein means an $—NR_8R_9$ group, as defined herein, appended to the parent molecular moiety through an alkylene group, as defined herein. Representative examples of $(NR_8R_9)alkyl$ include, but are not limited to, 2-(methylamino)ethyl, 2-(dimethylamino)ethyl, 2-(amino)ethyl, 2-(ethylmethylamino)ethyl, and the like.

The term "$(NR_8R_9)carbonyl$" as used herein means an $—NR_8R_9$ group, as defined herein, appended to the parent molecular moiety through a carbonyl group, as defined herein. Representative examples of $(NR_8R_9)carbonyl$ include, but are not limited to, aminocarbonyl, (methylamino)carbonyl, (dimethylamino)carbonyl, (ethylmethylamino)carbonyl, and the like.

The term "$—NR_8(C=O)Oalkyl$" as used herein means an amino group attached to the parent moiety to which is further appended a $R_8$ group as defined herein, and a (C=O), i.e. carbonyl, group to which is appended an Oalkyl, i.e. alkoxy, group. Representative examples of —$NR_8$(C=O)Oalkyl include, but are not limited to, methyl N-methylcarbamate, tert-butyl N-methylcarbamate, and the like.

The term "—$NR_8$(C=O)$NR_8R_9$" as used herein means an amino group attached to the parent moiety to which is further appended a $R_8$ group as defined herein, and a (C=O)$NR_8R_9$, i.e. ($NR_8R_9$)carbonyl, as defined herein. Representative examples of —$NR_8$(C=O)$NR_8R_9$ include, but are not limited to, methylurea, phenyl urea, and the like.

The term "($NR_8R_9$)sulfonyl" as used herein means a —$NR_8R_9$ group, as defined herein, appended to the parent molecular moiety through a sulfonyl group, as defined herein. Representative examples of ($NR_8R_9$)sulfonyl include, but are not limited to, aminosulfonyl, (methylamino)sulfonyl, (dimethylamino)sulfonyl and (ethylmethylamino)sulfonyl.

The term "—N($R_8$)$SO_2$($R_9$)" as used herein means an amino group attached to the parent moiety to which is further appended with a $R_8$ group as defined herein, and a $SO_2$ group to which is appended an ($R_9$) group as defined herein. Representative examples of —N($R_8$)$SO_2$($R_9$) include, but are not limited to, N-methylmethanesulfonamide.

The term "—$SO_2$($NR_8R_9$)" as used herein means a $NR_8R_9$ group attached to a $SO_2$ group, appended to the parent moiety through the sulfonyl group. Representative examples of —$SO_2$($NR_8R_9$) include, but are not limited to (dimethylamino)sulfonyl and N-cyclohexyl-N-methylsulfonyl.

The term "nitro" as used herein means a —$NO_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by an alkyl anhydride (alkyl-OC=O)$_2$O, a diaryl anhydride, for example as represented by (aryl-OC=O)$_2$O, an acyl halide, an alkylchloroformate, or an alkylsulfonylhalide, an arylsulfonylhalide, or halo-CON(alkyl)$_2$, for example acetyl chloride, benzoyl chloride, benzyl bromide, benzyloxycarbonyl chloride, formylfluoride, phenylsulfonyl chloride, pivaloyl chloride, (tert-butyl-O—C=O)$_2$O, trifluoroacetic anhydride, and triphenylmethylchloride.

The term "oxo" as used herein means (=O).

The term "sulfonyl" as used herein means a —S(O)$_2$— group.

Antagonists are ligands that block receptor activation by an agonist. In the case of the histamine $H_4$ receptor, a histamine $H_4$ receptor antagonist blocks activation of the histamine $H_4$ receptor by a histamine $H_4$ receptor agonist such as the endogenous agonist ligand histamine. Inverse agonists are ligands that block receptor activation more generally: they block intrinsic activation of a receptor that occurs in the absence of an agonist activation by an agonist, and also block receptor activation by an agonist. Partial agonists are ligands that bind to receptors but only partially activate the receptor; in so doing, partial agonists compete with full agonists and block full activation of the receptor. In the case of the histamine $H_4$ receptor, the endogenous agonist histamine is a full agonist.

Compounds of the Invention

Compounds of the invention can have the formula (I) as described in the Summary of the Invention. In addition, certain embodiments of the invention further describe compounds of formula (I):

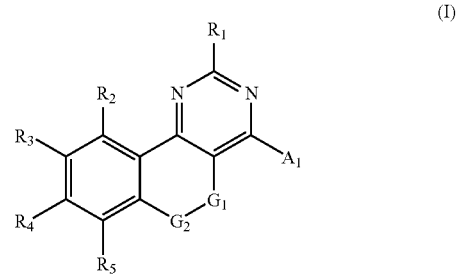

In compounds of formula (I), $G_1$ is oxygen, sulfur, S(O), S(O)$_2$, $NR_8$ or an alkylene group, for example a hydrocarbon chain of 1, 2, 3, 4, 5, 6, 7, 8, 9, or 10 carbons. Preferably, $G_1$ is —$CH_2CH_2$—.

$G_2$ is selected from alkylene, oxygen, sulfur, S(O), S(O)$_2$, $NR_8$, wherein each carbon of the alkylene groups of $G_1$ and $G_2$ may be optionally substituted with one or more groups selected from alkyl, fluoroalkyl, cyanoalkyl, cycloalkyl, fluorocycloalkyl, cycloalkoxyalkyl, alkylcycloalkyl, alkylfluorocycloalkyl, fluorine, acyl, acyloxy, alkenyl, alkoxy, alkoxyalkoxy, alkoxyalkyl, alkoxycarbonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, alkylthio, and oxo;

provided that when $G_1$ is oxygen, sulfur, S(O), S(O)$_2$ or $NR_8$, $G_2$ is alkylene;

provided that when $G_2$ is oxygen, sulfur, S(O), S(O)$_2$, or $NR_8$, $G_1$ is alkylene;

Preferably, $G_2$ is —$CH_2$—.

$R_1$ is selected from H, $NH_2$, —NH(acyl), —NH(alkyl), —N(alkyl)$_2$, NH(C=O)aryl, —NH-alkylene($NR_8R_9$), —NH(C=O)-alkylene($NR_8R_9$), —NH-alkylene-heteroaryl, —NHOH, —$NHOCH_3$, —O-alkylene($NR_8R_9$), alkyl, piperazine, fluoroalkyl, cyanoalkyl, cycloalkyl, fluorocycloalkyl, hydroxyalkyl, cyano, alkoxycarbonyl, carboxy, —(C=O)—($NR_8R_9$), —(C=O)—NH-alkylene($NR_8R_9$), and alkoxy.

$R_2$, $R_3$, $R_4$, and $R_5$ at each occurrence are each independently selected from hydrogen, alkyl, fluoroalkyl, cyanoalkyl, cycloalkyl, fluorocycloalkyl, cycloalkoxyalkyl, alkylcycloalkyl, alkylfluorocycloalkyl, aryl, heteroaryl, heterocycle, O-aryl, O-heteroaryl, S-aryl, $CONR_8R_9$, $NR_8COalkyl$, acyl, acyloxy, alkenyl, alkoxy, alkoxyalkoxy, alkoxyalkyl, alkoxycarbonyl, alkoxyimino, alkoxysulfonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, alkylthio, —$NR_8R_9$, -carbonyl($NR_8R_9$), —$SO_2$ ($NR_8R_9$), and N($R_8$)$SO_2$($R_9$).

Alternatively, $R_3$ and $R_4$ taken together form a ring, wherein $R_3$ and $R_4$ taken together are —$CH_2CH_2CH_2$—, —$CH_2CH_2CH_2CH_2$—, or —$CH_2OCH_2$—.

The preferred group for each of $R_2$, $R_3$, $R_4$, and $R_5$ is hydrogen, methoxy, chlorine, and fluorine.
$A_1$ is a group of structure $A_2$ or $A_3$
wherein $A_2$ is:
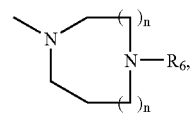
A
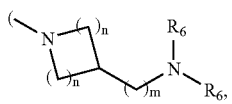
B
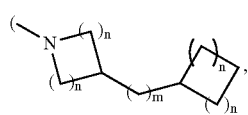
C
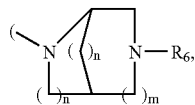
D
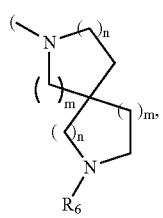
E
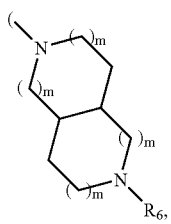
F
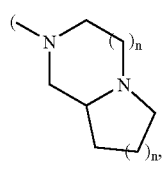
G
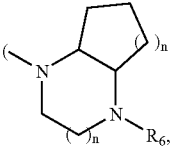
H
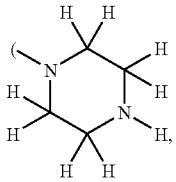
I
-continued
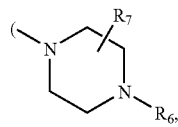
J
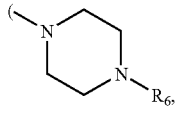
K
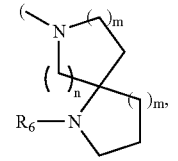
L
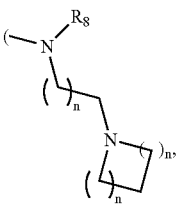
M
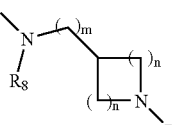
N
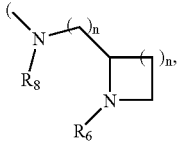
O
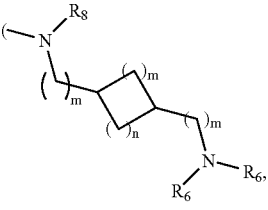
P
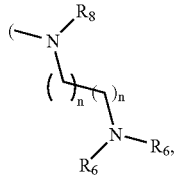
Q
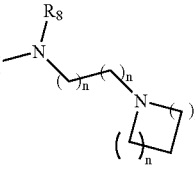
R

| | |
|---|---|
| S 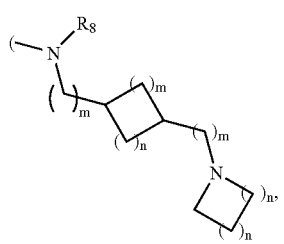 | Y4 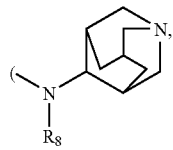 |
| T 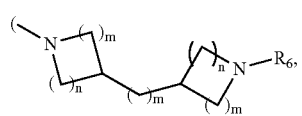 | Y5 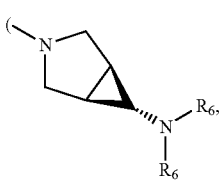 |
| U 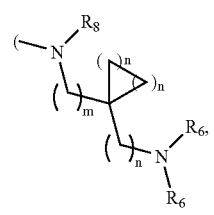 | Y6 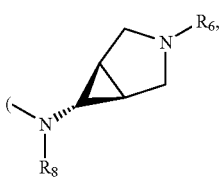 |
| V 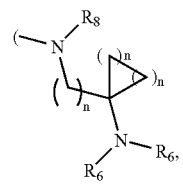 | Y7 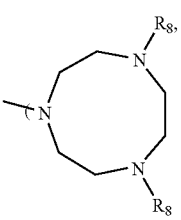 |
| W 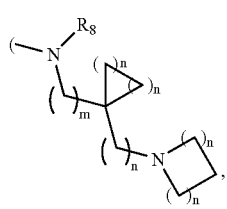 | Y8 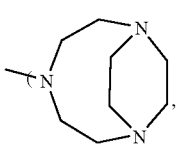 |
| X 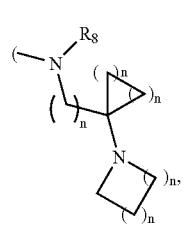 | Y9 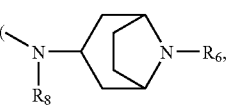 |
| Y1 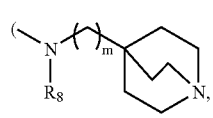 | Y10  |
| Y2 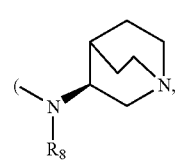 | Y11 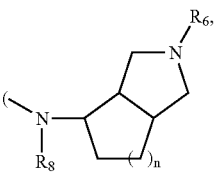 |
| Y3 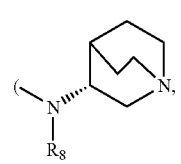 | Y12 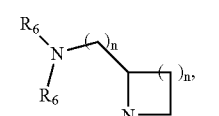 |
| | Y13 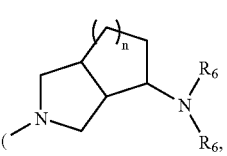 |

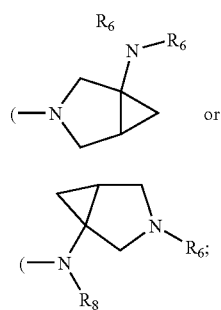
and A₃ is selected from
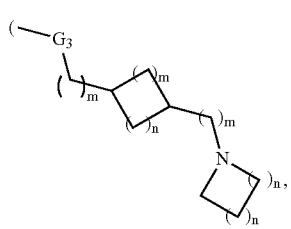  1M
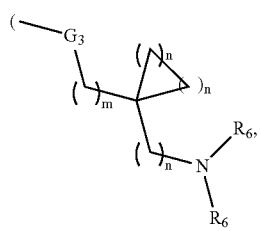  1N
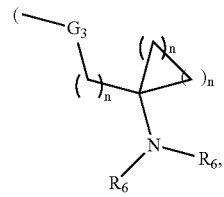  1O
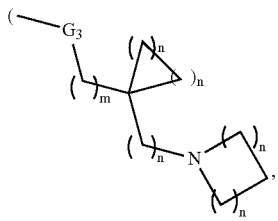  1P
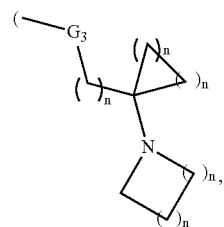  1Q
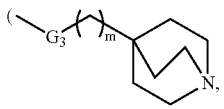  1R
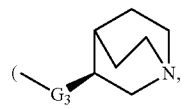  1S
  1U

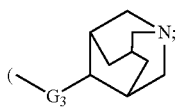

wherein G₃ is O, S, S(O), S(O)₂;

n is 1, 2, or 3;

m is 0, 1, or 2; and wherein each carbon atom of groups A₁ may be optionally substituted with one or more groups selected from alkyl, fluoroalkyl, cyanoalkyl, cycloalkyl, fluorocycloalkyl, cycloalkoxyalkyl, alkylcycloalkyl, alkylfluorocycloalkyl, fluorine, acyl, acyloxy, alkenyl, alkoxy, alkoxyalkoxy, alkoxyalkyl, alkoxycarbonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, alkylthio; provided that when G₁ is CH₂ and G₂ is selected from CH₂, CH₂CH₂, oxygen or sulfur and R₁ is selected from NH₂, NHalkyl, or alkyl, then A₁ is not a group of structure K; and further provided that when G₁ is CH₂CH₂ and G₂ is CH₂ and R₁ is selected from NH₂, NHalkyl, or alkyl, then A₁ is not a group of structure K.

Specific groups contemplated for A₁ have the structure:

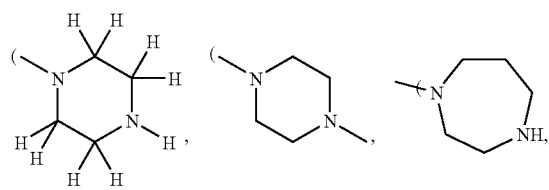

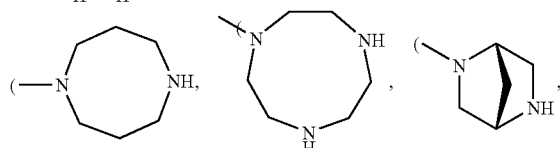

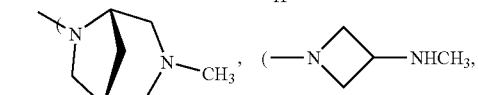

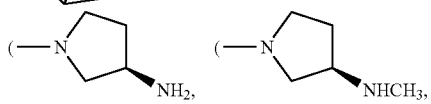

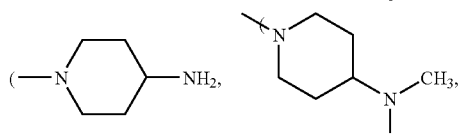

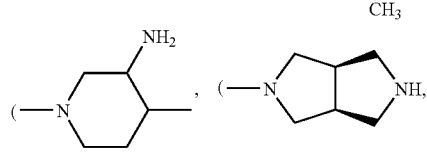

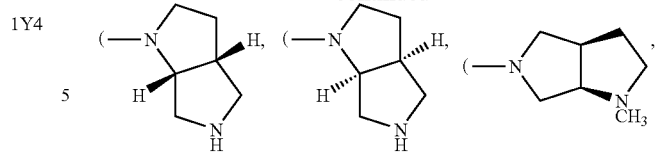

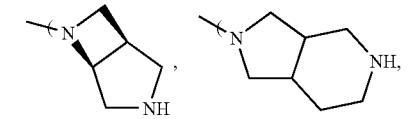

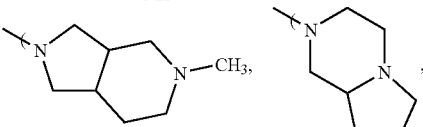

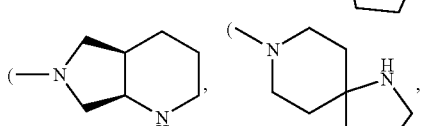

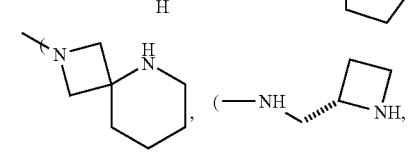

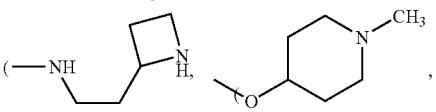

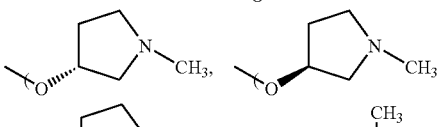

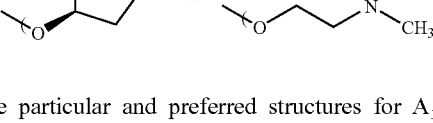

More particular and preferred structures for A₁ group groups of formulae (A)-(Y15) and (1M) to (1Y4) include, but are not limited to,

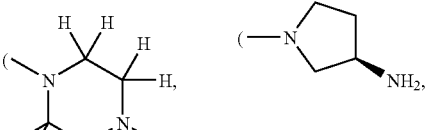

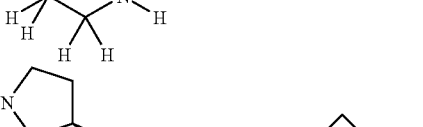

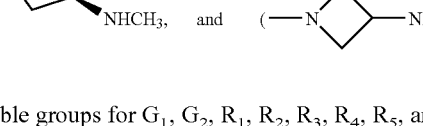

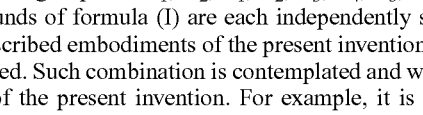

Suitable groups for G₁, G₂, R₁, R₂, R₃, R₄, R₅, and A₁ in compounds of formula (I) are each independently selected. The described embodiments of the present invention may be combined. Such combination is contemplated and within the scope of the present invention. For example, it is contemplated that preferred groups for any of G₁, G₂, R₁, R₂, R₃, R₄, R₅, and A₁ can be combined with groups defined for any other of G₁, G₂, R₁, R₂, R₃, R₄, R₅, and A₁ whether or not such group is preferred.

There also exist a pharmaceutical composition comprising a compound of formula (I) and a pharmaceutically acceptable carrier.

Representative examples of the invention are further described herein in the Examples. In particular, preferred embodiments contemplated as part of the invention also include, 4-piperazin-1-yl-6,7-dihydro-5H-benzo[6,7]cyclohepta[1,2-d]pyrimidin-2-ylamine, 4-(3-methylamino-azetidin-1-yl)-6,7-dihydro-5H-benzo[6,7]cyclohepta[1,2-d]pyrimidin-2-ylamine, 4-(3-(R)-methylamino-pyrrolidin-1-yl)-6,7-dihydro-5H-benzo[6,7]cyclohepta[1,2-d]pyrimidin-2-ylamine, and 4-((3R)-3-amino-pyrrolidin-1-yl)-6,7-dihydro-5H-benzo[6,7]cyclohepta[1,2-d]pyrimidin-2-ylamine. The practice of assigning names to chemical compounds from structures, and of assigning chemical structures from given chemical names is well known to those of ordinary skill in the art.

Compounds of the invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutanes and cyclohexanes may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention. It is also understood that the compounds of the invention may exist as isotopomers, wherein atoms may have different weights; for example, hydrogen, deuterium and tritium, or $^{12}C$, $^{11}C$ and $^{13}C$, or $^{19}F$ and $^{18}F$.

Methods of the Invention

Compounds and compositions of the invention are useful for modulating the histamine $H_4$ receptor, particularly by histamine $H_4$ receptor antagonism, partial agonism, or inverse agonism. In particular, the compounds and compositions of the invention can be used for treating and preventing disorders modulated by the histamine $H_4$ receptor. Typically, such disorders can be ameliorated by modulating histamine $H_4$ receptors in a mammal, preferably by administering a compound or composition of the invention, either alone or in combination with another active agent, for example, as part of a therapeutic regimen.

Certain substituted macrocyclic benzofused pyrimidine compounds, including but not limited to those specified as compounds of the invention, demonstrate the ability to affect histamine $H_4$ receptor activity, and particularly for histamine $H_4$ receptor antagonism. Such compounds can be useful for the treatment and prevention of a number of histamine $H_4$ receptor-mediated diseases or conditions. Compounds of the invention demonstrate such activity and have the formula (I), as previously defined herein.

There is also disclosed a method of treating a mammal having a condition where modulation of histamine $H_4$ receptor activity is of therapeutic benefit, said method comprising administering to a subject having or susceptible to said disorder with a therapeutically effective amount of a compound of the formula (I), or a pharmaceutically acceptable salt, ester, amide, or prodrug thereof, as previously in the Summary of the Invention and Detailed Description of the Invention herein.

There is also disclosed a method of treating a mammal having a condition where modulation of histamine $H_4$ receptor activity is of therapeutic benefit. The method comprises administering to a subject having or susceptible to said disorder a therapeutically effective amount of a compound of the formula (I), as previously defined.

The method is particularly beneficial when the condition or disorder is asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, or spinal cord injury pain.

In particular, it is particularly beneficial to administer compounds of formula (I) for the prevention and treatment of asthma.

It also is particularly beneficial to administer compounds of formula (I) for the prevention and treatment of inflammation.

It also is particularly beneficial to administer compounds of formula (I) for the prevention and treatment of pain. More particularly, it is beneficial to administer compounds of formula (I) for prevention and treatment of inflammatory pain. Compounds of formula (I) also demonstrate therapeutic benefit in treating and preventing non-inflammatory pain. In particular, compounds of formula (I) can be administered for treatment and prevention of neuropathic pain.

As an important consequence of the ability of the compounds of the invention to modulate the effects of histamine $H_4$ receptors in cells, the compounds described for the method of the invention can affect physiological processes in humans and animals. In this way, the compounds and compositions of formula (I) are useful for treating and preventing diseases and disorders modulated by histamine $H_4$ receptors. Typically, treatment or prevention of such diseases and disorders can be effected by modulating the histamine $H_4$ receptors in a mammal, by administering a compound or composition of the invention, either alone or in combination with another active agent as part of a therapeutic regimen.

Particularly preferred are compounds of formula (I) for the method, include, but are not limited to, 4-Piperazin-1-yl-6,7-dihydro-5H-benzo[6,7]cyclohepta[1,2-d]pyrimidin-2-ylamine, 4-(3-Methylamino-azetidin-1-yl)-6,7-dihydro-5H-benzo[6,7]cyclohepta[1,2-d]pyrimidin-2-ylamine, 4-(3-(R)-Methylamino-pyrrolidin-1-yl)-6,7-dihydro-5H-benzo[6,7]cyclohepta[1,2-d]pyrimidin-2-ylamine and 4-((3R)-3-Amino-pyrrolidin-1-yl)-6,7-dihydro-5H-benzo[6,7]cyclohepta[1,2-d]pyrimidin-2-ylamine.

Compounds of formula (I) can be administered to a subject having such a disorder or susceptible to such disorders in a therapeutically effective amount. The compounds are particularly useful for a method of treating a mammal having a condition where modulation of histamine $H_4$ receptor activity is of therapeutic benefit, wherein the method is accomplished by administering a therapeutically effective amount of a compound of formula (I) to a subject having, or susceptible to, such a disorder.

Compounds useful for the method of the invention, include but not limited to those specified in the examples, and possess an affinity for the histamine $H_4$ receptor. Such compounds therefore may be useful for the treatment and prevention of diseases or conditions related to histamine $H_4$ modulation. Examples of such diseases or conditions are, for example, asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain. The ability of histamine $H_4$ receptor modulators, and consequently the compounds of the invention, to prevent or treat such disorders is demonstrated by evidence and examples found in references which follow.

Histamine $H_4$ receptor ligands have utility in treatment of a number of diseases and conditions, including asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

The histamine $H_4$ receptor, or gene message coding for the histamine $H_4$ receptor (detected as cDNA by reverse transcriptase polymerase chain amplification (RTPCR) of cellular messenger (mRNA)) has been detected in a number of cells and tissues critically affected in disease conditions. For example, the histamine $H_4$ receptor plays a critical role in inflammation, in autoimmune disorders such as rheumatoid arthritis, and in disorders of the immune system. For example, the histamine $H_4$ receptor has been detected in cells of the immune system and in organs of the immune system: neutrophils, eosinophils, basophils, dendritic cells, mast cells, bone marrow, thymus, spleen, brain. For examples, see Liu, et al. Molecular Pharmacology (2001) vol. 59 pp. 420-426; de Esch, et al. Trends in Pharmacological Sciences Vol. 26 No. 9 pp. 462-469; Oda, et al. Journal of the Pharmocological Society (2005) vol. 98, pp. 319-322; Zhu, et al. Molecular Pharmacology, (2001), v. 59, pp. 434-441; Gutzmer, et al. Journal of Immunology (2005) vol. 174 pp. 5224-5232; Coge, et al., Biochemical and Biophysical Research Communications (2001) vol. 284, pp. 301-309.

Histamine $H_4$ receptor is found at high (compared to normal) levels in disease tissues in rheumatoid arthritis, see for example, Maslinska, et al. 34th Meeting of the European Histamine Research Society in Bled, Slovenia 2005 poster number 3; Jablonowska, et al. 35th Meeting of the European Histamine Research Society in Delphi, Greece (May 10-13, 2006) presentation O36; Ikawa, et al. Biol. Pharm. Bull. (2005) vol. 28(10) pp. 2016-2018.

The role of histamine $H_4$ receptors in allergy, asthma, and allergic airway inflammation is shown by the finding that transgenic mice without histamine $H_4$ receptors are resistant to the development of disease in an animal model of asthma. The observation that a selective synthetic $H_4$ ligand elicits the same benefit in the asthma model also supports the benefits of $H_4$ ligands in treatment of disease. For example, see Dunford, et al. The Journal of Immunology (2006) vol. 176, pp. 7062-7070.

General reviews and papers on the role of histamine receptor in disease include Akdis and Simons European Journal of Pharmacology (2006) vol. 533 pp. 69-76; de Esch, et al. Trends in Pharmacological Sciences Vol. 26 No. 9 pp. 462-469; Thurmond, et al. Journal of Pharmacology and Experimental Therapeutics (2004) vol. 309 pp. 404-413; Buckland, et al. British Journal of Pharmacology (2003) 140, 1117-1127. The utility for histamine $H_4$ receptor ligands in cancer is supported by the finding that the $H_4$ receptor has been found expressed on mammary cell carcinoma tissues, as reported by Maslinska, et al. 34th Meeting of the European Histamine Research Society in Bled, Slovenia (May 11-15, 2005) presentation. Histamine $H_4$ receptor activation was found to exert a proliferative effect in cancer tissues, Cianchi, et al. Clinical Cancer Research (2005) vol. 11(19) pp. 6807-6815. In gastritis and gastric lesions, histamine $H_4$ ligands were found to reduce the lesions induced by administration of indomethacin in vivo: Coruzzi, et al. Jablonowska, et al. 35th

Meeting of the European Histamine Research Society in Delphi, Greece (May 10-13, 2006) presentation O44. In colitis, histamine $H_4$ ligands were found to reduce the lesions induced by administration of trinitrobenzesulfonic acid in vivo: Varga, et al. European Journal of Pharmacology (2005) vol. 522 pp. 130-138; Fogel, et al. 35th Meeting of the European Histamine Research Society in Delphi, Greece (May 10-13, 2006) presentation P32. In itch and pruritis, the benefit of histamine $H_4$ receptor ligands has been shown by Bell, et al. British Journal of Pharmacology (2004) vol. 142, pp. 374-380.

The invention also relates to a new use of the compounds of the invention to treat histamine $H_4$ receptor ligands to treat pain, including distinctly different types of pain, including inflammatory pain, chemically induced pain, pain resulting from surgery, pain resulting from burns, pain resulting from osteoarthritis, non-inflammatory pain, and neuropathic pain. Neuropathic pain is distinct from other types of pain (e.g. inflammatory pain) in that it can develop in response to previous or ongoing tissue, nerve injury, or diabetes, but it persists long after signs of the original injury or damage have disappeared.

Neuropathic pain is associated with allodynia, hyperalgesia, or causalgia (Dworkin Clinical Journal of Pain (2002) vol. 18(6) pp. 343-9). Allodynia is the perception of pain following a stimulus that would not normally be painful. Hyperalgesia is an enhanced response to a mildly noxious stimulus. Causalgia is described as a chronic burning pain that shows persistence in the absence of obvious noxious stimuli.

Neuropathic pain is not well treated with current therapies and therefore there is a strong need for methods to treat this particular type of pain. The topic of neuropathic pain has been reviewed in the scientific literature, for example, Smith, et al. Drug Development Research (2001) vol. 54(3), pp. 140-153; Collins and Chessell Expert Opinion on Emerging Drugs (2005) vol. 10(1), pp. 95-108; Vinik and Mehrabyan Medical Clinics of North America (2004), vol. 88(4), pp. 947-999; Dray, Urban, and Dickenson Trends in Pharmacological Sciences (1994) vol. 15(6) pp. 190-7; Dworkin Clinical Journal of Pain (2002) vol. 18(6) pp. 343-9. A number of animal models of neuropathic pain that can be used to assess the ability of the compounds of the invention to treat neuropathic pain exist and are further discussed inter alia. Representative compounds of the invention are effective in treatment of neuropathic pain. Representative compounds of the invention are also effective in treating other types of pain, non-inflammatory pain, post surgical pain, and inflammatory pain.

Neuropathic pain is a description that encompasses more specific names of pain that are sub-categories of neuropathic pain (Dworkin Clinical Journal of Pain (2002) vol. 18(6) pp. 343-9) including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

In addition to neuropathic pain, there are other types of pain that are not inflammatory or not due to ongoing inflammation, including osteoarthritis pain, cancer pain, and visceral pain. A general review of animal models of pain is found in Joshi and Honore, Expert Opinion in Drug Discovery (2004) 1, pp. 323-334.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 5 to about 500 micromoles/kg of body weight. For purposes of oral administration, more preferable doses can be in the range of from about 30 to about 500 micromoles/kg body weight. If desired, the effective daily dose can be divided into multiple doses for purposes of administration; consequently, single dose compositions may contain such amounts or submultiples thereof to make up the daily dose.

Methods for Preparing Compounds of the Invention

The compounds of the invention can be better understood in connection with the following synthetic schemes and methods which illustrate a means by which the compounds can be prepared.

Abbreviations which have been used in the descriptions of the schemes and the examples that follow are: BINAP for 2,2'-bis(diphenylphosphino)-1,1'-binaphthyl; Boc for butyloxycarbonyl; DMF for N,N-dimethylformamide; DMSO for dimethyl sulfoxide; dppf for 1,1'-bis(diphenylphosphino)ferrocene; $Et_2O$ for diethyl ether; EtOAc for ethyl acetate; EtOH for ethanol; EtONa for sodium ethoxide; HPLC for high pressure liquid chromatography; IPA for isopropyl alcohol; MCPBA for 3-chloroperoxybenzoic acid; Me for methyl; MeOH for methanol; Ms for methanesulfonyl; Pd for palladium; tBu for tert-butyl; TEA for triethylamine; TFA for trifluoroacetic acid; THF for tetrahydrofuran; Tf represents trifluoromethane sulfonyl; and Ts for para-toluenesulfonyl; dba for dibenzylidine acetone, rt for "room temperature" or ambient temperature suitably ranging 17-30° C. As identifiers of compounds available from descriptions reported in the literature or available commercially, CAS numbers may be used; CAS numbers are identifier numbers assigned to compounds by Chemical Abstracts Service of the American Chemical Society, and are well known to those of ordinary skill in the art.

The compounds of this invention can be prepared by a variety of synthetic procedures. Representative procedures are shown in, but are not limited to Schemes 1-19.

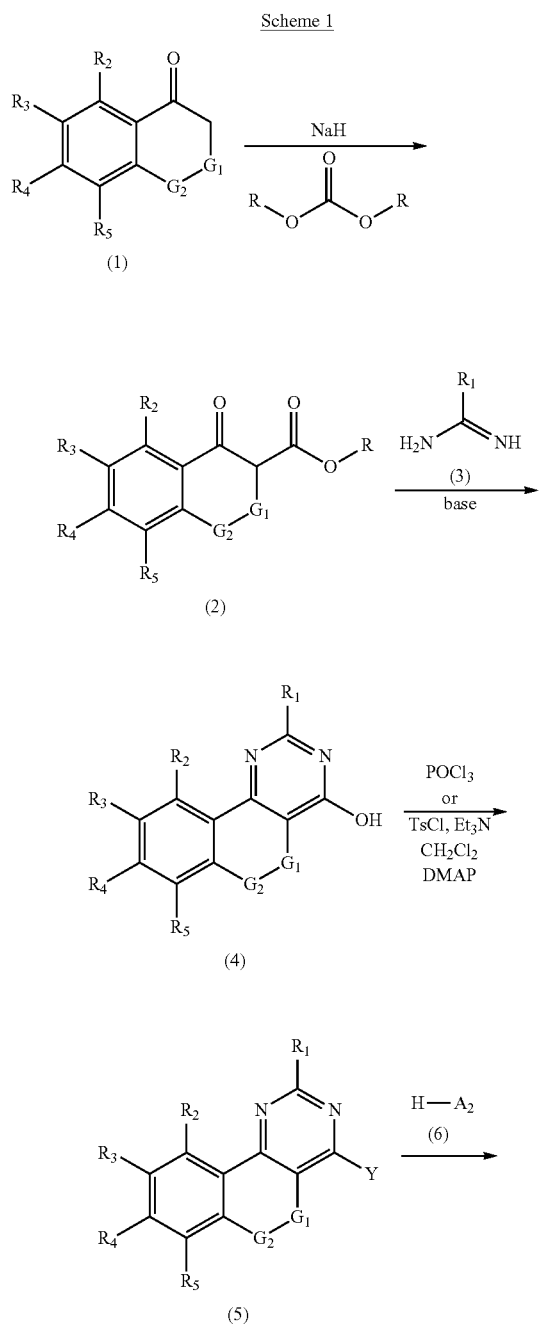

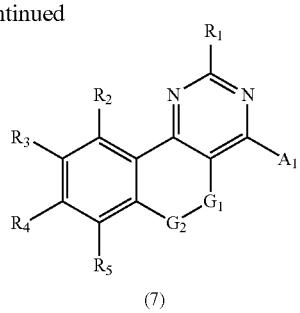

Compounds of formula (7), wherein $R_1$, $R_2$, $R_3$, $R_4$, $R_5$, $A_1$, $G_1$ and $G_2$ are defined in formula (I) may be prepared as outlined in Scheme 1. Ketones of formula (1), which are obtained either from commercial sources or synthesized through the methods outlined herein, when treated with a base such as sodium hydride, followed by treatment with either a carbonate such as dimethyl carbonate, or a chloroformate such as ethyl chloroformate, will provide keto-ester containing compounds of formula (2), wherein R is lower alkyl Compounds of formula (2) when treated with a compound of formula (3), such as guanidine nitrate, in the presence of a base such as potassium carbonate under heated conditions in a solvent such as DMF will provide compounds of formula (4). Compounds of formula (4) can exist as shown in the structure in scheme 1 or in a tautomeric form. Compounds of formula (4) when treated with a chlorinating reagent such as but not limited to $POCl_3$, with or without heating as needed, will provide compounds of formula (5), wherein Y=Cl. Alternatively, compounds of formula (4) may also be treated with reagents such as para-toluensulfonyl chloride, methylsulfonyl chloride or trifluoromethanesulfonyl chloride in the presence of a base such as triethylamine in a solvent such as pyridine or chloroform to provide compounds of formula (5) wherein Y=O—$SO_2$—R', wherein R' is lower alkyl, lower fluoroalkyl or aryl. Compounds of formula (5), wherein Y=Cl or —O—$SO_2$—R', when treated with compounds of formula (6), wherein (6) contains a primary or secondary nitrogen atom and H is a hydrogen atom on said nitrogen atom, under heated conditions in the presence or absence of a base such as triethylamine or diisopropyethylamine, in a solvent such as ethanol, 2-methoxyethanol, toluene or acetonitrile, will provide compounds of formula (7).

Compounds of formula (7) wherein $R_1$=H and $R_2$, $R_3$, $R_4$, $R_5$, $G_1$ and $G_2$ are defined in formula (I) may be prepared by treating a compound of formula (2) with thiourea with heating in the presence of a base such as sodium methoxide in a solvent such as methanol, followed by reduction of the resulting product using a reagent such as Raney nickel to provide compounds of formula (4) wherein $R_1$=H. Compounds of formula (4) wherein $R_1$=H can be treated according to the method above to provide compounds of formula (7) wherein $R_1$=H.

Compounds of formula (7), may be further treated according to conditions known to one skilled in the art to alter functional groups contained with in the compound, for example, the removal of a protecting group such as Boc or hydrolysis of an ester group that will generate compounds of the present invention or used within the scope of other schemes described herein.

Compounds of formula (6) that contain two different nitrogen atoms may selectively react with compounds of formula (5) to provide one isomer of formula (7). Such selectivity may be the result of substitution or protecting groups attached to one of the nitrogen atoms. Alternatively, compounds of formula (6) that contain two different N—H groups may react with compounds of formula (5) in a non-selective manner wherein a mixture of two different compounds of formula (7) are obtained from the reaction. Mixtures of compounds of formula (7) are generally separated by methods known to one skilled in the art, such as silica based column chromatography, selective recrystallization, or both.

Compounds of formula (7) generated through the methods outlined in Scheme 1, may contain a Br, I or —O-Tf functional group in one of the positions represented by $R_2$, $R_3$, $R_4$ or $R_5$. These functional groups may be utilized as a site for introducing a carbon or nitrogen atom containing substituent at that position. Such reactions are known to one skilled in the art. For example, compounds of formula (7), containing a Br, I or O-Tf functional group in one of the positions represented by $R_2$, $R_3$, $R_4$ or $R_5$ when treated with an aryl or heteroaryl boronic acids or boronic esters according to the conditions known to one skilled in the art as the Suzuki reaction will provide compounds wherein the Br, I or O-Tf has been replaced by an aryl or heteroaryl group. Alternatively, using the Stille coupling reaction, compounds of formula (7) wherein one of $R_2$, $R_3$, $R_4$ or $R_5$ is Br, I or O-Tf, when treated with a vinyl, aryl or heteroaryl stannanes will provide compounds wherein the Br, I or O-Tf has been replaced by the vinyl, aryl or heteroaryl group. Alternatively, compounds of formula (7) wherein one of $R_2$, $R_3$, $R_4$ or $R_5$ is Br, I or O-Tf, when treated with amines, heterocycles or heteroaryls containing an NH group will provide compounds of wherein the Br, I or O-Tf has been replaced by the amine, heterocycle or heteroaryl group. Procedures and condition describing these transformations may be found in the following references: J. Hartwig et al., Angew. Chem. Int. Ed. 37:2046-2067 (1998); J. P. Wolfe et al., Acc. Chem. Res., 13:805-818 (1998); M. Sugahara et al., Chem. Pharm. Bull., 45:719-721 (1997); J. P. Wolfe et al., J. Org. Chem., 65:1158-1174, (2000); F. Y. Kwong et al., Org. Lett., 4:581-584, (2002); A. Klapars et al., J. Amer. Chem. Soc., 123:7727-7729 (2001); B. H. Yang et al., J. Organomet. Chem., 576:125-146 (1999); A. Kiyomori et al., Tet. Lett., 40:2657-2640 (1999); and Hartwig, J. Org. Chem., 64(15):5575-5580 (1999). Alternatively, compounds of formula (7) wherein one of $R_2$, $R_3$, $R_4$ or $R_5$ is Br, I or O-Tf, may be subjected to conditions commonly known as the Heck and Sonogashira reaction, to introduce an alkene or alkyne group at the site of the Br, I or O-Tf moiety.

Scheme 2

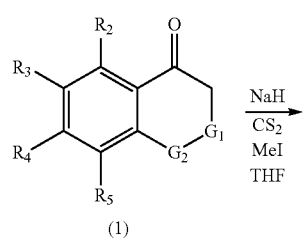

(1)

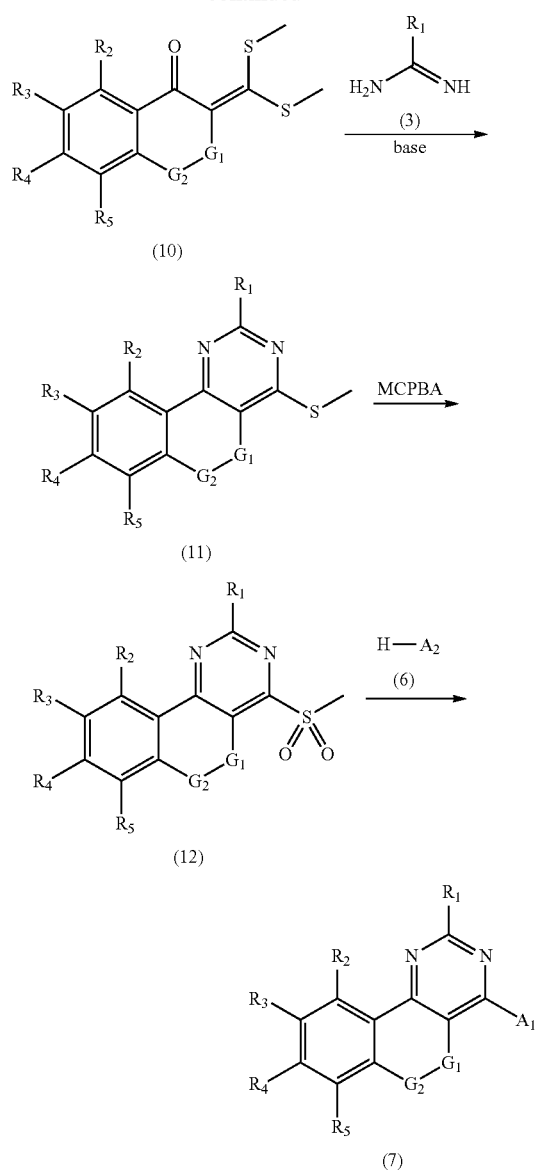

Alternatively, compounds of formula (7) which are representative of compounds of the present invention wherein $R_1$, $R_2$, $R_3$, $R_4$, $R_5$, $A_1$, $G_1$ and $G_2$ are defined in formula (I) may also be prepared as outlined in Scheme 2. Compounds of formula (1) when treated with carbon disulfide and iodomethane in the presence of a base such as but not limited to NaH in a solvent such as but not limited to THF will provide compounds of formula (10). Compounds of formula (10) when treated with a compound of formula (3), wherein $R_1$ is defined in formula (I), will provide sulfides of formula (11). Compounds of formula (11) when treated with an oxidizing agent such as MCPBA or Oxone® will provide sulfones of formula (12). Compounds of formula (12) when treated with compounds of formula (6), which contain a primary or secondary amine under heated conditions, in the presence or absence of a base such as triethyl amine or diisopropyethylamine, in a solvent such as ethanol or 2-methoxyethanol, will provide compounds of formula (7), which are representative of compounds of the present invention.

Scheme 3

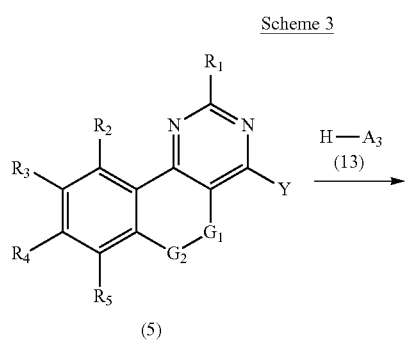

(5)

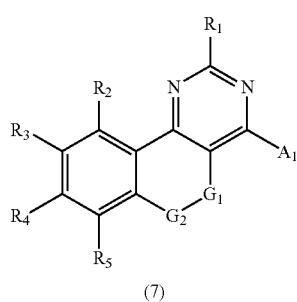

(7)

Compounds of formula (7), wherein $R_1$, $R_2$, $R_3$, $R_4$, $R_5$, $A_1$, $G_1$ and $G_2$ are defined in formula (I) may be prepared as outlined in Scheme 3. Alcohols and thiols of formula (13), and alcohols and thiols wherein the nitrogen atom is protected with synthetic protecting group such as a butoxycarbonyl group, which are obtained either from commercial sources or synthesized through the methods outlined herein, can be treated with a base such as sodium hydride, then treated with compounds of formula (5), wherein Y=Cl, p-toluenesulfonyl or $SO_2Me$, and then heated to provide compounds of formula (7). Alternative bases such as potassium tert-butoxide, potassium hydride, and potassium carbonate may also be employed. More generally, alcohols and thiols of formula 13 are described in the scientific literature and may be prepared by those or ordinary skill in the art of organic synthesis.

Compounds of formula (7), may be further reacted according to conditions known to those of ordinary skill in the art of organic synthesis to alter functional groups. For example, the removal of a protecting group such as Boc or hydrolysis of an ester group that will generate compounds of the present invention or be further transformed within the scope of other schemes described herein.

Compounds of formula (7) generated through the methods outlined in Scheme 1, 2 or 3 may contain a Br, I or —O-Tf functional group in one of the positions represented by $R_2$, $R_3$, $R_4$ or $R_5$. These functional groups may be utilized as a site for introducing a carbon or nitrogen atom containing substituent at that position. Such reactions are known to one skilled in the art. For example, compounds of formula (7), containing a Br, I or O-Tf functional group in one of the positions represented by $R_2$, $R_3$, $R_4$ or $R_5$ when treated with an aryl or heteroaryl boronic acids or boronic esters according to the conditions known to one skilled in the art as the Suzuki reaction will provide compounds wherein the Br, I or O-Tf has been replaced by an aryl or heteroaryl group. Alternatively, using the Stille coupling reaction, compounds of formula (7) wherein one of $R_2$, $R_3$, $R_4$ or $R_5$ is Br, I or O-Tf, when treated with a vinyl, aryl or heteroaryl stannanes will provide compounds wherein the Br, I or O-Tf has been replaced by the vinyl, aryl or heteroaryl group. Alternatively, compounds of formula (7) wherein one of $R_2$, $R_3$, $R_4$ or $R_5$ is Br, I or O-Tf, when treated with amines, heterocycles or heteroaryls containing an NH group will provide compounds of wherein the Br, I or O-Tf has been replaced by the amine, heterocycle or heteroaryl group. Procedures and conditions describing these transformations may be found in the following references: J. Hartwig et al., Angew. Chem. Int. Ed. 37:2046-2067 (1998); J. P. Wolfe et al., Acc. Chem. Res., 13:805-818 (1998); M. Sugahara et al., Chem. Pharm. Bull., 45:719-721 (1997); J. P. Wolfe et al., J. Org. Chem., 65:1158-1174, (2000); F. Y. Kwong et al., Org. Lett., 4:581-584, (2002); A. Klapars et al., J. Amer. Chem. Soc., 123:7727-7729 (2001); B. H. Yang et al., J. Organomet. Chem., 576:125-146 (1999); A. Kiyomori et al., Tet. Lett., 40:2657-2640 (1999); and Hartwig, J. Org. Chem., 64(15):5575-5580 (1999). Alternatively, compounds of formula (7) wherein one of $R_2$, $R_3$, $R_4$ or $R_5$ is Br, I or O-Tf, may be subjected to conditions commonly known as the Heck and Sonogashira reaction, to introduce an alkene or alkyne group at the site of the Br, I or O-Tf moiety.

Scheme 4

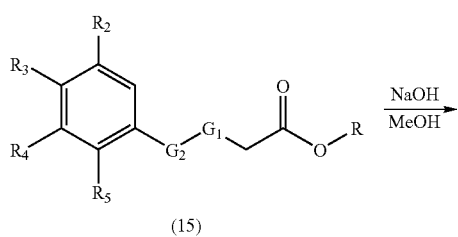

(15)

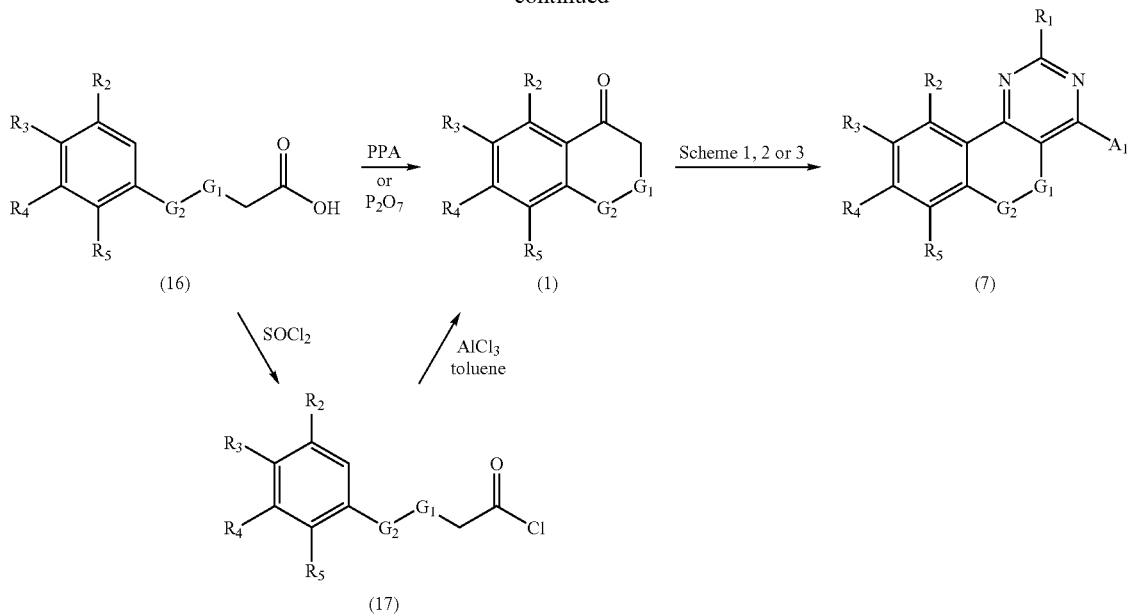

(16) (1) (7)

(17)

Compounds of formula (7), which are representative of compounds of the present invention wherein $R_1$, $R_2$, $R_3$, $R_4$, $R_5$, $A_1$, $G_1$ and $G_2$ are as defined in formula (I), may be prepared as outlined in Scheme 4. Compounds of formula (15), wherein R is lower alkyl or benzyl as obtained from commercial sources or prepared by those of ordinary skill in the art of organic synthesis, when treated with a base such as sodium hydroxide in a mixture of aqueous alcohol such as aqueous methanol or ethanol will provide compounds of formula (16). Compounds of formula (16) when heated in the presence of an acid such as polyphosphoric acid or heated in the presence of $P_2O_5$ (phosphorus pentoxide), will provide compounds of formula (1). Alternatively, compounds of formula (16) when treated with thionyl chloride under heated conditions will provide compounds of formula (17). Compounds of formula (17) when heated in the presence of a Lewis acid such as aluminum trichloride in a solvent such as toluene or carbon disulfide will provide compounds of formula (1). The compounds of formula (1) can be treated according to the methods outlined in Schemes 1, 2 or 3 to provide compounds of formula (7), which are representative of compounds of the present invention.

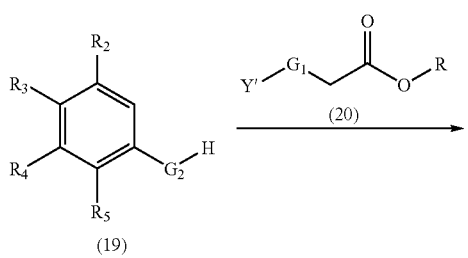

Scheme 5

(19)

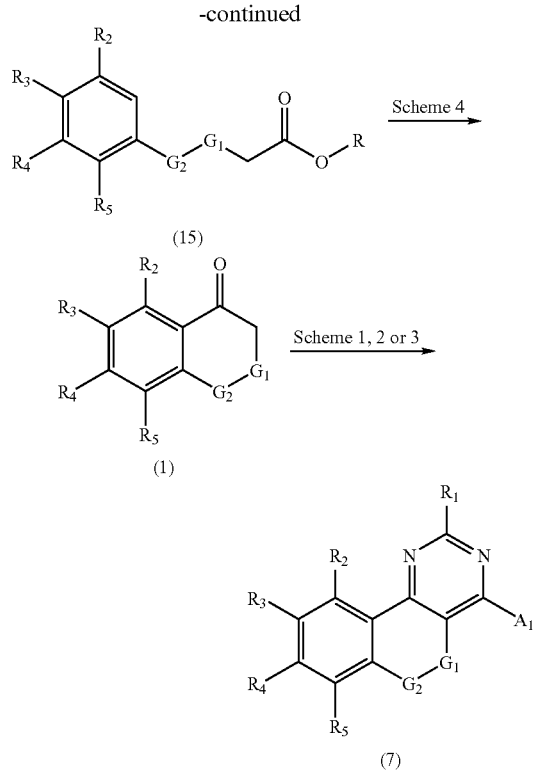

(15)

(1)

(7)

Compounds of formula (7), which are representative of compounds of the present invention wherein $R_1$, $R_2$, $R_3$, $R_4$, $R_5$ and $A_1$ are defined in formula (I), $G_1$ is alkylene, and $G_2$=O, S, $NR_8$ or $NR_a$, wherein $R_a$ is hydrogen, an alkyl group or a nitrogen protecting group such as Boc, alkylsulfonyl, arylsulfonyl or phosphate, may be prepared as outlined in Scheme 5. Compounds of formula (19), wherein $G_2$ is O, S, $NR_8$ or $NR_a$, wherein $R_a$ is hydrogen, alkyl or a nitrogen protecting group such as Boc, alkylsulfonyl, arylsulfonyl or phosphate, when treated with an ester of formula (20)

wherein R is lower alkyl, $G_1$ is alkylene, and wherein Y' is chloro, bromo, iodo or methanesulfonyl, in the presence of a base such as $K_2CO_3$, triethylamine or sodium hydride, in a solvent such as acetone, $CH_2Cl_2$, THF or DMF, will provide compounds of formula (15). Compounds of formula (15) can be cyclized according to the conditions described in Scheme 4 to provide compounds of formula (1). Compounds of formula (1) when processed as outlined in Schemes 1, 2 or 3 will provide compounds of formula (7), which are representative of compounds of the present invention.

wherein $R_2$, $R_3$, $R_4$ and $R_5$ are as defined in formula (I) which may be obtained from commercial sources or prepared by methods known in the art, when heated with succinic anhydride in the presence of a Lewis acid such as aluminum trichloride in a solvent such as benzene or toluene will provide compounds of formula (23). Compounds of formula (23) when treated with a catalyst such as 10% palladium on carbon in ethanol under an atmosphere of hydrogen, or treated with triethyl silane in the presence of trifluoroacetic acid will provide compounds of formula (24). Compounds of formula (24) can be cyclized according to the conditions described in Scheme 4 to provide compounds of formula (25), which can be processed as outlined in Schemes 1, 2 or 3 to provide compounds of formula (26), which are representative of compounds of the present invention.

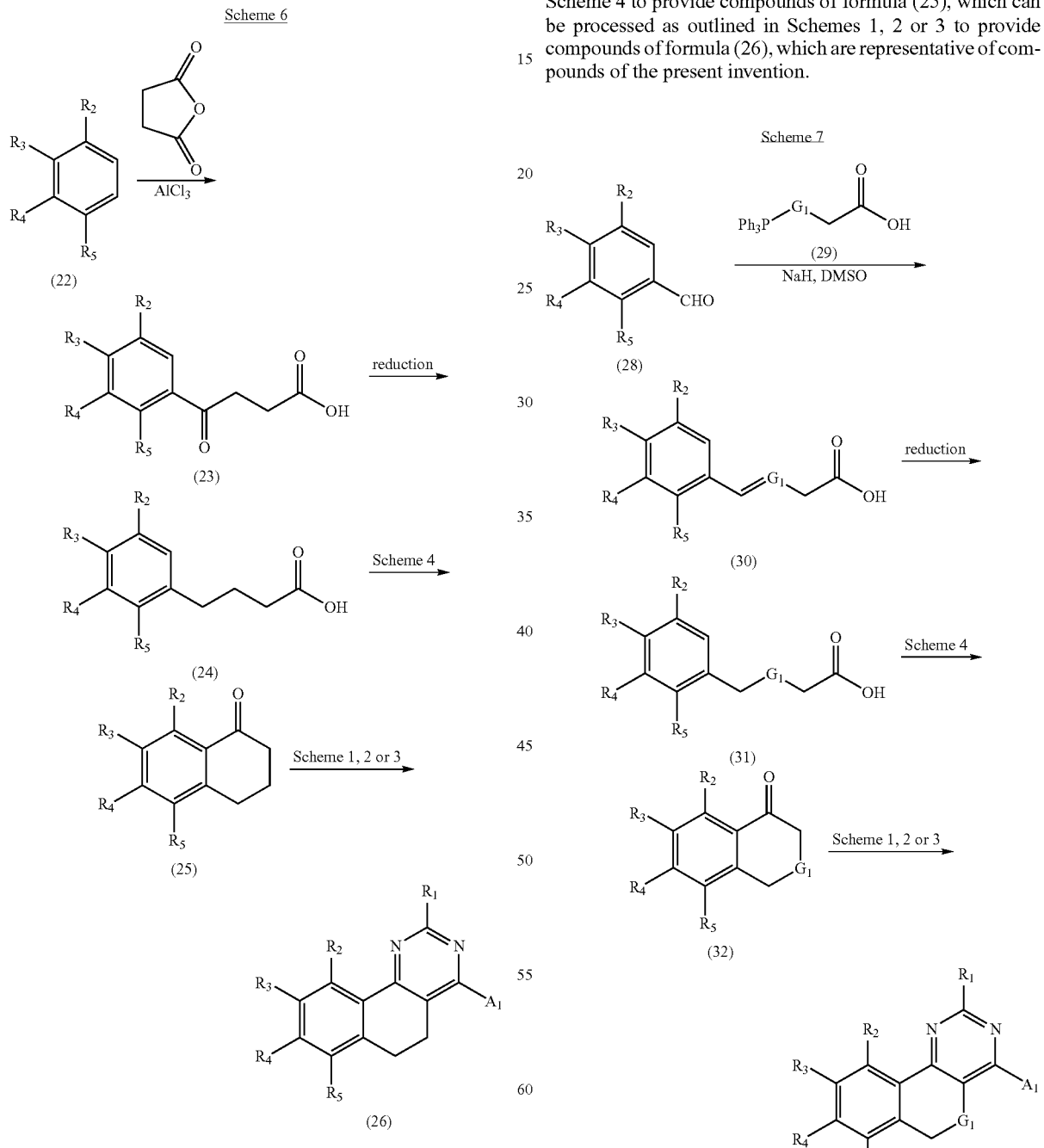

Compounds of formula (26), which are representative of compounds of the present invention wherein $R_1$, $R_2$, $R_3$, $R_4$, $R_5$, and $A_1$ are as defined in formula (I) may be prepared as outlined in Scheme 6. Phenyl compounds of formula (22), Compounds of formula (33) which are representative of compounds of the present invention wherein $R_1$, $R_2$, $R_3$, $R_4$, $R_5$ and $A_1$ are as defined in formula (I), and $G_1$ is alkylene, may be prepared as outlined in Scheme 7. Compounds of formula (28) when treated with a compound of formula (29) that has been pretreated with a base such as sodium hydride in a solvent such as THF or DMSO, will provide compounds of formula (30). Compounds of formula (30) when treated with a catalyst such as but not limited to 5-10% palladium on carbon in a solvent such as but not limited to ethanol under an atmosphere of hydrogen will provide compounds of formula (31). Compounds of formula (31) can be cyclized according to the conditions described in Scheme 4 to provide compounds of formula (32). Compounds of formula (32) when subjected to conditions outlined in Schemes 1, 2 or 3 will provide compounds of formula (33) which are representative of compounds of the present invention.

Compounds of formula (33), which are representative of compounds of the present invention wherein $R_1$, $R_2$, $R_3$, $R_4$, $R_5$ and $A_1$ are as defined in formula (I) and $G_1$ is alkylene, may be prepared as outlined in Scheme 8. Compounds of formula (34), wherein X=Br, I or OTf, when treated with compounds of formula (35), wherein Z=H and R is lower alkyl, according to the conditions of the Heck coupling reaction such as heating in the presence of a catalyst, such as palladium acetate, a base such as sodium acetate, in a solvent such as DMF and optionally using a ligand such as triphenylphosphine, will provide compounds of formula (36). Alternatively, compounds of formula (34), wherein X=Br, I or OTf, when treated with compounds formula (35), wherein R is lower alkyl and Z=Sn(R')$_3$, wherein R' is lower alkyl or phenyl, according to the conditions of the Stille coupling reaction such as heating in the presence of a palladium catalyst such as tetrakis(triphenylphosphine)palladium (0) in a

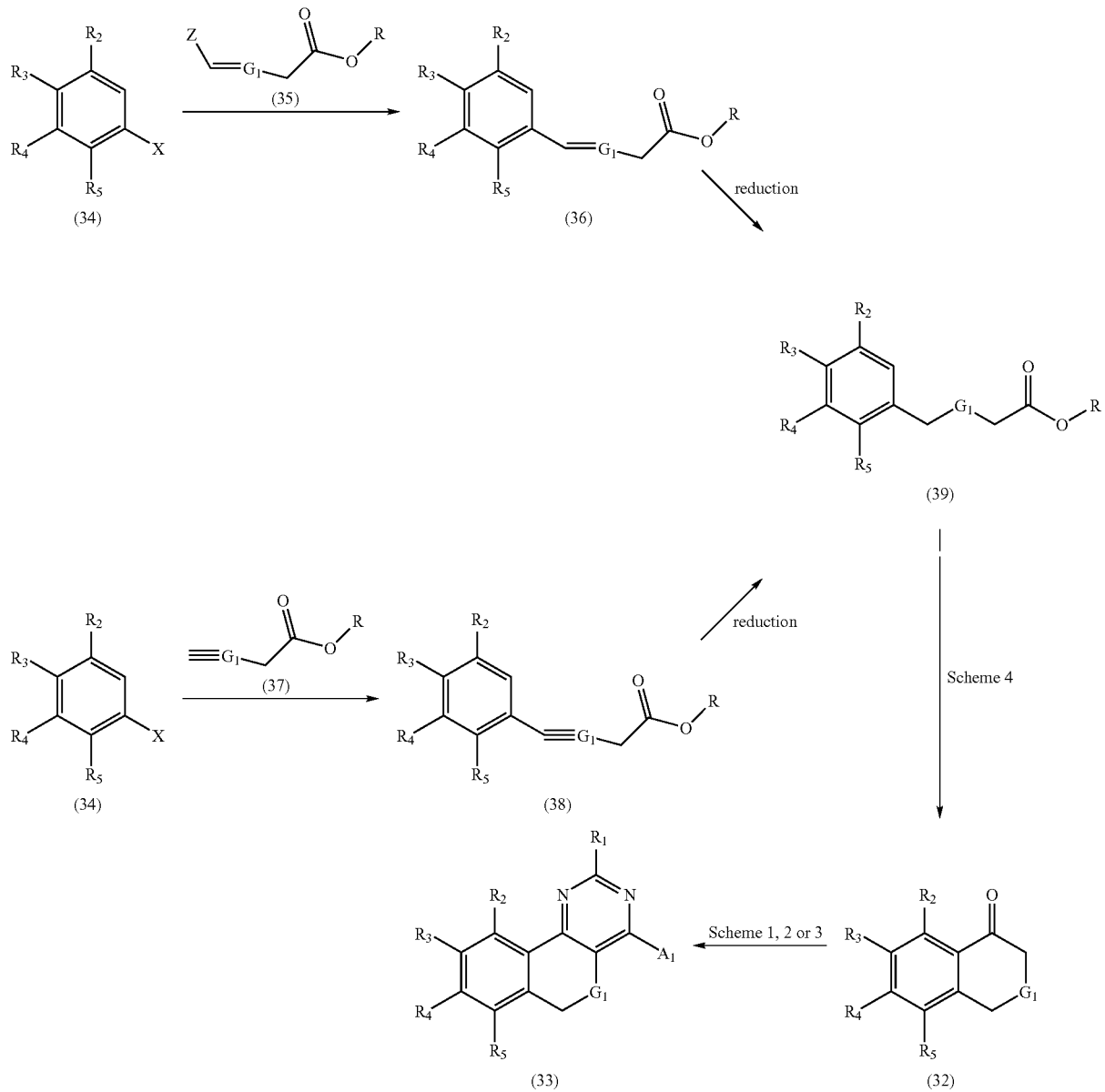

solvent such as toluene will provide compounds of formula (36). Similarly, compounds of formula (34), wherein X=Br, I or OTf, when treated with compounds of formula (37), wherein R is lower alkyl, according to the conditions of the Sonogashira coupling reaction such as heating in the presence of a catalyst such as bis(triphenylphosphine)palladium(II) chloride, a base such as triethyl amine, a source of copper such as copper(I) iodide in a solvent such as DMF, will provide compounds of formula (38). Examples of this methodology can be found in the following references: Deshmukh, A. R.; et al. J. Org. Chem. 57(2), 1992, 667-670; Chan, D. C. M.; et al. J. Med. Chem. 48(13), 2005, 4420-4431. The alkene group of compounds of formula (36) and the alkyne group of compounds of formula (38) may be reduced to their corresponding alkylene group by treatment with a catalyst such as but not limited to 5-10% palladium on carbon and an atmosphere of hydrogen in solvents such as but not limited to methanol, ethanol, THF and ethyl acetate to provide compounds of formula (39). Compounds of formula (39) can be cyclized according to the conditions described in Scheme 4 to provide compounds of formula (32). Compounds of formula (32) when treated according to the procedure outlined in Schemes 1, 2 or 3, will provide compounds of formula (33) which are representative of compounds of the present invention.

Scheme 9

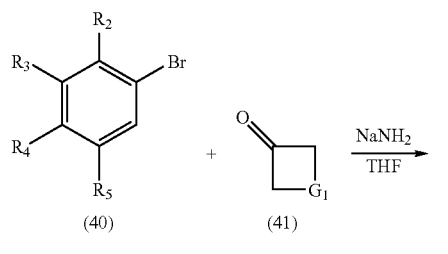

(40)  (41)

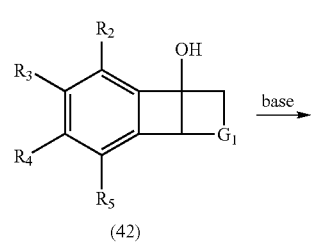

(42)

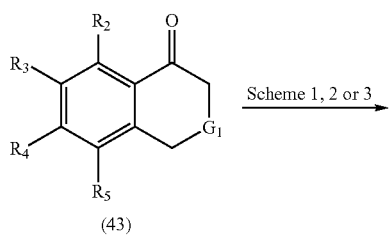

(43)

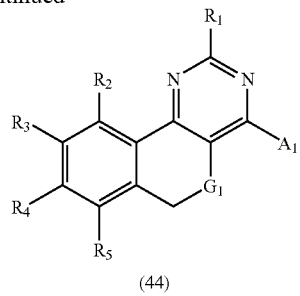

(44)

Compounds of formula (44), which are representative of compounds of the present invention wherein $R_1$, $R_2$, $R_3$, $R_4$, $R_5$ and $A_1$ are as defined in formula (I) and $G_1$ is alkylene, may be prepared as described in Scheme 9. Halobenzene rings of formula (40) when treated with a base such as sodium amide in a solvent such as THF followed by treatment with an enolate of a ketone of formula (41) will provide compounds of formula (42). Compounds of formula (42) when treated with a base such as potassium hydride or sodium amide in a solvent such as 1,2-dimethoxyethane or THF will provide compounds of formula (43). Further descriptions of this reaction can be found in the following references: Caubere, P., et al. Bull. Soc. Chim. Fr. 1974, 1415-1420.; Thies, R. W., et al. J. Org. Chem. 42(2), 1977, 280-281. Compounds of formula (43) when treated as outlined in Schemes 1, 2 or 3 will provide compounds of formula (44).

Scheme 10

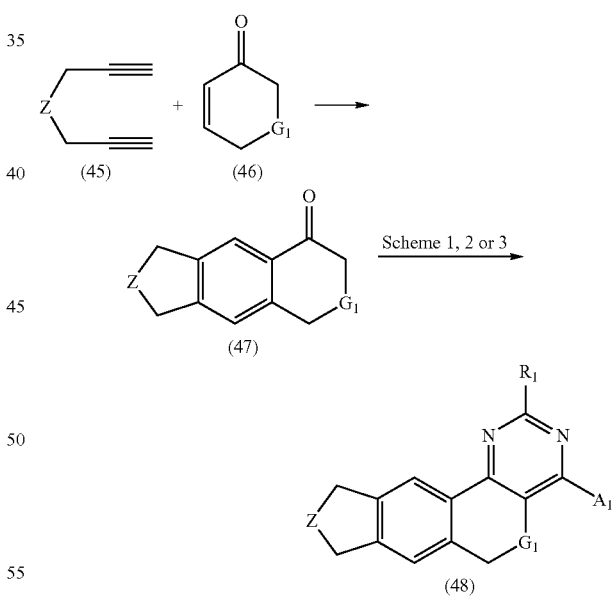

Compounds of formula (48), which are representative of compounds of the present invention wherein $R_1$, $G_1$ and $A_1$ are as defined in formula (I), and wherein Z is oxygen, —$CH_2$— or —$CH_2CH_2$—, may be prepared as outlined in Scheme 10. Compounds of formula (45) may be obtained from commercial sources or made through methods known to one skilled in the art. Compounds of formula (45), wherein Z is oxygen, —$CH_2$— or —$CH_2CH_2$—, when treated with a compound of formula (46) in the presence of a metal catalyst such as $NiI_2(PPh_3)_2$ and a Lewis acid such as $ZnI_2$ in a solvent such as THF will provide compounds of formula (47). Further examples describing similar reactions are found in the following reference: Sambaiah, T.; et al. J. Org. Chem. (1999) 64(10), 3663-3670. Compounds of formula (47) when treated as outlined in Schemes 1, 2 or 3 will provide compounds of formula (48), wherein Z is oxygen, —CH$_2$— or —CH$_2$CH$_2$—.

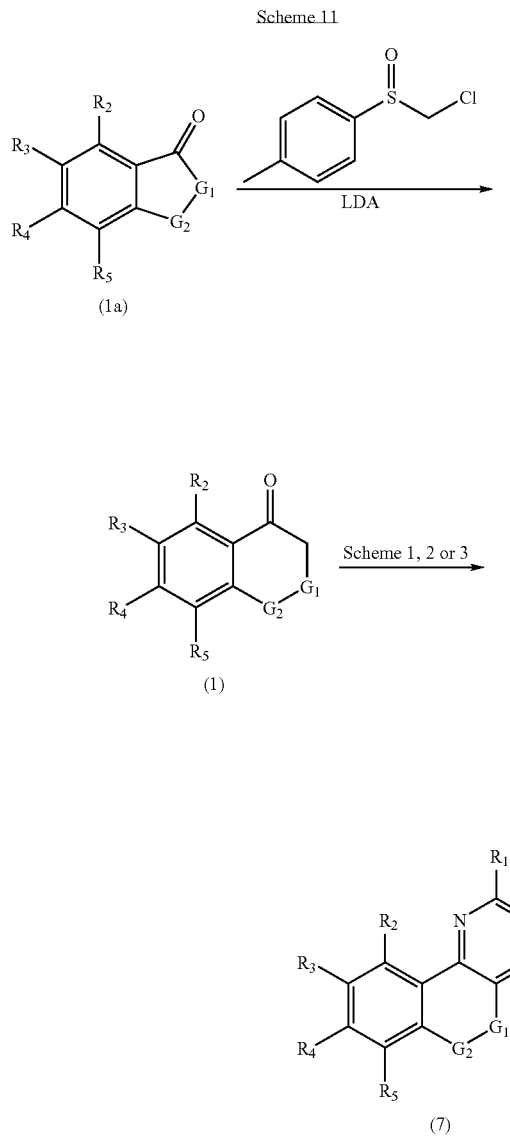

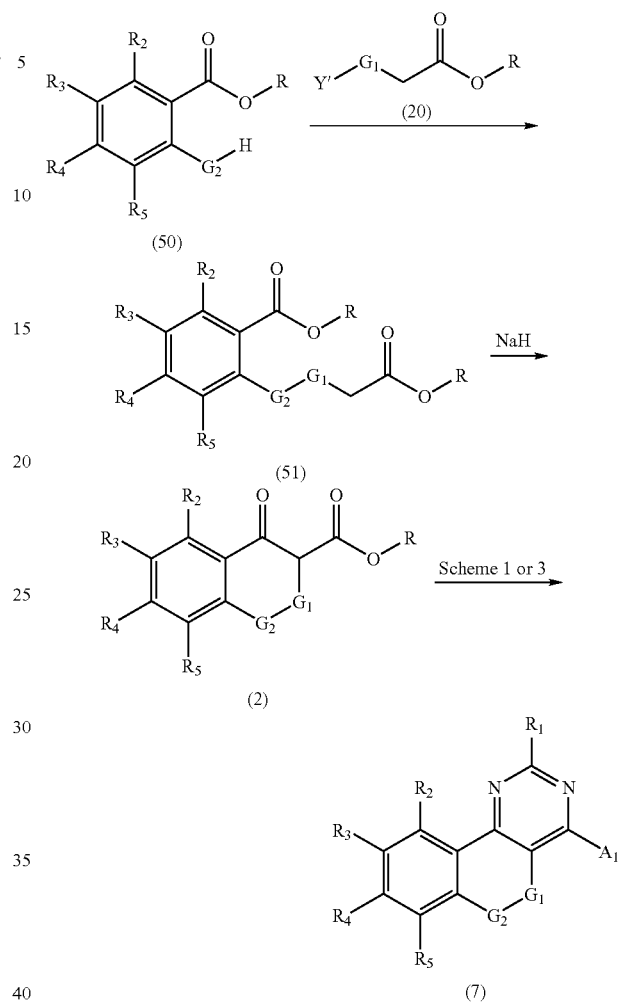

Compounds of formula (7), which are representative of compounds of the present invention wherein $R_1$, $R_2$, $R_3$, $R_4$ $R_5$, $A_1$ and $G_2$ are as defined in formula (I), and $G_1$ is alkylene, can be prepared as outlined in Scheme 11. Treatment of compounds of formula (1a) with p-toluenesulfonylmethyl chloride in the presence of a base such as lithium diisopropylamide will provide compounds of formula (1), wherein $G_1$ is alkylene. Further example describing similar reactions are found in the following reference: Satoh, T.; et al. Tetrahedron (1994), 50(41), 11839-52. Compounds of formula (1) when treated as outlined in Schemes 1, 2 or 3 will provide compounds of formula (7), which are representative of compounds of the present invention wherein $G_1$ is alkylene.

Compounds of formula (7), which are representative of compounds of the present invention wherein $R_1$, $R_2$, $R_3$, $R_4$, $R_5$ and $A_1$ have been defined in formula (I), wherein $G_1$ is alkylene, and wherein $G_2$ is O, S, $NR_8$ or $NR_a$, wherein $R_a$ is hydrogen, an alkyl group or a nitrogen protecting group such as Boc, alkylsulfonyl, arylsulfonyl or phosphate, may be prepared as outlined in Scheme 12. Compounds of formula (50), wherein R is lower alkyl, $G_2$=O, S, $NR_8$ or $NR_a$, wherein $R_a$ is hydrogen, alkyl or a nitrogen protecting group such as Boc, alkylsulfonyl, arylsulfonyl or phosphate, when treated with a compound of formula (20) wherein $G_1$ is $C_{1-5}$ alkylene, R is lower alkyl, and wherein Y' is a leaving group such as chloro, bromo, iodo or methanesulfonyl, in the presence of a base such as $K_2CO_3$, triethylamine or sodium hydride, in a solvent such as acetone, $CH_2Cl_2$, DMF or THF, will provide compounds of formula (51). Compounds of formula (51) when treated with a base such as sodium hydride in a solvent such as THF or DMF will provide compounds of formula (2). Compounds of formula (2) when treated as outlined in Scheme 1 or 3 will provide compounds of formula (7), which are representative of compounds of the present invention wherein $G_1$ is alkylene and $G_2$ is O, S, $NR_8$ or $NR_a$.

Scheme 13

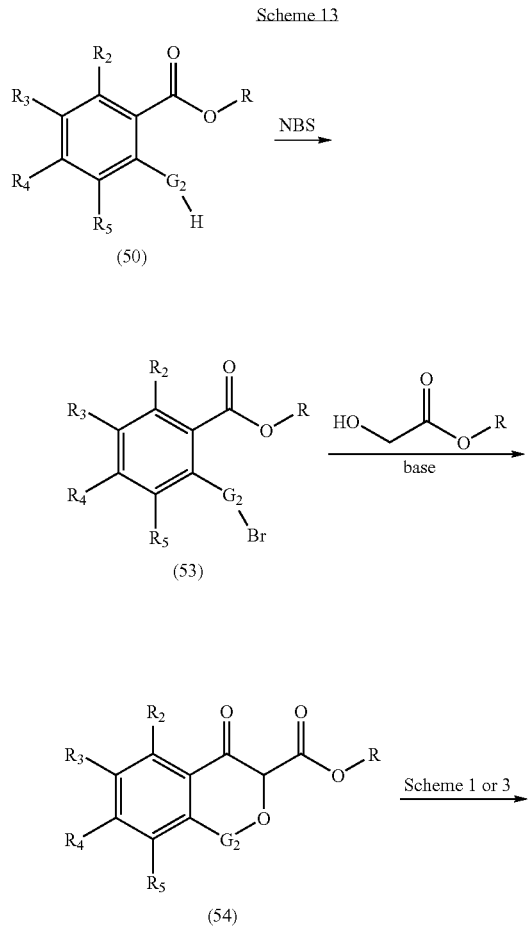

Compounds of formula (55) which are representative of compounds of the present invention, wherein $R_1$, $R_2$, $R_3$, $R_4$, $R_5$ and $A_1$ are as defined in formula (I) and wherein $G_2$ is methylene, may be prepared as outlined in Scheme 13. Compounds of formula (50), wherein R is lower alkyl and $G_2$ is methylene, when treated with a brominating agent such as N-bromosuccinimide, will provide compounds of formula (53) wherein R is lower alkyl. Compounds of formula (53) when treated with a glycolate, such as ethyl glycolate, in the presence of a base such as sodium hydride in a solvent including but not limited to THF will provide compounds of formula (54) wherein R is lower alkyl. Compounds of formula (54) when treated as outlined in Scheme 1 or 3 will provide compounds of formula (55) wherein $G_2$ is methylene.

Scheme 14

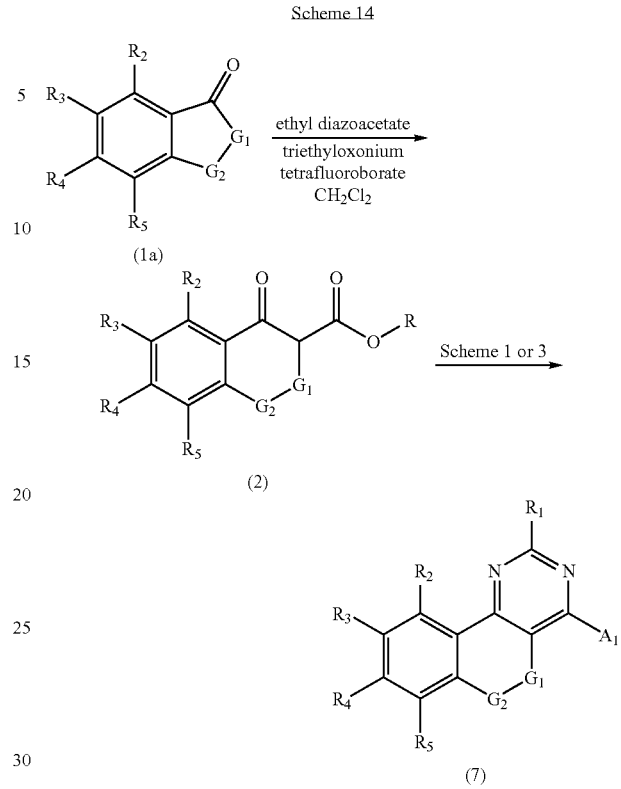

Compounds of formula (7) which are representative of compounds of the present invention, wherein $R_1$, $R_2$, $R_3$, $R_4$, $R_5$, $A_1$ and $G_2$ are as defined in formula (I) and $G_1$ is alkylene, may be prepared from compounds of formula (1a) as outlined in Scheme 14. Treatment of compounds of formula (1a) with ethyl diazoacetate in the presence of triethyloxonium tetrafluoroborate in a solvent such as $CH_2Cl_2$ will provide compounds of formula (2). An example of this methodology can be found in the following reference: Roever, S.; et al. J. Med. Chem. 43(7), 2000 1329-1338. Compounds of formula (2) when treated according to the procedures outlined in Scheme 1 or 3 will provide compounds of formula (7), which are representative of compounds of the present invention.

Scheme 15

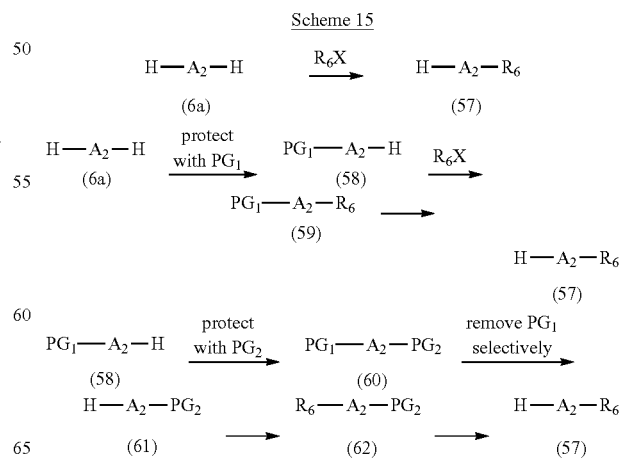

As outlined in Scheme 15, compounds of formula (6a) may contain two amine groups. The amine groups of compounds of formula (6a) may be either primary or secondary and can be used directly in Schemes 1 or Scheme 2 to provide compounds of formula (7). Alternatively, compounds of formula (6a), which contain two N—H groups, may be treated with an appropriate reagent such as $R_6$—X, wherein X is a leaving group such as chlorine, bromine, iodine, mesylate or triflate, to provide compounds of formula (57) wherein one of the two N—H groups is substituted with $R_6$. Substituting compounds of formula (57) for compounds of formula (6) in the procedures outlined in Scheme 1 or Scheme 2 will provide compounds of formula (7) that are representative of the present invention.

Furthermore, compounds of formula (6a) that contain two amine groups may be treated with a reagent which will introduce a nitrogen protecting group ($PG_1$) on one of the amine groups. Some typical examples of common nitrogen protecting groups include but are not limited to benzyl, tert-butoxycarbonyl, benzyloxycarbonyl, or acetyl which are introduced by treating amines of formula (6a) with 1 equivalent of an appropriate reagent such as benzyl bromide, di-tert-butyl dicarbonate, benzyl chloroformate or acetic anhydride, respectively, to provide mono-protected diamines of formula (58). Mono-amine protected compounds of formula (58) can be further treated with an appropriate reagent such as $R_6$—X, wherein $R_6$ is defined in formula (I) and X is a leaving group such as chlorine, bromine, iodine, mesylate or triflate, to provide compounds of formula (59). Compounds of formula (59) can be deprotected to provide compounds of formula (57) which can then be used to replace compounds of formula (6) in the procedures outlined in Scheme 1 and Scheme 2 to provide compounds of formula (7) which are representative of compounds of the present invention. Common conditions used for the deprotection of compounds of formula (59) to provide compounds of formula (57) include but are not limited to the following: catalytic hydrogenation (e.g. in the presence of palladium on carbon in a solvent such as ethanol under an atmosphere of hydrogen); acidic conditions (e.g. treatment with aqueous hydrochloric acid), or basic hydrolysis (e.g. treatment with aqueous sodium hydroxide and heat).

Alternatively, mono-protected diamines of formula (58) may be treated with an appropriate aldehyde or ketone under condition of reductive amination to provide diamines of formula (59). Conditions commonly used for reductive amination include treatment of an amine (58) with an aldehyde or ketone in the presence of $NaBH_3CN$ or $NaBH(OAc)_3$.

Mono-protected compounds of formula (58) can be treated with a second protecting group ($PG_2$) to provide di-protected compounds of formula (60). In di-protected compounds of formula (60), it is preferred that the choice of protecting groups is such that the protecting group $PG_1$ can be removed selectively without removing $PG_2$. Selective deprotection of $PG_1$ from compounds of formula (60) provide compounds of formula (61). Mono-protected compounds of formula (61) can be treated with an appropriate reagent such as $R_6$—X, wherein $R_6$ is as defined in formula (I) and X is a leaving group such as chlorine, bromine, iodine, mesylate or triflate, to provide compounds of formula (62). Alternatively, mono-protected compounds of formula (61) when treated with an appropriate aldehyde or ketone under condition of reductive amination will provide compounds of formula (62). Compounds of formula (62) can be deprotected to provide compounds of formula (57).

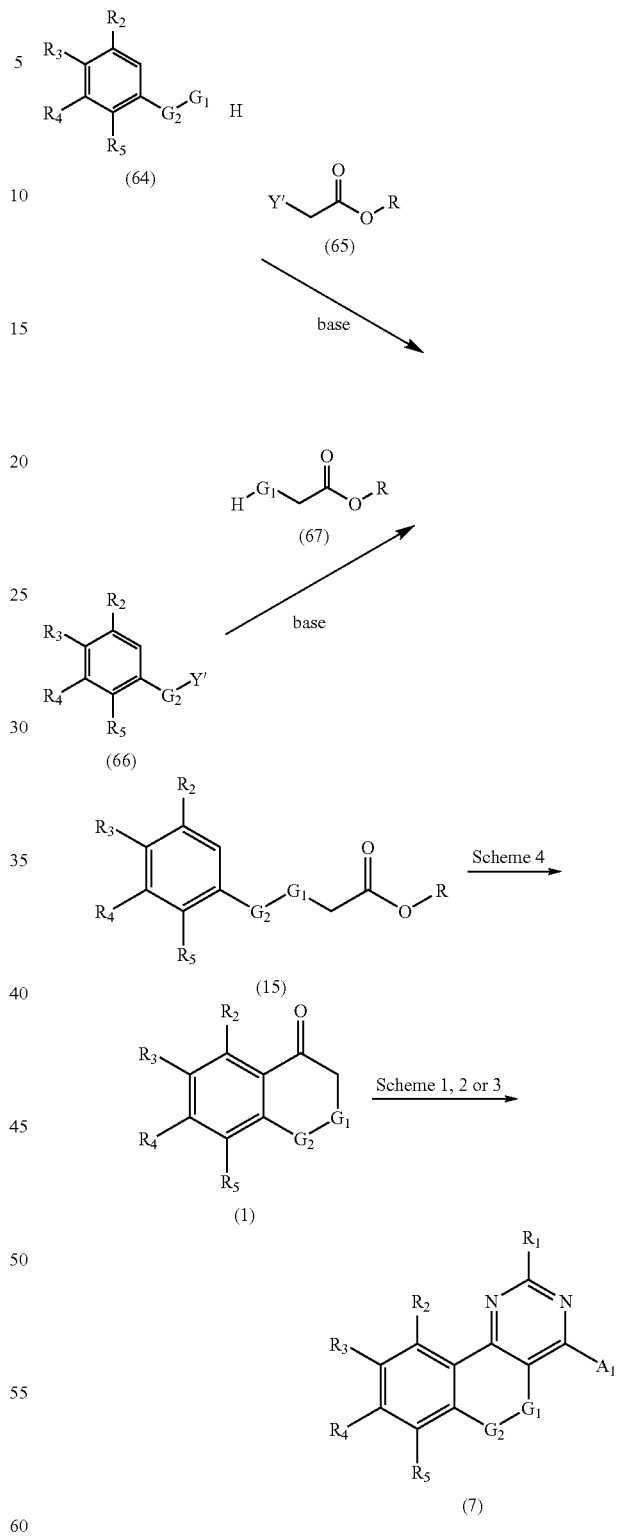

Compounds of formula (7), which are representative of compounds of the present invention wherein $R_1$, $R_2$, $R_3$, $R_4$, $R_5$ and $A_1$ are defined in formula (I), $G_2$ is alkylene, and $G_1$=O, S, $NR_8$ or $NR_a$, wherein $R_a$ is hydrogen, an alkyl group or a nitrogen protecting group such as Boc, alkylsulfonyl, arylsulfonyl or phosphate, may be prepared as outlined in Scheme 16. Compounds of formula (64), wherein $G_1$ is O, S, $NR_8$ or $NR_a$, wherein $R_a$ is hydrogen, an alkyl group or a nitrogen protecting group such as Boc, alkylsulfonyl, arylsulfonyl or phosphate, and $G_2$ is alkylene, can be treated with a base such as sodium hydride in a solvent such as DMF, followed by an ester of formula (65) wherein Y' is chloro, bromo, iodo or methanesulfonyl, and wherein R can be H or alkyl, to provide compounds of formula (15) wherein R can be H or alkyl. Compounds of formula (66), wherein $G_2$ is alkylene, and Y' is leaving group such as chloro, bromo, iodo or methanesulfonyl, can be treated with an ester of formula (67), wherein $G_1$ is S, $NR_8$ or $NR_a$, wherein $R_a$ is hydrogen, an alkyl group or a nitrogen protecting group such as Boc, alkylsulfonyl, arylsulfonyl or phosphate, and wherein R can be H or alkyl, in the presence of a base such as sodium hydride, sodium hydroxide or triethyl amine in a solvent such as DMF or methanol to provide compounds of formula (15) wherein R can be H or alkyl. Compounds of formula (15) can be cyclized according to the conditions described in Scheme 4 to provide compounds of formula (1). Compounds of formula (1) when processed as outlined in Schemes 1, 2 or 3 will provide compounds of formula (7), which are representative of compounds of the present invention.

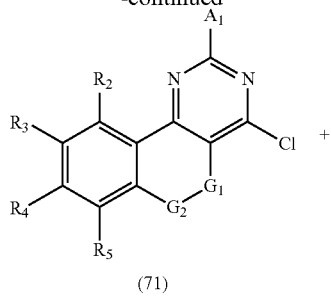

Compounds of formula (7), which are representative of compounds of the present invention wherein $R_1$, $R_2$, $R_3$, $R_4$, $R_5$, $G_1$, $G_2$ and $A_1$ are defined in formula (I), may be prepared as outlined in Scheme 17. Esters of formula (2), prepared as described in the above schemes, can be treated with an excess of urea and heated at 150-190° C. to provide compounds of formula (69). Compounds of formula (69) can exist as shown in the structure in scheme 17 or in a tautomeric form. Compounds of formula (69) can be treated with $POCl_3$ with heating to provide compounds of formula (70). Compounds of formula (70) can be treated with compounds of formula (6), wherein (6) contains a primary or secondary nitrogen atom and H is a hydrogen atom on said nitrogen atom, under heated conditions in the presence or absence of a base such as triethylamine or diisopropyethylamine, in a solvent such as ethanol, 2-methoxyethanol, toluene or acetonitrile, to provide a mixture of compounds of formula (71) and formula (72). Alternatively, compounds of formula (13) can be treated with a base such as sodium hydride or potassium carbonate in a solvent such as THF or DMF and then treated with a compound of formula (70) to provide a mixture of compounds of formula (71) and formula (72). Compounds of formula (71) and formula (72) can be separated by methods known to those skilled in the art, such as chromatography on silica gel or selective crystallization. Compounds of formula (72) can be reacted with a compound of formula (73), wherein $R_1$ is defined in formula (I), and compound (73) contains an alcohol or a primary or secondary nitrogen atom and H is a hydrogen atom on said oxygen or nitrogen atom, under heated conditions in the presence or absence of a base such as triethylamine, diisopropyethylamine or sodium hydride, in a solvent such as ethanol, 2-methoxyethanol, THF, toluene, DMF or acetonitrile, to provide compounds of formula (7).

Compounds of formula (72) can also be treated with a catalyst such as $PdCl_2(pddf)\text{-}CH_2Cl_2$ under an atmosphere of carbon monoxide in the presence of an alcohol such as methanol in the presence of a base such as triethyl amine while heating to provide compounds of formula (7) wherein $R_1$ is —(C=O)OR, wherein R is lower alkyl. Compounds of formula (7) wherein $R_1$ is —(C=O)OR can be treated with an aqueous base such as 1 M sodium hydroxide in the presence of a solvent such as methanol to provide compounds of formula (7) wherein $R_1$ is —(C=O)OH. Compounds of formula (7) wherein $R_1$ is —(C=O)OH can be coupled with amines under conditions known to those of ordinary skill in the art to provide compounds if formula (7) wherein $R_1$ is selected from —(C=O)—(NR$_8$R$_9$) and —(C=O)—NH-alkylene(NR$_8$R$_9$).

Compounds of formula (72) can also be treated with a reagent such as zinc cyanide in the presence of a catalyst such as $Pd(PPh_3)_4$ in a solvent such as DMF with heating to provide compounds if formula (7) wherein $R_1$ is cyano.

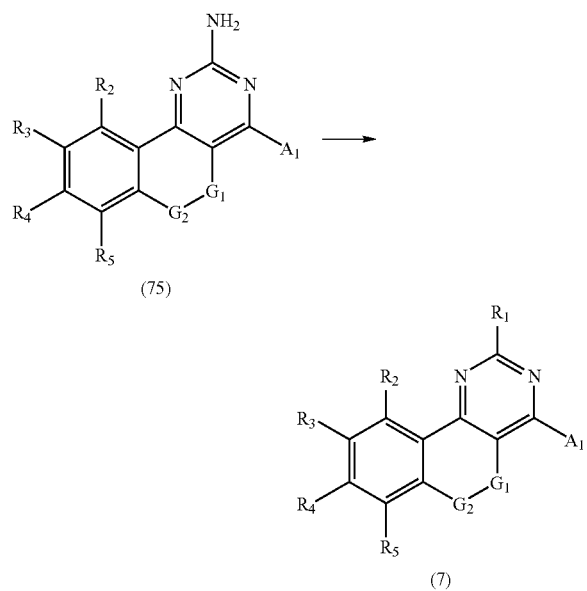

Compounds of formula (7), which are representative of compounds of the present invention wherein $R_2$, $R_3$, $R_4$, $R_5$, $G_1$, $G_2$ and $A_1$ are defined in formula (I), and wherein $R_1$ is limited to those compounds defined in formula (I) that are linked to the pyrimidine via nitrogen atom may be prepared as outlined in Scheme 18. 2-Aminopyrimidines of formula (75) can be prepared as described in the Schemes herein. 2-Aminopyrimidines of formula (75) can be reacted with reagents such as (alkylene-CO)$_2$O, Y'-alkyl, alkylene-CO—Y', aryl-CO—Y', Y'-alkylene(NR$_8$R$_9$), Y'—(C=O)-alkylene (NR$_8$R$_9$) and Y'-alkylene-heteroaryl, wherein Y' is a leaving group such as Cl, Br, OMs, OTs or N-hydroxysuccinimide optionally in the presence of a base such as Hunig's base or sodium hydride, pyridine or triethylamine, optionally in a solvent such as 2-methoxyethanol or DMF and optionally with heating to provide compounds of formula (7) wherein $R_2$, $R_3$, $R_4$, $R_5$, $G_1$, $G_2$ and $A_1$ are defined in formula (I) and $R_1$ is selected from —NH(acyl), —NH(alkyl), —N(alkyl)$_2$, —NH(C=O)aryl, —NH-alkylene(NR$_8$R$_9$), —NH(C=O)-alkylene(NR$_8$R$_9$), —NHOH, —NHOCH$_3$ and —NH-alkylene-heteroaryl.

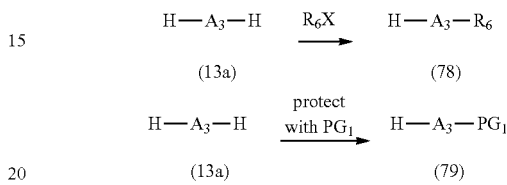

Compounds of formula (13a), wherein $A_3$ is defined in formula (I), are compounds wherein one of the H groups is a proton on an oxygen or sulfur atom and the other H group is a proton on a nitrogen atom of a primary or secondary amine. Compounds of formula (13a) can be directly reacted in Scheme 3 of the above in the presence of a strong base such as sodium hydride to provide compounds of formula (7). Alternatively, compounds of formula (13a) may be treated with an appropriate reagent such as $R_6$—X, wherein X is a leaving group such as chlorine, bromine, iodine, mesylate or triflate, to provide compounds of formula (78) wherein the nitrogen atom of (78) is substituted with $R_6$. Alternatively, monoprotected diamines of formula (13a) may be treated with an appropriate aldehyde or ketone under condition of reductive amination to provide compounds of formula (78). Conditions commonly used for reductive amination include treatment of an amine (13a) with an aldehyde or ketone in the presence of $NaBH_3CN$ or $NaBH(OAc)_3$. Substituting compounds of formula (78) for compounds of formula (13) in the procedure outlined in Scheme 3 will provide compounds of formula (7) that are representative of the present invention. Compounds of formula (13a) may be treated with a reagent that will introduce a nitrogen protecting group ($PG_1$) on the nitrogen atom of (13a). Some typical examples of common nitrogen protecting groups include but are not limited to tertbutoxycarbonyl or benzyloxycarbonyl, which are introduced by treating compounds of formula (13a) with 1 equivalent of an appropriate reagent such as di-tert-butyl dicarbonate or benzyl chloroformate, respectively, to provide compounds of formula (79) wherein the protecting group ($PG_1$) is connected to the nitrogen atom. Substituting compounds of formula (79) for compounds of formula (13) in the procedure outlined in Scheme 3 will provide compounds of formula (7), wherein the $A_1$ group of formula (7) contains a protected nitrogen atom. This said protected nitrogen atom of compounds of formula (7) can be deprotected using conditions known to one skilled in the art such as catalytic hydrogenation (e.g. in the presence of palladium on carbon in a solvent such as ethanol under an atmosphere of hydrogen) and acidic conditions (e.g. treatment with aqueous hydrochloric acid or with TFA) to provide compounds of formula (7) that are representative of the present invention.

There are many groups of formula (6), (6a), (13), (57), (58), (59) and (60) that are available commercially or that can be prepared as described in the scientific literature of synthetic organic chemistry. Non-exhaustive examples of diamine and aminoalcohol reagents for the synthesis of compounds of formula (I) are provided in Table 1, along with product compounds that may produced by application of the methods in the Schemes described above (Scheme 1 through Scheme 19).

TABLE 1

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 2-Methyl-2,6-Diazaspiro[3.4]octane | 135380-30-2 | WO2004056784 A1 | 4-(2-methyl-2,6-diazaspiro[3.4]oct-6-yl)-6,7-dihydro-5H-benzo[6,7]cyclohepta[1,2-d]pyrimidin-2-amine |
| 7-Methyl-2,7-diazaspiro[3.5]nonane | 135380-50-6 | Frohlich, Johannes, et al. Heterocycles (1994), 37(3), 1879-91. | 4-(7-methyl-2,7-diazaspiro[3.5]non-2-yl)-6,7-dihydro-5H-benzo[6,7]cyclohepta[1,2-d]pyrimidin-2-amine |
| 2,7-Diazaspiro[3.5]nonane-2-carboxylic acid, 1,1-dimethylethyl ester | 236406-55-6 | WO2005040159 A1 | |
| 2-(Phenylmethyl)-2,7-Diazaspiro[3.6]decane | 270257-44-8 | JP2001039950 A2 | 4-(2,7-diazaspiro[3.5]non-7-yl)-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 2-(Phenylmethyl)-2,7-Diazaspiro[3.6]decane | 270257-44-8 | JP2001039950 A2 | 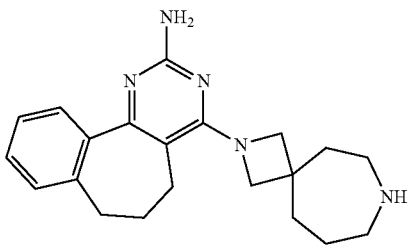<br>4-(2,7-diazaspiro[3.6]dec-2-yl)-6,7-dihydro-5H-benzo[6,7]cyclohepta[1,2-d]pyrimidin-2-amine |
| 1-(Phenylmethyl)-1,7-diazaspiro[4.4]nonane | 128244-01-9 | Culbertson, T. P., et al. Journal of Medicinal Chemistry (1990), 33(8), 2270-5. | 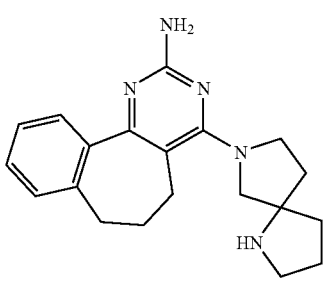<br>4-(1,7-diazaspiro[4.4]non-7-yl)-6,7-dihydro-5H-benzo[6,7]cyclohepta[1,2-d]pyrimidin-2-amine |
| 1-(Phenylmethyl)-1,7-diazaspiro[4.4]nonane | 128244-01-9 | Culbertson, T. P., et al. Journal of Medicinal Chemistry (1990), 33(8), 2270-5. | 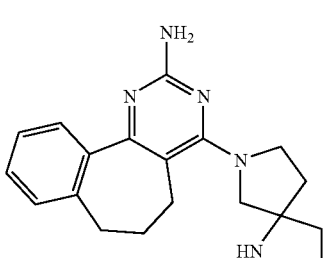<br>4-(1,7-diazaspiro[4.4]non-7-yl)-6,7-dihydro-5H-benzo[6,7]cyclohepta[1,2-d]pyrimidin-2-amine |
| 2,7-Diazaspiro[4.4]nonane | 175-96-2 | Culbertson, T. P., et al. Journal of Medicinal Chemistry (1990), 33(8), 2270-5. | 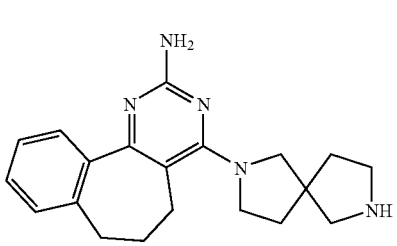<br>4-(2,7-diazaspiro[4.4]non-2-yl)-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 1-(Phenylmethyl)-1,7-diazaspiro[4.5]decane | 867009-85-6 | WO2005097794 A1 | 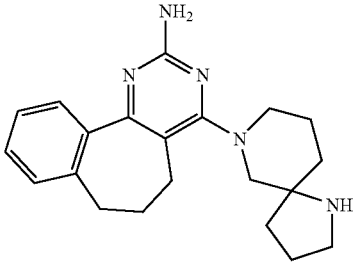<br>4-(1,7-diazaspiro[4.5]dec-7-yl)-6,7-dihydro-5H-benzo[6,7]cyclohepta[1,2-d]pyrimidin-2-amine |
| 1-(Phenylmethyl)-1,7-diazaspiro[4.5]decane | 867009-85-6 | WO2005097794 A1 | 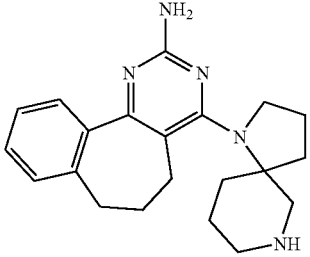<br>4-(1,7-diazaspiro[4.5]dec-1-yl)-6,7-dihydro-5H-benzo[6,7]cyclohepta[1,2-d]pyrimidin-2-amine |
| 2-Ethyl-2,8-Diazaspiro[4.5]decane | 64097-83-2 | Sueess, Rudolf. Helvetica Chimica Acta (1977), 60(5), 1650-6 | 4-(2-ethyl-2,8-diazaspiro[4.5]dec-8-yl)-6,7-dihydro-5H-benzo[6,7]cyclohepta[1,2-d]pyrimidin-2-amine<br>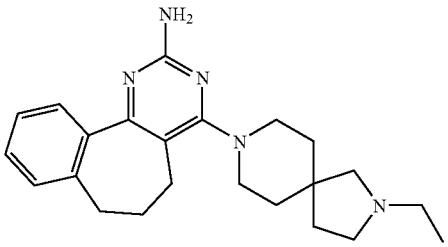 |
| 2,8-Diazaspiro[4.5]decane-8-carboxylic acid, 1,1-dimethylethyl ester | 236406-39-6 | US2006019985 A1 | 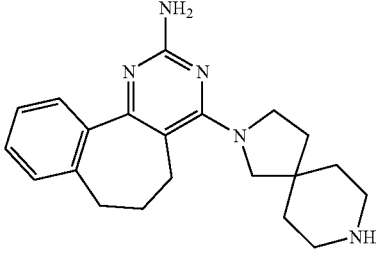<br>4-(2,8-diazaspiro[4.5]dec-2-yl)-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| (R)-1,8-Diazaspiro[5.5]undecane | 151746-68-8 | Zhu, Jieping; et al. Journal of Organic Chemistry (1993), 58(23), 6451-6 | 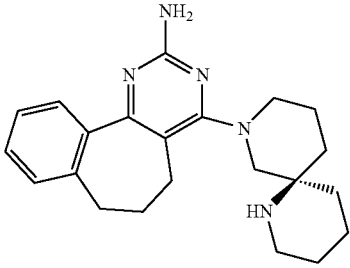<br>4-[(6R)-1,8-diazaspiro[5.5]undec-8-yl]-6,7-dihydro-5H-benzo[6,7]cyclohepta[1,2-d]pyrimidin-2-amine |
| (R)-1,8-Diazaspiro[5.5]undecane | 151746-68-8 | Zhu, Jieping; et al. Journal of Organic Chemistry (1993), 58(23), 6451-6 | 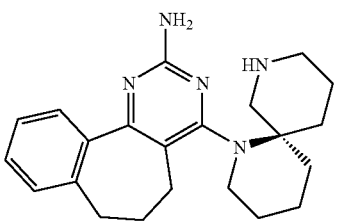<br>4-[(6R)-1,8-diazaspiro[5.5]undec-1-yl]-6,7-dihydro-5H-benzo[6,7]cyclohepta[1,2-d]pyrimidin-2-amine |
| 2,8-Diazaspiro[5.5]undecane | 180-50-7 | US2005084446 A1 | 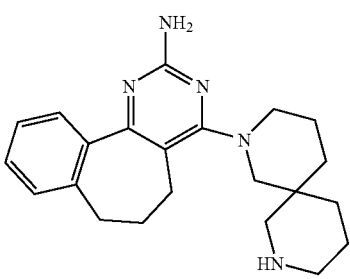<br>4-(2,8-diazaspiro[5.5]undec-2-yl)-6,7-dihydro-5H-benzo[6,7]cyclohepta[1,2-d]pyrimidin-2-amine |
| 3,9-Diazaspiro[5.5]undecane-3-carboxylic acid, 1,1-dimethylethyl ester | 173405-78-2 | WO2005040167 A1 | 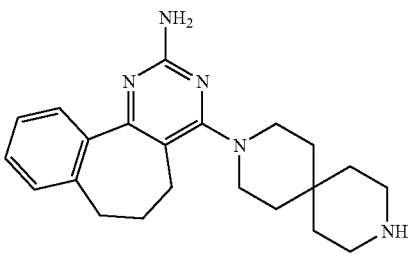<br>4-(3,9-diazaspiro[5.5]undec-3-yl)-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 2,5-Diazabicyclo[2.2.0]hexane | 186-07-2 | Krivdin, L. B.; et al. Russian Journal of Organic Chemistry (Translation of Zhurnal Organicheskoi Khimii) (2003), 39(5), 698-704 | 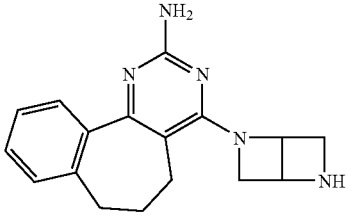<br>4-(2,5-diazabicyclo[2.2.0]hex-2-yl)-6,7-dihydro-5H-benzo[6,7]cyclohepta[1,2-d]pyrimidin-2-amine |
| 6-(Phenylmethyl)-2,6-diazabicyclo[3.2.0]heptane | 851526-88-0 | US2005101602 A1 | 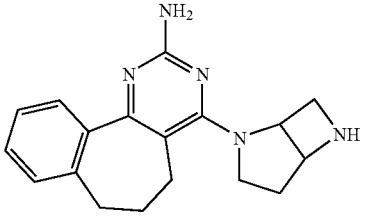<br>4-(2,6-diazabicyclo[3.2.0]hept-2-yl)-6,7-dihydro-5H-benzo[6,7]cyclohepta[1,2-d]pyrimidin-2-amine |
| 6-(Phenylmethyl)-2,6-diazabicyclo[3.2.0]heptane | 851526-88-0 | US2005101602 A1 | 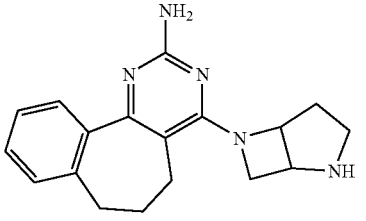<br>4-(2,6-diazabicyclo[3.2.0]hept-6-yl)-6,7-dihydro-5H-benzo[6,7]cyclohepta[1,2-d]pyrimidin-2-amine |
| tert-Butyl 3,7-diazabicyclo[4.2.0]octane-3-carboxylate | 885271-67-0 | MILESTONE PharmTec LLC 100 Jersey Avenue Building D, Box D-4 New Brunswick, NJ 08901 USA www.milestonepharm-tech.com cat # 6M-0032 | 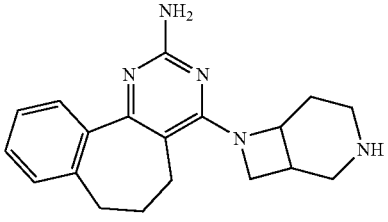<br>4-(3,7-diazabicyclo[4.2.0]oct-7-yl)-6,7-dihydro-5H-benzo[6,7]cyclohepta[1,2-d]pyrimidin-2-amine |

TABLE 1-continued

Prospective Examples of synthetic intermediate groups, and Product Compounds
that may be prepared by the methods described in Schemes 1-18.

| Group | CAS # | Commercial Source or Literature, or Patent Reference | Product from group |
|---|---|---|---|
| tert-Butyl 3,7-diazabicyclo[4.2.0]octane-7-carboxylate | 885271-73-8 | MILESTONE PharmTec LLC cat # 6M-0030 | 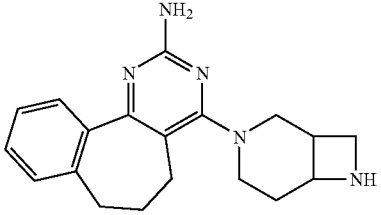 4-(3,7-diazabicyclo[4.2.0]oct-3-yl)-6,7-dihydro-5H-benzo[6,7]cyclohepta[1,2-d]pyrimidin-2-amine |
| ,8-Diazabicyclo[4.2.0]octane-8-carboxylic acid, 1,1-acid, 1,1-dimethylethyl ester | 848591-80-0 | US2005101602 A1 | 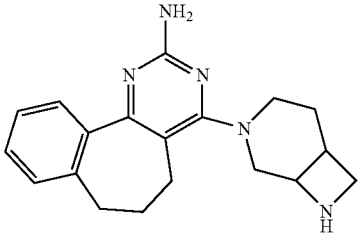 4-(3,8-diazabicyclo[4.2.0]oct-3-yl)-6,7-dihydro-5H-benzo[6,7]cyclohepta[1,2-d]pyrimidin-2-amine |
| ,8-Diazabicyclo[4.2.0]octane-8-carboxylic acid, 1,1-dimethylethyl ester | 848591-80-0 | US2005101602 A1 | 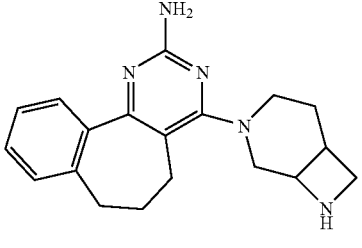 4-(3,8-diazabicyclo[4.2.0]oct-3-yl)-6,7-dihydro-5H-benzo[6,7]cyclohepta[1,2-d]pyrimidin-2-amine |
| Octahydro-pyrrolo[3,2-b]pyrrole | 5839-99-6 | US2932650 | 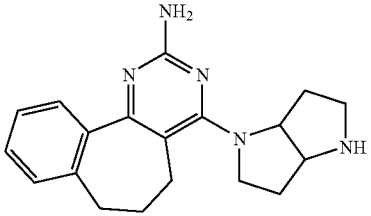 4-hexahydropyrrolo[3,2-b]pyrrol-1(2H)-yl-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| Hexahydro-pyrrolo[3,4-b]pyrrole-1-carboxylic acid tert-butyl ester | 185693-02-1 | ANICHEM LLC 7 Deer Park Drive Suite M6 Monmouth Junction, NJ 08852 www.anichemllc.com catalog # A21583 | 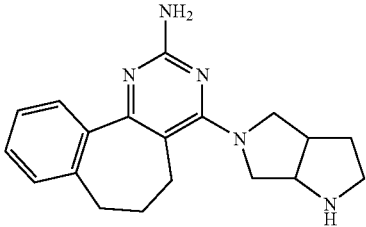 4-hexahydropyrrolo[3,4-b]pyrrol-5(1H)-yl-6,7-dihydro-5H-benzo[6,7]cyclohepta[1,2-d]pyrimidin-2-amine |
| Hexahydro-pyrrolo[3,4-b]pyrrole-1-carboxylic acid tert-butyl ester | 185693-02-1 | ANICHEM LLC cat # A21583 | 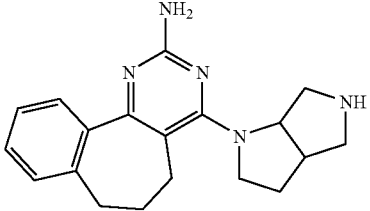 4-hexahydropyrrolo[3,4-b]pyrrol-1(2H)-yl-6,7-dihydro-5H-benzo[6,7]cyclohepta[1,2-d]pyrimidin-2-amine |
| 1H-Pyrrolo[3,2-c]pyridine, octahydro-1-methyl-, dihydrochloride | 172281-71-9 | US5442044A | 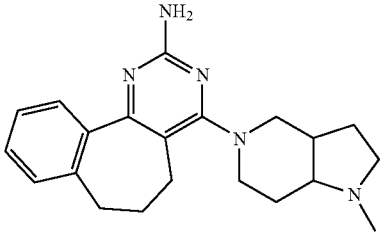 4-(1-methyloctahydro-5H-pyrrolo[3,2-c]pyridin-5-yl)-6,7-dihydro-5H-benzo[6,7]cyclohepta[1,2-d]pyrimidin-2-amine |
| 1H-Pyrrolo[2,3-c]pyridine-1-carboxylic acid, octahydro-, 1,1-dimethylethyl ester | 169750-88-3 | WO9510519A1 | 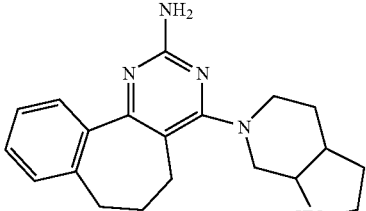 4-octahydro-6H-pyrrolo[2,3-c]pyridin-6-yl-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 1H-Pyrrolo[2,3-c]pyridine-1-carboxylic acid, octahydro-, 1,1-dimethylethyl ester | 169750-88-3 | WO9510519A1 | 4-octahydro-6H-pyrrolo[2,3-c]pyridin-6-yl-6,7-dihydro-5H-benzo[6,7]cyclohepta[1,2-d]pyrimidin-2-amine |
| Octahydro-6-(phenylmethyl)-1H-pyrrolo[3,4-b]pyridine | 128740-14-7 | TYGER (Aagile Labs Division of Tyger Scientific) 324 Stokes Ave. Ewing, NJ 08638 USA cat # B64518 | 4-octahydro-6H-pyrrolo[3,4-b]pyridin-6-yl-6,7-dihydro-5H-benzo[6,7]cyclohepta[1,2-d]pyrimidin-2-amine |
| Octahydro-6-(phenylmethyl)-1H-pyrrolo[3,4-b]pyridine | 128740-14-7 | TYGER (Aagile Labs Division of Tyger Scientific) 324 Stokes Ave. Ewing, NJ 08638 USA cat # B64518 | 4-octahydro-1H-pyrrolo[3,4-b]pyridin-1-yl-6,7-dihydro-5H-benzo[6,7]cyclohepta[1,2-d]pyrimidin-2-amine |
| 5H-Pyrrolo[3,4-c]pyridine-5-carboxylic acid, octahydro-, 1,1-dimethylethyl ester | 351370-99-5 | TYGER (Aagile Labs Division of Tyger Scientific) 324 Stokes Ave. Ewing, NJ 08638 USA) cat # B64520 | 4-octahydro-2H-pyrrolo[3,4-c]pyridin-2-yl-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| Octahydro-2-(phenylmethyl)-1H-pyrrolo[3,4-c]pyridine | 351370-98-4 | TYGER (Aagile Labs Division of Tyger Scientific) 324 Stokes Ave. Ewing, NJ 08638 USA) cat # B64521 | 4-octahydro-5H-pyrrolo[3,4-c]pyridin-5-yl-6,7-dihydro-5H-benzo[6,7]cyclohepta[1,2-d]pyrimidin-2-amine |
| Pyrrolo[3,4-c]azepine-2(1H)-carboxylic acid, octahydro-5-(phenylmethyl)-, 1,1-dimethylethyl ester | 236406-58-9 | WO9940070A1 | 4-octahydropyrrolo[3,4-c]azepin-5(1H)-yl-6,7-dihydro-5H-benzo[6,7]cyclohepta[1,2-d]pyrimidin-2-amine |
| Pyrrolo[3,4-c]azepine-2(1H)-carboxylic acid, octahydro-5-(phenylmethyl)-, 1,1-dimethylethyl ester | 236406-58-9 | WO9940070A1 | 4-octahydropyrrolo[3,4-c]azepin-2(1H)-yl-6,7-dihydro-5H-benzo[6,7]cyclohepta[1,2-d]pyrimidin-2-amine |
| Pyrrolo[3,4-d]azepine-2(1H)-carboxylic acid, octahydro-6-(phenylmethyl)-, 1,1-dimethylethyl ester | 801253-06-5 | WO2004103992A1 | 4-octahydropyrrolo[3,4-d]azepin-2(1H)-yl-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| Pyrrolo[3,4-d]azepine-2(1H)-carboxylic acid, octahydro-6-(phenylmethyl)-, 1,1-dimethylethyl ester | 801253-06-5 | WO2004103992 A1 | 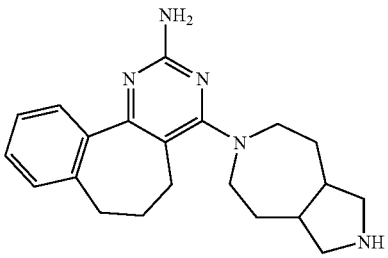<br>4-octahydropyrrolo[3,4-d]azepin-6(1H)-yl-6,7-dihydro-5H-benzo[6,7]cyclohepta[1,2-d]pyrimidin-2-amine |
| (4aS,8aS)-1,5-Naphthyridine, decahydro-1-(phenylmethyl)- | 574001-72-2 | Li, Xiaolin; et al. Journal of Organic Chemistry (2003), 68(14), 5500-5511. | 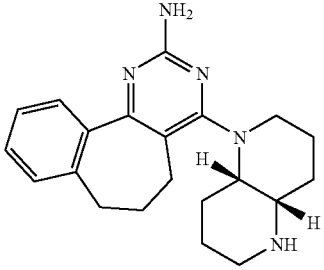<br>4-[(4aS,8aS)-octahydro-1,5-naphthyridin-1(2H)-yl]-6,7-dihydro-5H-benzo[6,7]cyclohepta[1,2-d]pyrimidin-2-amine |
| (4aR,8aR)-1,5-Naphthyridine, decahydro-1-methyl- | 381227-92-5 | Li, Xiaolin; et al. Journal of Organic Chemistry (2003), 68(14), 5500-5511. | 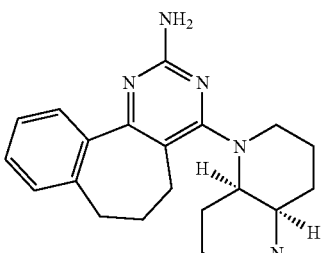<br>4-[(4aR,8aR)-5-methyloctahydro-1,5-naphthyridin-1(2H)-yl]-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| (4aR,8aR)-1,6-Naphthyridine-6(2H)-carboxylic acid, octahydro-1-(phenylmethyl)-, 1,1-dimethylethyl ester | 616875-95-7 | Kobashi, Seiichi; et al. Yakugaku Zasshi (2003), 123(5), 337-347. | 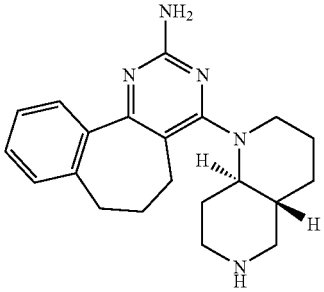<br>4-[(4aR,8aR)-octahydro-1,6-naphthyridin-1(2H)-yl]-6,7-dihydro-5H-benzo[6,7]cyclohepta[1,2-d]pyrimidin-2-amine |
| (4aR,8aR)-1,6-Naphthyridine-6(2H)-carboxylic acid, octahydro-1-(phenylmethyl)-, 1,1-dimethylethyl ester | 616875-95-7 | Kobashi, Seiichi; et al. Yakugaku Zasshi (2003), 123(5), 337-347. | 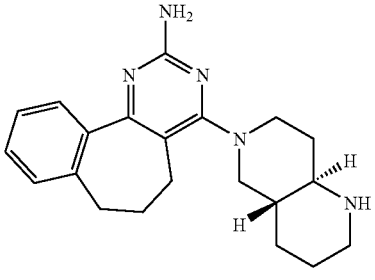<br>4-[(4aR,8aR)-octahydro-1,6-naphthyridin-6(2H)-yl]-6,7-dihydro-5H-benzo[6,7]cyclohepta[1,2-d]pyrimidin-2-amine |
| Decahydro-6-methyl-1,6-naphthyridine | 135037-28-4 | MicroChemistry Building Blocks MicroChemistry Ltd., Kosygina St. 4, Moscow, 119993; Russia; Email: sale@mch.ru; Web: http://www.mch.ru cat # mch-bb-2003 11276 | 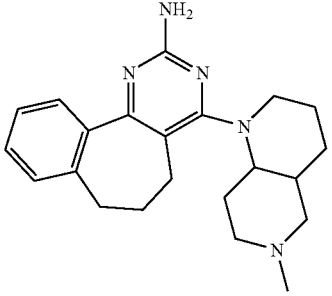<br>4-[(4aR,8aR)-octahydro-1,6-nephthyridin-6(2H)-yl]-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| trans-Decahydro-1,7-Naphthyridine | 13623-82-0 | Hanus, Vladimir; et al. Organic Mass Spectrometry (1984), 19(9), 459-60. | 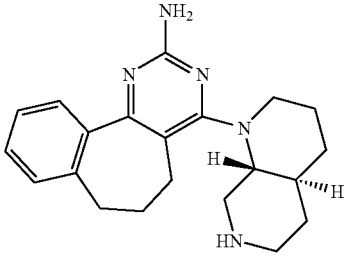<br>4-[(4aS,8aR)-octahydro-1,7-naphthyridin-1(2H)-yl]-6,7-dihydro-5H-benzo[6,7]cyclohepta[1,2-d]pyrimidin-2-amine |
| trans-Decahydro-1,7-Naphthyridine | 13623-82-0 | Hanus, Vladimir; et al. Organic Mass Spectrometry (1984), 19(9), 459-60. | 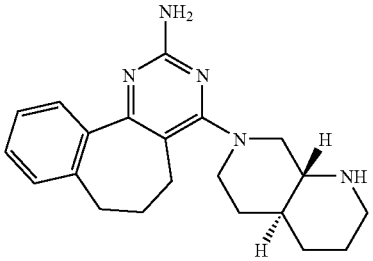<br>4-[(4aS,8aR)-octahydro-1,7-naphthyridin-7(1H)-yl]-6,7-dihydro-5H-benzo[6,7]cyclohepta[1,2-d]pyrimidin-2-amine |
| 2,7-Naphthyridine-2(1H)-carboxylic acid, octahydro-, 1,1-dimethylethyl ester | 885270-18-8 | MILESTONE PharmTec LLC cat # 6M-0007 | 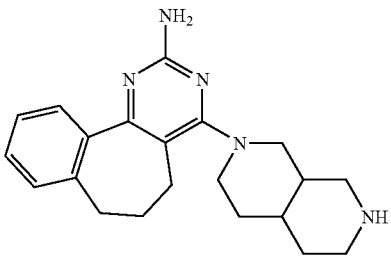<br>4-octahydro-2,7-naphthyridin-2(1H)-yl-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 8a-Ethyldecahydro-copyrine | 873999-52-1 | Iselin, B. M.; et al. Journal of the American Chemical Society (1954), 76 3220-2. | 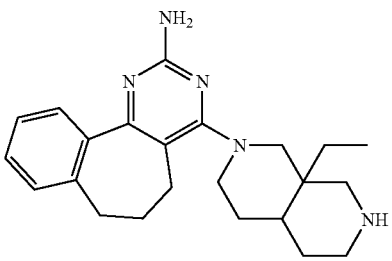<br>4-(8a-ethyloctahydro-2,7-naphthyridin-2(1H)-yl)-6,7-dihydro-5H-benzo[6,7]cyclohepta[1,2-d]pyrimidin-2-amine |
| decahydro-1H-Pyrido[3,2-c]azepine | 344460-81-7 | Linden, Anthony; et al. Acta Crystallographica, Section C: Crystal Structure Communications (2001), C57(6), 764-766. | 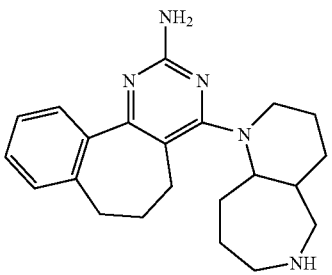<br>4-decahydro-1H-pyrido[3,2-c]azepin-1-yl-6,7-dihydro-5H-benzo[6,7]cyclohepta[1,2-d]pyrimidin-2-amine |
| Decahydro-1H-Pyrido[3,2-c]azepine | 344460-81-7 | Linden, Anthony; et al. Acta Crystallographica, Section C: Crystal Structure Communications (2001), C57(6), 764-766. | 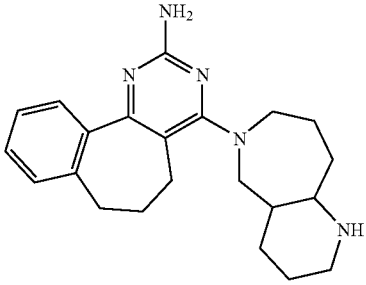<br>4-decahydro-6H-pyrido[3,2-c]azepin-6-yl-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| Octahydro-3-isobutyl-pyrrolo[1,2-a]pyrazine | 718631-71-1 | Chemstep Product List 20 Avenue Victor Hugo; Carbon Blanc, 33560; France; Email: info@chemstep.com; Web: http://www.chemstep.com cat # 71454 | 4-(3-isopropylhexahydropyrrolo[1,2-a]pyrazin-2(1H)-yl)-6,7-dihydro-5H-benzo[6,7]cyclohepta[1,2-d]pyrimidin-2-amine |
| Octahydro-1-methyl-pyrrolo[1,2-a]pyrazine | 155206-39-6 | WO2006048750 A2 | 4-(3-methylhexahydropyrrolo[1,2-a]pyrazin-2(1H)-yl)-6,7-dihydro-5H-benzo[6,7]cyclohepta[1,2-d]pyrimidin-2-amine |
| Octahydro-6-methyl-pyrrolo[1,2-a]pyrazine | 22177-06-6 | Ponomarev, A. A.; Set al. Metody Polucheniya Khimicheskikh Reaktivov i Preparatov (1967), (17), 5-6 | 4-(6-methylhexahydropyrrolo[1,2-a]pyrazin-2(1H)-yl)-6,7-dihydro-5H-benzo[6,7]cyclohepta[1,2-d]pyrimidin-2-amine |
| Octahydro-6-methyl-2H-Pyrido[1,2-a]pyrazine | 5762-99-2 | Chemstep Product List cat # 70166 | 4-(6-methyloctahydro-2H-pyrido[1,2-a]pyrazin-2-yl)-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| Octahydro-pyrido[1,2-a]pyrazine | 4430-75-5 | Oakwood Products Catalog cat # 032054 | 4-octahydro-2H-pyrido[1,2-a]pyrazin-2-yl-6,7-dihdyro-5H-benzo[6,7]cyclohepta[1,2-d]pyrimidin-2-amine |
| Octahydro-1H-Pyrrolo[1,2-a][1,4]diazepine | 109324-83-6 | MicroChemistry Building Blocks cat # mch-bb-2003 13717 | 4-hexahydro-1H-pyrrolo[1,2-a][1,4]diazepin-2(3H)-yl-6,7-dihydro-5H-benzo[6,7]cyclohepta[1,2-d]pyrimidin-2-amine |
| Decahydro-pyrazino[1,2-a]azepine | 49633-80-9 | Oakwood Products 1741 Old Dunbar Rd.; West Columbia, SC, 29172; USA; Email: sales@fluorochemusa.com; Web: http://www.oakwoodchemical.com Catalog cat # 032087 | 4-octahydropyrazino[1,2-a]azepin-2(1H)-yl-6,7-dihydro-5H-benzo[6,7]cyclohepta[1,2-d]pyrimidin-2-amine |
| Octahydro-1H-Cyclopenta-pyrazine | 154393-81-4 | Chemstep Product List cat # 53753 | 4-octahydropyrazino[1,2-a]azepin-2(1H)-yl-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
| --- | --- | --- | --- |
| Decahydro-quinoxaline | 90410-24-5 | MicroChemistry Building Blocks cat # mch-bb-2003 11269 | 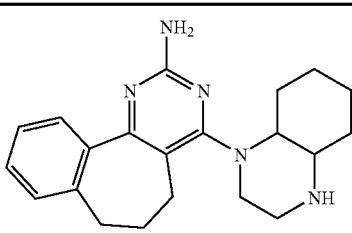<br>4-octahydroquinoxalin-1(2H)-yl-6,7-dihydro-5H-benzo[6,7]cyclohepta[1,2-d]pyrimidin-2-amine |
| Decahydro-2-methyl-quinoxaline, dihydrochloride | 114062-34-9 | Maffei, Silvio; et al. Gazzetta Chimica Italiana (1958), 88 556-63. | 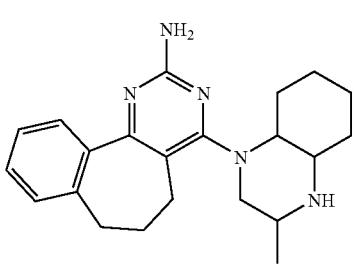<br>4-(3-methyloctahydroquinoxalin-1(2H)-yl)-6,7-dihydro-5H-benzo[6,7]cyclohepta[1,2-d]pyrimidin-2-amine |
| Octahydro-3,3,7,7-tetramethyl-5-diazocine | 17288-14-1 | Kemp, D. S.; et al. Journal of Organic Chemistry (1979), 44(25), 4473-6. | 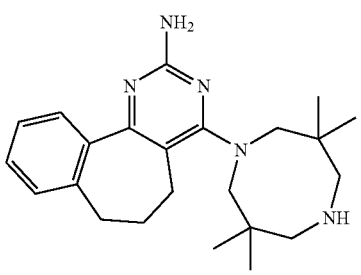<br>4-(3,3,7,7-tetramethyl-1,5-diazocan-1-yl)-6,7-dihydro-5H-benzo[6,7]cyclohepta[1,2-d]pyrimidin-2-amine |
| Octahydro-1-methyl-1,5-diazocine, dihydrobromide | 4318-35-8 | US3247206 | 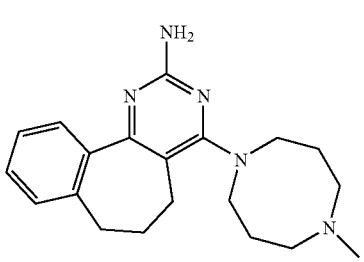<br>4-(5-methyl-1,5-diazocan-1-yl)-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| Octahydro-1H-1,5-diazonine, dihydrochloride | 118872-68-7 | Stetter, H.; et al. Chemische Berichte (1958), 91 1982-8. | 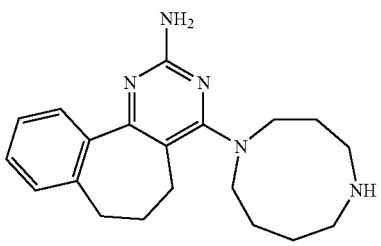<br>4-(1,5-diazonan-1-yl)-6,7-dihydro-5H-benzo[6,7]cyclohepta[1,2-d]pyrimidin-2-amine |
| Decahydro-1,6-diazecine, dihydrochloride | 118725-33-0 | Stetter, H.; et al. Chemische Berichte (1958), 91 1982-8. | 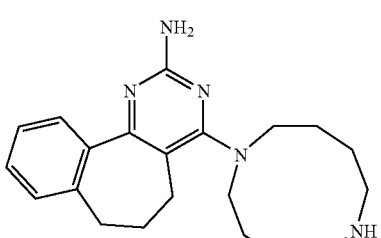<br>4-(1,6-diazecan-1-yl)-6,7-dihydro-5H-benzo[6,7]cyclohepta[1,2-d]pyrimidin-2-amine |
| Decahydro-1-methyl-1,6-diazecine | 68388-04-5 | Horner, L.; et al. Justus Liebigs Annalen der Chemie (1978), (9), 1505-17. | 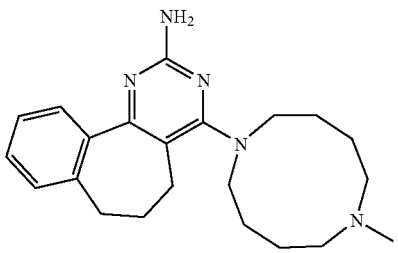<br>4-(6-methyl-1,6-diazecan-1-yl)-6,7-dihydro-5H-benzo[6,7]cyclohepta[1,2-d]pyrimidin-2-amine |
| Decahydro-1,5-diazecine | 6573-62-2 | Bergmann, D. J.; et al. Chemical Communications (1999), (14), 1279-1280. | 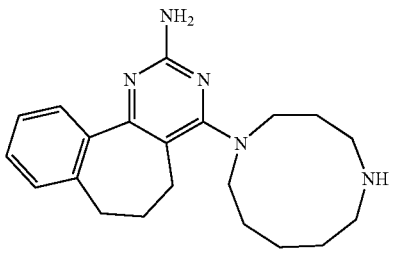<br>4-(1,5-diazecan-1-yl)-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 1,6-Diazacycloundecane | 294-51-9 | Stetter, H.; et al. Chemische Berichte (1958), 91 677-80. | 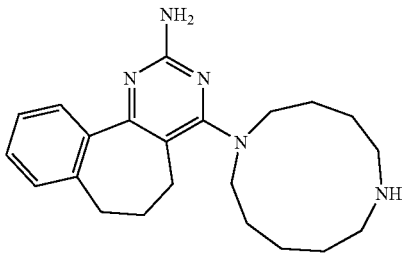 4-(1,6-diazacycloundecan-1-yl)-6,7-dihydro-5H-benzo[6,7]cyclohepta[1,2-d]pyrimidin-2-amine |
| Azetidin-3-ylmethyl-carbamic acid tert-butyl ester | 91188-15-7 | TYGER (Aagile Labs Division of Tyger Scientific) 324 Stokes Ave. Ewing, NJ 08638 USA) cat # A58187 | 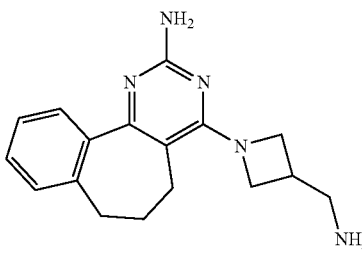 4-[3-(aminomethyl)azetidin-1-yl]-6,7-dihydro-5H-benzo[6,7]cyclohepta[1,2-d]pyrimidin-2-amine |
| (3-Pyrrolidinylmethyl)-carbamic acid tert-butyl ester | 149366-79-0 | TYGER (Aagile Labs Division of Tyger Scientific) 324 Stokes Ave. Ewing, NJ 08638 USA) cat #B64504 | 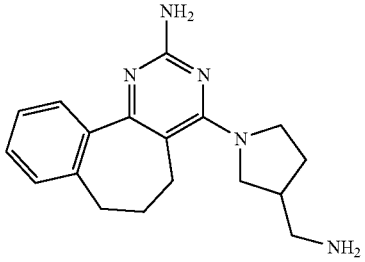 4-[3-(aminomethyl)pyrrolidin-1-yl]-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| (3R)-3-((Dimethylamino)methyl)pyrrolidine dihydrochloride | 859213-49-3 | WO2005082855 A1 | 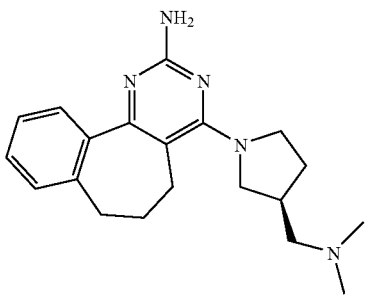<br>4-{(3S)-3-[(dimethylamino)methyl]pyrrolidin-1-yl}-6,7-dihydro-5H-benzo[6,7]cyclohepta[1,2-d]pyrimidin-2-amine |
| Piperidin-4-ylmethyl-carbamic acid tert-butyl ester | 135632-53-0 | Fluorochem Ltd.; Wesley Street; Old Glossop, Derbyshire, SK13 7RY; United Kingdom; Email: enquiries@fluorochem.co.uk; Web: http://www.fluorochem.net cat # 17246 | 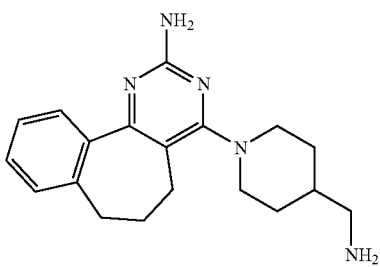<br>4-[4-(aminomethyl)piperidin-1-yl]-6,7-dihydro-5H-benzo[6,7]cyclohepta[1,2-d]pyrimidin-2-amine |
| Dimethyl-(2-piperidin-4-yl-ethyl)-amine | 102308-48-5 | MATRIX (Matrix Scientific; P O Box 25067; Columbia, SC, 29224-5067 USA; Email: sales@matrixscientific.com; Web: http://www.matrix-scientific.com) cat# 020420 | 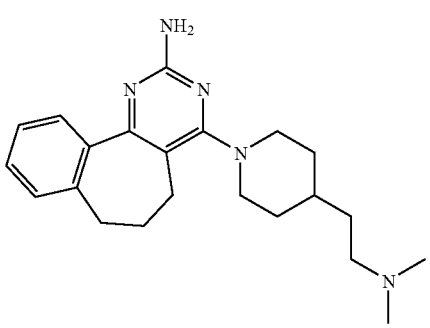<br>4-{4-[2-(dimethylamino)ethyl]piperidin-1-yl}-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 3-N-Boc-aminomethyl piperidine | 142643-29-6 | ALDRICH (Aldrich Chemical Company, Inc. 1001 West Saint Paul Avenue Milwaukee, WI 53233 USA) cat # 653896 | 4-[3-(aminomethyl)piperidin-1-yl]-6,7-dihydro-5H-benzo[6,7]cyclohepta[1,2-d]pyrimidin-2-amine |
| 3-(2-Boc-aminoethyl) piperidine | 215305-98-9 | TYGER (Aagile Labs Division of Tyger Scientific) 324 Stokes Ave. Ewing, NJ 08638 USA) cat # B28400 | 4-[3-(2-aminoethyl)piperidin-1-yl]-6,7-dihydro-5H-benzo[6,7]cyclohepta[1,2-d]pyrimidin-2-amine |
| 3-Aminomethyl-azetidine-1-carboxylic acid tert-butyl ester | 325775-44-8 | TYGER (Aagile Labs Division of Tyger Scientific) 324 Stokes Ave. Ewing, NJ 08638 USA) cat # A57126 | $N^4$-(azetidin-3-ylmethyl)-6,7-dihydro-5H-benzo[6,7]cyclohepta[1,2-d]pyrimidine-2,4-diamine |

TABLE 1-continued

Prospective Examples of synthetic intermediate groups, and Product Compounds
that may be prepared by the methods described in Schemes 1-18.

| Group | CAS # | Commercial Source or Literature, or Patent Reference | Product from group |
|---|---|---|---|
| 3-Aminomethyl-pyrrolidine-1-carboxylic acid tert-butyl ester | 270912-72-6 | FLROCHEM cat # 11395 | 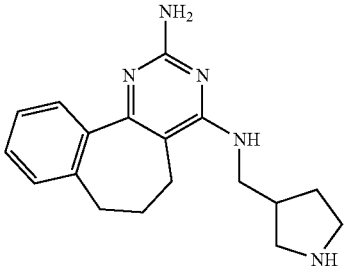<br>$N^4$-(pyrrolidin-3-ylmethyl)-6,7-dihydro-5H-benzo[6,7]cyclohepta[1,2-d]pyrimidine-2,4-diamine |
| Methyl-(1-methyl-pyrrolidin-3-ylmethyl)-amine | 89850-95-3 | MATRIX catalog # 019128 | 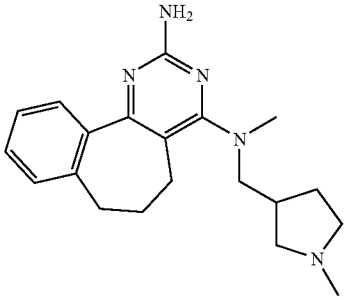<br>$N^4$-methyl-$N^4$-[(1-methylpyrrolidin-3-yl)methyl]-6,7-dihydro-5H-benzo[6,7]cyclohepta[1,2-d]pyrimidine-2,4-diamine |
| 3-Aminoethyl-1-n-cbz-pyrrolidine | 811842-07-6 | OAKWOOD cat # 11381 | 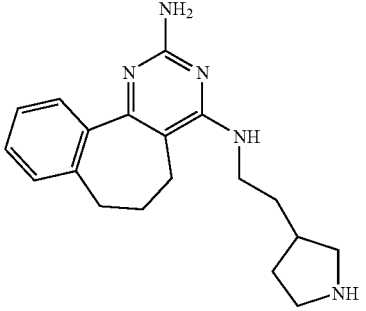<br>$N^4$-(2-pyrrolidin-3-ylethyl)-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 1-N-Boc-4-(aminomethyl)piperidine | 144222-22-0 | ALDRICH cat # 641472 | $N^4$-(piperidin-4-ylmethyl)-6,7-dihydro-5H-benzo[6,7]cyclohepta[1,2-d]pyrimidine-2,4-diamine |
| 4-(Pyrrolidin-1-ylmethyl)piperidine | 683772-11-4 | MATRIX cat # 016344 | 4-[4-(pyrrolidin-1-ylmethyl)piperidin-1-yl]-6,7-dihydro-5H-benzo[6,7]cyclohepta[1,2-d]pyrimidin-2-amine |
| 3-(Aminomethyl)-1-N-Boc-piperidine | 162167-97-7 | OAKWOOD cat # 11388 | $N^4$-(piperidin-3-ylmethyl)-6,7-dihydro-5H-bezno[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 4-(N-Boc-amino)piperidine | 73874-95-0 | ALDRICH cat # 540935 | 4-(4-aminopiperidin-1-yl)-6,7-dihydro-5H-benzo[6,7]cyclohepta[1,2-d]pyrimidin-2-amine |
| 4-(2-Boc-aminoethyl)piperidine | 165528-81-4 | Tyger catalog # B32000 | 4-[4-(2-aminoethyl)piperidin-1-yl]-6,7-dihydro-5H-benzo[6,7]cyclohepta[1,2-d]pyrimidin-2-amine |
| 3-Boc-aminopiperidine | 172603-05-3 | Tyger Scientific Product List cat # B50100 | 4-(3-aminopiperidin-1-yl)-6,7-dihydro-5H-benzo[6,7]cyclohepta[1,2-d]pyrimidin-2-amine |
| C-(1-Benzyl-piperidin-3-yl)-methylamine | 124257-62-1 | OAKWOOD cat # 30699 | $N^4$-(piperidin-3-ylmethyl)-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| (1-Methyl-piperidin-4-yl)-methylamine | 7149-42-0 | OAKWOOD cat # 32204 | 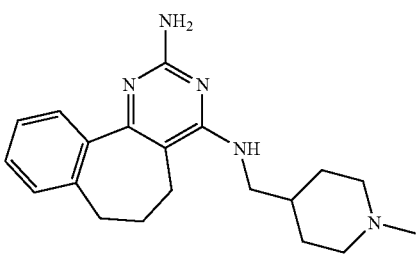<br>$N^4$-[(1-methylpiperidin-4-yl)methyl]-6,7-dihydro-5H-benzo[6,7]cyclohepta[1,2-d]pyrimidine-2,4-diamine |
| (1-Isopropyl-piperidin-3-ylmethyl)-methyl-amine | 876716-01-7 | Matrix Scientific catalog # 19173 | 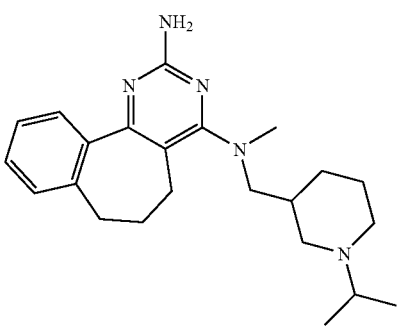<br>$N^4$-[(1-isopropylpiperidin-3-yl)methyl]-$N^4$-methyl-6,7-dihydro-5H-benzo[6,7]cyclohepta[1,2-d]pyrimidine-2,4-diamine |
| (1-Isopropyl-piperidin-4-ylmethyl)-methyl-amine | 876716-04-0 | Matrix Scientific catalog # 19174 | 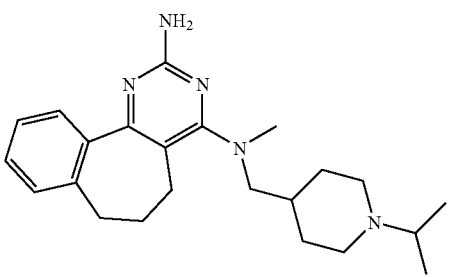<br>$N^4$-[(1-isopropylpiperidin-4-yl)methyl]-$N^4$-methyl-6,7-dihydro-5H-benzo[6,7]cyclohepta[1,2-d]pyrimidine-2,4-diamine |

TABLE 1-continued

Prospective Examples of synthetic intermediate groups, and Product Compounds
that may be prepared by the methods described in Schemes 1-18.

| Group | CAS # | Commercial Source or Literature, or Patent Reference | Product from group |
|---|---|---|---|
| 4-(1-Azetidinylmethyl)-piperidine, dihydrochloride | 864441-51-0 | WO2005082854 A1 | 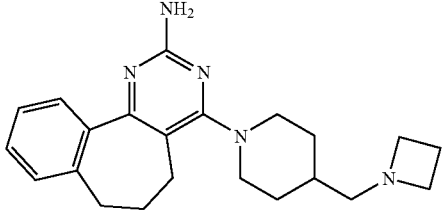<br>4-[4-(azetidin-1-ylmethyl)piperidin-1-yl]-6,7-dihydro-5H-benzo[6,7]cyclohepta[1,2-d]pyrimidin-2-amine |
| 4-(1-Azetidinyl)-piperidine, dihydrochloride | 864246-02-6 | WO2005082855 A1 | 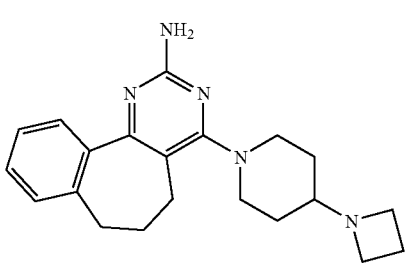<br>4-(4-azetidin-1-ylpiperidin-1-yl)-6,7-dihydro-5H-benzo[6,7]cyclohepta[1,2-d]pyrimidin-2-amine |
| 1-(3-Azetidinyl)-pyrrolidine, bis(trifluoroacetate) | 864248-58-8 | WO2005082854 A1 | 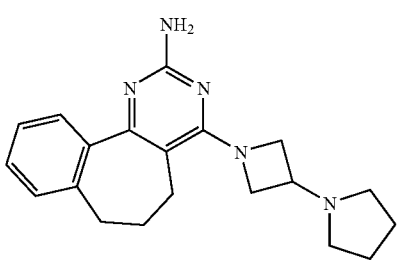<br>4-(3-pyrrolidin-1-ylazetidin-1-yl)-6,7-dihydro-5H-benzo[6,7]cyclohepta[1,2-d]pyrimidin-2-amine |
| [1,3']Bipyrrolidinyl | 267241-99-6 | Oakwood Products Catalog; catalog # 031602 | 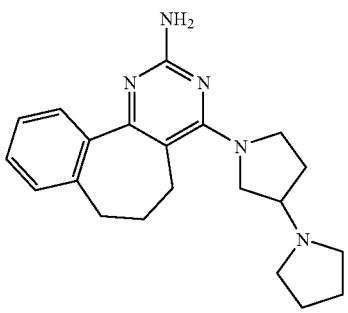<br>4-(1,3'-bipyrrolidin-1'-yl)-6,7-dihydro-5H-benzo[6,7]cyclohepta[1,2-d]pyrimidin-2-amine |

TABLE 1-continued

Prospective Examples of synthetic intermediate groups, and Product Compounds
that may be prepared by the methods described in Schemes 1-18.

| Group | CAS # | Commercial Source or Literature, or Patent Reference | Product from group |
|---|---|---|---|
| 4-(1-Pyrrolidinyl)piperidine | 5004-07-9 | Aldrich catalog #437352 | 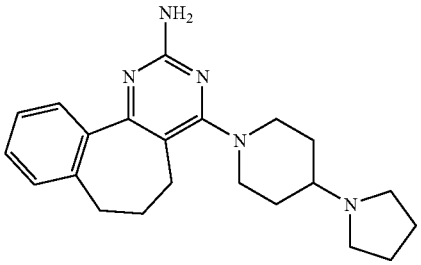<br>4-(4-pyrrolidin-1-ylpiperidin-1-yl)-6,7-dihydro-5H-benzo[6,7]cyclohepta[1,2-d]pyrimidin-2-amine |
| 3-Pyrrolidin-1-ylmethyl-piperidine | 514842-98-9 | Oakwood Products Catalog; catalog #032019 | 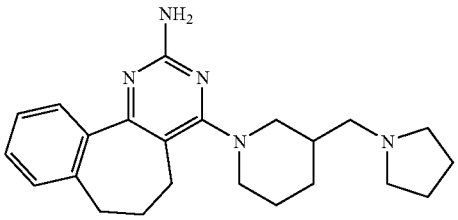<br>4-[3-(pyrrolidin-1-ylmethyl)piperidin-1-yl]-6,7-dihydro-5H-benzo[6,7]cyclohepta[1,2-d]pyrimidin-2-amine |
| 3-[2-(1-Pyrrolidinyl)ethyl]piperidine | 122373-96-0 | DE3726908A1 | 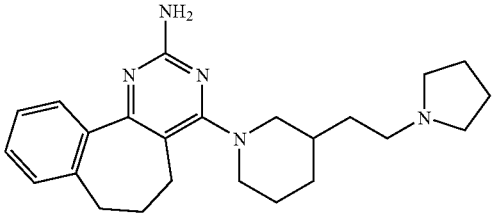<br>4-[3-(2-pyrrolidin-1-ylethyl)piperidin-1-yl]-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 4-(2-Pyrrolidin-1-yl-ethyl)-piperidine | 14759-08-1 | Oakwood Products Catalog; catalog #025057 | 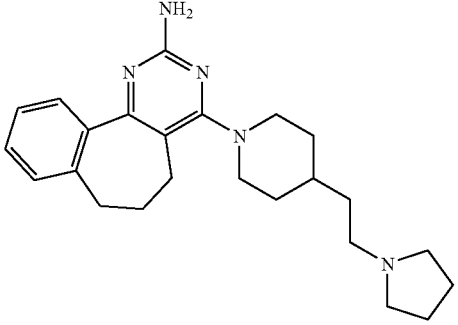<br>4-[4-(2-pyrrolidin-1-ylethyl)piperidin-1-yl]-6,7-dihydro-5H-benzo[6,7]cyclohepta[1,2-d]pyrimidin-2-amine |
| N-Methyl-1-azetidinepropan-amine | 864246-87-7 | WO2005082855 A1 | 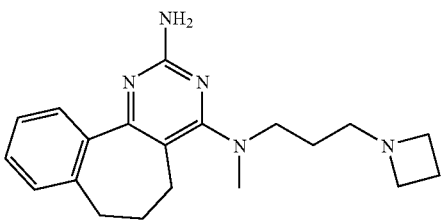<br>$N^4$-(3-azetidin-1-ylpropyl)-$N^4$-methyl-6,7-dihydro-5H-benzo[6,7]cyclohepta[1,2-d]pyrimidine-2,4-diamine |
| N-Methyl-1-Pyrrolidine-ethanamine | 32776-22-0 | Aurora Screening Library catalog #kec-0001338 | 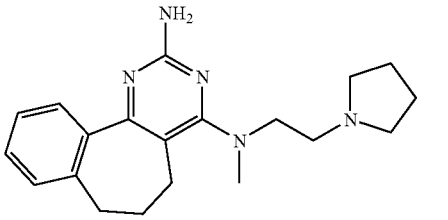<br>$N^4$-methyl-$N^4$-(2-pyrrolidin-1-ylethyl)-6,7-dihydro-5H-benzo[6,7]cyclohepta[1,2-d]pyrimidine-2,4-diamine |
| Methyl[3-(pyrrolidin-1-yl)propyl]amine | 99114-68-8 | Surleraux, D. L. N. G.; et al. Journal of Medicinal Chemistry 2005, 48(6), 1965-1973. | 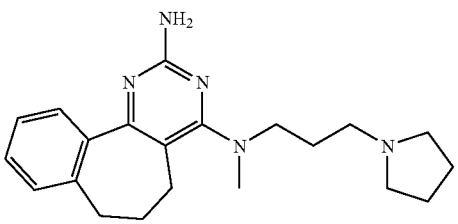<br>$N^4$-methyl-$N^4$-(3-pyrrolidin-1-ylpropyl)-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| N-Methyl-1-pyrrolidine-butanamine | 153905-93-2 | WO2005082855 A1 | 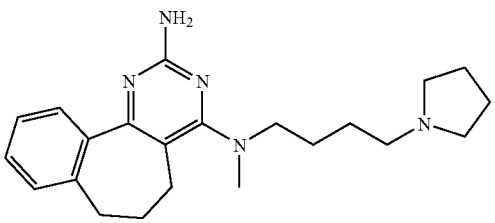<br>$N^4$-methyl-$N^4$-(4-pyrrolidin-1-ylbutyl)-6,7-dihydro-5H-benzo[6,7]cyclohepta[1,2-d]pyrimidine-2,4-diamine |
| 2-(Azetidin-1-yl)ethylamine | 795299-77-3 | WO2006021544 A1 | 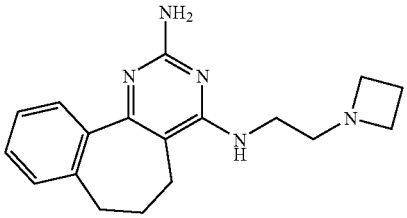<br>$N^4$-(2-azetidin-1-ylethyl)-6,7-dihydro-5H-benzo[6,7]cyclohepta[1,2-d]pyrimidine-2,4-diamine |
| N-(3-Aminopropyl)azetidine | 54262-75-8 | Murahashi, S.; et al. Journal of the American Chemical Society (1983), 105(15), 5002-11. | 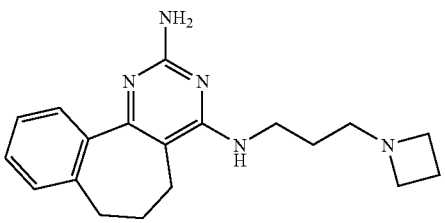<br>$N^4$-(3-azetidin-1-ylpropyl)-6,7-dihydro-5H-benzo[6,7]cyclohepta[1,2-d]pyrimidine-2,4-diamine |
| 1-(2-Aminoethyl)pyrrolidine | 7154-73-6 | ALDRICH catalog # A55357 | 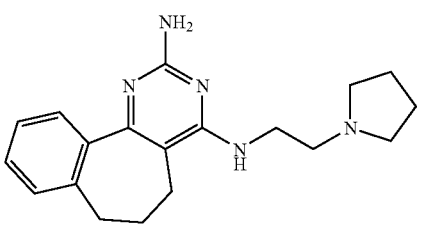<br>$N^4$-(2-pyrrolidin-1-ylethyl)-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 1-(3-Aminopropyl)pyrrolidine | 23159-07-1 | Lancaster Synthesis catalog # 4739 | 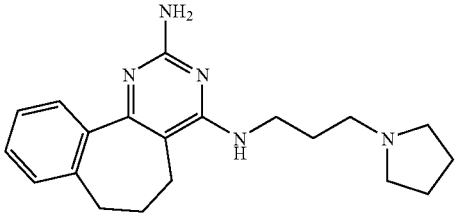 $N^4$-(3-pyrrolidin-1-ylpropyl)-6,7-dihydro-5H-benzo[6,7]cyclohepta[1,2-d]pyrimidine-2,4-diamine |
| 4-(1-Pyrrolidino)butylamine | 24715-90-0 | Matrix Scientific catalog # 7650 | 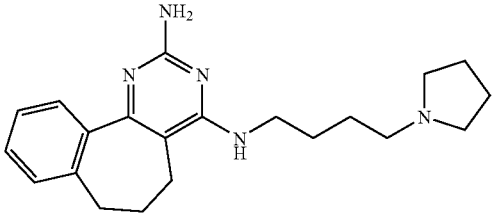 $N^4$-(4-pyrrolidin-1-ylbutyl)-6,7-dihydro-5H-benzo[6,7]cyclohepta[1,2-d]pyrimidine-2,4-diamine |
| (1-Benzyl-azetidin-2-yl)-methylamine | 46193-94-6 | PharmLab Product List catalog # 25-0007 | 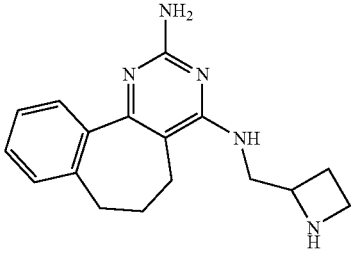 $N^4$-(azetidin-2-ylmethyl)-6,7-dihydro-5H-benzo[6,7]cyclohepta[1,2-d]pyrimidine-2,4-diamine |
| 2-(2-Aminoethyl)-1-methylpyrrolidine | 51387-90-7 | Aldrich catalog # 139505 | 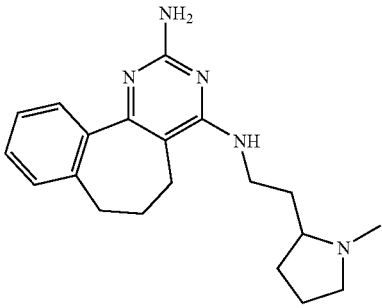 $N^4$-[2-(1-methylpyrrolidin-2-yl)ethyl]-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 2-(Aminomethyl)-1-N-Boc-piperidine | 370069-31-1 | Flrochem catalog # 11387 | 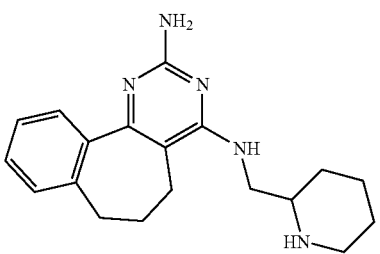<br>$N^4$-(piperidin-2-ylmethyl)-6,7-dihydro-5H-benzo[6,7]cyclohepta[1,2-d]pyrimidine-2,4-diamine |
| (+/−)-2-(Aminomethyl)-1-N-Boc-pyrrolidine | 177911-87-4 | Flrochem catalog # 11393 | 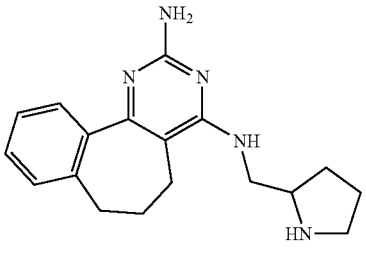<br>$N^4$-(pyrrolidin-2-ylmethyl)-6,7-dihydro-5H-benzo[6,7]cyclohepta[1,2-d]pyrimidine-2,4-diamine |
| 2-(Aminoethyl)-1-N-Boc-piperidine | 239482-98-5 | Flrochem catalog # 11378 | 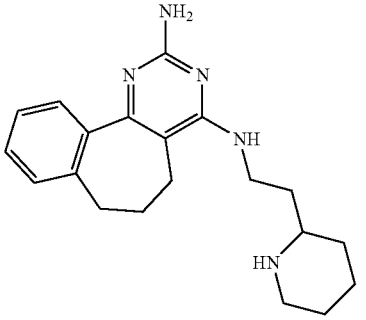<br>$N^4$-(2-piperidin-2-ylethyl)-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 2-(3-Amino-propyl)-pyrrolidine-1-carboxylic acid tert-butyl ester | 887587-47-5 | Tyger Scientific Product List catalog # A57685 | 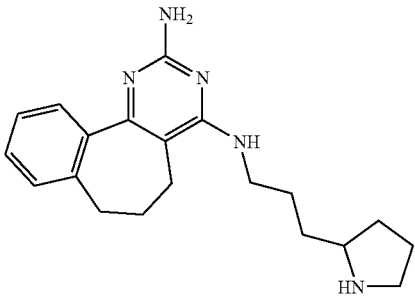<br>$N^4$-(3-pyrrolidin-2-ylpropyl)-6,7-dihydro-5H-benzo[6,7]cyclohepta[1,2-d]pyrimidine-2,4-diamine |
| 1,4-Cyclohexanedi-amine | 3114-70-3 | TCI-US catalog # C0814 | 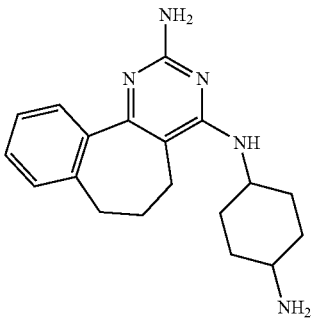<br>$N^4$-(4-aminocyclohexyl)-6,7-dihydro-5H-benzo[6,7]cyclohepta[1,2-d]pyrimidine-2,4-diamine |
| N,N-Dimethyl-cyclohexane-1,4-diamine | 42389-50-4 | PharmLab Product List catalog # 20-0268 | 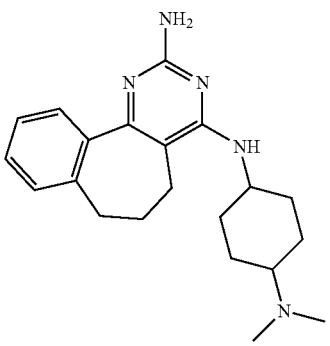<br>$N^4$-[4-(dimethylamino)cyclohexyl]-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 1,3-Cyclohexane-diamine | 3385-21-5 | TCI-US catalog # C0813 | $N^4$-(3-aminocyclohexyl)-6,7-dihydro-5H-benzo[6,7]cyclohepta[1,2-d]pyrimidine-2,4-diamine |
| 1,3-Cyclopentane-diamine | 73211-32-2 | Chemgenx Product List catalog # CX-01566 | $N^4$-(3-aminocyclopentyl)-6,7-dihydro-5H-benzo[6,7]cyclohepta[1,2-d]pyrimidine-2,4-diamine |
| Benzyl trans-4-aminomethylcyclo-hexylcarbamate | 177582-74-0 | AMRI Fine Chemicals catalog # A00095 | $N^4$-[(4-aminocyclohexyl)methyl]-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| tert-Butyl trans-4-aminocyclohex-ylmethylcarbamate | 192323-07-2 | AMRI Fine Chemicals catalog # A00096 | 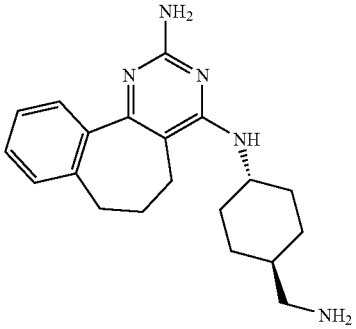<br>$N^4$-[4-(aminomethyl)cyclohexyl]-6,7-dihydro-5H-benzo[6,7]cyclohepta[1,2-d]pyrimidine-2,4-diamine |
| tert-Butyl trans-4-(2-aminoethyl)cyclo-hexylcarbamate | | AMRI Fine Chemicals catalog # A00049 | 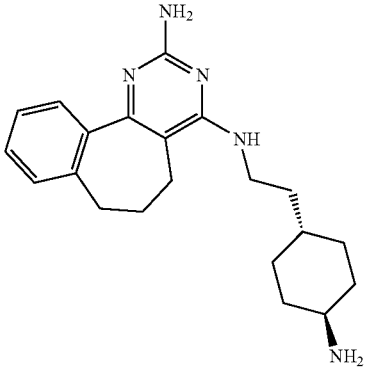<br>$N^4$-[2-(4-aminocyclohexyl)ethyl]-6,7-dihydro-5H-benzo[6,7]cyclohepta[1,2-d]pyrimidine-2,4-diamine |
| 1,3-Cyclohexanebis(methylamine) | 2579-20-6 | Aldrich catalog # 180467 | 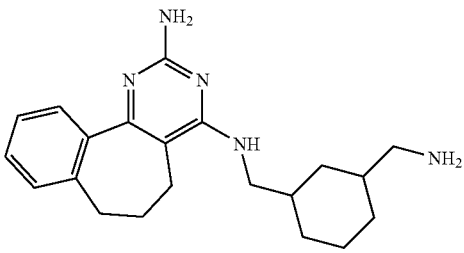<br>$N^4$-{[3-(aminomethyl)cyclohexyl]methyl}-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 1,4-Bis(aminomethyl)cyclohexane | 2549-93-1 | TCI-US catalog # B1083 | 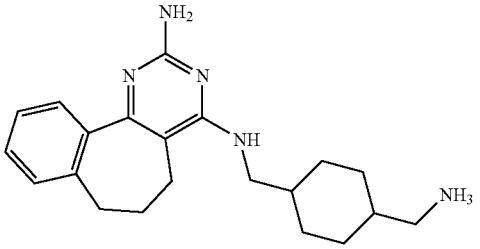<br>N⁴-{[4-(aminomethyl)cyclohexyl]methyl}-6,7-dihydro-5H-benzo[6,7]cyclohepta[1,2-d]pyrimidine-2,4-diamine |
| 1-(2-Aminoethyl)pyrrolidine | 7154-73-6 | Aldrich catalog # A55357 | 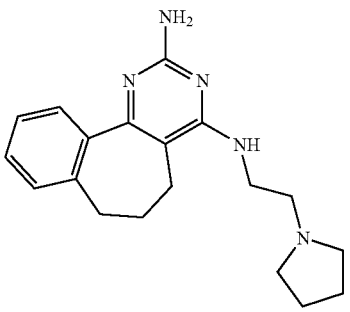<br>N⁴-(2-pyrrolidin-1-ylethyl)-6,7-dihydro-5H-benzo[6,7]cyclohepta[1,2-d]pyrimidine-2,4-diamine |
| 1-(3-Aminopropyl)pyrrolidine | 23159-07-1 | Acros catalog # 36809 | 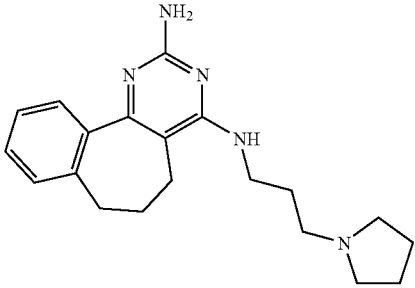<br>N⁴-(3-pyrrolidin-1-ylpropyl)-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 1-(4-Aminobutyl)pyrrolidine | 24715-90-0 | Matrix catalog # 007650 | 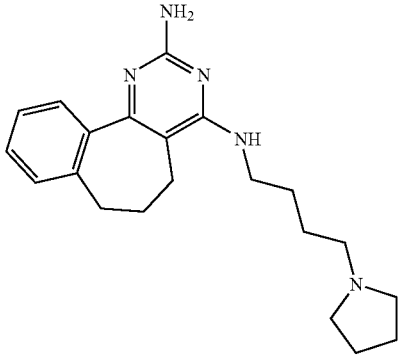 N$^4$-(4-pyrrolidin-1-ylbutyl)-6,7-dihydro-5H-benzo[6,7]cyclohepta[1,2-d]pyrimidine-2,4-diamine |
| Methyl-(3-piperidin-1-yl-propyl)-amine | 86010-41-5 | Matrix catalog # 018963 | 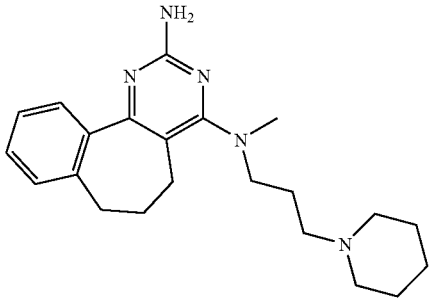 N$^4$-methyl-N$^4$-(3-piperidin-1-ylpropyl)-6,7-dihydro-5H-benzo[6,7]cyclohepta[1,2-d]pyrimidine-2,4-diamine |
| Methyl-(2-piperidin-1-yl-ethyl)-amine | 41239-39-8 | Matrix catalog # 018964 | 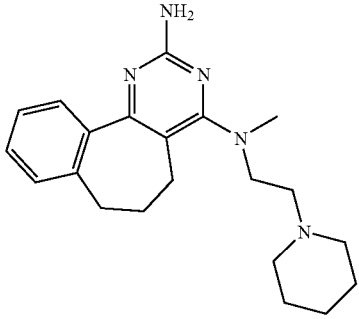 N$^4$-methyl-N$^4$-(2-piperidin-1-ylethyl)-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
| --- | --- | --- | --- |
| 4,4'-Bipiperidine dihydrochloride | 78619-84-8 | Aldrich catalog #180742 | 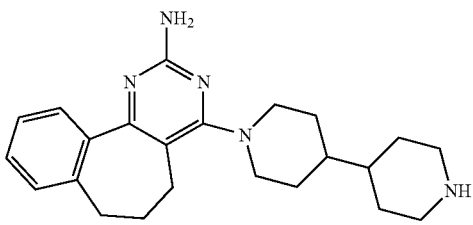 4-(4,4'-bipiperidin-1-yl)-6,7-dihydro-5H-benzo[6,7]cyclohepta[1,2-d]pyrimidin-2-amine |
| 4,4'-Ethylenedipiperidine dihydrochloride | 80997-86-0 | Aldrich catalog #214140 | 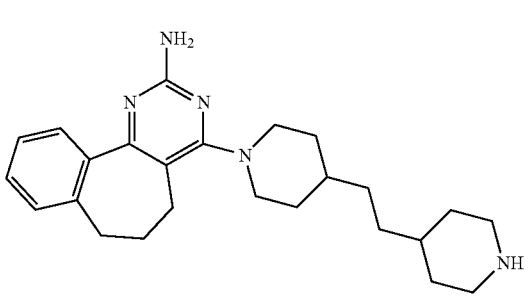 4-[4-(2-piperidin-4-ylethyl)piperidin-1-yl]-6,7-dihydro-5H-benzo[6,7]cyclohepta[1,2-d]pyrimidin-2-amine |
| 2-(1-N-Boc-Aminomethyl-cyclohexyl)-ethylamine | 886362-17-0 | AstaTech Product List catalog #46643 | 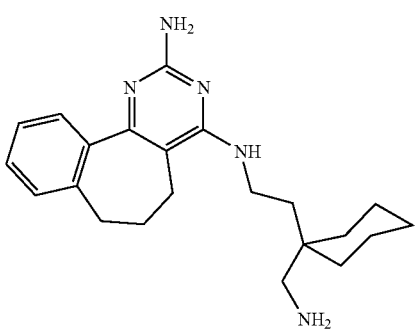 $N^4$-{2-[1-(aminomethyl)cyclohexyl]ethyl}-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| (1-Aminomethyl-cyclopentyl)-carbamic acid tert-butyl ester | 889949-09-1 | Tyger Scientific Product List catalog # A57914 | 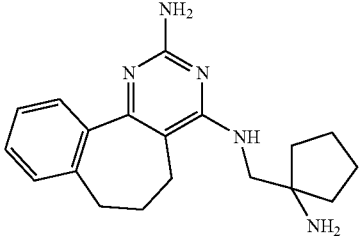<br>$N^4$-[(1-aminocyclopentyl)methyl]-6,7-dihydro-5H-benzo[6,7]cyclohepta[1,2-d]pyrimidine-2,4-diamine |
| 1-Pyrrolidin-1-ylmethyl-cylcohexylamine | 876717-44-1 | MATRIX catalog # 019232 | 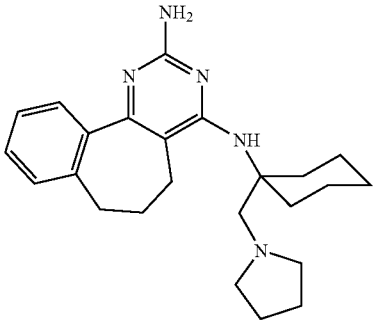<br>$N^4$-[1-(pyrrolidin-1-ylmethyl)cyclohexyl]-6,7-dihydro-5H-benzo[6,7]cyclohepta[1,2-d]pyrimidine-2,4-diamine |
| cis-N-methyl-4-(1-pyrrolidinyl)-Cyclohex-anamine, dihydrochloride | 883864-57-1 | WO2006040281 A1 | 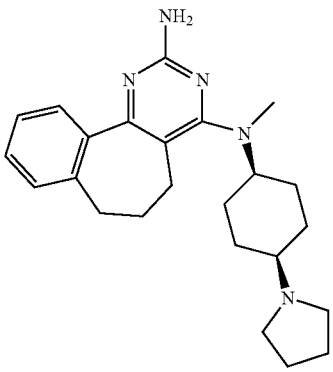<br>$N^4$-methyl-$N^4$-(4-pyrrolidin-1-ylcyclohexyl)-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| trans-3-(1-Pyrrolidinyl)-cyclobutanamine | 878156-28-6 | WO2006021544 A1 | 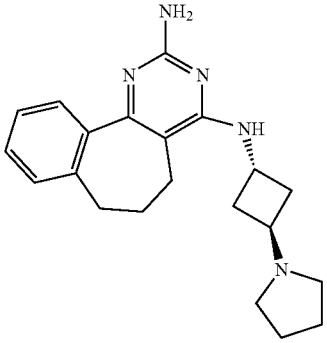<br>$N^4$-(3-pyrrolidin-1-ylcyclobutyl)-6,7-dihydro-5H-benzo[6,7]cyclohepta[1,2-d]pyrimidine-2,4-diamine |
| trans-4-(1-Azetidinylmethyl)-cyclohexanamine | 878155-27-2 | WO2006021544 A1 | 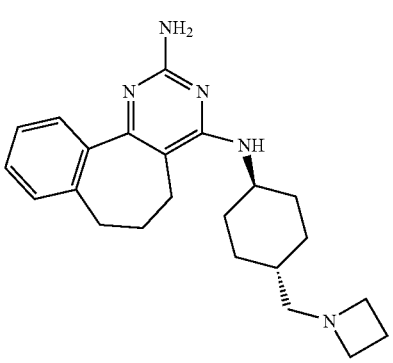<br>$N^4$-[4-(azetidin-1-ylmethyl)cyclohexyl]-6,7-dihydro-5H-benzo[6,7]cyclohepta[1,2-d]pyrimidine-2,4-diamine |
| trans-4-(1-Pyrrolidinyl)-cyclohexanamine | 734527-26-5 | Chemstep Product List catalog # 43301 | 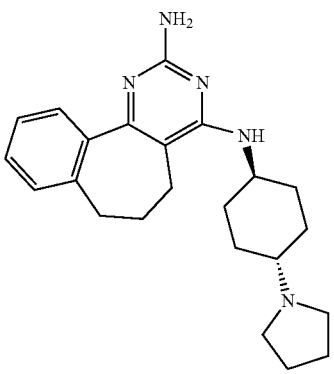<br>$N^4$-(4-pyrrolidin-1-ylcyclohexyl)-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 1-Methyl-4-(1-pyrrolidinyl)-cylcohexanamine, dihydrochloride | 412356-30-0 | WO2002030890 A1 | 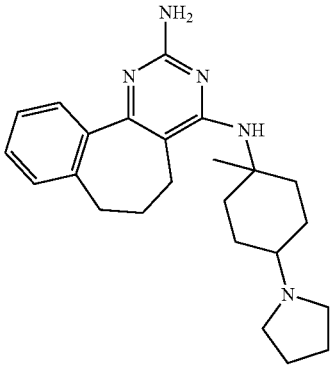 N4-(1-methyl-4-pyrrolidin-1-ylcyclohexyl)-6,7-dihydro-5H-benzo[6,7]cyclohepta[1,2-d]pyrimidine-2,4-diamine |
| 4-amino-quinuclidine | 22766-61-6 | Prepared from 4-cyano-quinuclidine (CAS # 26458-78-6), Fluorochem, catalog # 017382. EP0202062A2 | 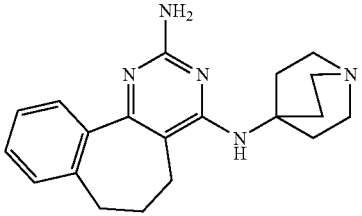 N4-(quinuclidin-4-yl)-6,7-dihydro-5H-benzo[6,7]cyclohepta[1,2-d]pyrimidine-2,4-diamine |
| 4-(aminomethyl)-quinuclidine | 67496-78-0 | Prepared from 4-cyano-quinuclidine (CAS # 26458-78-6), Fluorochem, catalog # 017382. WO99/21855 | 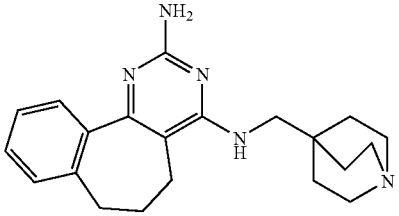 N4-(1-azabicyclo[2.2.2]oct-4-ylmethyl)-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| (S)-(−)-3-amino-quinuclidine dihydrochloride | 119904-90-4 | Aldrich catalog # 415,723 | 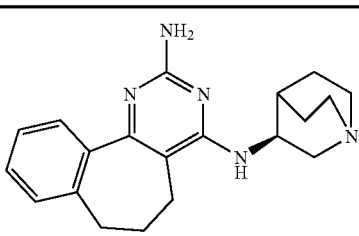<br>N4-(quinuclidin-3-(S)-yl)-6,7-dihydro-5H-benzo[6,7]cyclohepta[1,2-d]pyrimidin-2,4-diamine |
| (R)-(+)-3-amino-quinuclidine dihydrochloride | 123536-14-1 | Aldrich catalog # 415,715 | 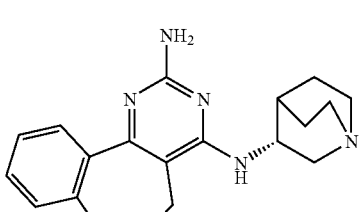<br>N4-(quinuclidin-3-(R)-yl)-6,7-dihydro-5H-benzo[6,7]cyclohepta[1,2-d]pyrimidine-2,4-diamine |
| 1-azatricyclo[3.3.1.1$^{3,7}$]decan-4r-amine | | Prepared from 1,4-cyclohexanedione monoethylene acetal (CAS # 4746-97-8), Aldrich catalog # 274879. Becker, D. P. and Flynn, D. L. Synthesis 1992, 1080-82 | 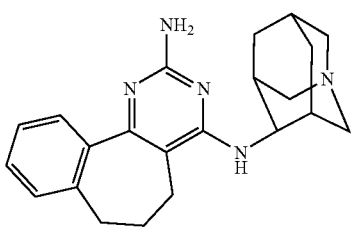<br>N4-(1-azatricyclo[3.3.1.13,7]decan-4r-yl)-6,7-dihydro-5H-benzo[6,7]cyclohepta[1,2-d]pyrimidine-2,4-diamine |
| 1-(2-hydroxyethyl)pyrrolidine | 2955-88-6 | ALDRICH catalog # H29404 | 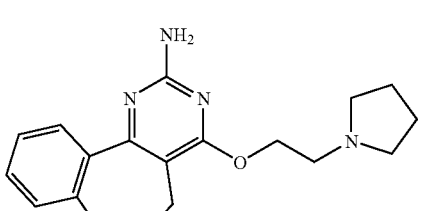<br>4-(2-pyrrolidin-1-ylethoxy)-6,7-dihydro-5H-benzo[6,7]cylcohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| N-BOC-D-prolinol | 83435-58-9 | ALDRICH catalog # 469440 | 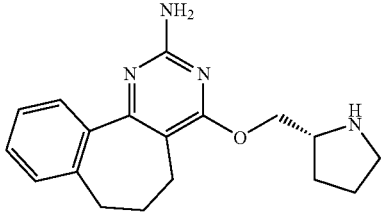 4-[(2R)-pyrrolidin-2-ylmethoxy]-6,7-dihydro-5H-benzo[6,7]cyclohepta[1,2-d]pyrimidin-2-amine |
| BOC-L-prolinol | 69610-40-8 | ALDRICH catalog # 446327 | 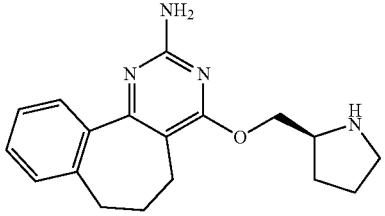 4-[(2S)-pyrrolidin-2-ylmethoxy]-6,7-dihydro-5H-benzo[6,7]cyclohepta[1,2-d]pyrimidin-2-amine |
| (R)-2-hydroxymethyl-piperidine-1-carboxylic acid tert-butyl ester | | CHEM-IMPEX catalog # 16141 | 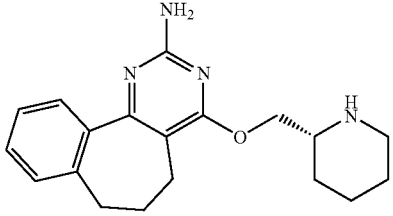 4-[(2R)-piperidin-2-ylmethoxy]-6,7-dihydro-5H-benzo[6,7]cyclohepta[1,2-d]pyrimidin-2-amine |
| BOC-S-PIP-2MEOH | | CHEM-IMPEX catalog # 16146 | 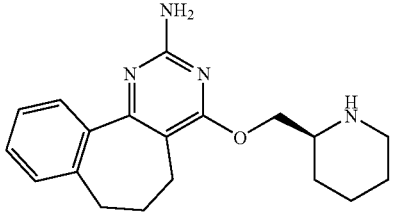 4-[(2S)-piperidin-2-ylmethoxy]-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 3-amino-cyclohexanol | 6850-39-1 | TYGER catalog # A58076 | 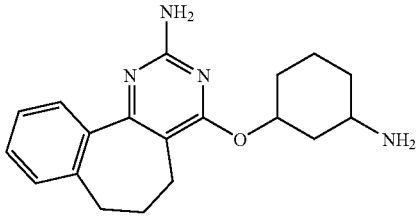<br>4-[(3-aminocyclohexyl)oxy]-6,7-dihydro-5H-benzo[6,7]cyclohepta[1,2-d]pyrimidin-2-amine |
| trans-4-aminocyclohex-anol | 27489-62-9 | ALFA catalog # B22365 | 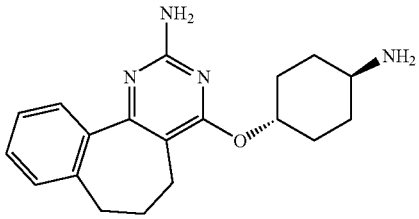<br>4-[(4-trans-aminocyclohexyl)oxy]-6,7-dihydro-5H-benzo[6,7]cyclohepta[1,2-d]pyrimidin-2-amine |
| tert-butyl cis-4-hydroxycyclohexyl-carbamate | 167081-25-6 | AMRI catalog # A00071 | 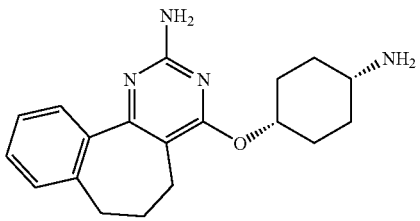<br>4-[(4-cis-aminocyclohexyl)oxy]-6,7-dihydro-5H-benzo[6,7]cyclohepta[1,2-d]pyrimidin-2-amine |
| (cis)-3-aminocyclo-butanol | | ALLWEYS catalog # 11331 | 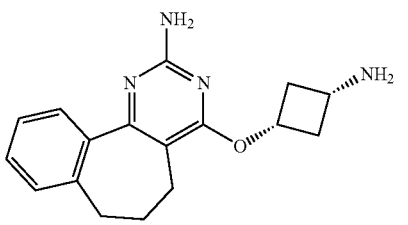<br>4-[(3-cis-aminocyclobutyl)oxy]-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| (trans)-3-aminocyclobutanol | 389890-42-0 | ALLWEYS catalog # 11361 | 4-[(3-trans-aminocyclobutyl)oxy]-6,7-dihydro-5H-benzo[6,7]cyclohepta[1,2-d]pyrimidin-2-amine |
| N-((3R,4S)-4-methylpyrrolidin-3-yl)acetamide | | | 4-((3R,4S)-3-amino-4-methylpyrrolidin-1-yl)-6,7-dihydro-5H-benzo[6,7]cyclohepta[1,2-d]pyrimidin-2-amine |
| (3S,4R)-1-benzyl-4-methylpyrrolidin-3-amine | | | 4-((3S,4R)-3-amino-4-methylpyrrolidin-1-yl)-6,7-dihydro-5H-benzo[6,7]cyclohepta[1,2-d]pyrimidin-2-amine |
| (3S,4R)-1-benzyl-4-methylpyrrolidin-3-amine | | | N4-[((3S,4R)-4-methylpyrrolidin-3-yl)]-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| tert-butyl (3S,4R)-4-(trifluoromethyl)pyrrolidin-3-ylcarbamate | 168544-95-4 | Qun Li, et al., Bioorganic & Medicinal Chemistry Letters (1998), 8(15), 1953-1958. | 4-((3S,4R)-3-amino-4-(trifluoromethyl)pyrrolidin-1-yl)-6,7-dihydro-5H-benzo[6,7]cyclohepta[1,2-d]pyrimidin-2-amine |
| tert-butyl (3S,4R)-4-(trifluoromethyl)pyrrolidin-3-ylcarbamate | | | N4-[(3S,4R)-4-(trifluoromethyl)pyrrolidin-3-yl]-6,7-dihydro-5H-benzo[6,7]cyclohepta[1,2-d]pyrimidine-2,4-diamine |
| tert-butyl ((3S,4S)-4-(trifluoromethyl)pyrrolidin-3-yl)methylcarbamate | 168544-90-9 | Qun Li, et al, Bioorganic & Medicinal Chemistry Letters (1998), 8(15), 1953-1958. | 4-((3R,4S)-3-aminomethyl-4-(trifluoromethyl)pyrrolidin-1-yl)-6,7-dihydro-5H-benzo[6,7]cyclohepta[1,2-d]pyrimidin-2-amine |
| tert-butyl ((3S,4S)-4-(trifluoromethyl)pyrrolidin-3-yl)methylcarbamate | | | N4-[((3S,4S)-4-(trifluoromethyl)pyrrolidin-3-yl)methyl]-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| tert-butyl (3S,5S)-5-methylpyrrolidin-3-ylcarbamate | 139161-75-4 | Qun Li, et al, Tetrahedron Letters (1995), 36(46), 8391-4 | 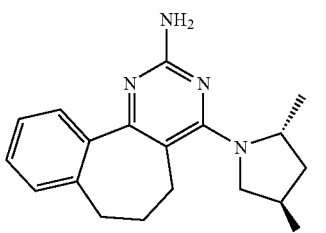<br>4-((3S,5S)-3-amino-5-methylpyrrolidin-1-yl)-6,7-dihydro-5H-benzo[6,7]cyclohepta[1,2-d]pyrimidin-2-amine |
| tert-butyl (3S,5S)-5-methylpyrrolidin-3-ylcarbamate | | | 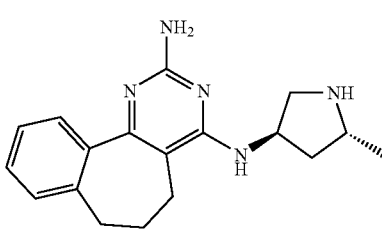<br>N4-[(3S,5S)-5-methylpyrrolidin-3-yl]-6,7-dihydro-5H-benzo[6,7]cyclohepta[1,2-d]pyrimidine-2,4-diamine |
| tert-butyl (3R,5S)-5-methylpyrrolidin-3-ylcarbamate | | | 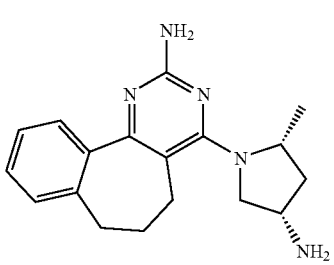<br>4-((3R,5S)-3-amino-5-methylpyrrolidin-1-yl)-6,7-dihydro-5H-benzo[6,7]cyclohepta[1,2-d]pyrimidin-2-amine |
| tert-butyl (3R,5S)-5-methylpyrrolidin-3-ylcarbamate | | | 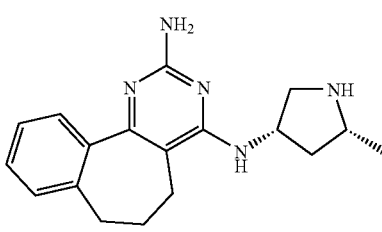<br>N4-[(3R,5S)-5-methylpyrrolidin-3-yl]-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| tert-butyl 1-benzyl-3-methylpyrrolidin-3-ylcarbamate | 181417-39-0 | T. Yoshida, et al, Chemical & Pharmaceutical Bulletin (1996), 44(7), 1376-1386. | 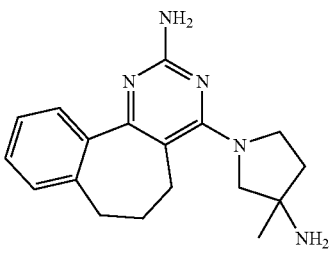 4-(3-amino-3-methylpyrrolidin-1-yl)-6,7-dihydro-5H-benzo[6,7]cyclohepta[1,2-d]pyrimidin-2-amine |
| tert-butyl 1-benzyl-3-methylpyrrolidin-3-ylcarbamate | | | 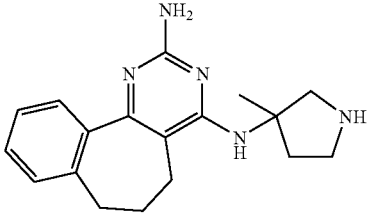 N4-[3-methylpyrrolidin-3-yl]-6,7-dihydro-5H-benzo[6,7]cyclohepta[1,2-d]pyrimidine-2,4-diamine |
| (R)-benzyl 2-((tert-butoxycarbonyl-amino)methyl)pyrrolidine-1-carboxylate | 141774-69-8 | R. M. Burch, WO 9203415 A1 (1992) | 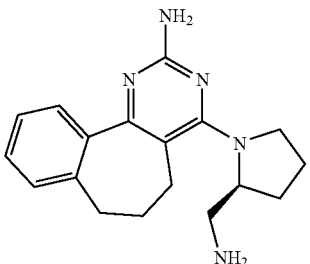 4-((R)-2-aminomethylpyrrolidin-1-yl)-6,7-dihydro-5H-benzo[6,7]cyclohepta[1,2-d]pyrimidin-2-amine |
| (R)-benzyl 2-((tert-butoxycarbonyl-amino)methyl)pyrrolidine-1-carboxylate | | | 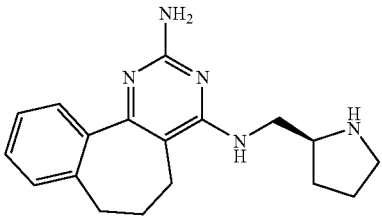 N4-[((R)-pyrrolidin-2-yl)methyl]-6,7-dihydro-5H-benzo[6,7]cyclohepta[1,2-d]pyrimidine-2,4-diamine |

149 150

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| tert-butyl (1-benzylpyrrolidin-3-yl)methylcarbamate | 155497-10-2 | Matrix 018167 | 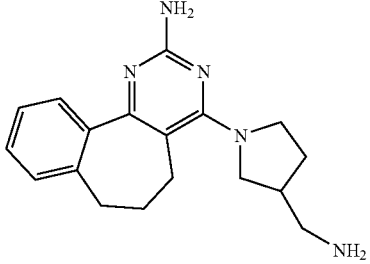<br>4-(3-aminomethylpyrrolidin-1-yl)-6,7-dihydro-5H-benzo[6,7]cyclohepta[1,2-d]pyrimidin-2-amine |
| tert-butyl (1-benzylpyrrolidin-3-yl)methylcarbamate | | | 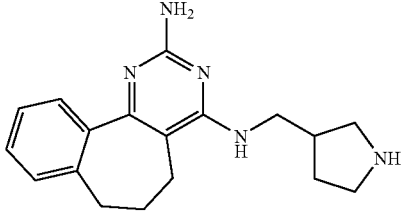<br>N4-[(pyrrolidin-3-yl)methyl]-6,7-dihydro-5H-benzo[6,7]cyclohepta[1,2-d]pyrimidine-2,4-diamine |
| N-((1-benzylpyrrolidin-3-yl)methyl)ethanamine | 91189-07-0 | Fulcrum B64503 | 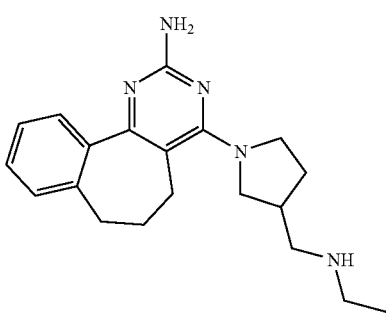<br>4-(3-(ethylamino)methylpyrrolidin-1-yl)-6,7-dihydro-5H-benzo[6,7]cyclohepta[1,2-d]pyrimidin-2-amine |
| N-((1-benzylpyrrolidin-3-yl)methyl)ethanamine | | | 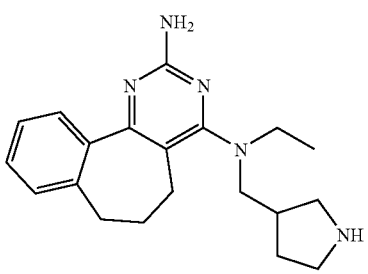<br>N4-ethyl-N4-[(pyrrolidin-3-yl)methyl]-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| tert-butyl ethyl(((5S)-5-methylpyrrolidin-3-yl)methyl)carbamate | | | 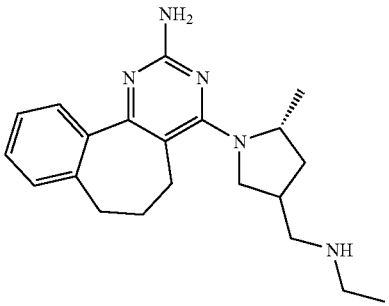<br>4-((5S)-3-ethylaminomethyl5-methylpyrrolidin-1-yl)-6,7-dihydro-5H-benzo[6,7]cyclohepta[1,2-d]pyrimidin-2-amine |
| tert-butyl ethyl(((5S)-5-methylpyrrolidin-3-yl)methyl)carbamate | | | 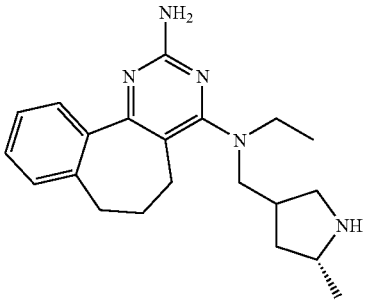<br>N4-ethyl-N4-[((5S)-5-methylpyrrolidin-3-yl)methyl]-6,7-dihydro-5H-benzo[6,7]cyclohepta[1,2-d]pyrimidine-2,4-diamine |
| (4S)-1-tert-butyl 3-methyl 4-aminopyrrolidine-1,3-dicarboxylate | 362491-96-1 | J. Duan, WO 2001070673 A2 (2001) | 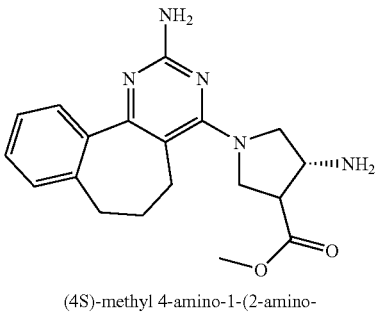<br>(4S)-methyl 4-amino-1-(2-amino-6,7-dihydro-5H-benzo[6,7]cyclohepta[1,2-d]pyrimidin-4-yl)pyrrolidine-3-carboxylate |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| (4S)-1-tert-butyl 3-methyl 4-aminopyrrolidine-1,3-dicarboxylate | | | 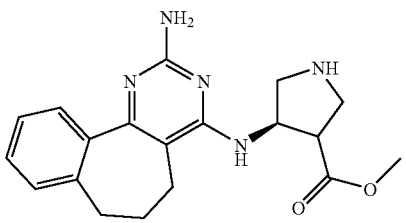<br>(4S)-methyl 4-(2-amino-6,7-dihydro-5H-benzo[6,7]cyclohepta[1,2-d]pyrimidine-4-ylamino)pyrrolidine-3-carboxylate |
| 1-cyclopropylpiperazine | 139256-79-4 | Fulcrunm C-1450 | 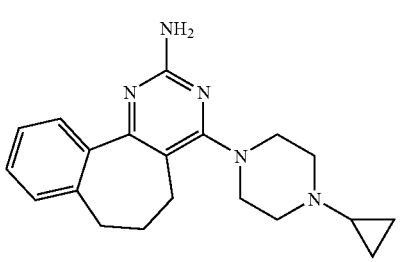<br>4-(4-Cyclopropyl-piperazin-1-yl)-6,7-dihydro-5H-benzo[6,7]cyclohepta[1,2-d]pyrimidin-2-ylamine |
| 1,3-dimethylpiperazine | 22317-01-7 | G. Steiner, et al, Journal of Medicinal Chemistry (1986), 29(10), 1877-88. | 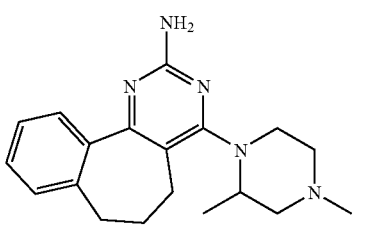<br>4-(2,4-Di-methyl-piperazin-1-yl)-6,7-dihydro-5H-benzo[6,7]cyclohepta[1,2-d]pyrimidin-2-ylamine |
| 2-(azetidin-2-yl)ethanamine | 90324-66-6 | H. Taniyama, et al, Yakugaku Zasshi (1961), 81 1497-500 | 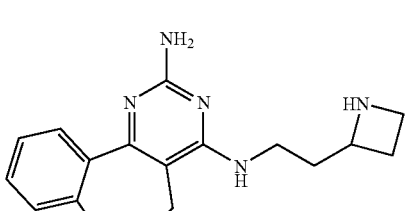<br>N4-[(azetidin-2-yl)ethyl]-6,7-dihydro-5H-benzo[6,7]cyclohepta[1,2-d]pyrimidine-2,4-diamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| 2-(azetidin-2-yl)ethanamine | | | 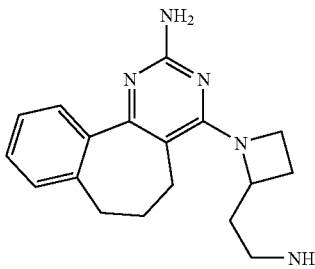<br>4-(2-aminoethylazetidin-1-yl)-6,7-dihydro-5H-benzo[6,7]cyclohepta[1,2-d]pyrimidin-2-amine |
| azetidin-2-ylmethanamine | 103550-76-1 | ABCHEM-INC AB1135 | 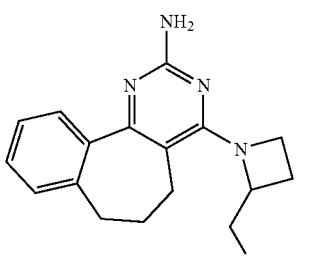<br>4-(2-aminomethylazetidin-1-yl)-6,7-dihydro-5H-benzo[6,7]cyclohepta[1,2-d]pyrimidin-2-amine |
| azetidin-2-ylmethanamine | | | 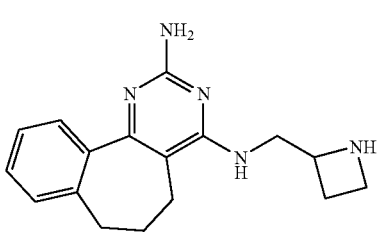<br>N4-[(azetidin-2-yl)methyl]-6,7-dihydro-5H-benzo[6,7]cyclohepta[1,2-d]pyrimidine-2,4-diamine |
| tert-butyl octahydro-1H-pyrrolo[3,4-b]pyridine-1-carboxylate | 159877-36-8 | Fulcrum B64519 | 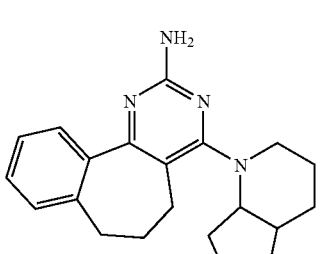<br>4-octahydro-6H-pyrrolo[3,4-b]pyridin-1-yl-6,7-dihydro-5H-benzo[6,7]cyclohepta[1,2-d]pyrimidin-2-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| ter-butyl (3aR,4R,7aS)-octahydro-1H-isoindol-4-ylcarbamate | 181141-44-6 | Qun Li, et al, Journal of Medicinal Chemistry (1996), 39(16), 3070-3088. | (3aR,4R,7aS)-2-(2-amino-6,7-dihydro-5H-benzo[6,7]cyclohepta[1,2-d]pyrimidin-4-yl)octahydro-1H-isoindol-4-amine |
| tert-butyl (3aR,4R,7aS)-octahydro-1H-isoindol-4-ylcarbamate | | | N4-((3aR,4R,7aS)-octahydro-1H-isoindol-4-yl)-6,7-dihydro-5H-benzo[6,7]cyclohepta[1,2-d]pyrimidin-2,4-diamine |
| tert-butyl (1R,5S)-3-azabicyclo[3.1.0]hexan-6-ylcarbamate | 134575-17-0 | G. Anquetin, et al, European Journal of Medicinal Chemistry (2006), 41(12), 1478-1493. | (1R,5S)-3-(2-amino-6,7-dihydro-5H-benzo[6,7]cyclohepta[1,2-d]pyrimidin-4-yl)-3-azabicyclo[3.1.0]hexan-6-amine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| tert-butyl (1R,5S)-3-azabicyclo[3.1.0]hexan-6-ylcarbamate | 134575-17-0 | G. Anquetin, et al, European Journal of Medicinal Chemistry (2006), 41(12), 1478-1493. | N4-((1R,5S)-3-azabicyclo[3.1.0]hexan-6-yl)-6,7-dihydro-5H-benzo[6,7]cyclohepta[1,2-d]pyrimidin-2,4-diamine |
| tert-butyl (1R)-3-(1-phenylethyl)-3-azabicyclo[3.1.0]hexan-1-ylcarbamate | 182075-89-4 | M. Takemura, WO 9623782 A1 (1996) | (1R)-3-(2-amino-6,7-dihydro-5H-benzo[6,7]cyclohepta[1,2-d]pyrimidin-4-yl)-3-azabicyclo[3.1.0]hexan-1-amine |
| tert-butyl (1R)-3-(1-phenylethyl)-3-azabicyclo[3.1.0]hexan-1-ylcarbamate | 182075-89-4 | M. Takemura, WO 9623782 A1 (1996) | N4-((1R)-3-azabicyclo[3.1.0]hexan-1-yl)-6,7-dihydro-5H-benzo[6,7]cyclohepta[1,2-d]pyrimidin-2,4-diamine |
| tert-butyl (1R)-3-(1-phenylethyl)-3-azabicyclo[3.1.0]hexan-1-ylcarbamate | 181941-43-5 | M. Takemura, WO 9623782 A1 (1996) | (1S)-3-(2-amino-6,7-dihydro-5H-benzo[6,7]cyclohepta[1,2-d]pyrimidin-4-yl)-3-azabicyclo[3.1.0]hexan-1-amine |

TABLE 1-continued

Prospective Examples of synthetic intermediate groups, and Product Compounds
that may be prepared by the methods described in Schemes 1-18.

| Group | CAS # | Commercial Source or Literature, or Patent Reference | Product from group |
|---|---|---|---|
| tert-butyl (1R)-3-(1-phenylethyl)-3-azabicyclo[3.1.0]hexan-1-ylcarbamate | 181941-43-5 | M. Takemura, WO 9623782 A1 (1996) | N4-((1S)-3-azabicyclo[3.1.0]hexan-1-yl)-6,7-dihydro-5H-benzo[6,7]cyclohepta[1,2-d]pyrimidin-2,4-diamine |
| tert-butyl 3-hydroxypyrrolidine-1-carboxylate | 40499-83-0 | Aldrich P74354 | 4-(Pyrrolidin-3-yloxy)-6,7-dihydro-5H-benzo[6,7]cyclohepta[1,2-d]pyrimidin-2-ylamine |
| (2S,4R)-tert-butyl 4-hydroxy-2-methylpyrrolidine-1-carboxylate | 114676-61-8 | Chu, Daniel T.; Li, Qun. US 5252747 A (1993) | 4-((3R,5S)-5-Methylpyrrolidin-3-yloxy)-6,7-dihydro-5H-benzo[6,7]cyclohepta[1,2-d]pyrimidin-2-ylamine |
| (3S,5S)-1-benzyl-5-methylpyrrolidin-3-ol | 152673-21-7 | Qun Li, et al, Tetrahedron Letters (1995), 36(46), 8391-4. | 4-((3S,5S)-5-Methylpyrrolidin-3-yloxy)-6,7-dihydro-5H-benzo[6,7]cyclohepta[1,2-d]pyrimidin-2-ylamine |

TABLE 1-continued

Prospective Examples of synthetic intermediate groups, and Product Compounds that may be prepared by the methods described in Schemes 1-18.

| Group | CAS # | Commercial Source or Literature, or Patent Reference | Product from group |
|---|---|---|---|
| (R)-tert-butyl 2-(hydroxymethyl) azetidine-1-carboxylate | 161511-90-6 | TCI-US B2174 | 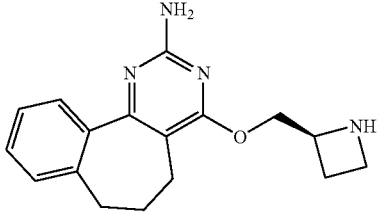<br>4-(((R)-azetidin-2-yl)methoxy)-6,7-dihydro-5H-benzo[6,7]cyclohepta[1,2-d]pyrimidin-2-amine |

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral, intravenous, subcutaneous, intramuscular, intraperitoneal, intra-arterial, or intradermal injection, for or for vaginal, nasal, topical, or rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals oral administration, by injection, including by intravenous, subcutaneous, intramuscular, intraperitoneal, intra-arterial, and intradermal injection. The pharmaceutical compositions of this invention can be administered to humans and other mammals topically (as by powders, lotions, ointments or drops applied to the skin), bucally, or inhaled, as an oral or nasal spray. The pharmaceutical compositions of this invention can be administered to humans and other mammals intrarectally, intravaginally. The term "parenterally," as used herein, refers to modes of administration which include intravenous, intramuscular, intraperitoneal, intrasternal, subcutaneous and intraarticular.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Ophthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts, esters, or amides derived from inorganic or organic acids. The term "pharmaceutically acceptable salts, esters and amides", as used herein, refer to carboxylate salts, amino acid addition salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acids suitable for formation of addition salts by combination with the compounds of the invention include, but are not limited to, ascorbic acid, (D)-tartaric acid, (L)-tartaric acid, maleic acid, phosphoric acid, citric acid, hydrochloric acid, sulfuric acid and trifluoroacetic acid. Other acids include acetic, adipic, aspartic, glutamic, benzoic, benzenesulfonic, 4-methylbenzenesulfonic, camphorsulfonic, propionic, hydrobromic, glucuronic, methanesulfonic, ethanesulfonic, naphthalene sulfonic, lactic, fumaric, oxalic, and succinic acid.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also may be prepared by reaction of the compound with an acid such as hydrochloric acid and an alkylcarboxylic acid such as acetic acid, or with acid and an arylcarboxylic acid such as benzoic acid.

The term "pharmaceutically acceptable amide", as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl acid chloride. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug", as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to compounds of formula (I).

The compounds and processes of the invention will be better understood by reference to the following examples, which are intended as an illustration of and not a limitation upon the scope of the invention.

Unless otherwise described, reactions were carried out under ambient conditions (ranging 17-27° C.), under nitrogen. Unless otherwise described, column chromatography means flash chromatography carried out using silica gel, a technique well known to those of ordinary skill in the art of organic synthesis.

EXAMPLES

Example 1

6-Methyl-4-[(3R)-3-methylamino-pyrrolidin-1-yl]-5,6-dihydro-benzo[h]quinazolin-2-ylamine

Example 1A 2-(Bis-methylsulfanyl-methylene)-4-methyl-3,4-dihydro-2H-naphthalen-1-one To a solution of 4-methyl-3,4-dihydro-2H-naphthalen-1-one (0.9 mL, 6.1 mmol), carbon disulfide (0.47 mL, 7.8 mmol), and methyl iodide (0.9 mL, 14 mmol) in anhydrous THF (20 mL) cooled in ice bath, was added NaH (60% in oil, 625 mg, 16 mmol). The mixture was stirred at ambient temperature for 16 hours, cooled to 0° C., treated slowly with 1 M HCl (20 mL) and extracted with EtOAc (100 mL). The layers were separated and the aqueous layer was extracted with EtOAc (100 mL). The combined organic layers were dried with $MgSO_4$, concentrated under reduced pressure and chromatographed on silica gel eluting with EtOAc:hexanes (10:90) to provide the title compound. $^1$H NMR ($CDCl_3$): δ 1.54 (s, 3H), 2.41 (s, 3H), 2.48 (s, 3H), 3.16 (m, 1H), 3.24 (m, 2H), 7.29 (d, J=9 Hz, 1H), 7.34 (d, J=9 Hz, 1H), 7.47 (t, J=9 Hz, 1H), 8.11 (d, J=9 Hz, 1H). MS (DCI-$NH_3$) m/z 265 (M+H)$^+$.

Example 1B

6-Methyl-4-methylsulfanyl-5,6-dihydro-benzo[h]quinazolin-2-ylamine

A solution consisting of Example 1A (1.12 g, 4.2 mmol), guanidine hydrochloride (520 mg, 5.5 mmol) and potassium t-butoxide (710 mg, 6.3 mmol) in anhydrous acetonitrile (30 mL) was heated at reflux for 3 hours. The mixture was cooled to room temperature and diluted with $H_2O$ (50 mL) and EtOAc (150 mL). The organic layer was separated and the aqueous layer was extracted with additional EtOAc. The combined organic layers were dried with $MgSO_4$, filtered, concentrated under reduced pressure and chromatographed on silica gel eluting with EtOAc:hexanes (15:85) to provide the title compound. $^1$H NMR ($CDCl_3$): δ 1.25 (d, J=6 Hz, 3H), 2.54 (s, 3H), 2.59 (dd, J=15 Hz, J=6 Hz, 1H), 2.84 (dd, J=15 Hz, J=6 Hz, 1H), 3.09 (q, J=9 Hz, 1H), 4.85 (s, 2H), 7.25 (d, J=9 Hz, 1H), 7.36 (m, 2H), 8.23 (d, J=9 Hz, 1H). MS (DCI-$NH_3$) m/z 258 (M+H)$^+$.

Example 1C

4-Methanesulfonyl-6-methyl-5,6-dihydrobenzo[h]quinazolin-2-ylamine

A solution of Example 1B (370 mg, 1.44 mmol) in dichloromethane (30 mL) and meta-chloroperoxybenzoic acid (77%, 810 mg, 3.6 mmol) were stirred for 3 hours at ambient temperature. The mixture was diluted with $CH_2Cl_2$ (50 mL) and extracted with a saturated aqueous solution of $Na_2S_2O_3$ (10 mL) and an aqueous solution of $Na_2CO_3$ (20 mL) sequentially. The aqueous layers were extracted with $CH_2Cl_2$ and EtOAc sequentially. The combined organic layers were dried with $MgSO_4$, filtered, concentrated under reduced pressure and chromatographed on silica gel eluting with EtOAc:hexanes (35:65) to provide the title compound. $^1$H NMR ($CDCl_3$): δ 1.28 (d, J=6 Hz, 3H), 3.12 (q, J=6 Hz, 1H), 3.26 (dd, J=6 Hz, J=3 Hz, 2H), 3.31 (s, 3H), 5.11 (s, 2H), 7.30 (d, J=9 z, 1H), 7.36 (t, J=9 Hz, 1H), 7.47 (t, J=9 Hz, 1H), 8.24 (d, J=9 Hz, 1H). MS (DCI-$NH_3$) m/z 290 (M+H)$^+$.

Example 1D (1-Benzyl-(3R)-pyrrolidin-3-yl)-methyl-carbamic acid tert-butyl ester To a solution of (3R)-(−)-1-benzyl-3-(methylamino)pyrrolidine (200 mg, 1.05 mmol) and di-tert-butyl-dicarbonate (230 mg, 1.06 mmol) in MeOH (10 mL) was added NaOH (10%, 4 mL) and the mixture stirred at ambient temperature for 1 hour. The mixture was diluted with $H_2O$ (20 mL) and EtOAc (100 mL). The organic layer was separated and the aqueous was extracted with additional EtOAc. The combined organic layers were dried with $MgSO_4$, filtered, concentrated under reduced pressure to provide the title compound. $^1$H NMR ($CD_3OD$): δ 1.43 (s, 9H), 1.8 (m, 1H), 2.07 (m, 1H), 2.53 (m, 2H), 2.73 (m, 1H), 2.81 (s, 3H), 2.60 (dd, J=27 Hz, J=15 Hz, 2H), 4.71 (m, 1H), 7.32 (m, 5H). MS (DCI-$NH_3$) m/z 291 (M+H)$^+$.

Example 1E (R)-Methyl-pyrrolidin-3-yl-carbamic acid tert-butyl ester

To a solution of Example 1D (285 mg, 0.98 mmol) in 4.4% $HCO_2H$/MeOH (20 mL) under a nitrogen atmosphere was added Pd(OH)$_2$ on carbon (20%, 40 mg) and the resulting mixture was heated at 60° C. for 16 hours. The mixture was cooled to room temperature, filtered through a layer of diatomaceous earth, washed with extra MeOH (30 mL) and concentrated under reduced pressure. The residue was diluted with $CH_2Cl_2$ (30 mL), washed with 1 M NaOH, dried ($MgSO_4$), filtered and concentrated under reduced pressure to provide the title compound. $^1$H NMR ($CD_3OD$): δ 1.46 (s, 9H), 1.79 (m, 1H), 1.99 (m, 1H), 2.76 (m, 1H), 2.79 (s, 3H), 2.87 (m, 1H), 3.03 (m, 2H), 4.57 (p, J=6 Hz, 1H). MS (DCI-$NH_3$) m/z 201 (M+H)$^+$.

Example 1F

[1-(2-Amino-6-methyl-5,6-dihydro-benzo[h]quinazolin-4-yl)-pyrrolidin-3-yl]-methyl-carbamic acid tert-butyl ester A solution consisting of Example 1C (80 mg, 0.28 mmol), Example 1E (89 mg, 0.45 mmol) and triethylamine (0.2 mL) in anhydrous acetonitrile (3 mL) was placed in a screw capped vial, and heated at 110° C. for 16 hours. The mixture was cooled, concentrated under reduced pressure, and the resulting residue chromatographed on silica gel eluting with EtOAc to provide the title compound. $^1$H NMR ($CD_3OD$) δ 1.24 (d, J=6 Hz, 3H), 1.45 (s, 9H), 1.83 (m, 1H), 2.07 (m, 1H), 2.47 (s, 3H), 2.66 (m, 1H), 2.95 (m, 1H), 3.28 (m, 1H), 3.44 (m, 1H), 3.65 (m, 1H), 3.77 (m, 2H), 4.65 (m, 1H), 4.73 (s, 2H), 7.22 (m, 1H), 7.33 (m, 2H), 8.13 (m, 1H). MS (M+H)$^+$ m/z 410.

Example 1G

6-Methyl-4-[(3R)-3-methylamino-pyrrolidin-1-yl]-5,6-dihydro-benzo[h]quinazolin-2-ylamine Example 1F (45 mg) was dissolved in $CH_2Cl_2$ (3 mL), treated with TFA (0.3 mL) and stirred at room temperature for 16 hours then partitioned between 1M NaOH and CH₂Cl₂. The organic layer was isolated, dried (MgSO₄), filtered, concentrated under reduced pressure, and chromatographed on silica gel eluting with 3% (9:1 MeOH: NH₄OH) in dichloromethane to provide the title compound. $^1$H NMR (CDCl₃) δ 1.25 (d, J=6 Hz, 3H), 1.78 (m, 1H), 2.07 (m, 1H), 2.48 (s, 3H), 2.68 (m, 1H), 2.96 (m, 1H), 3.28 (m, 1H), 3.44 (m, 1H), 3.64 (m, 1H), 3.76 (m, 2H), 4.65 (m, 1H), 4.73 (s, 2H), 7.22 (m, 1H), 7.33 (m, 2H), 8.13 (m, 1H). MS (M+H)⁺ m/z 310.

Example 2

6-Methyl-4-(3-methylamino-azetidin-1-yl)-5,6-dihydro-benzo[h]quinazolin-2-ylamine Example 2A 1-Benzhydryl-N-methylazetidin-3-amine A solution of 1-benzhydryl-azetidin-3-ol (15 g, 62.7 mmol) in pyridine (60 mL) was cooled to 0° C., treated with mesyl chloride (6.3 mL, 81 mmol) and stirred at room temperature for 3 hours. The mixture was partitioned between ether (300 mL) and H₂O (150 mL). The ether layer was washed with H₂O, washed with brine, dried (MgSO₄), filtered and concentrated to provide a greenish solid. The solid (23.3 g) was mixed with methyl amine (40% in H₂O, 90 mL) in DMF (60 mL), heated at 85° C. for 48 hours, cooled to room temperature, and partitioned between H₂O (200 mL) and EtOAc (400 mL). The aqueous was extracted with additional EtOAc. The combined organics were extracted twice with 2 N HCl (200 mL). The combined 2M HCl layers were basified with NaOH (50%) and extracted with diethyl ether. The ether layer was washed with brine, dried (MgSO₄), filtered, concentrated under reduced pressure and purified on a silica gel column eluting with NH₄OH/MeOH/CH₂Cl₂ (0.4/4/96) to provide the title compound. NMR (CDCl₃): δ 2.26 (s, 3H), 2.83 (t, J=6 Hz, 2H), 3.33 (m, 1H), 3.46 (t, J=6 Hz, 2H), 7.15-7.20 (m, 2H), 7.24-7.29 (m, 4H), 7.36-7.4 (m, 4H). MS (DCI-NH₃) m/z 254 (M+H)⁺.

Example 2B tert-Butyl azetidin-3-yl(methyl)carbamate

The title compound was prepared using the procedure outlined in Example 1D substituting Example 2A for the (3R)-(−)-1-benzyl-3-(methylamino)pyrrolidine followed by the procedure outlined in Example 1E. $^1$NMR (CDCl₃): δ 1.45 (s, 9H), 2.87 (s, 3H), 3.62 (t, J=6 Hz, 2H), 3.55 (m, 1H), 3.77 (t, J=6 Hz, 2H). MS (DCI-NH₃) m/z 187 (M+H)⁺.

Example 2C

6-Methyl-4-(3-methylamino-azetidin-1-yl)-5,6-dihydro-benzo[h]quinazolin-2-ylamine The title compound was prepared using the procedure outlined in Examples 1F substituting Example 2B for Example 1E followed by the procedure outlined in Example 1G. $^1$H NMR (CDCl₃) δ 1.24 (d, J=6.78 Hz, 3H), 2.44 (s, 3H), 2.48-2.58 (m, 1H), 2.79-2.88 (m, 1H), 2.93-3.04 (m, 1H), 3.62 (m, 1H), 3.89-3.89 (m, 2H), 4.37 (m, 2H), 4.67 (s, 2H), 7.21 (m, 1H), 7.27-7.38 (m, 2H), 8.15 (m, 1H). MS (M+H)⁺ m/z 296.

Example 3

4-(3-Methylamino-azetidin-1-yl)-6,7-dihydro-5H-benzo[6,7]cyclohepta[1,2-d]pyrimidin-2-ylamine Example 3A 4-Methanesulfonyl-6,7-dihydro-5H-benzo[6,7]cyclohepta[1,2-d]pyrimidin-2-ylamine The title compound was prepared using the procedures outlined in Example 1A through Example 1C substituting 6,7,8,9-tetrahydro-benzocyclohepten-5-one for 4-methyl-3,4-dihydro-2H-naphthalen-1-one in Example 1A. $^1$H NMR (CD₃OD) δ 2.21 (p, J=9 Hz, 2H), 2.57 (t, J=9 Hz, 2H), 2.73 (t, J=9 Hz, 2H), 3.35 (s, 3H), 7.28-7.31 (m, 1H), 7.36-7.47 (m, 2H), 7.65-7.68 (m, 1H). MS (M+H)⁺ m/z 290.

Example 3B 4-(3-Methylamino-azetidin-1-yl)-6,7-dihydro-5H-benzo[6,7]cyclohepta[1,2-d]pyrimidin-2-ylamine The title compound was prepared using the procedure outlined in Examples 1F followed by the procedure outlined in Example 1G, substituting Example 3A for 1C, and substituting Example 2B for Example 1E. $^1$H NMR (CD₃OD) δ 2.06-2.27 (m, 4H), 2.36 (s, 3H), 2.60 (t, J=6.78 Hz, 2H), 3.63 (m, 1H), 3.99 (dd, J=9.32, 4.92 Hz, 2H), 4.42 (dd, J=8.99, 7.63 Hz, 2H), 7.25 (m, 1H), 7.34 (m, 2H), 7.59 (m, 1H). MS (M+H)⁺ m/z 296.

Example 4

6-Methyl-4-piperazin-1-yl-5,6-dihydro-benzo[h]quinazolin-2-ylamine

A solution of Example 1C (50 mg, 0.17 mmol) and piperazine (38 mg, 0.44 mmol) in acetonitrile (2 mL) was heated at 110° C. for 16 hours. The mixture was cooled to room temperature and concentrated under reduced pressure. The residue was chromatographed on silica gel eluting with NH₄OH/MeOH/CH₂Cl₂ (0.8/8/92) to provide the title compound. $^1$H NMR (CDCl₃) δ 1.26 (d, J=7.12 Hz, 3H), 2.46 (dd, J=14.75, 7.97 Hz, 1H), 2.73-2.91 (m, 2H), 2.99 (m, 4H), 3.28 (m, 4H), 4.74 (s, 2H), 7.24 (m, 1H), 7.33 (m, 2H), 8.11 (m, 1H) MS (M+H)⁺ m/z 296.

Example 5

4-(4-Methyl-piperazin-1-yl)-6,7-dihydro-5H-benzo[6,7]cyclohepta[1,2-d]-pyrimidin-2-ylamine The title compound was prepared using the procedure outlined in Example 1F, substituting Example 3A for Example 1C, and substituting 1-methyl-piperazine for Example 1E. $^1$H NMR (CD₃OD) δ 2.18-2.33 (m, 4H), 2.35 (s, 3H), 2.59 (t, J=5.09 Hz, 4H), 2.65 (t, J=6.44 Hz, 2H), 3.46 (t, J=4.75 Hz, 4H), 7.26 (m, 1H), 7.36 (m, 2H), 7.62 (m, 1H). MS (M+H)⁺ m/z 310.

Example 6

4-(3-(R)-Methylamino-pyrrolidin-1-yl)-6,7-dihydro-5H-benzo[6,7]cyclohepta[1,2-d]pyrimidin-2-ylamine The title compound was prepared using the procedure outlined in Examples 1F substituting Example 3A for Example 1C followed by the procedure outlined in Example 1G. $^1$H NMR (CD$_3$OD) δ 1.84 (m, 1H), 2.13-2.24 (m, 3H), 2.33 (m, 2H), 2.43 (s, 3H), 2.65 (t, J=6.78 Hz, 2H), 3.50 (dd, J=10.85, 5.76 Hz, 1H), 3.64-3.88 (m, 3H), 7.25 (m, 1H), 7.33 (m, 2H), 7.62 (m, 1H). MS (M+H)$^+$ m/z 310.

Example 7

4-Piperazin-1-yl-6,7-dihydro-5H-benzo[6,7]cyclohepta[1,2-d]pyrimidin-2-ylamine The title compound was prepared using the procedure outlined in Example 1F, substituting Example 3A for Example 1C, and substituting piperazine for Example 1E. $^1$H NMR (CD$_3$OD) δ 2.17-2.35 (m, 4H), 2.65 (t, J=6.61 Hz, 2H), 2.94 (m, 4H), 3.39 (m, 4H), 7.26 (m, 1H), 7.35 (m, 2H), 7.62 (m, 1H) MS (M+H)$^+$ m/z 296.

Example 8

1-(3-Methylamino-azetidin-1-yl)-10H-9-oxa-2,4-diaza-phenanthren-3-ylamine

Example 8A

1-Methanesulfonyl-10H-9-oxa-2,4-diaza-phenanthren-3-ylamine

The title compound was prepared using the procedures outlined in Example 1A through 1C substituting chroman-4-one for 4-methyl-3,4-dihydro-2H-naphthalen-1-one in Example 1A. MS (M+H)$^+$ m/z 278.

Example 8B

1-(3-Methylamino-azetidin-1-yl)-10H-9-oxa-2,4-diaza-phenanthren-3-ylamine

The title compound was prepared using the procedure outlined in Example 1F substituting Example 8A for Example 1C, and substituting Example 2B for Example 1E followed by the procedure outlined in Example 1G. $^1$H NMR (CD$_3$OD) δ 2.35 (s, 3H), 3.62-3.63 (m, 1H), 3.93 (ddd, J=8.99, 4.92, 0.68 Hz, 2H), 4.36-4.37 (m, 2H), 5.13 (s, 2H), 6.89 (dd, J=8.31, 0.85 Hz, 1H), 7.02 (dd, J=7.46, 1.36 Hz, 1H), 7.31 (ddd, J=8.48, 6.78, 1.70 Hz, 1H), 7.92 (dd, J=7.80, 1.70 Hz, 1H). MS (M+H)$^+$ m/z 284.

Example 9

1-(3-(R)-Methylamino-pyrrolidin-1-yl)-10H-9-oxa-2,4-diaza-phenanthren-3-ylamine The title compound was prepared using the procedure outlined in Example 1F substituting Example 8A for Example 1C followed by the procedure outlined in Example 1G. $^1$H NMR (CD$_3$OD) δ 1.83 (m, 1H), 2.15 (m, 1H), 2.41 (s, 3H), 3.23-3.33 (m, 1H), 3.44 (dd, J=10.85, 5.09 Hz, 1H), 3.58-3.67 (m, 1H), 3.69-3.81 (m, 2H), 6.90 (dd, J=8.14, 1.02 Hz, 1H), 7.04 (td, J=7.54, 1.19 Hz, 1H), 7.31 (m, 1H), 7.91 (dd, J=8.14, 1.70 Hz, 1H). MS (M+H)$^+$ m/z 298.

Example 10

1-Piperazin-1-yl-10H-9-oxa-2,4-diaza-phenanthren-3-ylamine

The title compound was prepared using the procedure outlined in Example 1F, substituting Example 8A for Example 1C, and substituting piperazine for Example 1E. $^1$H NMR (CD$_3$OD) δ 2.93 (m, 4H), 3.24 (m, 4H), 5.00 (s, 2H), 6.92 (dd, J=8.14, 1.02 Hz, 1H), 7.06 (dt, J=7.54, 1.19 Hz, 1H), 7.33 (ddd, J=9.15, 7.46, 1.70 Hz, 1H), 7.92 (dd, J=7.80, 1.70 Hz, 1H). MS (M+H)$^+$ m/z 284.

Example 11

10-Fluoro-4-(3-(R)-methylamino-pyrrolidin-1-yl)-6,7-dihydro-5H-benzo[6,7]cyclohepta[1,2-d]pyrimidin-2-ylamine

Example 11A

10-Fluoro-4-methanesulfonyl-6,7-dihydro-5H-benzo[6,7]cyclohepta[1,2-d]pyrimidin-2-ylamine The title compound was prepared using the procedures outlined in Examples 1A through Example 1C, substituting 3-fluoro-6,7,8,9-tetrahydro-benzocyclohepten-5-one for 4-methyl-3,4-dihydro-2H-naphthalen-1-one in Example 1A.

Example 11B

10-Fluoro-4-(3-(R)-methylamino-pyrrolidin-1-yl)-6,7-dihydro-5H-benzo[6,7]cyclohepta[1,2-d]pyrimidin-2-ylamine The title compound was prepared using the procedure outlined in Example 1F substituting Example 11A for Example 1C followed by the procedure outlined in Example 1G. $^1$H NMR (CD$_3$OD) δ 1.85-1.86 (m, 1H), 2.18-2.18 (m, 3H), 2.34-2.34 (m, 2H), 2.43 (s, 3H), 2.63 (t, J=6.78 Hz, 2H), 3.51 (dd, J=11.19, 5.43 Hz, 1H), 3.69-3.70 (m, 1H), 3.75-3.87 (m, 2H), 7.09 (dt, J=8.48, 2.71 Hz, 1H), 7.27 (dd, J=8.31, 5.59 Hz, 1H), 7.37 (dd, J=9.83, 3.05 Hz, 1H). MS (M+H)$^+$ m/z 328.

Example 12

10-Fluoro-4-(3-methylamino-azetidin-1-yl)-6,7-dihydro-5H-benzo[6,7]cyclohepta[1,2-d]pyrimidin-2-ylamine The title compound was prepared using the procedure outlined in Example 1F substituting Example 11A for Example 1C, and substituting Example 2B for Example 1E followed by the procedure outlined in Example 1G. $^1$H NMR (CD$_3$OD) δ 2.06-2.25 (m, 4H), 2.36 (s, 3H), 2.58 (t, J=6.61 Hz, 2H), 3.63 (m, 1H), 3.99 (dd, J=9.66, 4.92 Hz, 2H), 4.42 (m, 2H), 7.08 (dt, J=8.48, 3.05 Hz, 1H), 7.26 (dd, J=8.31, 5.59 Hz, 1H), 7.32 (dd, J=9.66, 2.88 Hz, 1H). MS (M+H)$^+$ m/z 314.

Example 13

10-Fluoro-4-piperazin-1-yl-6,7-dihydro-5H-benzo[6,7]cyclohepta[1,2-d]pyrimidin-2-ylamine The title compound was prepared using the procedure outlined in Example 1F, substituting Example 11A for Example 1C, and substituting piperazine for Example 1E. $^1$H NMR (CD$_3$OD) δ 2.16-2.35 (m, 4H), 2.63 (t, J=6.61 Hz, 2H), 2.94-2.95 (m, 4H), 3.40-3.41 (m, 4H), 7.10 (dt, J=8.48, 2.71 Hz, 1H), 7.28 (dd, J=8.31, 5.59 Hz, 1H), 7.36 (dd, J=9.83, 2.71 Hz, 1H). MS (M+H)$^+$ m/z 314.

Example 14

4-[(3S)-3-Methylamino-pyrrolidin-1-yl]-6,7-dihydro-5H-benzo[6,7]cyclohepta[1,2-d]pyrimidin-2-ylamine

Example 14A (S)-Methyl-pyrrolidin-3-yl-carbamic acid tert-butyl ester

The title compound was prepared using the procedures outlined in Examples 1D followed by the procedure outlined in Example 1E, substituting (3S)-(+)-1-benzyl-3-(methylamino)pyrrolidine (CAS #169749-99-9) for (3R)-(−)-1-benzyl-3-(methylamino)pyrrolidine.

Example 14B

4-[(3S)-3-Methylamino-pyrrolidin-1-yl]-6,7-dihydro-5H-benzo[6,7]cyclohepta[1,2-d]pyrimidin-2-ylamine The title compound was prepared using the procedure outlined in Example 1F substituting Example 3A for Example 1C, and substituting the product described in Example 14A for Example 1E, followed by the procedure outlined in Example 1G. $^1$H NMR (CD$_3$OD) δ 1.85 (m, 1H), 2.18 (m, 3H), 2.33 (m, 2H), 2.43 (s, 3H), 2.65 (t, J=6.95 Hz, 2H), 3.51 (dd, J=10.85, 5.43 Hz, 1H), 3.64-3.88 (m, 3H), 7.25 (m, 1H), 7.34 (m, 2H), 7.63 (m, 1H). MS (M+H)$^+$ m/z 310.

Example 15

4-((3aR,6aR)-1-Methyl-hexahydro-pyrrolo[3,4-b]pyrrol-5-yl)-6,7-dihydro-5H-benzo[6,7]cyclohepta[1,2-d]pyrimidin-2-ylamine

Example 15A (3aR,6aR)-Hexahydro-pyrrolo[3,4-b]pyrrole-1,5-dicarboxylic acid 5-benzyl ester 1-tert-butyl ester (3aR,6aR)-Hexahydro-pyrrolo[3,4-b]pyrrole-1-carboxylic acid tert-butyl ester (CAS #370880-09-4) (3.0 g, 12.5 mmol) and N-(benzyloxycarbonyloxy)-succinimide (3.42 g, 13.7 mmol) were mixed in 15 ml of dichloromethane. The mixture was stirred at room temperature overnight and then concentrated under reduced pressure to provide the crude product. The residue was purified by flash chromatography (20% ethyl acetate in hexane) to provide the title compound. $^1$H NMR (CDCl$_3$) δ 7.29-7.43 (m, 5H), 5.13 (s, 2H), 4.15-4.33 (m, 1H), 3.39-3.74 (m, 5H), 3.20-3.37 (m, 1H), 2.84-2.96 (m, 1H), 1.92-2.03 (m, 1H), 1.66-1.82 (m, 1H), 1.46 (s, 9H). MS: (M+H)$^+$ m/z 347.

The starting material (3aR,6aR)-hexahydro-pyrrolo[3,4-b]pyrrole-1-carboxylic acid tert-butyl ester (CAS #370880-09-4) may be prepared as described in the literature, for example the method of Schenke, et al., "Preparation of 2,7-Diazabicyclo[3.3.0]octanes" U.S. Pat. No. 5,071,999 (1991) which provides a racemate which may be resolved by chromatography on a chiral column or by fractional crystallization of diasteromeric salts, or as described in Basha, et al. "Substituted diazabicycloalkane derivatives", US 2005101602 (2005).

Example 15B

Hexahydro-pyrrolo[3,4-b]pyrrole-1-carboxylic acid benzyl ester

A solution of the product from the Example 15A (500 mg) in CH$_2$Cl$_2$ (30 mL) was treated with TFA (1 mL) and stirred at room temperature for 16 hours. The mixture was basified with NaOH (10%) (pH>12) and partitioned. The organic was washed with H$_2$O, dried (MgSO$_4$) concentrated to provide the title compound. $^1$H NMR (CD$_3$OD) δ 1.39 (d, J=9 Hz, 3H), 1.88-1.97 (m, 1H), 2.17-2.25 (m, 1H), 2.62-2.78 (m, 5H), 3.15-3.22 (m, 1H), 3.45-3.52 (m, 1H) 7.19-7.33 (m, 5H). MS (M+H)$^+$ m/z 217.

Example 15C 4-((3aR,6aR)-1-Methyl-hexahydro-pyrrolo[3,4-b]pyrrol-5-yl)-6,7-dihydro-5H-benzo[6,7]cyclohepta[1,2-d]pyrimidin-2-ylamine The title compound was prepared using the procedure described in Example 1F, substituting the product from Example 3A for the product from Example 1C, and substituting the product from Example 15B for the product from Example 1E. The resulting intermediate was refluxed for 16 hours in 4.4% formic acid in methanol with the presence of Pd(OH)$_2$ (5% mol). The mixture was concentrated under reduced pressure and the residue was chromatographed on silica gel eluting with 3% (9:1 MeOH: NH$_4$OH) in dichloromethane to provide the title compound. $^1$H NMR (CDCl$_3$) δ 1.71-1.84 (m, 1H), 2.04-2.10 (m, 1H), 2.15-2.20 (m, 3H), 2.31-2.40 (m, 1H), 2.38 (s, 3H), 2.51-2.56 (m, 1H), 2.64 (t, J=6.44 Hz, 2H), 2.83 (m, 2H), 3.14-3.21 (m, 1H), 3.60-3.77 (m, 4H), 4.85 (s, 2H), 7.18-7.21 (m, 1H), 7.31-7.34 (m, 2H), 7.73-7.77 (m, 1H). MS (M+H)$^+$ m/z 336.

Example 16

4-((3R)-3-Amino-pyrrolidin-1-yl)-6,7-dihydro-5H-benzo[6,7]cyclohepta[1,2-d]pyrimidin-2-ylamine The title compound was prepared using the procedure outlined in Example 1F substituting Example 3A for Example 1C, and substituting (3R)-pyrrolidin-3-yl-carbamic acid tert-butyl ester for Example 1E followed by the procedure outlined in Example 1G. $^1$H NMR (CD$_3$OD) δ 1.79 (m, 1H), 2.10-2.25 (m, 3H), 2.35 (t, J=6.95 Hz, 2H), 2.65 (t, J=6.78 Hz, 2H), 3.42 (dd, J=10.51, 5.42 Hz, 1H), 3.56 (m, 1H), 3.69 (m, 1H), 3.82 (m, 2H), 7.25 (m, 1H), 7.34 (m, 2H), 7.63 (m, 1H). MS (M+H)$^+$ m/z 296.

Example 17

4-((1S,4S)-2,5-Diaza-bicyclo[2.2.1]hept-2-yl)-6,7-dihydro-5H-benzo[6,7]cyclohepta[1,2-d]pyrimidin-2-ylamine The title compound was prepared using the procedure outlined in Example 1F substituting Example 3A for Example 1C, and substituting tert-butyl (1S,4S)-(−)-2,5-diazabicyclo[2.2.1]heptane-2-carboxylate (CAS: 113451-59-5) for Example 1E followed by the procedure outlined in Example 1G. $^1$H NMR (CD$_3$OD) δ 1.75 (m, 1H), 1.90 (m, 1H), 1.97-2.30 (m, 3H), 2.44 (m, 1H), 2.56-2.71 (m, 2H), 2.99 (dd, J=10.17, 2.03 Hz, 1H), 3.25 (dd, J=10.17, 1.02 Hz, 1H), 3.41 (dd, J=9.15, 1.36 Hz, 1H), 3.76 (s, 1H), 3.89 (dd, J=9.49, 2.37 Hz, 1H), 4.81 (bs, 1H), 7.25 (m, 1H), 7.34 (m, 2H), 7.62 (m, 1H). MS (M+H)$^+$ m/z 308.

Example 18

4-(3-Piperidin-1-yl-pyrrolidin-1-yl)-6,7-dihydro-5H-benzo[6,7]cyclohepta[1,2-d]pyrimidin-2-ylamine The title compound was prepared using the procedure outlined in Example 1F, substituting Example 3A for Example 1C, and substituting 1-pyrrolidin-3-yl-piperidine (CAS #184970-32-9) for Example 1E. $^1$H NMR (CD$_3$OD) δ 1.51 (m, 2H), 1.66 (m, 4H), 1.82 (m, 1H), 2.01-2.31 (m, 4H), 2.44-2.73 (m, 7H), 2.88 (m, 1H), 3.56 (dd, J=10.17, 9.15 Hz, 1H), 3.71-3.78 (m, 2H), 3.82 (dd, J=10.17, 7.12 Hz, 1H), 7.25 (m, 1H), 7.35 (m, 2H), 7.63 (m, 1H). MS (M+H)$^+$ m/z 364.

Example 19

4-((3aR,6aR)-Hexahydro-pyrrolo[3,4-b]pyrrol-1-yl)-6,7-dihydro-5H-benzo[6,7]cyclohepta[1,2-d]pyrimidin-2-ylamine The title compound was prepared using the procedures outlined in Examples 1F substituting Example 3A for Example 1C, and substituting (3aR,6aR)-hexahydro-pyrrolo[3,4-b]pyrrole-5-carboxylic acid tert-butyl ester (CAS #370882-39-6) for Example 1E followed by the procedure outlined in Example 1G. $^1$H NMR (CD$_3$OD) δ 1.90 (m, 1H), 2.00-2.27 (m, 4H), 2.55-2.89 (m, 6H), 2.96 (dd, J=12.21, 2.37 Hz, 1H), 3.06-3.18 (m, 2H), 3.67 (m, 1H), 3.90 (dt, J=9.66, 6.78 Hz, 1H), 7.25 (m, 1H), 7.35 (m, 2H), 7.63 (m, 1H). MS (M+H)$^+$ m/z 322.

Example 20

4-Piperazin-1-yl-5,6,7,8-tetrahydro-1,3-diaza-dibenzo[a,c]cycloocten-2-ylamine

Example 20A

5-Oxo-5,6,7,8,9,10-hexahydro-benzocyclooctene-6-carboxylic acid methyl ester Dimethyl carbonate (20 mL) was treated with NaH (60% dispersed in oil, 660 mg, 46 mmol), heated at 85° C., treated dropwise with a solution of 7,8,9,10-tetrahydro-6H-benzocycloocten-5-one (prepared according to Richard W. Thies, J. Org. Chem. 42(2), 280-281, 1977) (950 mg, 5.5 mmol) in dimethyl carbonate (10 mL), stirred at 85-90° C. for three hours, cooled to 0° C., acidified by the slow addition of 1 M HCl (50 mL) and extracted with ether (150 mL). The organic was isolated, washed with brine, dried (MgSO$_4$) and concentrated to provide the title compound.

Example 20B

2-Amino-5,6,7,8-tetrahydro-1,3-diaza-dibenzo[a,c]cycloocten-4-ol

A mixture of Example 20A (1.49 g, 6.4 mmol), guanidine hydrochloride (2.1 g, 22 mmol) and K$_2$CO$_3$ (3.26 g, 24 mmol) in anhydrous DMF (20 mL) was heated at 120° C. for 8 hours under a nitrogen atmosphere. The mixture was cooled to room temperature and partitioned between EtOAc (200 mL) and H$_2$O (150 mL). The aqueous layer was extracted with EtOAc three times. The organic layers were combined, washed with brine, dried (MgSO$_4$), filtered and concentrated to provide a residue. The residue was chromatographed on silica gel eluting with MeOH:EtOAc:CHCl$_3$ (10:45:45) to provide the title compound.

Example 20C

Toluene-4-sulfonic acid 2-amino-5,6,7,8-tetrahydro-1,3-diaza-dibenzo[a,c]cycloocten-4-yl ester To a solution of Example 20B (950 mg, 2.4 mmol) in CH$_2$Cl$_2$ (30 mL) was added para-toluenesulfonyl chloride (1.09 g, 5.7 mmol), 4-dimethylaminopyridine (50 mg, 0.41 mmol) and triethylamine (1.1 mL. 7.9 mmol) and the mixture was stirred at room temperature for 16 hours. The mixture was diluted with CH$_2$Cl$_2$ (100 mL), washed with H$_2$O, dried (MgSO$_4$), filtered and concentrated under reduced pressure. The residue was purified on silica gel eluting with EtOAc: hexanes (25:75) to provide the title compound.

Example 20D

4-Piperazin-1-yl-5,6,7,8-tetrahydro-1,3-diaza-dibenzo[a,c]cycloocten-2-ylamine A solution of Example 20C (80 mg 0.20 mmol), piperazine (26 mg, 0.30 mmol) and triethylamine (0.1 mL, 0.72 mmol) in anhydrous acetonitrile (3 mL) was heated at 160° C. in a microwave reactor for 20 minutes. The mixture was concentrated under reduced pressure and chromatographed on silica gel eluting with NH$_4$OH:MeOH:CH$_2$Cl$_2$ (0.6:6:94) to provide the title compound. $^1$H NMR (CD$_3$OD) δ 1.45 (m, 2H), 1.86 (m, 1H), 2.00-2.15 (m, 2H), 2.34 (m, 1H), 2.73 (dd, J=14.58, 8.48 Hz, 1H), 2.80-3.02 (m, 5H), 3.37 (m, 4H), 7.22 (m, 1H), 7.24-7.31 (m, 2H), 7.33-7.41 (m, 1H). MS (M+H)$^+$ m/z 310.

Example 21

4-Piperazin-1-yl-6,7,8,9-tetrahydro-5H-1,3-diaza-dibenzo[a,c]cyclononen-2-ylamine

Example 21A

Toluene-4-sulfonic acid 2-amino-6,7,8,9-tetrahydro-5H-1,3-diaza-dibenzo[a,c]cyclononen-4-yl ester The title compound was prepared using the procedures outlined in Example 20A through 20C substituting 6,7,8,9,10,11-hexahydro-benzocyclononen-5-one [prepared according to Richard W. Thies, J. Org. Chem. 42(2), 280-281, 1977] for 7,8,9,10-tetrahydro-6H-benzocycloocten-5-one in Example 20A.

Example 21B

4-Piperazin-1-yl-6,7,8,9-tetrahydro-5H-1,3-diaza-dibenzo[a,c]cyclononen-2-ylamine The title compound was prepared using the procedures outlined in Example 20D substituting Example 21A for Example 20C. $^1$H NMR (CD$_3$OD) δ 1.30 (m, 2H), 1.53 (m, 3H), 1.83 (m, 1H), 2.00 (m, 1H), 2.31 (m, 1H), 2.60-2.81 (m, 2H), 2.91 (m, 4H), 3.32-3.50 (m, 4H), 7.06 (m, 1H), 7.24 (m, 2H), 7.33 (m, 1H). MS (M+H)+ m/z 310.

Example 22

4-(Hexahydro-pyrrolo[3,4-c]pyrrol-2-yl)-6,7-dihydro-5H-benzo[6,7]cyclohepta[1,2-d]pyrimidin-2-ylamine The title compound was prepared using the procedure outlined in Example 1F substituting Example 3A for Example 1C, and substituting hexahydro-pyrrolo[3,4-c]pyrrole-2-carboxylic acid tert-butyl ester (CAS #141449-85-6) for Example 1E followed by the procedure outlined in Example 1G. $^1$H NMR (CD$_3$OD) δ 2.19 (m, 2H), 2.34 (t, J=6.61 Hz, 2H), 2.64 (t, J=6.78 Hz, 2H), 2.78 (dd, J=11.36, 4.24 Hz, 2H), 2.90 (m, 2H), 3.15 (dd, J=11.53, 7.12 Hz, 2H), 3.56 (dd, J=11.19, 3.39 Hz, 2H), 3.77 (dd, J=11.19, 7.46 Hz, 2H), 7.25 (m, 1H), 7.35 (m, 2H), 7.63 (m, 1H). MS (M+H)+ m/z 322.

Example 23

4-(3-(R)-Methylamino-pyrrolidin-1-yl)-6,7,8,9-tetrahydro-5H-1,3-diaza-dibenzo[a,c]cyclononen-2-ylamine

Example 23A

[1-(2-Amino-6,7,8,9-tetrahydro-5H-1,3-diaza-dibenzo[a,c]cyclononen-4-yl)-(3R)-pyrrolidin-3-yl]-methyl-carbamic acid tert-butyl ester The title compound was prepared using the procedures outlined in Example 20D, substituting Example 21A for Example 20C, and substituting Example 1E for piperazine and chromatographed on silica gel, eluting with EtOAc.

Example 23B

4-(3-(R)-Methylamino-pyrrolidin-1-yl)-6,7,8,9-tetrahydro-5H-1,3-diaza-dibenzo[a,c]cyclononen-2-ylamine The title compound was prepared using the procedures outlined in Example 1G substituting Example 23A for Example 1F. $^1$H NMR (CD$_3$OD) δ 1.15-1.97 (m, 8H), 2.17 (m, 1H), 2.25-2.40 (m, 1H), 2.41 and 2.42 (s and s, 3H), 2.66-2.92 (m, 2H), 3.22-3.33 (m, 1H), 3.48 (ddd, J=20.94, 10.94, 5.76 Hz, 1H), 3.60-3.97 (m, 3H), 7.07 (m, 1H), 7.24 (m, 2H), 7.32 (m, 1H). MS (M+H)+ m/z 338.

Example 24

4-((R)-3-Amino-pyrrolidin-1-yl)-6,7,8,9-tetrahydro-5H-1,3-diaza-dibenzo[a,c]cyclononen-2-ylamine The title compound was prepared using the procedures outlined in Example 23 substituting (R)-3-(Boc-amino)pyrrolidine (CAS #122536-77-0) for Example 1E. $^1$H NMR (CD$_3$OD) δ 1.19-1.96 (m, 8H), 2.13 (m, 1H), 2.33 (m, 1H), 2.66-2.91 (m, 2H), 3.33-3.95 (m, 5H), 7.07 (m, 1H), 7.24 (m, 2H), 7.32 (m, 1H). MS (M+H)+ m/z 324.

Example 25

4-((S)-3-Amino-pyrrolidin-1-yl)-6,7,8,9-tetrahydro-5H-1,3-diaza-dibenzo[a,c]cyclononen-2-ylamine The title compound was prepared using the procedures outlined in Example 23 substituting (S)-(−)-3-(Boc-amino)pyrrolidine (CAS #122536-76-9) for Example 1E. $^1$H NMR (CD$_3$OD) δ 1.19-1.96 (m, 8H), 2.12 (m, 1H), 2.34 (m, 1H), 2.67-2.90 (m, 2H), 3.32-3.95 (m, 5H), 7.06 (m, 1H), 7.23 (m, 2H), 7.31 (m, 1H). MS (M+H)+ m/z 324.

Example 26

4-(3-Methylamino-azetidin-1-yl)-6,7,8,9-tetrahydro-5H-1,3-diaza-dibenzo[a,c]cyclononen-2-ylamine The title compound was prepared using the procedures outlined in Example 23 substituting Example 2B for Example 1E. $^1$H NMR (CD$_3$OD) δ 1.11-1.59 (m, 3H), 1.60-1.86 (m, 4H), 2.28-2.40 (m, 1H), 2.35 (s, 3H), 2.55-2.76 (m, 2H), 3.58 (m, 1H), 3.98 (ddd, J=20.17, 9.32, 5.09 Hz, 2H), 4.39 (m, 2H), 7.07 (m, 1H), 7.21-7.37 (m, 3H). MS (M+H)+ m/z 324.

Example 27

4-((3aS,6aS)-Hexahydro-pyrrolo[3,4-b]pyrrol-1-yl)-6,7,8,9-tetrahydro-5H-1,3-diaza-dibenzo[a,c]cyclononen-2-ylamine The title compound was prepared using the procedures outlined in Example 23 substituting (3aS,6aS)-hexahydro-pyrrolo[3,4-b]pyrrole-5-carboxylic acid tert-butyl ester (CAS #180975-51-3) for Example 1E. $^1$H NMR (CD$_3$OD) δ 0.99-2.31 (m, 10H), 2.51-2.94 (m, 5H), 3.00-3.25 (m, 2H), 3.56-3.90 (m, 2H), 4.72 (m, 1H), 7.08 (m, 1H), 7.20-7.36 (m, 3H).

Example 28

4-((1S,4S)-2,5-Diaza-bicyclo[2.2.1]hept-2-yl)-6,7,8,9-tetrahydro-5H-1,3-diaza-dibenzo[a,c]cyclononen-2-ylamine The title compound was prepared using the procedures outlined in Example 23 substituting tert-butyl (1S,4S)-(−)-2,5-diazabicyclo[2.2.1]heptane-2-carboxylate (CAS: 113451-59-5) for Example 1E. $^1$H NMR (CD$_3$OD) δ 1.26-2.03 (m, 11H), 2.35-2.82 (m, 3H), 3.01 (dt, J=10.43, 2.42 Hz, 1H), 3.71-3.82 (m, 2H), 4.90 (m, 1H), 7.06 (m, 1H), 7.20-7.37 (m, 3H). MS (M+H)+ m/z 336.

Example 29

4-(4-Methyl-piperazin-1-yl)-5,6-dihydro-7-oxa-1,3-diaza-dibenzo[a,c]cyclohepten-2-ylamine

Example 29A

2-(3-Ethoxycarbonyl-propoxy)-benzoic acid methyl ester

Methyl salicylate (4.6 g, 30 mmol) was treated with ethyl 4-bromobutyrate (6.5 g, 33 mmol) followed by the addition of potassium carbonate (4.6 g, 33 mmol), potassium iodide (61 mg, 0.36 mmol) and acetone (75 mL). The mixture was heated at reflux for 16 hours, cooled and filtered to remove the solids. The solids were washed with additional acetone and the combined filtrates were concentrated under reduced pressure. The residue was dissolved in ether (150 mL), cooled to 0° C., washed with 40 mL of 0.5 M sodium hydroxide, washed with brine, dried (MgSO$_4$), filtered, concentrated under reduced pressure and the residue chromatographed on silica gel eluting with a gradient of hexane:EtOAc (10:1, 5:1 and 4:1) to provide the title compound. $^1$H NMR (CDCl$_3$) δ 1.25 (t, J=7.12 Hz, 3H), 2.09-2.22 (m, 2H), 2.59 (t, J=7.29 Hz, 2H), 3.89 (s, 3H), 4.06-4.19 (m, 4H), 6.93-7.03 (m, J=8.14, 8.14 Hz, 2H), 7.40-7.48 (m, 1H), 7.78 (dd, J=7.63, 1.86 Hz, 1H); MS (M+H)$^+$ m/z 267.

Example 29B

5-Oxo-2,3,4,5-tetrahydro-benzo[b]oxepine-4-carboxylic acid methyl ester and 5-Oxo-2,3,4,5-tetrahydro-benzo[b]oxepine-4-carboxylic acid ethyl ester To a solution of Example 29A (3.43 g, 12.9 mmol) in anhydrous DMF (32 mL) under nitrogen was added EtOH (3 drops) followed by sodium hydride (1.13 g of a 60% dispersion in oil, 28 mmol). The mixture was stirred for 16 hours, heated at 100° C. for 30 minutes, cooled to ambient temperature then diluted with a 0° C. solution of 0.15 M HCl and extracted with ether (3×100 mL). The combined ether extractions were washed with water (2×100 mL), washed with brine, dried (MgSO$_4$), filtered, concentrated under reduced pressure and chromatographed on silica gel eluting with a gradient of hexane:EtOAc (20:1, 10:1 and 5:1) to provide the title compound as a 1:1 ratio of methyl and ethyl esters. MS (M+NH$_4$)$^+$ m/z 238 and 252.

Example 29C

2-Amino-5,6-dihydro-7-oxa-1,3-diaza-dibenzo[a,c]cyclohepten-4-ol

A solution of Example 29B (1.15 g, 4.9 mmol) in DMF (5 mL) was treated with guanidine nitrate (1.8 g, 15 mmol) followed by the addition of potassium carbonate (2.0 g, 15 mmol) and the mixture stirred at 110° C. for 16 hours. The mixture was cooled to ambient temperature, diluted with water (40 mL) and neutralized to pH 6 with acetic acid. The solid was collected by filtration, washed with water and dried under vacuum to provide the title compound. $^1$H NMR (DMSO-d6) δ 2.58 (t, J=5.93 Hz, 2H), 4.35 (t, J=5.93 Hz, 2H), 6.44 (bs, 2H), 7.04 (dd, J=7.97, 1.19 Hz, 1H), 7.11-7.23 (m, 1H), 7.31-7.41 (m, 1H), 7.83 (dd, J=7.80, 2.03 Hz, 1H), 10.92 (bs, 1H); MS (M+H)$^+$ m/z 230.

Example 29D

4-Chloro-5,6-dihydro-7-oxa-1,3-diaza-dibenzo[a,c]cyclohepten-2-ylamine

A mixture of Example 29C (0.63 g, 2.7 mmol) and phosphorus oxychloride (10 mL) was heated at reflux for 1 hour, cooled, concentrated under reduced pressure followed by the addition of water (20 mL). The mixture was filtered and the resulting solid was taken up in 1 M HCl (20 mL) and heated at reflux for 5 minutes. The cooled mixture was basified with 1M NaOH and extracted with CH$_2$Cl$_2$ (3×), filtering each extraction through diatomaceous earth. The combined CH$_2$Cl$_2$ layers were dried (MgSO$_4$), filtered, concentrated under reduced pressure and chromatographed on silica gel eluting with a gradient of CH$_2$Cl$_2$:EtOAc (20:1 and 10:1) to provide the title compound. $^1$H NMR (CDCl$_3$) δ 2.94 (t, J=6.10 Hz, 2H), 4.52 (t, J=6.27 Hz, 2H), 5.15 (s, 2H), 7.13 (dd, J=7.97, 1.19 Hz, 1H), 7.21-7.30 (m, 1H), 7.41-7.49 (m, 1H), 7.82 (dd, J=7.80, 1.70 Hz, 1H); MS (M+H)$^+$ m/z 248.

Example 29E 4-(4-Methyl-piperazin-1-yl)-5,6-dihydro-7-oxa-1,3-diaza-dibenzo[a,c]cyclohepten-2-ylamine Example 29D (29 mg, 0.12 mmol) in 2-methoxy-ethanol (0.5 mL) was treated with Hunig's base (0.14 mL, 0.82 mmol) and 1-methyl-piperazine (27 µL, 0.24 mmol), heated at 115° C. for 24 hours, cooled, concentrated under reduced pressure, diluted with CH$_2$Cl$_2$ (25 mL) and washed with 1 M NaOH (10 mL). The layers were separated and the aqueous was extracted with CH$_2$Cl$_2$ (25 mL). The combined CH$_2$Cl$_2$ layers were dried (MgSO$_4$), filtered, concentrated and chromatographed on silica gel eluting with a gradient of 5 and 10% (9:1 MeOH: saturated aqueous NH$_4$OH) in CH$_2$Cl$_2$ to provide the title compound. $^1$H NMR (CDCl$_3$) δ 2.35 (s, 3H), 2.48-2.60 (m, 4H), 2.71 (t, J=5.93 Hz, 2H), 3.39 (s, 4H), 4.54 (t, J=5.93 Hz, 2H), 4.78 (s, 2H), 7.08 (dd, J=7.97, 1.19 Hz, 1H), 7.17-7.24 (m, 1H), 7.33-7.41 (m, 1H), 7.89 (dd, J=7.80, 1.70 Hz, 1H). MS (M+H)$^+$ m/z 312.

Example 30

4-Piperazin-1-yl-5,6-dihydro-7-oxa-1,3-diaza-dibenzo[a,c]cyclohepten-2-ylamine

Example 30A 4-(2-Amino-5,6-dihydro-7-oxa-1,3-diaza-dibenzo[a,c]cyclohepten-4-yl)-piperazine-1-carboxylic acid tert-butyl ester To a solution of Example 29D (29 mg, 0.12 mmol) in ethanol (0.5 mL) was added triethylamine (0.12 mL, 0.82 mmol), piperazine-1-carboxylic acid tert-butyl ester (33 mg, 0.18 mmol) and the mixture heated at 90° C. for 16 hours. The mixture was diluted with CH$_2$Cl$_2$ (25 mL) and washed with 1 M NaOH (10 mL). The layers were separated and the aqueous was extracted with CH$_2$Cl$_2$ (25 mL). The combined CH$_2$Cl$_2$ layers were dried (MgSO$_4$), filtered, concentrated under reduced pressure and chromatographed on silica gel eluting with a gradient of CH$_2$Cl$_2$:EtOAc (5:1, 2:1 and 1:1) to provide the title compound. $^1$H NMR (CDCl$_3$) δ 1.49 (s, 9H), 2.72 (t, J=5.93 Hz, 2H), 3.26-3.32 (m, 4H), 3.52-3.57 (m, 4H), 4.54 (t, J=5.93 Hz, 2H), 4.78 (s, 2H), 7.09 (dd, J=8.14, 1.36 Hz, 1H), 7.17-7.24 (m, 1H), 7.35-7.42 (m, 1H), 7.89 (dd, J=7.80, 1.70 Hz, 1H).

Example 30B

4-Piperazin-1-yl-5,6-dihydro-7-oxa-1,3-diaza-dibenzo[a,c]cyclohepten-2-ylamine

A solution of Example 30A (38 mg, 0.096 mmol) in CH$_2$Cl$_2$ (1 mL) was treated with TFA (2 mL), heated at 60° C. for 2 minutes, cooled, concentrated under reduced pressure and chromatographed on silica gel eluting with a gradient of 2, 3.5, 5 and 10% (9:1 MeOH: saturated aqueous NH$_4$OH) in CH$_2$Cl$_2$ to provide the title compound. $^1$H NMR (CDCl$_3$) δ

2.72 (t, J=5.93 Hz, 2H), 2.91-3.09 (m, 4H), 3.26-3.46 (m, 4H), 4.54 (t, J=5.93 Hz, 2H), 4.79 (s, 2H), 7.09 (dd, J=7.97, 1.19 Hz, 1H), 7.17-7.26 (m, 1H), 7.34-7.41 (m, 1H), 7.89 (dd, J=7.63, 1.86 Hz, 1H); MS (M+H)$^+$ m/z 298.

Example 31

4-((R)-3-Methylamino-pyrrolidin-1-yl)-5,6-dihydro-7-oxa-1,3-diaza-dibenzo[a,c]cyclohepten-2-ylamine Example 29D (29 mg, 0.12 mmol) was processed as outlined in Example 30, substituting Example 1E for piperazine-1-carboxylic acid tert-butyl ester to provide the title compound. $^1$H NMR (CDCl$_3$) δ 1.75-1.89 (m, 1H), 2.06-2.19 (m, 1H), 2.49 (s, 3H), 2.73 (td, J=6.19, 1.86 Hz, 2H), 3.26-3.36 (m, 1H), 3.43 (dd, J=10.85, 4.75 Hz, 1H), 3.59-3.69 (m, 1H), 3.72-3.84 (m, 2H), 4.54 (t, J=6.10 Hz, 2H), 4.71 (s, 2H), 7.09 (dd, J=7.97, 1.19 Hz, 1H), 7.20-7.26 (m, 1H), 7.34-7.41 (m, 1H), 7.86 (dd, J=7.80, 1.70 Hz, 1H); MS (M+H)$^+$ m/z 312.

Example 32

4-(3-Methylamino-azetidin-1-yl)-5,6-dihydro-7-oxa-1,3-diaza-dibenzo[a,c]cyclohepten-2-ylamine Example 29D (29 mg, 0.12 mmol) was processed as outlined in Example 30, substituting Example 2B for piperazine-1-carboxylic acid tert-butyl ester to provide the title compound. $^1$H NMR (CDCl$_3$) δ 2.45 (s, 3H), 2.60 (t, J=6.10 Hz, 2H), 3.61-3.71 (m, 1H), 3.92 (dd, J=9.16, 5.09 Hz, 2H), 4.34-4.42 (m, 2H), 4.48 (t, J=6.10 Hz, 2H), 4.76 (s, 2H), 7.08 (dd, J=7.97, 1.19 Hz, 1H), 7.23 (td, J=7.54, 1.19 Hz, 1H), 7.37 (td, J=7.63, 1.70 Hz, 1H), 7.84 (dd, J=7.80, 1.70 Hz, 1H); MS (M+H)$^+$ m/z 298.

Example 33

4-(3-Methylamino-azetidin-1-yl)-5,6-dihydro-7-thia-1,3-diaza-dibenzo[a,c]cyclohepten-2-ylamine

Example 33A

2-(3-Ethoxycarbonyl-propylsulfanyl)-benzoic acid methyl ester

A mixture of methyl thiosalicylate (3.25 g, 19.3 mmol), ethyl 4-bromobutyrate (5.7 g, 29 mmol) and potassium carbonate (5.4 g, 39 mmol) in acetone (40 mL) was heated at reflux for 1 hour, cooled and filtered to remove the solids. The solids were washed with acetone and the combined filtrates were concentrated under reduced pressure and chromatographed on silica gel eluting with a gradient of hexane:EtOAc (20:1, 10:1, 5:1 and 2:1) to provide the title compound. $^1$H NMR (CDCl$_3$) δ 1.26 (t, J=7.12 Hz, 3H), 2.05 (m, 2H), 2.51 (t, J=7.29 Hz, 2H), 2.99 (t, J=7.29 Hz, 2H), 3.91 (s, 3H), 4.14 (q, J=7.12 Hz, 2H), 7.11-7.21 (m, 1H), 7.35 (m, 1H), 7.45 (m, 1H), 7.95 (dd, J=7.80, 1.70 Hz, 1H); MS (M+NH4)+ m/z 300.

Example 33B

5-Oxo-2,3,4,5-tetrahydro-benzo[b]thiepine-4-carboxylic acid methyl ester and 5-Oxo-2,3,4,5-tetrahydro-benzo[b]thiepine-4-carboxylic acid ethyl ester Example 33A (3.43 g, 12.9 mmol) was processed as outlined in Example 29B to provide of the title compound as a 1:1 ratio of methyl and ethyl esters.

Example 33C

2-Amino-5,6-dihydro-7-thia-1,3-diaza-dibenzo[a,c]cyclohepten-4-ol

Example 33B (1.27 g, 5.2 mmol) processed as outlined in Example 29C to provide the title compound which was contaminated with some 3,4-dihydro-2H-benzo[b]thiepin-5-one. $^1$H NMR (DMSO-d6) δ 2.43 (t, J=6.44 Hz, 2H), 3.28 (t, J=6.44 Hz, 2H), 6.49 (s, 2H), 7.36 (m, 1H), 7.47 (m, 1H), 7.56 (dd, J=7.63, 1.19 Hz, 1H), 7.60 (dd, J=7.63, 1.53 Hz, 1H), 11.01 (bs, 1H); MS (M+H)$^+$ m/z 246.

Example 33D

4-Chloro-5,6-dihydro-7-thia-1,3-diaza-dibenzo[a,c]cyclohepten-2-ylamine

A mixture of Example 33C (0.59 g, 2.4 mmol) and triethylamine (0.67 mL, 4.8 mmol) in CHCl$_3$ (10 mL) was cooled to 0° C. and treated dropwise with phosphorus oxychloride (0.29 mL, 3.1 mmol). The mixture was stirred at ambient temperature for 16 hours, treated with a stream of HCl gas for 5 minutes, stirred for 4 hours, heated at 70° C. for 10 minutes, cooled to 0° C., poured into 1 M NaOH, and extracted with CH$_2$Cl$_2$ (3×), filtering each extraction through diatomaceous earth. The combined organic layers were dried (MgSO$_4$), filtered, concentrated under reduced pressure and chromatographed on silica gel eluting with a gradient of CH$_2$Cl$_2$:EtOAc (20:1 and 10:1) to provide the title compound. $^1$H NMR (CDCl$_3$) δ 2.85 (t, J=6.61 Hz, 2H), 3.37 (t, J=6.61 Hz, 2H), 5.17 (s, 2H), 7.41 (td, J=7.54, 1.53 Hz, 1H), 7.49 (dt, J=7.54, 1.53 Hz, 1H), 7.63 (dd, J=7.46, 1.36 Hz, 1H), 7.68 (dd, J=7.46, 1.70 Hz, 1H). MS (M+H)$^+$ m/z 264.

Example 33E

4-(3-Methylamino-azetidin-1-yl)-5,6-dihydro-7-thia-1,3-diaza-dibenzo[a,c]cyclohepten-2-ylamine The title compound was prepared using the procedure outlined in Example 30, substituting Example 33D for Example 29D, and substituting Example 2B for piperazine-1-carboxylic acid tert-butyl ester. $^1$H NMR (DMSO-d6) δ 2.24 (s, 3H), 2.42 (t, J=6.27 Hz, 2H), 3.31 (t, J=6.26 Hz, 2H), 3.50-3.52 (m, 1H), 3.86 (dd, J=8.65, 5.26 Hz, 2H), 4.27 (t, J=7.80 Hz, 2H), 5.99 (s, 2H), 7.37 (td, J=7.46, 1.70 Hz, 1H), 7.47 (td, J=7.54, 1.53 Hz, 1H), 7.54 (dd, J=7.46, 1.36 Hz, 1H), 7.61 (dd, J=7.80, 1.36 Hz, 1H). MS (M+H)$^+$ m/z 314.

Example 34

4-(3-(R)-Methylamino-pyrrolidin-1-yl)-5,6-dihydro-7-thia-1,3-diaza-dibenzo[a,c]cyclohepten-2-ylamine The title compound was prepared using the procedure outlined in Example 30, substituting Example 33D for Example 29D, and substituting Example 1E for piperazine-1-carboxylic acid tert-butyl ester. $^1$H NMR (CDCl$_3$) δ 1.84 (m, 1H), 2.13 (m, 1H), 2.49 (s, 3H), 2.68 (m, 2H), 3.27-3.42 (m, 3H), 3.48 (dd, J=10.68, 4.92 Hz, 1H), 3.67 (m, 1H), 3.81 (m, 2H), 4.72 (s, 2H), 7.34 (dt, J=7.54, 1.53 Hz, 1H), 7.46 (dt, J=7.54, 1.19 Hz, 1H), 7.60 (dd, J=7.63, 1.19 Hz, 1H), 7.74 (dd, J=7.63, 1.53 Hz, 1H). MS (M+H)⁺ m/z 328.

Example 35

4-(3-(R)-Amino-pyrrolidin-1-yl)-5,6-dihydro-7-thia-1,3-diaza-dibenzo[a,c]cyclohepten-2-ylamine The title compound was prepared using the procedure outlined in Example 30, substituting Example 33D for Example 29D, and substituting (R)-(+)-3-(Boc-amino)pyrrolidine for piperazine-1-carboxylic acid tert-butyl ester. $^1$H NMR (CD$_3$OD) δ 1.81-1.82 (m, 1H), 2.16-2.17 (m, 1H), 2.67 (d, J=11.19 Hz, 2H), 3.38 (t, J=6.44 Hz, 2H), 3.45 (dd, J=10.68, 4.92 Hz, 1H), 3.58-3.59 (m, 1H), 3.72-3.73 (m, 1H), 3.82-3.91 (m, 2H), 7.39 (dt, J=7.54, 1.53 Hz, 1H), 7.49 (dt, J=7.54, 1.53 Hz, 1H), 7.60 (dd, J=7.46, 1.02 Hz, 1H), 7.63 (dd, J=8.14, 1.70 Hz, 1H). MS (M+H)⁺ m/z 314.

Example 36

4-Piperazin-1-yl-5,6-dihydro-7-thia-1,3-diaza-dibenzo[a,c]cyclohepten-2-ylamine

The title compound was prepared using the procedure outlined in Example 30, substituting Example 33D for Example 29D. $^1$H NMR (CDCl$_3$) δ 2.66-2.66 (m, 4H), 3.04-3.04 (m, 2H), 3.41-3.41 (m, 6H), 4.83 (s, 2H), 7.36 (dt, J=7.54, 1.53 Hz, 1H), 7.47 (dt, J=7.46, 1.36 Hz, 1H), 7.61 (dd, J=7.63, 1.19 Hz, 1H), 7.69 (td, J=7.80, 1.86 Hz, 1H). MS (M+H)⁺ m/z 314

Example 37

4-(3-Methylamino-azetidin-1-yl)-7-oxo-6,7-dihydro-5H-7λ4-thia-1,3-diaza-dibenzo[a,c]cyclohepten-2-ylamine

Example 37A

4-Chloro-7-oxo-6,7-dihydro-5H-7λ4-thia-1,3-diaza-dibenzo[a,c]cyclohepten-2-ylamine Example 33D (70 mg, 0.27 mmol) was dissolved in CH$_2$Cl$_2$ (6 mL), cooled to 0° C., treated with 70% meta-chloroperbenzoic acid (110 mg, 0.50 mmol), stirred at ambient temperature overnight, treated with 1 M NaOH (5 mL), and extracted with CH$_2$Cl$_2$ (3×25 mL). The combined CH$_2$Cl$_2$ layers were dried (MgSO$_4$), filtered, concentrated under reduced pressure and chromatographed on silica gel eluting with a gradient of CH$_2$Cl$_2$:EtOAc:EtOH (9:1:0, 1:1:0, 0:1:0 and 0:9:1) to provide the title compound as the slower eluting component. $^1$H NMR (DMSO-d6) δ 2.41-2.56 (m, 1H), 2.91-3.06 (m, 2H), 4.23 (dt, J=11.53, 6.78 Hz, 1H), 7.25 (s, 2H), 7.73 (m, 2H), 7.83 (m, 2H). MS (M+H)⁺ m/z 280.

Example 37B

4-Chloro-7,7-dioxo-6,7-dihydro-5H-7λ6-thia-1,3-diaza-dibenzo[a,c]cyclohepten-2-ylamine Example 33D (70 mg, 0.27 mmol) was processed as outlined in Example 37A to provide the title compound as the faster eluting component. $^1$H NMR (DMSO-d6) δ 2.90 (t, J=6.61 Hz, 2H), 3.81 (t, J=6.61 Hz, 2H), 7.24 (s, 2H), 7.77-7.84 (m, 2H), 7.92 (dt, J=7.46, 1.36 Hz, 1H), 8.01 (dd, 1H). MS (M+H)⁺ m/z 296.

Example 37C 4-(3-Methylamino-azetidin-1-yl)-7-oxo-6,7-dihydro-5H-7λ4-thia-1,3-diaza-dibenzo[a,c]cyclohepten-2-ylamine The title compound was prepared using the procedure outlined in Example 30, substituting Example 37A for Example 29D, and substituting Example 2B for piperazine-1-carboxylic acid tert-butyl ester. $^1$H NMR (DMSO-d6) δ 2.13-2.27 (m, 2H), 2.31 (s, 3H), 2.64 (dd, J=14.75, 6.27 Hz, 1H), 2.96 (dd, J=11.70, 6.95 Hz, 1H), 3.61 (t, J=6.44 Hz, 1H), 3.92 (dd, J=8.31, 4.92 Hz, 1H), 4.02 (dd, J=6.78, 5.09 Hz, 1H), 4.18-4.29 (m, 2H), 4.44 (t, J=8.48 Hz, 1H), 6.19 (s, 2H), 7.65-7.73 (m, 2H), 7.76 (dd, J=6.27, 2.20 Hz, 1H), 7.82 (m, 1H). MS (M+H)⁺ m/z 330.

Example 38

4-(3-Methylamino-azetidin-1-yl)-7,7-dioxo-6,7-dihydro-5H-7λ6-thia-1,3-diaza-dibenzo[a,c]cyclohepten-2-ylamine The title compound was prepared using the procedure outlined in Example 30, substituting Example 37B for Example 29D, and substituting Example 2B for piperazine-1-carboxylic acid tert-butyl ester. $^1$H NMR (DMSO-d6) δ 2.26 (s, 3H), 2.66 (t, J=6.78 Hz, 2H), 3.53-3.54 (m, 1H), 3.78 (t, J=6.44 Hz, 2H), 3.87 (dd, J=8.82, 5.42 Hz, 2H), 4.27 (t, J=7.97 Hz, 2H), 6.15 (s, 2H), 7.70 (dt, J=7.46, 1.70 Hz, 1H), 7.77 (dd, J=7.80, 1.36 Hz, 1H), 7.84 (dt, J=7.46, 1.36 Hz, 1H), 7.95 (dd, J=7.80, 1.02 Hz, 1H). MS (M+H)⁺ m/z 346.

Example 39

4-(3-(R)-Methylamino-pyrrolidin-1-yl)-5,6-dihydro-benzo[h]quinazolin-2-ylamine

Example 39A

1-Oxo-1,2,3,4-tetrahydro-naphthalene-2-carboxylic acid methyl ester

A suspension of 60% dispersion of sodium hydride in mineral oil (1.64 g, 41 mmol) in dimethyl carbonate (50 mL) was treated dropwise with alpha-tetralone (4.6 mL, 34 mmol). The mixture was heated at 90° C. for 20 minutes, cooled to ambient temperature, treated with 2 M HCl (40 mL), and extracted with EtOAc (100 mL and 25 mL). The combined EtOAc layers were washed with brine, dried (MgSO$_4$), filtered, concentrated under reduced pressure and chromatographed on silica gel eluting with a gradient of hexane:EtOAc (20:1 and 10:1) to provide the title compound. MS (M+H)⁺ m/z 205.

Example 39B

2-Amino-5,6-dihydro-benzo[h]quinazolin-4-ol

Example 39A (1.87 g, 9.2 mmol) was processed as outlined in Example 29C to provide the title compound. $^1$H NMR (DMSO-d6) δ 2.48-2.55 (m, 2H), 2.78 (t, J=7.63 Hz, 2H), 6.37 (s, 2H), 7.21-7.36 (m, 3H), 7.95-8.00 (m, 1H), 10.82 (s, 1H). MS (M+H)$^+$ m/z 214.

Example 39C

4-Chloro-5,6-dihydro-benzo[h]quinazolin-2-ylamine

Example 39B was processed as outlined in Example 29D to provide the title compound. $^1$H NMR (CDCl$_3$) δ 2.93-2.93 (m, 4H), 5.06 (s, 2H), 7.21-7.27 (m, 1H), 7.30-7.43 (m, 2H), 8.21 (dd, J=7.63, 1.53 Hz, 1H). MS (M+H)$^+$ m/z 232.

Example 39D 4-(3-(R)-Methylamino-pyrrolidin-1-yl)-5,6-dihydro-benzo[h]quinazolin-2-ylamine The title compound was prepared using the procedure outlined in Example 30, substituting Example 39C for Example 29D, and substituting Example 1E for piperazine-1-carboxylic acid tert-butyl ester. $^1$H NMR (CDCl$_3$) δ 1.78-1.79 (m, 1H), 2.07-2.08 (m, 1H), 2.47 (s, 3H), 2.78-2.80 (m, 2H), 2.84-2.93 (m, 2H), 3.26-3.27 (m, 1H), 3.43 (dd, J=11.02, 4.92 Hz, 1H), 3.58-3.68 (m, 1H), 3.71-3.82 (m, 2H), 4.69 (s, 2H), 7.17-7.18 (m, 1H), 7.27-7.35 (m, 2H), 8.09-8.10 (m, 1H). MS (M+H)$^+$ m/z 296.

Example 40

4-(3-Methylamino-azetidin-1-yl)-5,6-dihydro-benzo[h]quinazolin-2-ylamine

The title compound was prepared using the procedure outlined in Example 30, substituting Example 39C for Example 29D, and substituting Example 2B for piperazine-1-carboxylic acid tert-butyl ester. $^1$H NMR (CDCl$_3$) δ 2.43 (s, 3H), 2.71 (m, 2H), 2.83 (dd, J=9.83, 7.12 Hz, 2H), 3.62 (m, 1H), 3.89 (dd, J=8.98, 4.92 Hz, 2H), 4.36 (m, 2H), 4.69 (s, 2H), 7.16 (m, 1H), 7.27-7.35 (m, 2H), 8.13 (m, 1H). MS (M+H)$^+$ m/z 282.

Example 41

1-(4-Methyl-piperazin-1-yl)-9H-10-oxa-2,4-diaza-phenanthren-3-ylamine

Example 41A 3-(Bis-methylsulfanyl-methylene)-isochroman-4-one

Isochroman-4-one (Anzalone, L. et al. J. Org. Chem. 1985, 50(12), p. 2128-2133) (0.42 g, 2.8 mmol) was processed as outlined in Example 1A to provide the title compound. $^1$H NMR (CDCl$_3$) δ 2.49 (s, 3H), 2.51 (s, 3H), 5.16 (s, 2H), 7.19-7.20 (m, 1H), 7.43-7.44 (m, 1H), 7.52 (dd, J=7.46, 1.36 Hz, 1H), 8.08 (dd, J=7.63, 1.19 Hz, 1H). MS (M+H)$^+$ m/z 253.

Example 41B

1-Methylsulfanyl-9H-10-oxa-2,4-diaza-phenanthren-3-ylamine

A solution of guanidine nitrate (1.5 g, 12 mmol) in EtOH (9 mL) was treated with 3 mL of 1 M EtONa in EtOH, refluxed for 15 minutes, cooled, treated with a solution of Example 41A in EtOH (5 mL), heated at reflux overnight, cooled, treated with water (25 mL) and extracted with CH$_2$Cl$_2$ (3×25 mL). The combined CH$_2$Cl$_2$ layers were dried (MgSO$_4$), filtered, concentrated under reduced pressure and chromatographed on silica gel eluting with a gradient of CH$_2$Cl$_2$: EtOAc (1:0 and 20:1) to provide the title compound. $^1$H NMR (DMSO-d6) δ 2.46 (s, 3H), 5.18 (s, 2H), 6.31 (s, 2H), 7.29 (m, 1H), 7.42-7.51 (m, 2H), 7.96 (m, 1H). MS (M+H)$^+$ m/z 246.

Example 41C

1-Methanesulfonyl-9H-10-oxa-2,4-diaza-phenanthren-3-ylamine

Example 41B (60 mg, 0.24 mmol) was processed as outlined in Example 1C to provide the title compound. MS (M+H)$^+$ m/z 278.

Example 41D 1-(4-Methyl-piperazin-1-yl)-9H-10-oxa-2,4-diaza-phenanthren-3-ylamine A mixture of Example 41C, 1-methyl-piperazine (0.5 mL) and 2-methoxy-ethanol (1 mL) was heated at 110° C. for 60 hours, cooled, concentrated under reduced pressure and chromatographed on silica gel eluting with a gradient of 2, 3.5 and 5% (9:1 MeOH: saturated aqueous NH$_4$OH) to provide the title compound. $^1$H NMR (CDCl$_3$) δ 2.34 (s, 3H), 2.52 (t, J=4.75 Hz, 4H), 3.83 (t, J=4.75 Hz, 4H), 4.61 (s, 2H), 5.06 (s, 2H), 7.12 (m, 1H), 7.34-7.44 (m, 2H), 8.05 (m, 1H); MS (M+H)$^+$ m/z 298.

Example 42

4-(4-Methyl-piperazin-1-yl)-5,6-dihydro-benzo[h]quinazolin-2-ylamine

The title compound was prepared using the procedure outlined in Example 29E, substituting Example 39C for Example 29D. $^1$H NMR (CDCl$_3$) δ 2.35 (s, 3H), 2.53 (t, J=4.75 Hz, 4H), 2.67 (dd, J=7.80, 5.09 Hz, 2H), 2.82 (dd, J=9.16, 6.44 Hz, 2H), 3.34 (t, J=4.75 Hz, 4H), 4.72 (s, 2H), 7.19 (m, 1H), 7.31 (m, 2H), 8.09 (m, 1H); MS (M+H)$^+$ m/z 296.

Example 43

7-Bromo-4-(4-methyl-piperazin-1-yl)-5,6-dihydro-benzo[h]quinazolin-2-ylamine

The title compound was prepared using the procedure outlined in Example 41, substituting 5-bromo-1-tetralone for isochroman-4-one. $^1$H NMR (CDCl$_3$) δ 2.37 (s, 3H), 2.56 (t, J=4.75 Hz, 4H), 2.68 (dd, J=7.80, 6.10 Hz, 2H), 2.97 (dd, 2H), 3.38 (t, J=4.75 Hz, 4H), 4.76 (s, 2H), 7.19 (t, J=7.97 Hz, 1H), 7.56 (dd, J=8.14, 1.36 Hz, 1H), 8.09 (dd, J=7.80, 1.02 Hz, 1H); MS (M+H)$^+$ m/z 274.

Example 44

4-Piperazin-1-yl-5,6-dihydro-benzo[h]quinazolin-2-ylamine

The title compound was prepared using the procedure outlined in Example 30, substituting Example 39C for Example 29D. $^1$H NMR (CDCl$_3$) δ 2.68 (dd, J=7.80, 5.09 Hz, 2H), 2.82

(dd, J=8.82, 6.10 Hz, 2H), 2.99 (m, 4H), 3.28 (m, 4H), 4.74 (s, 2H), 7.19 (m, 1H), 7.31 (m, 2H), 8.10 (m, 1H); MS (M+H)$^+$ m/z 282.

Example 45

10-chloro-4-[(3R)-3-(methylamino)pyrrolidin-1-yl]-5,6-dihydro[1]benzoxepino[5,4-d]pyrimidin-2-amine Example 45A methyl 5-chloro-2-(4-ethoxy-4-oxobutoxy)benzoate To a solution of methyl 5-chloro-2-hydroxybenzoate (1.12 g, 6.0 mmol) in acetone (15 mL) was added ethyl 4-bromobutyrate (1.3 mL, 9.0 mmol) and K$_2$CO$_3$ (1.24 g, 9.0 mmol) and a catalytic amount of potassium iodide. The mixture was heated at reflux overnight, cooled, filtered, concentrated under reduced pressure and chromatographed using hexane:EtOAc to provide the title compound. $^1$H NMR (CDCl$_3$) δ 1.25 (t, J=7.12 Hz, 3H) 2.13 (m, 2H) 2.57 (t, J=7.29 Hz, 2H) 3.89 (s, 3H) 4.07 (t, J=6.10 Hz, 2H) 4.14 (q, J=7.12 Hz, 2H) 6.90 (d, J=8.82 Hz, 1H) 7.38 (dd, J=8.82, 2.71 Hz, 1H) 7.76 (d, J=2.71 Hz, 1H); MS (M+H)$^+$ m/z 301.

Example 45B

Methyl 7-chloro-5-oxo-2,3,4,5-tetrahydrobenzo[b]oxepine-4-carboxylate and ethyl 7-chloro-5-oxo-2,3,4,5-tetrahydrobenzo[b]oxepine-4-carboxylate To a solution of Example 45A (1.5 g, 5.1 mmol) in DMF (13 mL) under nitrogen was added EtOH (3 drops) and NaH (60% dispersion in mineral oil 0.45 g, 11.3 mmol). The mixture was stirred overnight at room temp, heated at 100° C. for 30 minutes, cooled to 0° C., poured into a 0° C. of 0.15 M HCl (100 mL) and extracted with Et$_2$O (3×). The combined Et$_2$O layers were washed with water (2×), washed with brine, dried (MgSO$_4$), filtered, concentrated under reduced pressure and chromatographed (hexane:EtOAc) to provide the title compound. MS (M+NH$_4$)$^+$ m/z 272 and 286.

Example 45C 2-amino-10-chloro-5,6-dihydro[1]benzoxepino[5,4-d]pyrimidin-4-ol

To a solution of Example 45B (0.73 g, 2.7 mmol) in DMF (2.7 mL) was added guanidine nitrate (0.66 g, 5.4 mmol) and K$_2$CO$_3$ (0.75 g, 5.4 mmol). The mixture was stirred at 110° C. overnight, cooled, diluted with water (10 mL), acidified to pH 6 with acetic acid, allowed to stand for 15 minutes and the solid was collected by filtration. The solid was washed with water and dried overnight under reduced pressure to provide the title compound. $^1$H NMR (DMSO-d6) δ 2.65 (t, J=5.76 Hz, 2H) 4.35 (t, J=5.76 Hz, 2H) 6.49 (s, 2H) 7.06 (d, J=8.48 Hz, 1H) 7.39 (dd, J=8.65, 2.88 Hz, 1H) 7.96 (d, J=2.71 Hz, 1H) 11.00 (s, 1H); MS (M+H)$^+$ m/z 264.

Example 45D 4,10-dichloro-5,6-dihydro[1]benzoxepino[5,4-d]pyrimidin-2-amine

A mixture of Example 45C (0.56 g, 2.1 mmol) in CHCl$_3$ (4.2 mL) was treated with POCl$_3$ (0.97 mL, 10.5 mmol), cooled to 0° C., treated with triethylamine (0.59 mL, 4.2 mmol), stirred at ambient temperature for 4 hours, diluted with CHCl$_3$ (5 mL), treated with a stream of HCl gas for 2 minutes, stirred at ambient temperature overnight and partitioned between cold 1 M NaOH (50 mL) and CH$_2$Cl$_2$ (50 mL). The layers were separated and the aqueous was extracted with CH$_2$Cl$_2$ (2×50 mL). The combined CH$_2$Cl$_2$ layers were dried (MgSO$_4$), filtered, concentrated under reduced pressure and chromatographed eluting with CH$_2$Cl$_2$ and then 9:1 CH$_2$Cl$_2$:EtOAc to provide the title compound. $^1$H NMR (DMSO-d6) δ 2.87 (t, J=5.76 Hz, 2H) 4.43 (t, J=5.93 Hz, 2H) 7.12 (s, 2H) 7.15 (d, J=8.81 Hz, 1H) 7.52 (dd, J=8.65, 2.88 Hz, 1H) 7.88 (d, J=2.71 Hz, 1H); MS (M+H)$^+$ m/z 282.

Example 45E 10-chloro-4-[(3R)-3-(methylamino)pyrrolidin-1-yl]-5,6-dihydro[1]benzoxepino[5,4-d]pyrimidin-2-amine To a mixture of Example 45D (48 mg, 0.17 mmol) in EtOH (1 mL) was added Example 1E (51 mg, 0.25 mmol) followed by triethylamine (0.17 mL, 1.2 mmol) and the resulting mixture heated at 80° C. overnight, cooled, concentrated under reduced pressure and chromatographed on silica gel eluting with a gradient of CH$_2$Cl$_2$:EtOAc (5:1, 2:1 and 1:1) to provide the intermediate Boc-protected product. This intermediate Boc-protected product was taken up in CH$_2$Cl$_2$ (2 mL), treated with trifluoroacetic acid (2 mL), heated at 60° C. for 1 minute, cooled, concentrated under reduced pressure and chromatographed on silica gel eluting with a gradient of 2, 10 and 20% (9:1 MeOH: saturated aqueous NH$_4$OH) in CH$_2$Cl$_2$ to provide the title compound. $^1$H NMR (CDCl$_3$) δ 1.84 (m, 1H), 2.11 (m, 1H), 2.49 (s, 3H), 2.73 (dt, J=6.02, 1.86 Hz, 2H), 3.32 (m, 1H), 3.43 (dd, J=10.85, 4.75 Hz, 1H), 3.61 (m, 1H), 3.72-3.81 (m, 2H), 4.51 (t, J=5.93 Hz, 2H), 4.70 (s, 2H), 7.01 (d, J=8.82 Hz, 1H), 7.31 (dd, J=8.48, 2.71 Hz, 1H), 7.86 (d, J=2.71 Hz, 1H); MS (M+H)$^+$ m/z 346.

Example 46

10-methyl-4-[(3R)-3-(methylamino)pyrrolidin-1-yl]-5,6-dihydro[1]benzoxepino[5,4-d]pyrimidin-2-amine The title compound was prepared by using the procedures outlined in Example 45, substituting methyl 2-hydroxy-5-methylbenzoate for methyl 5-chloro-2-hydroxybenzoate in Example 45A. $^1$H NMR (CDCl$_3$) δ 1.82 (m, 1H), 2.12 (m, 1H), 2.38 (s, 3H), 2.49 (s, 3H), 2.71 (dt, J=6.10, 2.03 Hz, 2H), 3.31 (m, 1H), 3.43 (dd, J=10.51, 4.75 Hz, 1H), 3.58-3.68 (m, 1H), 3.72-3.83 (m, 2H), 4.50 (t, J=6.10 Hz, 2H), 4.73 (s, 2H), 6.98 (d, J=7.80 Hz, 1H), 7.18 (ddd, J=8.14, 2.37, 0.68 Hz, 1H), 7.64 (d, J=2.37 Hz, 1H); MS (M+H)$^+$ m/z 326.

Example 47

10-methoxy-4-[(3R)-3-(methylamino)pyrrolidin-1-yl]-5,6-dihydro[1]benzoxepino[5,4-d]pyrimidin-2-amine The title compound was prepared by using the procedures outlined in Example 45, substituting 2-hydroxy-5-methoxybenzoate for methyl 5-chloro-2-hydroxybenzoate in Example 45A. $^1$H NMR (CDCl$_3$) δ 1.82 (m, 1H), 2.12 (m, 1H), 2.49 (s, 3H), 2.69 (dt, J=6.19, 1.86 Hz, 2H), 3.31 (m, 1H), 3.43 (dd, J=10.85, 4.75 Hz, 1H), 3.59-3.69 (m, 1H), 3.73-3.83 (m, 2H), 3.85 (s, 3H), 4.48 (t, J=6.10 Hz, 2H), 4.72

(s, 2H), 6.92 (dd, J=8.82, 3.39 Hz, 1H), 7.02 (d, J=8.82 Hz, 1H), 7.36 (d, J=3.05 Hz, 1H); MS (M+H)⁺ m/z 342.

Example 48

9-chloro-4-[(3R)-3-(methylamino)pyrrolidin-1-yl]-5,6-dihydro[1]benzoxepino[5,4-d]pyrimidin-2-amine The title compound was prepared by using the procedures outlined in Example 45, substituting methyl 4-chloro-2-hydroxybenzoate for methyl 5-chloro-2-hydroxybenzoate in Example 45A. $^1$H NMR (CDCl$_3$) δ 1.82 (m, 1H), 2.11 (m, 1H), 2.49 (s, 3H), 2.74 (dt, J=6.02, 1.53 Hz, 2H), 3.30 (m, 1H), 3.41 (dd, J=10.51, 4.75 Hz, 1H), 3.61 (m, 1H), 3.70-3.81 (m, 2H), 4.53 (t, J=5.93 Hz, 2H), 4.68 (s, 2H), 7.09 (d, J=2.03 Hz, 1H), 7.20 (dd, J=8.31, 2.20 Hz, 1H), 7.83 (d, J=8.48 Hz, 1H); MS (M+H)⁺ m/z 346.

Example 49

9-methyl-4-[(3R)-3-(methylamino)pyrrolidin-1-yl]-5,6-dihydro[1]benzoxepino[5,4-d]pyrimidin-2-amine The title compound was prepared by using the procedures outlined in Example 45, substituting ethyl 2-hydroxy-4-methylbenzoate for methyl 5-chloro-2-hydroxybenzoate in Example 45A. $^1$H NMR (CDCl$_3$) δ 1.82 (m, 1H), 2.12 (m, 1H), 2.37 (s, 3H), 2.49 (s, 3H), 2.72 (dt, J=6.02, 1.53 Hz, 2H), 3.31 (m, 1H), 3.43 (dd, J=10.51, 4.75 Hz, 1H), 3.62 (m, 1H), 3.71-3.82 (m, 2H), 4.52 (t, J=6.10 Hz, 2H), 4.76 (s, 2H), 6.90 (d, J=0.68 Hz, 1H), 7.05 (ddd, J=7.80, 1.70, 0.68 Hz, 1H), 7.75 (d, J=7.80 Hz, 1H); MS (M+H)⁺ m/z 326.

Example 50

9-methoxy-4-[(3R)-3-(methylamino)pyrrolidin-1-yl]-5,6-dihydro[1]benzoxepino[5,4-d]pyrimidin-2-amine The title compound was prepared by using the procedures outlined in Example 45, substituting methyl 2-hydroxy-4-methoxybenzoate for methyl 5-chloro-2-hydroxybenzoate in Example 45A. $^1$H NMR (CDCl$_3$) δ 1.81 (m, 1H), 2.10 (m, 1H), 2.49 (s, 3H), 2.74 (m, 2H), 3.30 (m, 1H), 3.41 (dd, J=10.85, 5.09 Hz, 1H), 3.61 (m, 1H), 3.70-3.81 (m, 2H), 3.83 (s, 3H), 4.53 (t, J=5.93 Hz, 2H), 4.72 (s, 2H), 6.63 (d, J=2.71 Hz, 1H), 6.79 (dd, J=8.65, 2.54 Hz, 1H), 7.83 (d, J=8.82 Hz, 1H); MS (M+H)⁺ m/z 342.

Example 51

8-chloro-4-[(3R)-3-(methylamino)pyrrolidin-1-yl]-5,6-dihydro[1]benzoxepino[5,4-d]pyrimidin-2-amine The title compound was prepared by using the procedures outlined in Example 45, substituting 3-chloro-2-hydroxybenzoate for methyl 5-chloro-2-hydroxybenzoate in Example 45A. $^1$H NMR (CDCl$_3$) δ 1.83 (m, 1H), 2.13 (m, 1H), 2.49 (s, 3H), 2.71 (dt, J=6.19, 3.56 Hz, 2H), 3.32 (m, 1H), 3.43 (dd, J=10.51, 4.75 Hz, 1H), 3.63 (m, 1H), 3.73-3.83 (m, 2H), 4.61 (t, J=6.10 Hz, 2H), 4.70 (s, 2H), 7.16 (t, J=7.80 Hz, 1H), 7.46 (dd, J=7.80, 1.70 Hz, 1H), 7.73 (dd, J=7.80, 1.70 Hz, 1H); MS (M+H)⁺ m/z 346.

Example 52

8-Methyl-4-((R)-3-methylamino-pyrrolidin-1-yl)-5,6-dihydro-7-oxa-1,3-diaza-dibenzo[a,c]cyclohepten-2-ylamine The title compound was prepared by using the procedures outlined in Example 45, substituting methyl 2-hydroxy-3-methylbenzoate for methyl 5-chloro-2-hydroxybenzoate in Example 45A. $^1$H NMR (CDCl$_3$) δ 1.81 (m, 1H), 2.12 (m, 1H), 2.32 (s, 3H), 2.49 (s, 3H), 2.69 (dt, J=6.19, 1.86 Hz, 2H), 3.31 (m, 1H), 3.43 (dd, J=10.85, 5.09 Hz, 1H), 3.63 (m, 1H), 3.72-3.84 (m, 2H), 4.51 (t, J=6.27 Hz, 2H), 4.70 (s, 2H), 7.13 (t, J=7.63 Hz, 1H), 7.25 (m, 1H), 7.63 (m, 1H); MS (M+H)⁺ m/z 326.

Example 53

8-methoxy-4-[(3R)-3-(methylamino)pyrrolidin-1-yl]-5,6-dihydro[1]benzoxepino[5,4-d]pyrimidin-2-amine The title compound was prepared by using the procedures outlined in Example 45, substituting methyl 2-hydroxy-3-methoxybenzoate for methyl 5-chloro-2-hydroxybenzoate in Example 45A. $^1$H NMR (CDCl$_3$) δ 1.82 (m, 1H), 2.12 (m, 1H), 2.49 (s, 3H), 2.71 (dt, J=6.19, 2.54 Hz, 2H), 3.31 (m, 1H), 3.44 (dd, J=10.51, 4.75 Hz, 1H), 3.63 (m, 1H), 3.73-3.83 (m, 2H), 3.89 (s, 3H), 4.57 (t, J=6.27 Hz, 2H), 4.74 (s, 2H), 7.00 (dd, J=8.14, 1.70 Hz, 1H), 7.17 (t, J=7.97 Hz, 1H), 7.40 (dd, J=7.80, 1.70 Hz, 1H); MS (M+H)⁺ m/z 342.

Example 54

4-[(3R)-3-(methylamino)pyrrolidin-1-yl]-5,6,7,8-tetrahydrobenzo[7,8]cycloocta[1,2-d]pyrimidin-2-amine The title compound was prepared using the procedure outlined in Example 20D substituting Example 1E for piperazine, followed by the procedure outlined in Example 1G. $^1$H NMR (CDCl$_3$) δ 1.4-1.5 (m, 1H), 1.53-1.62 (m, 1H), 1.92 (s, 2H), 1.93 (t, J=6 Hz, 2H), 1.99-2.15 (m, 2H), 2.28-2.45 (m, 2H), 2.60 (d, J=3 Hz, 3H), 2.86-3.05 (m, 2H), 3.56-3.62 (m, 1H), 3.81-4.1 (m, 4H), 7.31-7.36 (m, 3H), 7.48-7.42 (m, 1H); MS (M+H)⁺ m/z 324.

Example 55

4-[(3R)-3-aminopyrrolidin-1-yl]-5,6,7,8-tetrahydrobenzo[7,8]cycloocta[1,2-d]pyrimidin-2-amine The title compound was prepared using the procedure outlined in Example 20D substituting (R)-tert-butyl pyrrolidin-3-ylcarbamate for piperazine, followed by the procedure outlined in Example 1G. $^1$H NMR (CDCl$_3$) δ 1.36-1.65 (m, 2H), 1.92 (s, 2H), 2.28-2.45 (m, 6H), 2.26-2.45 (m, 2H), 2.85-3.04 (m, 2H), 3.76-4.1 (m, 5H), 7.30-7.34 (m, 3H), 7.41-7.46 (m, 1H); MS (M+H)⁺ m/z 310.

Example 56

4-[(3S)-3-aminopyrrolidin-1-yl]-5,6,7,8-tetrahydrobenzo[7,8]cycloocta[1,2-d]pyrimidin-2-amine The title compound was prepared using the procedure outlined in Example 20D substituting (S)-tert-butyl pyrrolidin- 3-ylcarbamate for piperazine, followed by the procedure outlined in Example 1G. $^1$H NMR (CDCl$_3$) δ 1.36-1.65 (m, 2H), 1.92 (s, 2H), 2.28-2.45 (m, 6H), 2.26-2.45 (m, 2H), 2.85-3.04 (m, 2H), 3.76-4.1 (m, 5H), 7.30-7.34 (m, 3H), 7.41-7.46 (m, 1H); MS (M+H)$^+$ m/z 310.

Example 57

4-(3-aminoazetidin-1-yl)-5,6,7,8-tetrahydrobenzo[7,8]cycloocta[1,2-d]pyrimidin-2-amine The title compound was prepared using the procedure outlined in Example 20D substituting Example 2B for piperazine, followed by the procedure outlined in Example 1G. $^1$H NMR (CDCl$_3$) δ 1.36-1.53 (m, 2H), 1.75-1.82 (m, 1H), 1.94 (s, 4H), 2.09-2.17 (m, 1H), 2.33-2.41 (t, J=9 Hz, 1H), 2.66-2.74 (m, 1H), 2.85-2.93 (m, 1H), 3.91-3.98 (m, 1H), 4.11-4.19 (m, 2H), 4.58-4.69 (m, 2H), 7.32-7.36 (m, 3H), 7.43-7.48 (m, 1H); MS (M+H)$^+$ m/z 296.

Example 58

4-[(3aR,6aR)-hexahydropyrrolo[3,4-b]pyrrol-1(2H)-yl]-5,6,7,8-tetrahydrobenzo[7,8]cycloocta[1,2-d]pyrimidin-2-amine The title compound was prepared using the procedure outlined in Example 20D substituting (3aR,6aR)-hexahydropyrrolo[3,4-b]pyrrole-5-carboxylic acid tert-butyl ester (CAS #370882-39-6) for piperazine, followed by the procedure outlined in Example 1G. $^1$H NMR (CDCl$_3$) δ 1.42-1.59 (m, 2H), 1.86-2.0 (m, 2H), 1.91 (s, 4H), 2.04-2.15 (m, 2H), 2.22-2.44 (m, 2H), 2.82-2.93 (m, 2H), 3.13-3.21 (m, 1H), 3.71-3.96 (m, 3H), 4.04-4.26 (m, 2H), 7.27-7.32 (m, 3H), 7.39-7.44 (m, 1H); MS (M+H)$^+$ m/z 336.

Example 59

4-octahydro-6H-pyrrolo[3,4-b]pyridin-6-yl-6,7-dihydro-5H-benzo[6,7]cyclohepta[1,2-d]pyrimidin-2-amine Example 59A Methyl 5-Oxo-6,7,8,9-tetrahydro-5H-benzo[7]annulene-6-carboxylate A mixture of benzosuberone (8 g, 50 mmol) and neat dimethyl carbonate (45 mL) at ambient temperature under N$_2$ was treated with NaH (60% in mineral oil, 4 g, 100 mmol) in 0.1 mL of dry MeOH, heated at 80° C. for 3 hours, cooled to ambient temperature, treated with 2 N HCl (55 mL) and extracted with ethyl acetate. The organic layer was washed with brine, dried (MgSO$_4$) and concentrated to provide the title compound as an oil, as a 3:1 mixture of enol and keto forms of product by NMR spectroscopy. The NMR of the main enol form was: $^1$H NMR (CDCl$_3$) δ 2.03-2.16 (m, 4H), 2.64 (m, 2H), 3.82 (s, 3H), 7.23 (m, 1H), 7.33 (m, 2H), 7.62 (m, 1H), 12.6 (bs, 1H). MS (M+H)$^+$ m/z 219.

Example 59B 2-amino-6,7-dihydro-5H-benzo[6,7]cyclohepta[1,2-d]pyrimidin-4-ol

The product from Example 59A (5.45 g, 25 mmol) was dissolved in DMF (25 mL), treated with guanidine nitrate (6.1 g, 50 mmol), treated with potassium carbonate (6.9 g, 50 mmol), stirred at 110° C. for 16 hours, cooled, diluted with water and neutralized to pH 6 with acetic acid. The solid was collected by filtration, washed with water and dried under vacuum to provide the title compound. $^1$H NMR (DMSO-d6) δ 2.0 (m, 2H), 2.13 (t, J=6.78 Hz, 2H), 2.47 (m, 2H), 6.37 (bs, 2H), 7.25 (m, 1H), 7.31 (m, 2H), 7.53 (m, 1H), 10.83 (s, 1H); MS (M+H)$^+$ m/z 228.

Example 59C 2-amino-6,7-dihydro-5H-benzo[6,7]cyclohepta[1,2-d]pyrimidin-4-yl 4-methylbenzenesulfonate The product from Example 59B (1.37 g, 6 mmol) was suspended in CH$_2$Cl$_2$ (100 mL), treated with TsCl (2.28 g, 12 mmol), treated with 4-dimethylaminopyridine (100 mg, 0.82 mmol), treated with triethylamine (2.2 mL, 16 mmol), and heated at reflux for 4 hours. The mixture was washed with H$_2$O, dried (MgSO$_4$), concentrated under reduced pressure and chromatographed on silica gel eluting with EtOAc:hexanes (25:75) to provide the title compound. $^1$H NMR (DMSO-d6) δ 1.99 (t, J=6.95 Hz, 2H), 2.23 (t, J=6.95 Hz, 2H), 2.45 (s, 3H), 2.47 (m, 2H), 6.91 (bs, 2H), 7.31 (m, 1H), 7.4 (m, 2H), 7.55 (dd, J=7.29, 1.87 Hz, 1H), 7.5 (d, J=8.48 Hz, 2H), 8.03 (d, J=8.14 Hz, 2H). MS (M+H)$^+$ m/z 382.

Example 59D tert-butyl 6-(2-amino-6,7-dihydro-5H-benzo[6,7]cyclohepta[1,2-d]pyrimidin-4-yl)octahydro-1H-pyrrolo[3,4-b]pyridine-1-carboxylate A solution of the product from Example 59C (76 mg, 0.2 mmol), t-butyl octahydro-1H-pyrrolo[3,4-b]pyridine-1-carboxylate (CAS #159877-36-8) (59 mg, 0.22 mmol) and triethylamine (0.1 mL) in acetonitrile (1 mL) was heated in a microwave reactor at 160° C. for 1 hour. The mixture was concentrated and chromatographed on silica gel eluting with EtOAc:hexane (1:1) mixture to yield the title compound.

Example 59E 4-octahydro-6H-pyrrolo[3,4-b]pyridin-6-yl-6,7-dihydro-5H-benzo[6,7]cyclohepta[1,2-d]pyrimidin-2-amine A solution of Example 59D in CH$_2$Cl$_2$ (2 mL) was treated with trifluoroacetic acid (0.5 mL), stirred for 2 hours, concentrated and partitioned between 1M NaOH solution and CH$_2$Cl$_2$. The organic layer was isolated, dried over MgSO$_4$ and concentrated to yield the title product. $^1$H NMR (CDCl$_3$) δ 0.86 (m, 1H), 1.77 (m, 5H), 2.16 (m, 2H), 2.30 (m, 1H), 2.64 (m, 3H), 3.03 (m, 1H), 3.43 (m, 3H), 3.87 (m, 2H), 4.73 (bs, 2H), 7.19 (m, 1H), 7.33, (m, 2H), 7.75 (m, 1H). MS (M+H)$^+$ m/z 336.

Example 60

4-(2,8-diazaspiro[4.5]dec-8-yl)-6,7-dihydro-5H-benzo[6,7]cyclohepta[1,2-d]pyrimidin-2-amine Example 60A 4-(2-benzyl-2,8-diazaspiro[4.5]dec-8-yl)-6,7-dihydro-5H-benzo[6,7]cyclohepta[1,2-d]pyrimidin-2-amine A solution of the product from Example 59C (76 mg, 0.2 mmol) and 2-benzyl-2,8-diazospiro[4.5]decane (CAS

867009-61-8) (50 mg, 0.22 mmol) were treated as described in Example 59D to provide the title product.

Example 60B 4-(2,8-diazaspiro[4.5]dec-8-yl)-6,7-dihydro-5H-benzo[6,7]cyclohepta[1,2-d]pyrimidin-2-amine A solution of 40 mg of the product from the Example 60A in MeOH (4 mL) and a catalytic amount of 10% Pd on carbon was stirred under an atmosphere of hydrogen for 16 hour at ambient temperature. The mixture was filtered and concentrated under reduced pressure. The residue was chromatographed on silica gel, eluting with 10% EtOH/CH$_2$Cl$_2$ containing 1% NH$_4$OH to provide the title compound. $^1$H NMR (DMSO-d6) δ1.65 (m, 5H), 1.80 (t, 1H), 2.19 (m, 4H), 2.45 (m, 2H), 2.57 (m, 2H), 2.97 (bs, 2H), 3.05 (m, 4H), 6.08 (s, 2H), 7.27 (m, 1H), 7.34 (m, 2H), 7.64 (m, 1H). MS (M+H)$^+$ m/z 350.

Example 61

4-(1,5-diazocan-1-yl)-6,7-dihydro-5H-benzo[6,7]cyclohepta[2-d]pyrimidin-2-amine

The title compound was prepared using the procedure outlined in Example 59D substituting 1-benzyl-1,5-diazocane for t-butyl octahydro-1H-pyrrolo[3,4-b]pyridine-1-carboxylate (CAS #223797-64-6) followed by the procedure outlined in Example 60B. $^1$H NMR (DMSO-d6) δ1.95 (m, 1H), 2.07 (m, 2H), 2.19 (m, 4H), 2.29 (m, 1H), 2.45 (m, 2H), 2.64 (m, 2H), 3.19 (m, 4H), 6.0 (bs, 2H), 7.36 (m, 3H), 7.61 (m, 1H), 8.37 (bs, 1H) MS (M+H)$^+$ m/z 324.

Example 62

4-(4-aminopiperidin-1-yl)-6,7-dihydro-5H-benzo[6,7]cyclohepta[1,2-d]pyrimidin-2-amine The title compound was prepared using the procedure outlined in Example 59D substituting t-butyl piperidine-4-ylcarbamate for t-butyl octahydro-1H-pyrrolo[3,4-b]pyridine-1-carboxylate (CAS #73874-95-0) followed by the procedure outlined in Example 59E. $^1$H NMR (DMSO-d6) δ1.35 (t, J=10.68 Hz, 1H), 1.68-1.92 (m, 2H), 2.12-1.23 (m, 4H), 2.41-2.47 (m, 2H), 2.53-2.66 (m, 2H), 2.80-3.00 (m, 2H), 3.67 (d, J=13.22 Hz, 2H), 6.04 (s, 2H), 7.21-7.30 (m, 1H), 7.31-7.41 (m, 2H), 7.53-7.69 (m, 1H) MS (M+H)$^+$ m/z 310.

Example 63

N$^4$-(2-azetidin-2-ylethyl)-6,7-dihydro-5H-benzo[6,7]cyclohepta[1,2-d]pyrimidine-2,4-diamine The title compound was prepared using the procedure outlined in Example 59D substituting 2-(2-amino-ethyl)-azetidine-1-carboxylic acid tert-butyl ester, toluene-4-sulfonic acid, for t-butyl octahydro-1H-pyrrolo[3,4-b]pyridine-1-carboxylate followed by the procedure outlined in Example 59E. $^1$H NMR (DMSO-d6) δ 1.78 (m, 2H), 1.99 (m, 4H), 2.13 (m, 4H), 2.43 (m, 2H), 3.2 (m, 1H), 3.5 (m, 1H), 3.9 (m, 1H), 5.78 (s, 2H), 6.8 (bs, 1H), 7.24 (m, 1H), 7.3 (m, 2H), 7.5 (m, 1H); MS (M+H)$^+$ m/z 310.

Example 64

N$^4$-[(2R)-azetidin-2-ylmethyl]-6,7-dihydro-5H-benzo[6,7]cyclohepta[1,2-d]pyrimidine-2,4-diamine The title compound was prepared using the procedure outlined in Example 59D substituting ((R)-2-Aminomethyl-azetidine-1-carboxylic acid tert-butyl ester, toluene-4-sulfonic acid, (CAS #887626-82-6) for t-butyl octahydro-1H-pyrrolo[3,4-b]pyridine-1-carboxylate followed by the procedure outlined in Example 59E. $^1$H NMR (DMSO-d6) δ 2.1-2.3 (m, 4H), 2.3-2.42 (m, 1H), 2.6 (m, 2H), 3.62-4.0 (m, 4H), 4.55 (m, 1H), 7.45 (m, 1H), 7.53 (m, 3H), 8.5 bs, 1H), 8.8 (bs, 1H), 12.35 (bs, 1H) MS (M+H)$^+$ m/z 296.

Example 65

N$^4$-(1-methylpiperidin-4-yl)-6,7-dihydro-5H-benzo[6,7]cyclohepta[1,2-d]pyrimidine-2,4-diamine The title compound was prepared using the procedure outlined in Example 59D substituting 1-methyl-piperidin-4-ylamine (CAS #41838-46-4) for t-butyl octahydro-1H-pyrrolo[3,4-b]pyridine-1-carboxylate. $^1$H NMR (DMSO-d6) δ 1.44-1.65 (m, 2H), 1.72-1.85 (m, 2H), 1.95-2.05 (m, 3H), 2.15 (m, 2H), 2.20 (s, 3H), 2.45 (m, 2H), 2.70-2.859 m, 3H0, 3.85-3.95 (m, 1H), 6.23 (d, J=6.23 Hz 1H), 7.21 (m, 1H), 7.28 (m, 2H), 7.51 (m, 1H); MS (M+H)$^+$ m/z 324.

Example 66

N$^4$-[(1R,5S)-8-methyl-8-azabicyclo[3.2.1]oct-3-yl]-6,7-dihydro-5H-benzo[6,7]cyclohepta[1,2-d]pyrimidine-2,4-diamine The title compound was prepared using the procedure outlined in Example 59D substituting 8-methyl-8-azabicyclo[3.2.1]octan-3-amine dihydrochloride (CAS #646477-45-4) for t-butyl octahydro-1H-pyrrolo[3,4-b]pyridine-1-carboxylate. $^1$H NMR (CDCl$_3$) δ1.75-1.85 (m, 2H), 2.05-2.20 (m, 7H), 2.2-2.30 (m, 3H), 2.32 (s, 3H), 2.58 (t, 2H), 3.2 (m, 2H), 4.28 (m, 1H), 4.68 (bs, 2H), 5.08 (d, 1H), 7.2 (m, 1H), 7.34 (m, 2H), 7.66 (m, 1H); MS (M+H)$^+$ m/z 350.

Example 67

4-(5-methyl-1,4-diazepan-1-yl)-6,7-dihydro-5H-benzo[6,7]cyclohepta[1,2-d]pyrimidin-2-amine The title compound was prepared using the procedure outlined in Example 59D substituting benzyl 7-methyl-1,4-diazepane-1-carboxylate for t-butyl octahydro-1H-pyrrolo[3,4-b]pyridine-1-carboxylate followed by the procedure outlined in Example 60B. $^1$H NMR (CDCl$_3$) δ 1.16 (d, J=6.44 Hz, 3H), 1.60-1.77 (m, 2H), 1.88-2.02 (m, 1H), 2.10-2.25 (m, 2H), 2.27-2.44 (m, 2H), 2.62-2.71 (m, 2H), 2.83-2.96 (m, 1H), 2.97-3.09 (m, 1H), 3.22 (dt, J=13.90, 4.07 Hz, 1H), 3.44-3.61 (m, 2H), 3.72-3.91 (m, 2H), 4.66 (s, 2H), 7.18-7.24 (m, 1H), 7.29-7.39 (m, 2H), 7.73-7.80 (m, 1H); MS (M+H)$^+$ m/z 324.

Example 68

4-(1-Methyl-piperidin-4-yloxy)-6,7-dihydro-5H-benzo[6,7]cyclohepta[1,2-d]pyrimidin-2-ylamine

Example 68A 4-chloro-6,7-dihydro-5H-benzo[6,7]cyclohepta[1,2-d]pyrimidin-2-amine Example 59B (1.05 g, 4.62 mmol), triethylamine (1.1 mL, 7.85 mmol), and 4-dimethylamino pyridine (56 mg, 0.462 mmol) were combined in chloroform (30 mL) to form a suspension. 4-Nitrobenzene-1-sulfonyl chloride (1.54 g, 6.93 mmol) was added and the mixture was stirred overnight at room temperature. A 4 M solution of hydrochloric acid in dioxane (5.8 mL, 23.1 mmol) was added and the mixture was stirred for two hours. The mixture was diluted with ethyl acetate, washed with 1 N NaOH, dried with a saturated solution of sodium chloride, and the organic layer was absorbed on silica gel and purified using silica gel chromatography (40 g column) eluting with a gradient of ethyl acetate in hexane (15-55%) to afford the title compound. $^1$H NMR (CDCl$_3$) δ 7.63-7.68 (m, 1H), 7.36-7.42 (m, 2H), 7.22-7.25 (m, 1H), 5.07 (s, 2H), 2.52-2.62 (m, 4H), 2.12-2.24 (m, 2H); MS (M+H)$^+$ m/z 246.

Example 68B 4-(1-Methyl-piperidin-4-yloxy)-6,7-dihydro-5H-benzo[6,7]cyclohepta[1,2-d]pyrimidin-2-ylamine Sodium hydride (30 mg, 1.22 mmol) was added to 4-hydroxy-1-methylpiperdine (478 μL, 4.07 mmol) and the mixture was stirred for five minutes at room temperature. Example 68A (50 mg, 0.203 mmol) was added and the mixture was heated at 80° C. for two hours. The mixture was then diluted with methylene chloride, washed with water, dried over sodium sulfate. After filtration, the reaction mixture was absorbed on silica gel and purified using silica gel chromatography, eluting with a gradient of methanol in methylene chloride (4-15%) to afford the title compound. $^1$H NMR (CDCl$_3$) δ 7.60-7.68 (m, 1H), 7.30-7.37 (m, 2H), 7.18-7.24 (m, 1H), 5.12-5.22 (m, 1H), 4.78 (s, 2H), 2.60-2.73 (m, 2H), 2.56 (t, J=7.12 Hz, 2H), 2.35-2.48 (m, 4H), 2.33 (s, 3H), 1.98-2.19 (m, 4H), 1.81-1.97 (m, 2H); MS (M+H)$^+$ m/z 325.

Example 69

4-(1-Methyl-piperidin-3-yloxy)-6,7-dihydro-5H-benzo[6,7]cyclohepta[1,2-d]pyrimidin-2-ylamine The title compound was prepared using the procedure outlined in Example 68B substituting 1-methylpiperidin-3-ol for 4-hydroxy-1-methylpiperdine. $^1$H NMR (CDCl$_3$) δ 7.60-7.66 (m, 1H), 7.29-7.38 (m, 2H), 7.18-7.23 (m, 1H), 5.15-5.27 (m, 1H), 4.81 (s, 2H), 3.09 (dd, J=10.31, 3.17 Hz, 1H), 2.64-2.75 (m, 1H), 2.55 (t, J=6.94 Hz, 2H), 2.29-2.41 (m, 5H), 2.01-2.18 (m, 5H), 1.77-1.90 (m, 1H), 1.62-1.76 (m, 1H), 1.39-1.54 (m, 1H); MS (M+H)$^+$ m/z 325.

Example 70

4-((R)-1-Methyl-pyrrolidin-3-yloxy)-6,7-dihydro-5H-benzo[6,7]cyclohepta[1,2-d]pyrimidin-2-ylamine The title compound was prepared using the procedure outlined in Example 68B substituting (R)-1-methylpyrrolidin-3-ol for 4-hydroxy-1-methylpiperdine. $^1$H NMR (CDCl$_3$) δ 7.61-7.66 (m, 1H), 7.29-7.38 (m, 2H), 7.19-7.24 (m, 1H), 5.41-5.51 (m, 1H), 4.79 (s, 2H), 2.93 (dd, J=11.02, 6.61 Hz, 1H), 2.73-2.84 (m, 2H), 2.55 (t, J=7.12 Hz, 2H), 2.43-2.51 (m, 1H), 2.30-2.43 (m, 6H), 2.06-2.18 (m, 2H), 1.94-2.07 (m, 1H); MS (M+H)$^+$ m/z 311.

Example 71

4-((S)-1-Methyl-pyrrolidin-3-yloxy)-6,7-dihydro-5H-benzo[6,7]cyclohepta[1,2-d]pyrimidin-2-ylamine The title compound was prepared using the procedure outlined in Example 68B substituting (S)-1-methylpyrrolidin-3-ol for 4-hydroxy-1-methylpiperdine. $^1$H NMR (CDCl$_3$) δ 7.61-7.66 (m, 1H), 7.29-7.37 (m, 2H), 7.19-7.23 (m, 1H), 5.42-5.51 (m, 1H), 4.79 (s, 2H), 2.97 (dd, J=11.02, 6.27 Hz, 1H), 2.73-2.85 (m, 2H), 2.47-2.59 (m, 3H), 2.31-2.44 (m, 6H), 2.08-2.18 (m, 2H), 1.96-2.08 (m, 1H); MS (M+H)$^+$ m/z 311.

Example 72

4-(Piperidin-4-yloxy)-6,7-dihydro-5H-benzo[6,7]cyclohepta[1,2-d]pyrimidin-2-ylamine

72A tert-butyl 4-[(2-amino-6,7-dihydro-5H-benzo[6,7]cyclohepta[1,2-d]pyrimidin-4-yl)oxy]piperidine-1-carboxylate The title compound was prepared using the procedure outlined in Example 68B substituting tert-butyl 4-hydroxypiperidine-1-carboxylate for 4-hydroxy-1-methylpiperdine.

Example 72B 4-(Piperidin-4-yloxy)-6,7-dihydro-5H-benzo[6,7]cyclohepta[1,2-d]pyrimidin-2-ylamine The product from Example 72A was dissolved in methylene chloride (2 mL) and treated with a solution of 4 N hydrochloric acid in dioxane (2 mL). The mixture was stirred at room temperature overnight. The solvents were removed and the mixture was diluted with 1 N NaOH. The product was extracted with methylene chloride three times and the organic washes were combined to afford the title compound. $^1$H NMR (CDCl$_3$) δ 7.61-7.67 (m, 1H), 7.31-7.37 (m, 2H), 7.19-7.24 (m, 1H), 5.17-5.27 (m, 1H), 4.78 (s, 2H), 3.08-3.18 (m, 2H), 2.75-2.86 (m, 2H), 2.56 (t, J=6.95 Hz, 2H), 2.39 (t, J=7.12 Hz, 2H), 2.13 (q, J=7.01 Hz, 2H), 1.97-2.08 (m, 2H), 1.65-1.77 (m, 3H); MS (M+H)$^+$ m/z 311.

Example 73

4-((S)-Pyrrolidin-3-yloxy)-6,7-dihydro-5H-benzo[6,7]cyclohepta[1,2-d]pyrimidin-2-ylamine The title compound was prepared using the procedure outlined in Example 72 substituting (S)-tert-butyl 3-hydroxypyrrolidine-1-carboxylate for 4-hydroxy-1-methylpiperdine in Example 72A. $^1$H NMR (CDCl$_3$) δ 7.61-7.67 (m, 1H), 7.31-7.37 (m, 2H), 7.19-7.24 (m, 1H), 5.48-5.55 (m, 1H), 4.81 (s, 2H), 3.10-3.22 (m, 3H), 2.90-3.00 (m, 1H), 2.56 (t, J=7.12 Hz, 2H), 2.35 (t, J=7.12 Hz, 2H), 2.05-2.20 (m, 3H), 1.92-2.04 (m, 1H); MS (M+H)$^+$ m/z 297.

Example 74

4-(2-Dimethylamino-ethoxy)-6,7-dihydro-5H-benzo[6,7]cyclohepta[1,2-d]pyrimidin-2-ylamine The title compound was prepared using the procedure outlined in Example 68B substituting 2-(dimethylamino)ethanol for 4-hydroxy-1-methylpiperdine. The amine was converted to the hydrochloride salt by first dissolving it in tetrahydrofuran (1 mL). A 2 N solution of hydrochloric acid in diethyl ether (67 μL, 0.134 mmol) was added and the mixture was stirred at room temperature for two hours. The solvents were removed under reduced pressure and the resulting solids were triturated with diethyl ether to afford the title compound. After conversion to the free base by basification, extraction with organic solvent, and concentration, a free base of the product was obtained: $^1$H NMR (CDCl$_3$) δ 7.64 (s, 1H), 7.29-7.38 (m, 2H), 7.19-7.24 (m, 1H), 4.81 (s, 2H), 4.46 (t, J=5.95 Hz, 2H), 2.75 (t, J=5.95 Hz, 2H), 2.55 (t, J=7.14 Hz, 2H), 2.32-2.44 (m, 8H), 2.05-2.18 (m, 2H); MS (M+H)$^+$ m/z 299.

Example 75

4-(1,9-Diaza-spiro[5.5]undec-9-yl)-6,7-dihydro-5H-benzo[6,7]cyclohepta[1,2-d]pyrimidin-2-ylamine Example 59C (75 mg, 0.20 mmol) was mixed with 2,2,2-trifluoro-1-(1,9-diazaspiro[5.5]undecan-1-yl)ethanone (58.9 mg, 0.24 mmol), KOtBu (44 mg, 0.4 mmol) and palladium (I) tri-tert-butylphosphine bromide (10 mg, 0.013 mmol), in anhydrous toluene (1.5 mL), and heated at reflux under nitrogen for 20 hours, then cooled, diluted with CH$_2$Cl$_2$ and washed with 1 M NaOH. The aqueous layer was extracted with CH$_2$Cl$_2$. The combined organics were dried (MgSO$_4$), filtered, concentrated and chromatographed and eluted with 10% (9:1 MeOH: saturated aqueous ammonium hydroxide) to provide the title compound. $^1$H NMR (CDCl$_3$) δ 1.50-1.66 (m, 6H), 1.75 (t, J=5.59 Hz, 4H), 2.16-2.36 (m, 5H), 2.64 (t, J=6.78 Hz, 2H), 2.83-2.91 (m, 2H), 3.40 (q, J=4.97 Hz, 4H), 4.73 (s, 2H), 7.18-7.24 (m, 1H), 7.29-7.38 (m, 2H), 7.69-7.76 (m, 1H); MS (M+H)$^+$ m/z 364.

Example 76

4-((R)-3-Dimethylamino-pyrrolidin-1-yl)-6,7-dihydro-5H-benzo[6,7]cyclohepta[1,2-d]pyrimidin-2-ylamine Example 59C (100 mg, 0.26 mmol) was mixed with (3R)-(+)-3-(dimethylamino)pyrrolidine (45 mg, 0.39 mmol) and to this was added 2-methoxyethanol (1 mL) and N,N-diisopropylethylamine (0.22 mL, 1.3 mmol); the reaction was heated at 115° C. for 2 hours, cooled, diluted with CH$_2$Cl$_2$ and washed with 1 M NaOH. The aqueous layer was extracted with CH$_2$Cl$_2$. The combined organics were dried (MgSO$_4$), filtered, concentrated and chromatographed and eluted with a gradient of 1:0 to 35:65 CH$_2$Cl$_2$:[10% (9:1 MeOH:saturated aqueous ammonium hydroxide)] to provide the title compound. $^1$H NMR (CDCl$_3$) δ 1.78-1.93 (m, 1H), 2.10-2.21 (m, 4H), 2.33 (s, 6H), 2.53 (dd, J=9.49, 4.75 Hz, 1H), 2.61-2.69 (m, 2H), 2.69-2.79 (m, 1H), 3.54 (dd, J=10.17, 8.82 Hz, 1H), 3.69-3.80 (m, 3H), 4.76 (s, 2H), 7.18-7.24 (m, 1H), 7.29-7.39 (m, 2H), 7.75-7.80 (m, 1H); MS (M+H)$^+$ m/z 324.

Example 77

4-(2,6-Diaza-spiro[3.5]non-2-yl)-6,7-dihydro-5H-benzo[6,7]cyclohepta[1,2-d]pyrimidin-2-ylamine Example 77A 6-benzyl-2,6-diazaspiro[3.5]nonane 2,2,2-trifluoroacetate tert-butyl 6-benzyl-2,6-diazaspiro[3.5]nonane-2-carboxylate (0.18 g) was mixed with CH$_2$Cl$_2$ (1 mL) and TFA (1 mL), then heated at 60° C. for 2 minutes and concentrated to dryness to provide the title compound as the trifluoroacetic acid salt.

Example 77B 4-(6-benzyl-2,6-diazaspiro[3.5]non-2-yl)-6,7-dihydro-5H-benzo[6,7]cyclohepta[1,2-d]pyrimidin-2-amine The product from Example 77A was mixed with the product from Example 59C (135 mg, 0.35 mmol) in 2-methoxyethanol (1.2 mL) and N,N-diisopropylethylamine (0.74 mL, 1.74 mmol), then heated at 115° C. overnight, then cooled, diluted with CH$_2$Cl$_2$, and washed with 1 M NaOH. The aqueous layer was extracted with CH$_2$Cl$_2$. The combined organic extracts were dried (MgSO$_4$), filtered, concentrated and purified by chromatography on silica gel, eluting with a gradient of 1:0 to 1:2 CH$_2$Cl$_2$:[10% (9:1 MeOH:saturated aqueous ammonium hydroxide)] to provide the title compound. MS (M+H)$^+$ m/z 426.

Example 77C 4-(2,6-Diaza-spiro[3.5]non-2-yl)-6,7-dihydro-5H-benzo[6,7]cyclohepta[1,2-d]pyrimidin-2-ylamine The product from Example 77B (0.19 g) was dissolved in EtOH (1.5 mL), and to this was added Pd(OH)$_2$ (20 mg); the mixture was heated overnight at 50° C. under an atmosphere of hydrogen gas (H$_2$), then more Pd(OH)$_2$ (30 mg) was added, and the reaction further heated under an atmosphere of H$_2$ for 3 hours, cooled, diluted with EtOH, filtered to remove the Pd(OH)$_2$ and concentrated to provide the title compound. $^1$H NMR (CDCl$_3$) δ 1.61-1.80 (m, 3H), 1.82-1.89 (m, 1H), 2.08-2.27 (m, 4H), 2.54-2.64 (m, 2H), 2.89-2.97 (m, 1H), 3.13 (s, 1H), 3.43-3.60 (m, 1H), 3.92-4.06 (m, 2H), 4.10-4.18 (m, 1H), 5.37-5.63 (m, 2H), 7.18-7.26 (m, 1H), 7.31-7.43 (m, 2H), 7.68-7.80 (m, 1H); MS (M+H)$^+$ m/z 336.

Example 78

4-(2,5-Diaza-spiro[3.5]non-2-yl)-6,7-dihydro-5H-benzo[6,7]cyclohepta[1,2-d]pyrimidin-2-ylamine The title compound was prepared using the procedure described in Example 77, substituting tert-butyl 5-benzyl-2,5-diazaspiro[3.5]nonane-2-carboxylate for tert-butyl 6-benzyl-2,6-diazaspiro[3.5]nonane-2-carboxylate. $^1$H NMR (CDCl$_3$) δ 1.49-1.65 (m, 5H), 1.81-1.92 (m, 2H), 2.09-2.25 (m, 4H), 2.61-2.86 (m, 4H), 3.96-4.12 (m, 3H), 5.11 (s, 1H), 7.21-7.27 (m, 1H), 7.32-7.40 (m, 2H), 7.67-7.73 (m, 1H); MS (M+H)$^+$ m/z 336.

Example 79

4-(Octahydro-pyrrolo[3,4-c]pyridin-2-yl)-6,7-dihydro-5H-benzo[6,7]cyclohepta[1,2-d]pyrimidin-2-ylamine Example 79A tert-Butyl 2-(2-amino-6,7-dihydro-5H-benzo[6,7]cyclohepta[1,2-d]pyrimidin-4-yl)octahydro-5H-pyrrolo[3,4-c]pyridine-5-carboxylate The product from Example 68A (40 mg, 0.16 mmol) was mixed with tert-butyl hexahydro-1H-pyrrolo[3,4-c]pyridine-5(6H)-carboxylate (55 mg, 0.24 mmol) and to this was added 2-methoxyethanol (0.65 mL), and N,N-diisopropylethylamine (0.20 mL, 1.2 mmol); the reaction was heated at 115°

C. for 16 hours, cooled, diluted with CH$_2$Cl$_2$ (25 mL) and washed with 1 M NaOH (10 mL). The aqueous layer was extracted with CH$_2$Cl$_2$ (15 mL). The combined organics were dried (MgSO$_4$), filtered, concentrated and chromatographed and eluted with a gradient of 1:0 to 0:1 CH$_2$Cl$_2$:EtOAc to provide the title compound.

Example 79B 4-(Octahydro-pyrrolo[3,4-c]pyridin-2-yl)-6,7-dihydro-5H-benzo[6,7]cyclohepta[1,2-d]pyrimidin-2-ylamine The compound from Example Example 79A (70 mg) was treated with TFA (2 mL), and heated at 60° C. for 1 minute, then concentrated and purified by chromatography on silica gel (eluting step wise with 2, 3.5, 5 and 10% (9:1 MeOH: saturated aqueous NH$_4$OH) in CH$_2$Cl$_2$) to provide the title compound. $^1$H NMR (CDCl$_3$) δ 1.49-1.62 (m, 1H), 1.66-1.78 (m, 1H), 2.10-2.21 (m, 2H), 2.25-2.50 (m, 4H), 2.65 (t, J=6.78 Hz, 2H), 2.68-2.77 (m, 1H), 2.81-3.02 (m, 3H), 3.51-3.65 (m, 2H), 3.67-3.75 (m, 2H), 4.68 (s, 2H), 7.18-7.23 (m, 1H), 7.29-7.38 (m, 2H), 7.74-7.78 (m, 1H); MS (M+H)$^+$ m/z 336.

Example 80

4-(Octahydro-pyrrolo[1,2-a]pyrazin-2-yl)-6,7-dihydro-5H-benzo[6,7]cyclohepta[1,2-d]pyrimidin-2-ylamine The product from Example 68A (40 mg, 0.16 mmol) was treated with octahydro-pyrrolo[1,2-A]pyrazine (31 mg, 0.24 mmol), and to this was added 2-methoxyethanol (0.65 mL) and N,N-diisopropylethylamine (0.20 mL, 1.2 mmol); the reaction was heated at 115° C. for 16 hours, cooled, diluted with CH$_2$Cl$_2$ (25 mL) and washed with 1 M NaOH (10 mL). The aqueous layer was extracted with CH$_2$Cl$_2$ (15 mL). The combined organic layers were dried (MgSO$_4$), filtered, concentrated and purified by chromatography (eluting with 2, 3.5, 5 and 10% (9:1 MeOH:saturated aqueous NH$_4$OH) in CH$_2$Cl$_2$) to provide the title compound. $^1$H NMR (CDCl$_3$) δ 1.43-1.57 (m, 1H), 1.71-1.94 (m, 3H), 2.13-2.29 (m, 4H), 2.30-2.45 (m, 3H), 2.66 (t, J=6.78 Hz, 2H), 2.81 (dd, J=12.21, 10.17 Hz, 1H), 3.06-3.23 (m, 3H), 3.81-3.89 (m, 1H), 3.98 (dt, J=12.29, 2.33 Hz, 1H), 4.76 (s, 2H), 7.20-7.24 (m, 1H), 7.31-7.39 (m, 2H), 7.71-7.76 (m, 1H); MS (M+H)$^+$ m/z 336.

Example 81

4-(3,6-Diaza-bicyclo[3.2.1]oct-6-yl)-6,7-dihydro-5H-benzo[6,7]cyclohepta[1,2-d]pyrimidin-2-ylamine

Example 81A 4-(3-benzyl-3,6-Diaza-bicyclo[3.2.1]oct-6-yl)-6,7-dihydro-5H-benzo[6,7]cyclohepta[1,2-d]pyrimidin-2-ylamine The title compound was prepared using the procedure described in Example 80, substituting 3-benzyl-3,6-diazabicyclo[3.2.1]octane (CAS #286947-23-7) for octahydro-pyrrolo[1,2-A]pyrazine. MS (M+H)$^+$ m/z 412.

Example 81B 4-(3,6-Diaza-bicyclo[3.2.1]oct-6-yl)-6,7-dihydro-5H-benzo[6,7]cyclohepta[1,2-d]pyrimidin-2-ylamine The product from Example 81A (69 mg) in EtOH (1.5 mL) was treated with 20% Pd(OH)$_2$/C (35 mg), stirred under an atmosphere of H$_2$ for 16 hours at room temperature, then at 60° C. for 3 hours, after which the reaction was cooled, diluted with 5:1 CH$_2$Cl$_2$:EtOH, stirred for 20 minutes, filtered, concentrated and purified by chromatography (eluting with 2, 3.5, 5 and 10% (9:1 MeOH:saturated aqueous NH$_4$OH) in CH$_2$Cl$_2$) to provide the title compound. $^1$H NMR (CDCl$_3$) δ 1.83 (d, J=11.19 Hz, 1H), 1.97-2.08 (m, 1H), 2.09-2.20 (m, 2H), 2.24-2.42 (m, 2H), 2.52 (dt, J=14.50, 5.47 Hz, 1H), 2.61-2.75 (m, 3H), 2.84-2.92 (m, 1H), 2.93-3.01 (m, 1H), 3.31-3.38 (m, 1H), 3.63 (d, J=10.17 Hz, 1H), 3.93 (dd, J=9.83, 5.43 Hz, 1H), 4.43 (dd, J=5.26, 3.56 Hz, 1H), 4.65 (s, 2H), 7.18-7.23 (m, 1H), 7.29-7.39 (m, 2H), 7.72-7.79 (m, 1H); MS (M+H)$^+$ m/z 322.

Example 82

4-(2,6-Diaza-bicyclo[3.2.1]oct-2-yl)-6,7-dihydro-5H-benzo[6,7]cyclohepta[1,2-d]pyrimidin-2-ylamine

Example 82A

Benzyl 2-(2-amino-6,7-dihydro-5H-benzo[6,7]cyclohepta[1,2-d]pyrimidin-4-yl)-2,6-diazabicyclo[3.2.1]octane-6-carboxylate The title compound was prepared using the procedure described in Example 79A, substituting benzyl 2,6-diazabicyclo[3.2.1]octane-6-carboxylate (CAS #286946-67-6) for tert-butyl hexahydro-1H-pyrrolo[3,4-c]pyridine-5(6H)-carboxylate.
MS (M+H)$^+$ m/z 456

Example 82B 4-(2,6-Diaza-bicyclo[3.2.1]oct-2-yl)-6,7-dihydro-5H-benzo[6,7]cyclohepta[1,2-d]pyrimidin-2-ylamine The product from Example 82A was treated with EtOH (1.5 mL) and 20% Pd(OH)$_2$/C (15 mg), then stirred at ambient temperature under an H$_2$ atmosphere for 16 hours, then diluted with 5:1 CH$_2$Cl$_2$:EtOH, filtered, concentrated and purified by chromatography (eluting with 2, 3.5, 5 and 10% (9:1 MeOH:saturated aqueous NH$_4$OH) in CH$_2$Cl$_2$) to provide the title compound. $^1$H NMR (CDCl$_3$) δ 1.65-1.86 (m, 2H), 2.01 (d, J=11.53 Hz, 2H), 2.20-2.27 (m, 3H), 2.40-2.49 (m, 1H), 2.62-2.69 (m, 2H), 3.20 (dd, J=11.53, 4.75 Hz, 1H), 3.32 (d, J=12.21 Hz, 1H), 3.46-3.58 (m, 2H), 3.76-3.81 (m, 1H), 4.50 (t, J=4.41 Hz, 1H), 4.71 (s, 2H), 7.20-7.24 (m, 1H), 7.31-7.39 (m, 2H), 7.71-7.75 (m, 1H); MS (M+H)$^+$ m/z 322.

Example 83

N-(4-Piperazin-1-yl-6,7-dihydro-5H-benzo[6,7]cyclohepta[1,2-d]pyrimidin-2-yl)-acetamide

Example 83A tert-Butyl 4-(2-amino-6,7-dihydro-5H-benzo[6,7]cyclohepta[1,2-d]pyrimidin-4-yl)piperazine-1-carboxylate The title compound was prepared using the procedure described in Example 79A, substituting substituting 1-Boc-piperazine for tert-butyl hexahydro-1H-pyrrolo[3,4-c]pyridine-5(6H)-carboxylate. $^1$H NMR (CDCl$_3$) δ 1.49 (s, 9H), 2.16-2.27 (m, 2H), 2.34 (t, J=6.44 Hz, 2H), 2.65 (t, J=6.78 Hz, 2H), 3.34-3.40 (m, 4H), 3.53-3.59 (m, 4H), 4.75 (s, 2H), 7.20-7.25 (m, 1H), 7.32-7.39 (m, 2H), 7.69-7.76 (m, 1H); MS (M+H)+ m/z 396.

Example 83B tert-Butyl 4-[2-(acetylamino)-6,7-dihydro-5H-benzo[6,7]cyclohepta[1,2-d]pyrimidin-4-yl]piperazine-1-carboxylate The product from Example 83A (20 mg, 0.051 mmol) was treated with CHCl$_3$ (0.080 mL), pyridine (0.020 mL, 0.25 mmol), and acetic anhydride (0.006 mL, 0.061 mmol), then heated at 60° C. overnight, cooled and purified by chromatography (eluting with 9:1, 4:1 and 2:1 CH$_2$Cl$_2$:EtOAc) to provide the title compound. MS (M+H)+ m/z 438.

Example 83C

N-(4-Piperazin-1-yl-6,7-dihydro-5H-benzo[6,7]cyclohepta[1,2-d]pyrimidin-2-yl)-acetamide The title compound was prepared using the procedure described in Example 79B, substituting Example 83B for Example 79A. $^1$H NMR (CDCl$_3$) δ 2.25-2.34 (m, 2H), 2.40 (t, J=6.44 Hz, 2H), 2.61 (s, 3H), 2.66 (t, J=6.78 Hz, 2H), 3.03-3.10 (m, 4H), 3.48-3.55 (m, 4H), 7.23-7.29 (m, 1H), 7.35-7.42 (m, 2H), 7.71-7.77 (m, 1H), 7.81 (bs, 1H); MS (M+H)+ m/z 338.

Example 84

N-(4-Piperazin-1-yl-6,7-dihydro-5H-benzo[6,7]cyclohepta[1,2-d]pyrimidin-2-yl)-benzamide The title compound was prepared using the procedure described in Example 83B, substituting benzoyl chloride for acetic anhydride, and then further processing as described in Example 83C. $^1$H NMR (CDCl$_3$) δ 2.25-2.36 (m, 2H), 2.42 (t, J=6.44 Hz, 2H), 2.67 (t, J=6.78 Hz, 2H), 3.04-3.12 (m, 4H), 3.57-3.64 (m, 4H), 7.23-7.29 (m, 1H), 7.36-7.42 (m, 2H), 7.44-7.59 (m, 3H), 7.78-7.84 (m, 1H), 7.89-7.95 (m, 2H), 8.42 (s, 1H); MS (M+H)+ m/z 400.

Example 85

4-(5-Methyl-octahydro-pyrrolo[3,4-c]pyridin-2-yl)-6,7-dihydro-5H-benzo[6,7]cyclohepta[1,2-d]pyrimidin-2-ylamine The product from Example 79B (20.4 mg, 0.061 mmol) was treated with 0.091 M formaldehyde in CH$_3$CN (0.80 mL, 0.073 mmol), diluted with CH$_3$CN (2.24 mL), treated with NaCNBH$_3$ (7.6 mg, 0.12 mmol), treated dropwise with a solution of 0.48 M HCl in CH$_3$CN to keep the reaction at approximately a pH of 6 and then stirred for 1 hour. The mixture was directly purified by chromatography on silica gel (2, 3.5 and 5% (9:1 MeOH:saturated aqueous NH$_4$OH) in CH$_2$Cl$_2$) to provide 9.6 mg of the title compound. The 0.48 M HCl in CH$_3$CN was prepared by diluting 1 mL of concentrated HCl to 25 mL with CH$_3$CN. The 0.091 M formaldehyde solution was prepared by diluting 37% aqueous formaldehyde with CH$_3$CN. $^1$H NMR (CDCl$_3$) δ 1.63-1.76 (m, 1H), 1.76-1.89 (m, 1H), 2.10-2.21 (m, 2H), 2.21-2.36 (m, 3H), 2.28 (s, 3H), 2.37-2.55 (m, 5H), 2.65 (t, J=6.78 Hz, 2H), 3.55 (dd, J=10.85, 5.43 Hz, 1H), 3.62-3.75 (m, 3H), 4.77 (s, 2H), 7.18-7.23 (m, 1H), 7.29-7.39 (m, 2H), 7.75-7.79 (m, 1H); MS (M+H)+ m/z 350.

Example 86

4-(3-Methyl-3,6-diaza-bicyclo[3.2.1]oct-6-yl)-6,7-dihydro-5H-benzo[6,7]cyclohepta[1,2-d]pyrimidin-2-ylamine The title compound was prepared using the procedure described in Example 85, substituting Example 81B for Example 79B. $^1$H NMR (CDCl$_3$) δ 1.55 (d, J=11.19 Hz, 1H), 1.82-1.93 (m, 1H), 2.01 (d, J=10.51 Hz, 1H), 2.08-2.19 (m, 2H), 2.22 (d, J=10.51 Hz, 1H), 2.26 (s, 3H), 2.29-2.37 (m, 1H), 2.43-2.53 (m, 2H), 2.58-2.74 (m, 2H), 2.86 (dd, J=10.00, 3.22 Hz, 1H), 3.36 (dd, J=10.85, 3.73 Hz, 1H), 3.62 (d, J=9.49 Hz, 1H), 3.84 (dd, J=9.32, 5.59 Hz, 1H), 4.56 (t, J=4.07 Hz, 1H), 4.75 (s, 2H), 7.18-7.22 (m, 1H), 7.29-7.39 (m, 2H), 7.73-7.77 (m, 1H); MS (M+H)+ m/z 336.

Example 87

2-Dimethylamino-N-(4-piperazin-1-yl-6,7-dihydro-5H-benzo[6,7]cyclohepta[1,2-d]pyrimidin-2-yl)-acetamide The title compound was prepared using the procedures described in Example 83B and Example 83C, substituting dimethylaminoacetyl chloride hydrochloride for acetic anhydride in Example 83B, and chromatographed (2, 10, 20 and 40% (9:1 MeOH:saturated aqueous NH$_4$OH) in CH$_2$Cl$_2$). $^1$H NMR (CD$_3$OD) δ 2.29-2.48 (m, 4H), 2.68 (t, J=6.44 Hz, 2H), 2.86 (s, 6H), 3.37-3.43 (m, 4H), 3.73-3.78 (m, 4H), 7.31-7.35 (m, 1H), 7.37-7.47 (m, 2H), 7.77-7.81 (m, 1H); MS (M+H)+ m/z 381.

Example 88

2-Methylamino-N-(4-piperazin-1-yl-6,7-dihydro-5H-benzo[6,7]cyclohepta[1,2-d]pyrimidin-2-yl)-acetamide The title compound was prepared using the procedures described in Example 83B and Example 83C, substituting 2,5-dioxopyrrolidin-1-yl 2-(tert-butoxycarbonyl(methyl)amino)acetate (CAS #80621-90-5) for acetic anhydride, and then chromatographed (2, 10, 20 and 40% (9:1 MeOH:saturated aqueous NH$_4$OH) in CH$_2$Cl$_2$). $^1$H NMR (CD$_3$OD) δ 2.29-2.44 (m, 4H), 2.53 (s, 3H), 2.67 (t, J=6.44 Hz, 2H), 2.99-3.04 (m, 4H), 3.52-3.57 (m, 4H), 3.91 (s, 2H), 7.29-7.33 (m, 1H), 7.35-7.45 (m, 2H), 7.75-7.79 (m, 1H); MS (M+H)+ m/z 367.

Example 89

2-Amino-N-(4-piperazin-1-yl-6,7-dihydro-5H-benzo[6,7]cyclohepta[1,2-d]pyrimidin-2-yl)-acetamide The title compound was prepared using the procedures described in Example 83B and Example 83C, substituting 2,5-dioxopyrrolidin-1-yl 2-(tert-butoxycarbonylamino)acetate (CAS #3392-07-2) for acetic anhydride, and chromatographed (2, 10, 20 and 40% (9:1 MeOH:saturated aqueous NH$_4$OH) in CH$_2$Cl$_2$). $^1$H NMR (CD$_3$OD) δ 2.28-2.44 (m, 4H), 2.67 (t, J=6.44 Hz, 2H), 2.99-3.05 (m, 4H), 3.52-3.57

(m, 4H), 3.99 (bs, 2H), 7.28-7.33 (m, 1H), 7.34-7.45 (m, 2H), 7.75-7.79 (m, 1H); MS (M+H)+ m/z 353.

Example 90

1-Methyl-3-(4-piperazin-1-yl-6,7-dihydro-5H-benzo[6,7]cyclohepta[1,2-d]pyrimidin-2-yl)-urea A vial containing product from Example 83A (50 mg, 0.126 mmol) in chloroform (1264 μl) was treated with isocyanatomethane (22.54 μl, 0.379 mmol), stirred overnight at 80° C., cooled, treated with more isocyanatomethane (0.05 mL), stirred at 80° C. overnight, cooled and directly purified by chromatography on silica gel eluting with 9:1, 2:1 and 1:1 EtOAc:CH$_2$Cl$_2$ to provide the Boc protected intermediate which was further process as described in Example 83C and purified by chromatography on silica gel eluting with 2 and then 10% (9:1 MeOH:concentrated NH$_4$OH) in CH$_2$Cl$_2$ to provide the title product. $^1$H NMR (CDCl$_3$) δ 2.23-2.41 (m, 4H), 2.67 (t, J=6.61 Hz, 2H), 2.93 (d, J=4.75 Hz, 3H), 3.02-3.07 (m, 4H), 3.44-3.49 (m, 4H), 7.13 (bs, 1H), 7.26-7.30 (m, 1H), 7.37-7.44 (m, 2H), 7.67-7.71 (m, 1H), 9.23 (bq, J=4.41 Hz, 1H); MS (M+H)+ m/z at 353.

Example 91

4-Amino-N-(4-piperazin-1-yl-6,7-dihydro-5H-benzo[6,7]cyclohepta[1,2-d]pyrimidin-2-yl)-butyramide

Example 91A

2,5-dioxopyrrolidin-1-yl 4-(tert-butoxycarbonylamino)butanoate

A 100 mL round bottomed flask containing 4-(tert-butoxycarbonylamino)butanoic acid (1 g, 4.92 mmol) was treated with N-hydroxysuccinimide (0.680 g, 5.90 mmol), treated with DMF (8 ml), cooled to 0° C., treated with N-(3-dimethylaminopropyl)-N'-ethylcarbodiimide hydrochloride (1.226 g, 6.40 mmol), stirred at ambient temperature for 2 hours, diluted with Et$_2$O (100 mL), washed with H$_2$O (2×25 mL), dried (MgSO$_4$), filtered and concentrated to provide the title compound. $^1$H NMR (CDCl$_3$) δ 1.44 (s, 9H), 1.90-2.00 (m, 2H), 2.66 (t, J=7.54 Hz, 2H), 2.84 (s, 4H), 3.15-3.28 (m, 2H), 4.73 (bs, 1H).

Example 91B

4-Amino-N-(4-piperazin-1-yl-6,7-dihydro-5H-benzo[6,7]cyclohepta[1,2-d]pyrimidin-2-yl)-butyramide The title compound was prepared using the procedures described in Example 83B and Example 83C, substituting the product from Example 91A for acetic anhydride, and chromatographed (2, 10, 20 and 40% (9:1 MeOH:saturated aqueous NH$_4$OH) in CH$_2$Cl$_2$). $^1$H NMR (CD$_3$OD) δ 1.97-2.08 (m, 2H), 2.30-2.46 (m, 4H), 2.68 (t, J=6.78 Hz, 2H), 2.83 (t, J=6.95 Hz, 2H), 3.03 (t, J=7.80 Hz, 2H), 3.12-3.17 (m, 4H), 3.59-3.65 (m, 4H), 7.30-7.34 (m, 1H), 7.35-7.46 (m, 2H), 7.76-7.80 (m, 1H); MS (M+H)+ m/z 381.

Example 92

6-(2-pyridin-3-ylmethylamino-6,7-dihydro-5H-benzo[6,7]cyclohepta[1,2-d]pyrimidin-4-yl)octahydro-1H-pyrrolo[3,4-b]pyridine

Example 92A tert-butyl 6-(2-chloro-6,7-dihydro-5H-benzo[6,7]cyclohepta[1,2-d]pyrimidin-4-yl)octahydro-1H-pyrrolo[3,4-b]pyridine-1-carboxylate Example 103B (945.8 mg, 3.57 mmol) in EtOH (25 mL) was treated with triethylamine (1.75 mL), cooled to 0° C., treated with a solution of tert-butyl octahydro-1H-pyrrolo[3,4-b]pyridine-1-carboxylate (888 mg, 3.92 mmol) in EtOH (7 mL) and triethylamine (1.75 mL), stirred at room temperature overnight, concentrated to near dryness and partitioned between 1 M NaOH (25 mL) and CH$_2$Cl$_2$ (50 mL). The layers were separated and the aqueous was extracted with CH$_2$Cl$_2$ (2×50 mL). The combined CH$_2$Cl$_2$ layers were dried (MgSO$_4$), filtered, concentrated and purified by chromatography on silica gel eluting with CH$_2$Cl$_2$:EtOAc:hexane (9:1: 20, 9:1:10, 9:1:5 and 9:1:0) to provide 2 products, a faster moving isomer and a slower moving isomer. The slower moving isomer is the title compound. $^1$H NMR (CDCl$_3$) δ 1.34-1.45 (m, 1H), 1.49 (s, 9H), 1.69-1.85 (m, 2H), 2.11-2.33 (m, 5H), 2.51-2.74 (m, 3H), 2.77-2.90 (m, 1H), 3.45 (d, J=11.2 Hz, 1H), 3.62-3.70 (m, 1H), 3.75 (t, J=10.2 Hz, 1H), 3.93 (dd, J=11.2, 5.8 Hz, 1H), 4.00-4.08 (m, 1H), 7.20-7.26 (m, 2H), 7.34-7.42 (m, 2H), 7.79-7.86 (m, 1H); MS (M+H)+ m/z 455.

Example 92B

6-(2-pyridin-3-ylmethylamino-6,7-dihydro-5H-benzo[6,7]cyclohepta[1,2-d]pyrimidin-4-yl)octahydro-1H-pyrrolo[3,4-b]pyridine A tapered microwave vial was charged with a stirbar, Example 92A (20 mg, 0.043 mmol), pyridin-3-ylmethanamine (14 mg, 0.13 mmol) and ethylene glycol (0.750 mL). The vial was capped and heated at 160° C. for 2400 seconds. The Boc group came off during the reaction. The solvent was evaporated with a stream of hot nitrogen and then redissolved in DMSO/MeOH. The product was purified by preparative HPLC on a Waters Nova-Pak® HR C18 6 um 60 Å Prep-Pak® cartridge column (25 mm×100 mm) eluting with a gradient of (A) acetonitrile and (B) 0.1% trifluoroacetic acid in water to provide the title compound as the tri-trifluoroacetic acid salt. MS (M+H)+ m/z 427.

Example 93

3-Amino-N-(4-piperazin-1-yl-6,7-dihydro-5H-benzo[6,7]cyclohepta[1,2-d]pyrimidin-2-yl)-propionamide The product from Example 83A (50 mg, 0.126 mmol) was processed as described in Example 83B substituting 2,5-dioxopyrrolidin-1-yl 3-(tert-butoxycarbonylamino)propanoate (CAS #32703-87-0) for acetic anhydride and then further processed as described in Example 83C and purified by chromatography on silica gel (eluting with 2, 10, 20 and 40% (9:1 MeOH:saturated aqueous NH$_4$OH) in CH$_2$Cl$_2$) to provide the title compound. $^1$H NMR (CD$_3$OD) δ 2.29-2.44 (m, 4H), 2.67 (t, J=6.61 Hz, 2H), 2.94-3.05 (m, 6H), 3.14 (t, J=5.93 Hz, 2H), 3.50-3.55 (m, 4H), 7.28-7.33 (m, 1H), 7.34-7.44 (m, 2H), 7.76-7.80 (m, 1H); MS (M+H)+ m/z 367.

Example 94

4-[1,4,7]Triazonan-1-yl-6,7-dihydro-5H-benzo[6,7]cyclohepta[1,2-d]pyrimidin-2-ylamine The product from Example 68A (52 mg, 0.212 mmol) was treated with 1,4,7-triazonane trihydrochloride (202 mg, 0.847 mmol), treated with Hunig's base (554 µl, 3.17 mmol), treated with 2-methoxyethanol (2116 µl), stirred at 110° C. for 19 hours, cooled, diluted with Et$_2$O (25 mL), washed with 0.1 M NaOH (2×10 mL), washed with brine, dried (MgSO$_4$), filtered, concentrated and purified by chromatography on silica gel (eluting with 2, 10 and 50% (9:1 MeOH:concentrated NH$_4$OH) in CH$_2$Cl$_2$) to provide the title compound. $^1$H NMR (CD$_3$OD) δ 2.08-2.24 (m, 2H), 2.40 (t, J=6.94 Hz, 2H), 2.67 (t, J=6.74 Hz, 2H), 2.94 (s, 4H), 3.10-3.16 (m, 4H), 3.71-3.77 (m, 4H), 7.24-7.29 (m, 1H), 7.32-7.41 (m, 2H), 7.63-7.68 (m, 1H); MS (M+H)+ m/z 339.

Example 95

N,N-Dimethyl-N'-(4-piperazin-1-yl-6,7-dihydro-5H-benzo[6,7]cyclohepta[1,2-d]pyrimidin-2-yl)-ethane-1,2-diamine The product from Example 83A (25 mg, 0.063 mmol) under nitrogen was treated with DMF (630 µl), treated with a 60% dispersion of sodium hydride (7.6 mg, 0.19 mmol), stirred at ambient temperature for 30 minutes, treated with 3-chloro-N,N-dimethylpropan-1-amine hydrochloride (10 mg, 0.063 mmol), stirred over three days at ambient temperature, diluted with ether, washed with water (2×), washed with brine, dried (MgSO$_4$), filtered, concentrated and purified by chromatography on silica gel (eluting with 2, 3.5, 5 and 10% (9:1 MeOH:concentrated NH$_4$OH) in CH$_2$Cl$_2$) to provide the Boc-protected intermediate. The Boc-protected intermediate further processed as described in Example 83C and purified by chromatography on silica gel (eluting with 2, 3.5, 5, 10 and 20% (9:1 MeOH:concentrated NH$_4$OH) in CH$_2$Cl$_2$) to provide the title product. MS (M+H)+ m/z 367.

Example 96

4-(Octahydro-pyrrolo[3,4-b]pyridin-6-yl)-5,6-dihydro-7-thia-1,3-diaza-dibenzo[a,c]cyclohepten-2-ylamine The title compound was prepared using the procedure outlined in Example 30, substituting Example 33D for Example 29D, and substituting t-butyloctahydro-1H-pyrrolo[3,4-b]pyridine-1-carboxylate (CAS #159877-36-8) for piperazine-1-carboxylic acid tert-butyl ester. $^1$H NMR (CDCl$_3$) δ 1.44-1.81 (m, 7H), 2.24-2.37 (m, 1H), 2.40-2.54 (m, 1H), 2.62-2.73 (m, 1H), 2.91 (dt, J=15.6, 5.1 Hz, 1H), 2.99-3.08 (m, 1H), 3.17-3.29 (m, 1H), 3.39 (t, J=3.9 Hz, 1H), 3.46-3.62 (m, 3H), 3.80-3.93 (m, 2H), 4.67 (s, 2H), 7.33 (dt, J=7.5, 1.7 Hz, 1H), 7.46 (dt, J=7.5, 1.5 Hz, 1H), 7.59 (dd, J=7.6, 1.2 Hz, 1H), 7.73 (dd, J=7.5, 1.9 Hz, 1H); MS (M+H)+ m/z 354.

Example 97

4-((R)-3-Methylamino-pyrrolidin-1-yl)-6,7,9,10,11,12-hexahydro-5H-1,3-diaza-benzo[3,4]cyclohepta[1,2-b]naphthalen-2-ylamine Example 97A methyl 6-oxo-2,3,4,6,7,8,9,10-octahydro-1H-cyclohepta[b]naphthalene-7-carboxylate 2,3,4,6,7,8,9,10-Octahydro-1H-cyclohepta[b]naphthalen-6-one (prepared as described in Sambaiah, T.; et al. J. Org. Chem. 64(10), 1999, 3663-3670) was processed as described in Example 59A to provide the title compound. MS (M+H)+ m/z 273 (100%), (M+NH$_4$)+ m/z 290 (20%).

Example 97B

2-Amino-6,7,9,10,11,12-hexahydro-5H-naphtho[2',3':6,7]cyclohepta[1,2-d]pyrimidin-4-ol The product from Example Example 97A was processed as described in Example 59B to provide the title compound. $^1$H NMR (DMSO-d6) δ 1.68-1.80 (m, 4H), 1.89-2.01 (m, 2H), 2.14 (t, J=6.9 Hz, 2H), 2.42 (t, J=6.7 Hz, 2H), 2.66-2.77 (m, 4H), 6.41 (s, 2H), 6.92 (s, 1H), 7.24 (s, 1H), 10.93 (s, 1H); MS (M+H)+ m/z at 282.

Example 97C

4-Chloro-6,7,9,10,11,12-hexahydro-5H-naphtho[2',3':6,7]cyclohepta[1,2-d]pyrimidin-2-amine The product from Example 97B was processed as described in Example 68A to provide the title compound. $^1$H NMR (CDCl$_3$) δ 1.78-1.84 (m, 4H), 2.08-2.18 (m, 2H), 2.50 (t, J=7.1 Hz, 2H), 2.57 (t, J=7.0 Hz, 2H), 2.76-2.84 (m, 4H), 5.06 (bs, 2H), 6.93 (s, 1H), 7.36 (s, 1H); MS (M+H)+ m/z 300.

Example 97D 4-((R)-3-Methylamino-pyrrolidin-1-yl)-6,7,9,10,11,12-hexahydro-5H-1,3-diaza-benzo[3,4]cyclohepta[1,2-b]naphthalen-2-ylamine The title compound was prepared using the procedure outlined in Example 30, substituting Example 97C for Example 29D, and substituting Example 1E for piperazine-1-carboxylic acid tert-butyl ester. $^1$H NMR (CDCl$_3$) δ 1.76-1.83 (m, 5H), 2.06-2.18 (m, 3H), 2.33-2.41 (m, 2H), 2.49 (s, 3H), 2.57 (t, J=6.8 Hz, 2H), 2.73-2.85 (m, 4H), 3.26-3.35 (m, 1H), 3.44 (dd, J=10.7, 4.9 Hz, 1H), 3.60-3.69 (m, 1H), 3.72-3.84 (m, 2H), 4.66 (s, 2H), 6.89 (s, 1H), 7.47 (s, 1H); MS (M+H)+ m/z at 364.

Example 98

4-(Octahydro-pyrrolo[3,4-b]pyridin-6-yl)-6,7,9,10,11,12-hexahydro-5H-1,3-diaza-benzo[3,4]cyclohepta[1,2-b]naphthalen-2-ylamine The title compound was prepared using the procedure outlined in Example 30, substituting Example 97C for Example 29D, and substituting t-butyl octahydro-1H-pyrrolo[3,4-b]pyridine-1-carboxylate (CAS #159877-36-8) for piperazine-1-carboxylic acid tert-butyl ester. $^1$H NMR (CDCl$_3$) δ 1.53-

1.67 (m, 1H), 1.73-1.84 (m, 6H), 2.06-2.22 (m, 3H), 2.23-2.35 (m, 1H), 2.52-2.86 (m, 9H), 3.00-3.09 (m, 1H), 3.34-3.55 (m, 3H), 3.81-3.94 (m, 2H), 4.61 (s, 2H), 6.89 (s, 1H), 7.46 (s, 1H); MS (M+H)$^+$ m/z 390.

Example 99

4-Piperazin-1-yl-6,7,9,10,11,12-hexahydro-5H-1,3-diaza-benzo[3,4]cyclohepta[1,2b]naphthalen-2-ylamine

The title compound was prepared using the procedure outlined in Example 30, substituting Example 97C for Example 29D. $^1$H NMR (CDCl$_3$) δ 1.76-1.84 (m, 4H), 2.12-2.23 (m, 2H), 2.35 (t, J=6.6 Hz, 2H), 2.58 (t, J=6.6 Hz, 2H), 2.63-2.69 (m, 1H), 2.74-2.86 (m, 4H), 3.00-3.05 (m, 3H), 3.39-3.46 (m, 4H), 4.92 (s, 2H), 6.92 (s, 1H), 7.46 (s, 1H); MS (M+H)$^+$ m/z 350.

Example 100

9-Iodo-4-((R)-3-methylamino-pyrrolidin-1-yl)-5,6-dihydro-7-oxa-1,3-diaza-dibenzo[a,c]cyclohepten-2-ylamine

Example 100A

2-Amino-9-iodo-5,6-dihydro[1]benzoxepino[5,4-d]pyrimidin-4-ol

The title compound was prepared using the procedures outlined in Examples 45A, 45B and 45C, substituting methyl 2-hydroxy-4-iodobenzoate for methyl 5-chloro-2-hydroxybenzoate in Example 45A. $^1$H NMR (DMSO-d6) δ 2.60 (t, J=5.8 Hz, 2H), 4.36 (t, J=5.8 Hz, 2H), 6.46 (s, 2H), 7.42 (d, J=1.7 Hz, 1H), 7.52 (dd, J=8.5, 1.7 Hz, 1H), 7.65 (d, J=8.5 Hz, 1H), 10.96 (s, 1H); MS (M+H)$^+$ m/z at 356.

Example 100B

4-Chloro-9-iodo-5,6-dihydro[1]benzoxepino[5,4-d]pyrimidin-2-amine

The title compound was prepared using the procedures outlined in Example 68A, substituting Example 100A for Example 59B. $^1$H NMR (DMSO-d6) δ 2.84 (t, J=5.9 Hz, 2H), 4.44 (t, J=5.9 Hz, 2H), 7.07 (s, 2H), 7.52 (d, J=1.6 Hz, 1H), 7.59 (d, J=8.3 Hz, 1H), 7.64 (dd, J=8.3, 1.6 Hz, 1H); MS (M+H)$^+$ m/z at 374.

Example 100C

9-Iodo-4-((R)-3-methylamino-pyrrolidin-1-yl)-5,6-dihydro-7-oxa-1,3-diaza-dibenzo[a,c]cyclohepten-2-ylamine

The title compound was prepared using the procedure outlined in Example 30, substituting Example 100B for Example 29D, and substituting Example 1E for piperazine-1-carboxylic acid tert-butyl ester. $^1$H NMR (CD$_3$OD) δ 1.80-1.93 (m, 1H), 2.12-2.24 (m, 1H), 2.43 (s, 3H), 2.73 (t, J=5.9 Hz, 2H), 3.48 (dd, J=10.8, 5.1 Hz, 1H), 3.62-3.85 (m, 3H), 4.54 (t, J=5.9 Hz, 2H), 7.46 (d, J=8.1 Hz, 1H), 7.48 (d, J=1.7 Hz, 1H), 7.60 (dd, J=8.1, 1.7 Hz, 1H); MS (M+H)$^+$ m/z at 438.

Example 101

9-Iodo-4-piperazin-1-yl-5,6-dihydro-7-oxa-1,3-diaza-dibenzo[a,c]cyclohepten-2-ylamine

The title compound was prepared using the procedure outlined in Example 30, substituting Example 100B for Example 29D. $^1$H NMR (CD$_3$OD) δ 2.68 (t, J=5.9 Hz, 2H), 2.92-2.98 (m, 4H), 3.32-3.36 (m, 4H), 4.53 (t, J=5.9 Hz, 2H), 7.47 (d, J=1.7 Hz, 1H), 7.51 (d, J=8.5 Hz, 1H), 7.57 (dd, J=8.1, 1.7 Hz, 1H); MS (M+H)$^+$ m/z at 424.

Example 102

9-Iodo-4-octahydro-pyrrolo[3,4-b]pyridin-6-yl-5,6-dihydro-7-oxa-1,3-diaza-dibenzo[a,c]cyclohepten-2-ylamine

Example 102A tert-Butyl 6-(2-amino-9-iodo-5,6-dihydro[1]benzoxepino[5,4-d]pyrimidin-4-yl)octahydro-1 H-pyrrolo[3,4-b]pyridine-1-carboxylate

The title compound was prepared using the procedure outlined in Example 30A, substituting Example 100B for Example 29D, and substituting t-butyl octahydro-1H-pyrrolo[3,4-b]pyridine-1-carboxylate (CAS #159877-36-8) for piperazine-1-carboxylic acid tert-butyl ester. $^1$H NMR (CDCl$_3$) δ 1.25-1.62 (m, 3H), 1.48 (s, 9H), 1.68-1.80 (m, 2H), 2.14-2.26 (m, 1H), 2.56-2.68 (m, 1H), 2.75-2.88 (m, 2H), 3.32 (d, J=10.7 Hz, 1H), 3.51 (t, J=9.3 Hz, 1H), 3.70 (t, J=10.1 Hz, 1H), 3.85 (dd, J=10.7, 5.6 Hz, 1H), 3.98-4.09 (m, 1H), 4.44-4.61 (m, 2H), 4.64-4.81 (m, 1H), 4.68 (s, 2H), 7.47 (d, J=1.6 Hz, 1H), 7.56 (dd, J=7.9, 1.6 Hz, 1H), 7.60 (d, J=8.3 Hz, 1H); MS (M+H)$^+$ m/z at 564.

Example 102B

9-Iodo-4-octahydro-pyrrolo[3,4-b]pyridin-6-yl-5,6-dihydro-7-oxa-1,3-diaza-dibenzo[a,c]cyclohpten-2-ylamine

The title compound was prepared using the procedure outlined in Example 30B, substituting Example 102A for Example 30A. $^1$H NMR (CD$_3$OD) δ 1.44-1.55 (m, 1H), 1.58-1.83 (m, 3H), 2.30-2.43 (m, 1H), 2.56-2.68 (m, 2H), 2.84-3.00 (m, 2H), 3.32-3.39 (m, 1H), 3.46-3.60 (m, 2H), 3.80-3.89 (m, 2H), 4.46-4.64 (m, 2H), 7.45 (d, J=7.9 Hz, 1H), 7.47 (d, J=1.6 Hz, 1H), 7.60 (dd, J=8.1, 1.8 Hz, 1H); MS (M+H)$^+$ m/z at 464.

Example 103

2,4-Di-piperazin-1-yl-6,7-dihydro-5H-benzo[6,7]cyclohepta[1,2-d]pyrimidine

Example 103A

6,7-Dihydro-1H-benzo[6,7]cyclohepta[1,2-d]pyrimidine-2,4(3H,5H)-dione

In a 150 mL beaker, urea (32 g, 533 mmol) (previously pulverized in a mortar and pestle) was treated with Example 59A (4.3 g, 19.70 mmol) and the mixture was manually stirred with a spatula to thoroughly mix the reaction components. While manually stirring with a spatula, the reaction was heated at increasing temperatures of 160° C. for 5 minutes, 170° C. for 5 minutes, 180° C. for 20 minutes, and then 190° C. for 30 minutes, then allowed to cool. When the reaction was approximately half solidified on cooling, water (50 mL) was added and mixture was stirred with a spatula. After stirring for about 10 minutes, more water (50 mL) and a magnetic stir bar were added. The mixture was stirred until all of the urea had dissolved from the bottom of the flask (30 minutes) and then stirred for an additional 15 minutes. The solid was collected by filtration, washed with water and dried overnight under house vacuum with heating in a vacuum oven to obtain the title compound.

Example 103B 2,4-dichloro-6,7-dihydro-5H-benzo[6,7]cyclohepta[1,2-d]pyrimidine The product from Example 103A (4.14 g, 18.14 mmol) was treated with phosphoryl trichloride (40 ml, 430 mmol), stirred at 100° C. for 1 hour, cooled, poured into a flask containing ice and water (400 mL), swirled for 5 minutes (became hot), allowed to stand for 5 minutes, cooled in an ice bath, allowed to stand at ambient temperature for 15 minutes and the solid was collected by filtration and washed with water. The solid was dissolved in $CH_2Cl_2$ (50 mL) and transferred to a separatory funnel to remove the water/emulsion (~5 mL) present. The organic and aqueous layers were separated, and the residual water/emulsion was extracted with $CH_2Cl_2$. The combined $CH_2Cl_2$ layers were dried ($MgSO_4$), filtered, and concentrated to provide the title compound. $^1$H NMR ($CDCl_3$) δ 2.25-2.36 (m, 2H), 2.58 (t, J=7.3 Hz, 2H), 2.69 (t, J=7.1 Hz, 2H), 7.27-7.31 (m, 1H), 7.39-7.50 (m, 2H), 7.74-7.78 (m, 1H); MS (M+H)$^+$ m/z 265.

Example 103C di-tert-butyl 4,4'-(6,7-dihydro-5H-benzo[6,7]cyclohepta[1,2-d]pyrimidin-2,4-diyl)dipiperazine-1-carboxylate The product from Example 103B (33.4 mg, 0.126 mmol) was treated with tert-butyl piperazine-1-carboxylate (94 mg, 0.504 mmol) and Hunig's base (diisopropylethylamine, 154 µl, 0.882 mmol) in 2-methoxyethanol (504 µl) at 110° C. overnight, cooled, treated with 1 M NaOH (5 mL) and extracted with $CH_2Cl_2$ (2×25 mL). The combined $CH_2Cl_2$ layers were dried ($MgSO_4$), filtered, concentrated and purified by chromatography on silica gel eluting with (1:0, 9:1 and 2:1 $CH_2Cl_2$:EtOAc) to provide the title compound. $^1$H NMR ($CDCl_3$) δ 1.49 (s, 18H), 2.16-2.28 (m, 2H), 2.34 (t, J=6.5 Hz, 2H), 2.65 (t, J=6.5 Hz, 2H), 3.35-3.42 (m, 4H), 3.48-3.53 (m, 4H), 3.54-3.60 (m, 4H), 3.78-3.85 (m, 4H), 7.20-7.24 (m, 1H), 7.32-7.38 (m, 2H), 7.76-7.81 (m, 1H); MS (M+H)$^+$ m/z at 565.

Example 103D 2,4-Di-piperazin-1-yl-6,7-dihydro-5H-benzo[6,7]cyclohepta[1,2-d]pyrimidine The product from Example 103C (71 mg, 0.13 mmol) was treated with TFA (2 mL), heated at 60° C. for 1 minute, concentrated, dissolved in 1:1 MeOH: $CH_2Cl_2$ (2 mL), diluted with $CH_2Cl_2$ (25 mL), washed with 1 M NaOH (10 mL) and the layers were separated. The aqueous layer was extracted with $CH_2Cl_2$ (25 mL) and the combined organic layers were dried ($MgSO_4$), filtered, concentrated and purified by chromatography on silica gel eluting with 10 and 40% (9:1 MeOH:concentrated $NH_4OH$) in $CH_2Cl_2$ to provide the title compound. $^1$H NMR ($CD_3OD$) δ 2.24-2.40 (m, 4H), 2.65 (t, J=6.5 Hz, 2H), 3.27-3.32 (m, 4H), 3.37-3.42 (m, 4H), 3.66-3.70 (m, 4H), 4.07-4.12 (m, 4H), 7.27-7.31 (m, 1H), 7.32-7.43 (m, 2H), 7.72-7.76 (m, 1H); MS (M+H)$^+$ m/z at 365.

Example 104

2-Amino-4-octahydro-pyrrolo[3,4-b]pyridin-6-yl-5,6-dihydro-7-oxa-1,3-diaza-dibenzo[a,c]cyclohepten-9-carbonitrile

Example 104A tert-butyl 6-(2-amino-9-cyano-5,6-dihydro[1]benzoxepino[5,4-d]pyrimidin-4-yl)octahydro-1H-pyrrolo[3,4-b]pyridine-1-carboxylate The product from Example 102A (24.7 mg, 0.044 mmol) was treated with copper(I) cyanide (27.5 mg, 0.307 mmol) in DMF (0.5 mL) heated at 110° C. overnight, cooled, diluted with $Et_2O$ (25 mL), washed with water (2×20 mL), washed with brine, dried ($MgSO_4$), filtered, concentrated and purified by chromatography on silica gel eluting with hexane:EtOAc (2:1, 1:1, 4:1) to provide the title compound. MS (M+H)$^+$ m/z 463.

Example 104B

2-Amino-4-octahydro-pyrrolo[3,4-b]pyridin-6-yl-5,6-dihydro-7-oxa-1,3-diaza-dibenzo[a,c]cyclohepten-9-carbonitrile The title compound was prepared using the procedure outlined in Example 30B, substituting Example 104A for Example 30A. $^1$H NMR ($CDCl_3$) δ 0.78-0.93 (m, 2H), 1.43-1.86 (m, 6H), 2.32-2.45 (m, 1H), 2.63-2.76 (m, 3H), 2.90 (dt, J=16.1, 4.6, 4.4 Hz, 1H), 3.06-3.16 (m, 1H), 3.41-3.62 (m, 4H), 3.85 (dd, J=11.5, 4.8 Hz, 1H), 3.88-3.95 (m, 1H), 4.48-4.67 (m, 2H), 4.78 (s, 2H), 7.37 (d, J=1.6 Hz, 1H), 7.49 (dd, J=7.9, 1.6 Hz, 1H), 7.98 (d, J=7.9 Hz, 1H); MS (M+H)$^+$ m/z 363.

Example 105

4-Octahydro-pyrrolo[3,4-b]pyridin-6-yl-9-phenyl-5,6-dihydro-7-oxa-1,3-diaza-dibenzo[a,c]cyclohepten-2-ylamine

Example 105A tert-Butyl 6-(2-amino-9-phenyl-5,6-dihydro[1]benzoxepino[5,4-d]pyrimidin-4-yl)octahydro-1H-pyrrolo[3,4-b]pyridine-1-carboxylate The product from Example 102A (32 mg, 0.057 mmol) was treated with phenylboronic acid (10 mg, 0.085 mmol), $Pd(PPh)_4$ (6.6 mg, 5.7 µmol), and 2 M $Na_2CO_3$ (63 µl, 0.12 mmol) in 1,2-dimethoxyethane (170 µl), heated overnight at 90° C., cooled, diluted with $CH_2Cl_2$ (25 mL) and washed with 1 M NaOH (10 mL). The layers were separated and the aqueous was extracted with CH$_2$Cl$_2$ (25 mL). The combined CH$_2$Cl$_2$ layers were dried (MgSO$_4$), filtered, concentrated and purified by chromatography on silica gel eluting with a gradient of 5:1 to 1:2 hexane:EtOAc to provide the title compound. $^1$H NMR (CDCl$_3$) δ 1.32-1.46 (m, 2H), 1.49 (s, 9H), 1.52-1.82 (m, 3H), 2.15-2.28 (m, 1H), 2.64-2.89 (m, 3H), 3.35 (d, J=10.5 Hz, 1H), 3.54 (t, J=9.2 Hz, 1H), 3.72 (t, J=10.0 Hz, 1H), 3.87 (dd, J=10.7, 5.6 Hz, 1H), 4.00-4.09 (m, 1H), 4.72 (s, 3H), 4.72 (s, 2H), 7.32-7.40 (m, 1H), 7.41-7.50 (m, 3H), 7.61-7.66 (m, 2H), 8.14 (d, J=8.1 Hz, 1H); MS (M+H)$^+$ m/z at 514.

Example 105B

4-Octahydro-pyrrolo[3,4-b]pyridin-6-yl-9-phenyl-5,6-dihydro-7-oxa-1,3-diaza-dibenzo[a,c]cyclohepten-2-ylamine The title compound was prepared using the procedure outlined in Example 30B, substituting Example 105A for Example 30A. $^1$H NMR (CDCl$_3$) δ 1.46-1.57 (m, 1H), 1.63-1.84 (m, 2H), 2.25-2.36 (m, 1H), 2.63-2.80 (m, 2H), 2.89 (dt, J=15.8, 4.4, 4.2 Hz, 1H), 3.00-3.08 (m, 1H), 3.36-3.55 (m, 3H), 3.81-3.94 (m, 2H), 4.51-4.68 (m, 3H), 4.68 (s, 2H), 7.34 (d, J=1.7 Hz, 1H), 7.35-7.40 (m, 1H), 7.41-7.50 (m, 3H), 7.61-7.66 (m, 2H), 7.93 (d, J=7.8 Hz, 1H); MS (M+H)$^+$ m/z 414.

Example 106

4-Octahydro-pyrrolo[3,4-b]pyridin-6-yl-9-pyridin-3-yl-5,6-dihydro-7-oxa-1,3-diaza-dibenzo[a,c]cyclohepten-2-ylamine The title compound was prepared using the procedure outlined in Example 105, substituting pyridin-3-ylboronic acid for phenylboronic acid. $^1$H NMR (CDCl$_3$) δ 1.47-1.57 (m, 1H), 1.64-1.84 (m, 3H), 2.25-2.37 (m, 1H), 2.63-2.80 (m, 2H), 2.90 (dt, J=15.8, 4.2, 4.1 Hz, 1H), 3.00-3.09 (m, 1H), 3.36-3.55 (m, 3H), 3.81-3.94 (m, 2H), 4.52-4.67 (m, 2H), 4.68 (s, 2H), 7.33 (d, J=1.7 Hz, 1H), 7.37 (dd, J=8.0, 4.9 Hz, 1H), 7.46 (dd, J=8.0, 1.5 Hz, 1H), 7.91 (dd, J=8.1, 2.0 Hz, 1H), 7.99 (d, J=8.1 Hz, 1H), 8.61 (dd, J=4.9, 1.5 Hz, 1H), 8.89 (d, J=2.4 Hz, 1H); MS (M+H)$^+$ m/z 415.

Example 107

4-((R)-3-Methylamino-pyrrolidin-1-yl)-6,7-dihydro-5-thia-1,3-diaza-dibenzo[a,c]cyclohepten-2-ylamine Example 107A 2-(Phenethylthio)acetic acid In a 1 L flask, solid sodium hydroxide (10.50 g, 0.263 mol) was dissolved in MeOH (150 ml), and then slowly combined with 2-mercaptoacetic acid (11.51 g, 0.125 mol). The mixture was then treated in portions with (2-chloroethyl)benzene (19.33 g, 0.138 mol), heated at reflux for 10 hours, stirred for 6 hours at ambient temperature, concentrated to dryness on a rotovap, treated with water (500 mL) and extracted with Et$_2$O (2×150 mL). These Et$_2$O extractions were discarded. The aqueous layer was acidified to pH ~2 with concentrated HCl and extracted with Et$_2$O (2×150 mL). These Et$_2$O extractions were combined, washed with brine, dried (MgSO$_4$), filtered and concentrated to provide the title compound. $^1$H NMR (CDCl$_3$) δ 2.93 (s, 4H), 3.25 (s, 2H), 7.17-7.34 (m, 5H); MS (M+NH$_4$)$^+$ m/z 214.

Example 107B 2-(Phenethylthio)acetyl chloride

A flask containing the product from Example 107A (10 g, 51.0 mmol) was treated with SOCl$_2$ (18.59 ml, 255 mmol), heated at 55° C. overnight under nitrogen, cooled and concentrated to provide the desired product. $^1$H NMR (CDCl$_3$) δ 2.91 (s, 4H), 3.64 (s, 2H), 7.17-7.35 (m, 5H).

Example 107C 4,5-Dihydrobenzo[d]thiepin-1(2H)-one

A suspension of aluminum chloride (12.21 g, 92 mmol) in CH$_2$Cl$_2$ (200 mL) was treated dropwise with a solution of Example 107B (9.83 g, 45.8 mmol) in CH$_2$Cl$_2$ (100 mL) over 35 minutes, stirred at ambient temperature for 30 minutes, poured into a flask containing ice water (~400 mL) and transferred to a separatory funnel using ~50 mL CH$_2$Cl$_2$. The layers were separated and the aqueous was extracted with CH$_2$Cl$_2$ (100 mL). The combined CH$_2$Cl$_2$ layers were dried (MgSO$_4$), filtered, concentrated and purified by chromatography on silica gel eluting with 20:1, 10:1 and 5:1 hexane:EtOAc to provide the title compound. $^1$H NMR (CDCl$_3$) δ 2.99 (t, J=6.4 Hz, 2H), 3.19 (t, J=6.4 Hz, 2H), 3.55 (s, 2H), 7.21-7.26 (m, 1H), 7.40 (dt, J=7.6, 1.4 Hz, 1H), 7.50 (dt, J=7.5, 1.4 Hz, 1H), 7.93 (dd, J=7.8, 1.4 Hz, 1H); MS (M+H)$^+$ m/z 179 (20%), (M+NH$_4$)$^+$ m/z 196 (100%).

Example 107D

Methyl 1-oxo-1,2,4,5-tetrahydrobenzo[d]thiepine-2-carboxylate

A solution of Example 107C (1.25 g, 7.01 mmol) in dimethyl carbonate (14.77 ml, 175 mmol) under nitrogen was treated with sodium hydride (0.841 g, 21.04 mmol), stirred for 2 days, poured into a flask containing a mixture of ice and 1 M HCl (25 mL) and extracted with ether (2×75 mL). The combined ether layers were washed with brine, dried (MgSO$_4$), filtered, concentrated and purified by chromatography on silica gel eluting with 20:1, 10:1 and 5:1 hexane:EtOAc to provide the title compound. $^1$H NMR (CDCl$_3$) δ 2.88 (t, J=6.8 Hz, 2H), 3.29 (t, J=6.8 Hz, 2H), 3.90 (s, 3H), 7.23-7.27 (m, 1H), 7.36-7.46 (m, 2H), 7.60-7.64 (m, 1H), 13.48 (s, 1H); MS (M+H)$^+$ m/z 237 (70%), (M+NH$_4$)$^+$ m/z 254 (100%).

Example 107E

4-Hydroxy-6,7-dihydro-5-thia-1,3-diaza-dibenzo[a,c]cyclohepten-2-ylamine

In a 25 mL microwave vial were combined pulverized guanidine carbonate (1.07 g, 5.97 mmol), sodium bicarbonate (500 mg, 5.97 mmol), and Example 107D (282 mg, 1.193 mmol), in DMF (4 mL). The reaction mixture was heated at 120° C. in the microwave for 1 hour (the temperature shot up to 170° C. and slowly came back down to 120° C. during the first 5 minutes of the reaction). The mixture was cooled, transferred to a separatory funnel using 1 M NaOH (5 mL) and water (5 mL). The mixture was washed with Et$_2$O (20 mL). The Et$_2$O layer was extracted with 1 M NaOH (3 mL). The combined NaOH layers were acidified with concentrated HCl until a solid started to form (pH ~8) and then further acidified with concentrated acetic acid until pH 6. After sitting at ambient temperature for 15 minutes, the solid was collected by filtration, washed with water and dried for 3 days under house vacuum to provide the title compound. $^1$H NMR (DMSO-d6) δ 2.72 (t, J=6.6 Hz, 2H), 3.16 (t, J=6.6 Hz, 2H), 6.78 (bs, 2H), 7.26-7.40 (m, 3H), 7.46-7.50 (m, 1H), 11.10 (bs, 1H); MS (M+H)$^+$ m/z 246.

Example 107F

4-Chloro-6,7-dihydro-5-thia-1,3-diaza-dibenzo[a,c]cyclohepten-2-ylamine

The title compound was prepared using the procedures outlined in Example 68A, substituting Example 107E for Example 59B. $^1$H NMR (DMSO-d6) δ 2.76 (t, J=6.6 Hz, 2H), 3.28 (t, J=6.8 Hz, 2H), 7.32-7.50 (m, 5H), 7.54 (dd, J=7.1, 1.7 Hz, 1H); MS (M+H)$^+$ m/z 264.

Example 107G 4-((R)-3-Methylamino-pyrrolidin-1-yl)-6,7-dihydro-5-thia-1,3-diaza-dibenzo[a,c]cyclohepten-2-ylamine The title compound was prepared using the procedure outlined in Example 30, substituting Example 107F for Example 29D, and substituting Example 1E for piperazine-1-carboxylic acid tert-butyl ester. $^1$H NMR (CDCl$_3$) δ 1.75-1.88 (m, 1H), 2.06-2.19 (m, 1H), 2.50 (s, 3H), 2.78-2.88 (m, 2H), 3.09-3.25 (m, 2H), 3.27-3.35 (m, 1H), 3.60-3.71 (m, 1H), 3.78-4.06 (m, 3H), 4.82 (s, 2H), 7.16-7.23 (m, 1H), 7.33-7.43 (m, 2H), 7.67-7.74 (m, 1H); MS (M+H)$^+$ m/z 328.

Example 108

2-Amino-4-octahydro-pyrrolo[3,4-b]pyridin-6-yl-5,6-dihydro-7-oxa-1,3-diaza-dibenzo[a,c]cycloheptene-9-carboxylic acid methyl ester Example 108A Methyl 2-amino-4-[1-(tert-butoxycarbonyl)octahydro-6H-pyrrolo[3,4-b]pyridin-6-yl]-5,6-dihydro[1]benzoxepino[5,4-d]pyrimidine-9-carboxylate A mixture of the product from Example 102A (55 mg, 0.098 mmol), PdCl$_2$(pddf).CH$_2$Cl$_2$ (4 mg, 0.0049 mmol), triethylamine (0.027 mL, 0.19 mmol) and MeOH (2 mL) was heated at 100° C. in an atmosphere of carbon monoxide at a pressure of 60 psi for 3 hours. The mixture was cooled and filtered to remove the solids. The filtrate was concentrated and purified by chromatography on silica gel using a gradient of 4:1 to 0:1 CH$_2$Cl$_2$:EtOAc to provide the title compound. $^1$H NMR (CDCl$_3$) δ 1.31-1.43 (m, 1H), 1.49 (s, 9H), 1.54-1.86 (m, 4H), 2.21-2.33 (m, 1H), 2.54-2.68 (m, 1H), 2.75-2.89 (m, 2H), 3.45 (d, J=11.1 Hz, 1H), 3.60-3.78 (m, 2H), 3.85-3.92 (m, 1H), 3.94 (s, 3H), 4.01-4.10 (m, 1H), 4.50-4.68 (m, 2H), 4.79 (s, 2H), 7.80 (d, J=1.6 Hz, 1H), 7.98 (dd, J=7.9, 1.6 Hz, 1H), 8.12 (d, J=8.3 Hz, 1H);
MS (M+H)$^+$ m/z 496.

Example 108B

2-Amino-4-octahydro-pyrrolo[3,4-b]pyridin-6-yl-5,6-dihydro-7-oxa-1,3-diaza-dibenzo[a,c]cycloheptene-9-carboxylic acid methyl ester The title compound was prepared using the procedure outlined in Example 30B, substituting Example 108A for Example 30A. $^1$H NMR (CDCl$_3$) δ 1.46-1.56 (m, 1H), 1.65-1.82 (m, 3H), 2.25-2.36 (m, 1H), 2.58-2.73 (m, 2H), 2.85 (dt, J=15.9, 4.1 Hz, 1H), 2.99-3.08 (m, 1H), 3.36-3.54 (m, 3H), 3.78-3.92 (m, 2H), 3.93 (s, 3H), 4.48-4.65 (m, 2H), 4.69 (s, 2H), 7.76 (d, J=1.4 Hz, 1H), 7.88 (dd, J=8.1, 1.7 Hz, 1H), 7.93 (d, J=7.8 Hz, 1H); MS (M+H)$^+$ m/z 396.

Example 109

4-Piperazin-1-yl-6,7-dihydro-5-thia-1,3-diaza-dibenzo[a,c]cyclohepten-2-ylamine

The title compound was prepared using the procedure outlined in Example 30, substituting Example 107F for Example 29D. $^1$H NMR (CD$_3$OD) δ 2.83 (t, J=6.4 Hz, 2H), 3.07-3.12 (m, 4H), 3.26 (t, J=6.6 Hz, 2H), 3.79-3.85 (m, 4H), 7.26-7.30 (m, 1H), 7.35-7.44 (m, 2H), 7.58-7.63 (m, 1H); MS (M+H)$^+$ m/z 314.

Example 110

4-(Octahydro-pyrrolo[3,4-b]pyridin-6-yl)-6,7-dihydro-5-thia-1,3-diaza-dibenzo[a,c]cyclohepten-2-ylamine The title compound was prepared using the procedure outlined in Example 30, substituting Example 107F for Example 29D, and substituting t-butyl octahydro-1H-pyrrolo[3,4-b]pyridine-1-carboxylate (CAS #159877-36-8) for piperazine-1-carboxylic acid tert-butyl ester. $^1$H NMR (CDCl$_3$) δ 1.40-1.83 (m, 5H), 2.24-2.36 (m, 1H), 2.62-2.73 (m, 1H), 2.80-2.93 (m, 1H), 2.99-3.30 (m, 3H), 3.37-3.46 (m, 1H), 3.54-4.08 (m, 3H), 4.79 (s, 2H), 7.18-7.24 (m, 1H), 7.34-7.43 (m, 2H), 7.67-7.72 (m, 1H); MS (M+H)$^+$ m/z 354.

Example 111

4-((R)-3-Methylamino-pyrrolidin-1-yl)-5,5-dioxo-6,7-dihydro-5H-5λ6-thia-1,3-diaza-dibenzo[a,c]cyclohepten-2-ylamine Example 111A 4-Chloro-5-oxo-6,7-dihydro-5H-5-thia-1,3-diaza-dibenzo[a,c]cyclohepten-2-ylamine and 4-Chloro-5,5-dioxo-6,7-dihydro-5H-5-thia-1,3-diaza-dibenzo[a,c]cyclohepten-2-ylamine Example 107F (37.5 mg, 0.142 mmol) in CH$_2$Cl$_2$ (5 mL) was treated with MCPBA (44.6 mg, 0.199 mmol), stirred at ambient temperature overnight, diluted with CH$_2$Cl$_2$ (25 mL) and washed with 1 M NaOH (5 mL). The aqueous layer was extracted with CH$_2$Cl$_2$ (25 mL). The combined CH$_2$Cl$_2$ layers were dried (MgSO$_4$), filtered and concentrated to provide a 1:1 ratio of the title compounds.

Example 111B tert-butyl (3R)-1-(2-amino-5,5-dioxo-6,7-dihydro-5H-5l6-thia-1,3-diaza-dibenzo[a,c]cyclohepten-4-yl)pyrrolidin-3-yl(methyl)carbamate The products from Example 111A (40 mg) were treated with the product from Example 1E (42.7 mg, 0.213 mmol) and triethylamine (139 µl, 0.995 mmol), in ethanol (0.57 mL), heated at 80° C. for overnight, cooled, diluted with $CH_2Cl_2$ (25 mL) and washed with 1 M NaOH (5 mL). The layers were separated and the aqueous was extracted with $CH_2Cl_2$ (2×25 mL). The combined $CH_2Cl_2$ layers were dried ($MgSO_4$), filtered, concentrated and purified by chromatography on silica gel eluting with 1:1:0 hexane:EtOAc:EtOH, then a gradient to 0:1:0 over 10 minutes followed by a gradient to 0:1:9 over 10 minutes to provide the title compound as the faster moving less polar product. $^1H$ NMR ($CDCl_3$) δ 1.49 (s, 9H), 2.03-2.13 (m, 2H), 2.84 (s, 3H), 3.16 (dd, J=14.2, 5.1 Hz, 1H), 3.33-3.44 (m, 1H), 3.57-3.67 (m, 1H), 3.70-3.77 (m, 3H), 3.78-3.89 (m, 2H), 4.67-4.81 (m, 1H), 5.18 (s, 2H), 7.23-7.28 (m, 1H), 7.38-7.47 (m, 2H), 7.95-8.01 (m, 1H); MS $(M+H)^+$ m/z 460.

Example 111C 4-((R)-3-Methylamino-pyrrolidin-1-yl)-5,5-dioxo-6,7-dihydro-5H-5λ6-thia-1,3-diaza-dibenzo[a,c]cyclohepten-2-ylamine The title compound was prepared using the procedure outlined in Example 30B, substituting Example 111B for Example 30A. $^1H$ NMR (DMSO-d6) δ 1.69-1.83 (m, 1H), 1.94-2.08 (m, 1H), 2.33 (s, 3H), 3.16-3.43 (m, 2H), 3.53-3.65 (m, 1H), 3.67-3.81 (m, 4H), 7.00 (s, 2H), 7.31-7.44 (m, 3H), 7.82-7.87 (m, 1H); MS $(M+H)^+$ m/z 360.

Example 112

4-((R)-3-Methylamino-pyrrolidin-1-yl)-5-oxo-6,7-dihydro-5-thia-1,3-diaza-dibenzo[a,c]cyclohepten-2-ylamine

Example 112A tert-butyl(3R)-1-(2-amino-5-oxo-6,7-dihydro-5-thia-1,3-diaza-dibenzo[a,c]cyclohepten-4-yl)pyrrolidin-3-yl(methyl)carbamate The products from Example 111A (40 mg) were processed as described in Example 111B to provide the title compound as the slower moving more polar product. $^1H$ NMR ($CDCl_3$) δ 1.48 and 1.49 (s and s, 9H), 1.98-2.21 (m, 2H), 2.80 and 2.83 (s and s, 3H), 3.07-3.15 (m, 1H), 3.21-3.56 (m, 4H), 3.58-3.84 (m, 2H), 4.01-4.14 (m, 1H), 4.69-4.81 (m, 1H), 5.07 (s, 2H), 7.26-7.31 (m, 1H), 7.37-7.45 (m, 2H), 7.79-7.86 (m, 1H); MS $(M+H)^+$ m/z 444.

Example 112B 4-((R)-3-Methylamino-pyrrolidin-1-yl)-5-oxo-6,7-dihydro-5-thia-1,3-diaza-dibenzo[a,c]cyclohepten-2-ylamine The title compound was prepared using the procedure outlined in Example 30B, substituting Example 112A for Example 30A. $^1H$ NMR ($CD_3OD$) δ 1.67-1.81 (m, 0.5H), 2.00-2.11 (m, 1H), 2.22-2.34 (m, 0.5H), 2.41 and 2.46 (s and s, 3H), 3.13-3.26 (m, 1H), 3.27-3.37 (m, 2H), 3.37-3.59 (m, 2H), 3.59-3.67 (m, 1H), 3.79-4.05 (m, 3H), 7.32-7.44 (m, 3H), 7.72-7.77 (m, 1H); MS $(M+H)^+$ m/z 344.

Example 113

$N^4$-(3-Piperidin-1-yl-propyl)-6,7-dihydro-5H-benzo[6,7]cyclohepta[1,2-d]pyrimidine-2,4-diamine The title compound was prepared using the procedure outlined in Example 59D substituting 3-piperidinyl-1-propylamine (CAS 3529-08-6) for t-butyl octahydro-1H-pyrrolo[3,4-b]pyridine-1-carboxylate. The product was purified by preparative HPLC on a Waters Nova-Pak® HR C18 6 um 60 Å Prep-Pak® cartridge column (25 mm×100 mm) eluting with a gradient of 10 mM ammonium acetate in water. $^1H$ NMR ($CDCl_3$) δ 1.48 (m, 2H), 1.64 (m, 4H), 1.85 (m, 2H), 2.15 (m, 8H), 2.56 (m, 6H), 5.44 (s, 2H), 7.20 (dd, J=6.95, 1.87 Hz, 1H), 7.33 (m, 2H), 7.64 (m, 1H); MS $(M+H)^+$ m/z 352.

Example 114

4-(4-Dimethylamino-piperidin-1-yl)-6,7-dihydro-5H-benzo[6,7]cyclohepta[1,2-d]pyrimidin-2-ylamine The title compound was prepared using the procedure outlined in Example 59D substituting 4-dimethylaminopiperidine (CAS 50533-97-6) for t-butyl octahydro-1H-pyrrolo[3,4-b]pyridine-1-carboxylate. The product was purified by preparative HPLC on a Waters Nova-Pak® HR C18 6 um 60 Å Prep-Pak® cartridge column (25 mm×100 mm) eluting with a gradient of 10 mM ammonium acetate in water. $^1H$ NMR ($CDCl_3$) δ 1.64 (m, 2H), 1.93 (d, J=13.22 Hz, 2H), 2.24 (m, 2H), 2.33 (m, 4H), 2.36 (s, 6H), 2.41 (m, 1H), 2.65 (t, J=6.78 Hz, 2H), 2.90 (t, J=12.21 Hz, 2H), 3.92 (d, J=14.58 Hz, 2H), 4.74 (s, 2H), 7.22 (m, 1H), 7.34 (m, 2H), 7.72 (m, 1H); MS $(M+H)^+$ m/z 352.

Example 115

10-fluoro-4-octahydro-6H-pyrrolo[3,4-b]pyridin-6-yl-6,7-dihydro-5H-benzo[6,7]cyclohepta[1,2-d]pyrimidin-2-amine

Example 115A methyl 3-fluoro-5-oxo-6,7,8,9-tetrahydro-5H-benzo[7]annulene-6-carboxylate The title compound was prepared as in Example 59A, substituting 8-fluoro-1-benzosuberone for benzosuberone. NMR in $CDCl_3$ indicates enol form. $^1H$ NMR ($CDCl_3$) δ 0.87 (q, J=6.74 Hz, 4H), 2.60 (t, J=6.74 Hz, 2H), 7.03 (td, J=8.33, 2.78 Hz, 1H), 7.17 (dd, J=8.33, 5.55 Hz, 1H), 7.33 (dd, J=9.52, 2.78 Hz, 1H), 12.55 (s, 1H); MS $(M+H)^+$ m/z 237.

Example 115B 2-amino-10-fluoro-6,7-dihydro-5H-benzo[6,7]cyclohepta[1,2-d]pyrimidin-4-ol The title compound was prepared as described in Example 59B, substituting Example 115A for the product from the example 59A. $^1H$ NMR (DMSO-d6) δ 1.73 (m, 2H), 2.00 (q, J=7.01 Hz, 2H), 2.15 (t, J=6.95 Hz, 2H), 2.70 (m, 1H), 2.90 (m, 1H), 6.42 (s, 2H), 7.15 (td, J=8.56, 2.88 Hz, 1H), 7.30 (m, 2H), 10.91 (s, 1H)

Example 115C 2-amino-10-fluoro-6,7-dihydro-5H-benzo[6,7]cyclohepta[1,2-d]pyrimidin-4-yl 4-methylbenzenesulfonate The title compound was prepared as described in Example 59C substituting the product from the Example 115B for Example 59B. $^1$H NMR (DMSO-d6) δ 1.99 (m, J=6.74 Hz, 2H), 2.22 (t, J=6.94 Hz, 2H), 2.45 (m, 5H), 6.95 (s, 2H), 7.32 (m, 3H), 7.50 (d, J=7.93 Hz, 2H), 8.03 (d, J=8.33 Hz, 2H); MS (M+H)$^+$ m/z 400.

Example 115D tert-butyl 6-(2-amino-10-fluoro-6,7-dihydro-5H-benzo[6,7]cyclohepta[1,2-d]pyrimidin-4-yl)octahydro-1H-pyrrolo[3,4-b]pyridine-1-carboxylate The title compound was prepared as described in Example 59D, substituting the product from the Example 115C for Example 59C.

Example 115E 10-fluoro-4-octahydro-6H-pyrrolo[3,4-b]pyridin-6-yl-6,7-dihydro-5H-benzo[6,7]cyclohepta[1,2-d]pyrimidin-2-amine The compound, obtained from Example 115D was dissolved in MeOH and treated with 4N HCl in dioxane at reflux for 1 hour. The reaction mixture was concentrated and triturated with ethyl acetate to yield the title product as the HCl salt. $^1$H NMR (DMSO-d6) δ 1.73 (m, 4H), 2.25 (m, J=16.62 Hz, 2H), 2.76 (m, 2H), 2.90 (m, 1H), 3.22 (d, J=12.55 Hz, 1H), 3.89 (m, J=23.06 Hz, 3H), 4.04 (q, 1H), 7.42 (td, J=8.48, 2.71 Hz, 2H), 7.51 (m, 1H), 7.57 (dd, J=9.66, 2.54 Hz, 1H); (M+H)$^+$ m/z 354.

Example 116

4-[1,4]Diazepan-1-yl-6,7-dihydro-5H-benzo[6,7] cyclohepta[1,2-d]pyrimidin-2-ylamine The title compound was prepared using the procedure outlined in Example 59D substituting homopiperazine for t-butyl octahydro-1H-pyrrolo[3,4-b]pyridine-1-carboxylate. The product was purified by chromatography eluting with NH$_4$OH:MeOH:CHCl$_3$ (0.8:8:92) to provide the title compound. $^1$H NMR (CD$_3$OD) δ 1.95-2.03 (m, 2H), 2.18-2.24 (m, 2H), 2.31 (t, J=6 Hz, 2H), 2.68 (t, J=6 Hz, 2H), 2.91-2.95 (m, 2H), 3.05-3.11 (m, 2H), 3.71-3.76 (m, 4H), 7.25-7.28 (m, 1H), 7.34-7.37 (m, 2H), 7.64-7.67 (m, 1H); MS (M+H)$^+$ m/z 310.

Example 117

(1R,5S)-4-(3,6-Diaza-bicyclo[3.2.0]hept-6-yl)-6,7-dihydro-5H-benzo[6,7]cyclohepta[1,2-d]pyrimidin-2-ylamine The title compound was prepared using the procedure outlined in Example 59D substituting (1S,5S)-tert-butyl 3,6-diazabicyclo[3.2.0]heptane-3-carboxylate for t-butyl octahydro-1H-pyrrolo[3,4-b]pyridine-1-carboxylate followed by the procedure outlined in Example 59E. $^1$H NMR (CD$_3$OD) δ 2.07 (s, 3H), 2.29-2.40 (m, 1H), 2.53-2.68 (m, 3H), 2.77 (dd, J=12.21, 6.10 Hz, 1H), 3.20 (d, J=12.21 Hz, 1H), 3.39 (d, J=12.88 Hz, 1H), 4.00 (dd, J=8.48, 4.07 Hz, 1H), 4.33 (t, J=8.31 Hz, 1H), 5.09 (dd, J=6.27, 3.90 Hz, 1H), 7.21-7.28 (m, 1H), 7.22-7.27 (m, 1H), 7.34 (d, J=9.83 Hz, 2H), 7.57 (d, J=8.81 Hz, 1H); MS (M+H)$^+$ m/z 308.

Example 118

4-Piperazin-1-yl-6,7-dihydro-5H-benzo[6,7]cyclohepta[1,2-d]pyrimidine

Example 118A 2-thioxo-1,2,3,5,6,7-hexahydro-4H-benzo[6,7]cyclohepta[1,2-d]pyrimidin-4-one A solution of Example 59A (1 g, 4.6 mmol), thiourea (500 mg, 6.9 mmol) and sodium methoxide (670 mg, 11.5 mmol) in anhydrous methanol (15 mL) was heated at reflux for 16 hours. The mixture was filtered through diatomaceous earth and washed with small amount of methanol. The filtrate was concentrated in vacuo, dissolved in water (120 mL) and acidified with acetic acid to pH=5. The precipitate formed was collected by filtration, washed with NaHCO$_3$ and water, and dried under vacuum. The solid was recrystallized in EtOAc/hexanes to provide the title compound. $^1$H NMR (DMSO-d6) δ 2.08 (s, 4H), 2.58 (t, J=6.27 Hz, 2H), 7.32-7.55 (m, J=51.20 Hz, 4H), 12.43 (d, J=13.56 Hz, 2H). MS (M+H)$^+$ m/z 245.

Example 118B 3,5,6,7-tetrahydro-4H-benzo[6,7]cyclohepta[1,2-d] pyrimidin-4-one A solution of Example 118A (170 mg, 0.7 mmol) in methanol (15 mL) was treated with Raney nickel (slurry in H$_2$O, 1 spatula) and refluxed for 16 hours. The mixture was filtered through diatomaceous earth and washed with methanol. The filtrate was concentrated under vacuum to provide the title compound. $^1$H NMR (CD$_3$OD) δ 2.24 (t, 2H), 2.40 (t, 2H), 2.59 (t, 2H), 7.27-7.34 (m, 1H), 7.36-7.42 (m, 2H), 7.60-7.66 (m, 1H), 8.14-8.18 (m, 1H). MS (M+H)$^+$ m/z 213

Example 118C 6,7-dihydro-5H-benzo[6,7]cyclohepta[1,2-d]pyrimidin-4-yl 4-methylbenzenesulfonate The product from Example 118B (154 mg, 0.72 mmol), p-toluenesulfonyl chloride (278 mg, 1.44 mmol), DMAP (17 mg, 0.14 mmol) in CH$_2$Cl$_2$ (20 mL) was treated with triethylamine (0.25 mL, 1.8 mmol) and stirred at room temperature for 16 hours. The mixture was concentrated under reduced pressure and the residue was chromatographed on silica gel eluting with 40% EtOAc/hexanes to provide the title compound. $^1$H NMR (CDCl$_3$) δ 2.18-2.40 (m, 4H), 2.48 (d, 3H), 2.51-2.58 (m, 2H), 7.25-7.29 (m, 1H), 7.35-7.45 (m, 4H), 7.66-7.73 (m, J=17.63 Hz, 1H), 8.07 (dd, J=15.60, 8.48 Hz, 2H), 8.85 (d, J=8.48 Hz, 1H). MS (M+H)$^+$ m/z 367

Example 118D

4-Piperazin-1-yl-6,7-dihydro-5H-benzo[6,7]cyclohepta[1,2-d]pyrimidine

The title compound was prepared using the procedure outlined in Example 59D substituting piperazine for t-butyl octahydro-1H-pyrrolo[3,4-b]pyridine-1-carboxylate, and substituting the product from Example 118C for the product from Example 59C. The product was purified by chromatography on silica gel eluting with NH$_4$OH:MeOH:CHCl$_3$ (0.8:8:92) to provide the title compound. $^1$H NMR (CD$_3$OD) δ 2.32-2.49 (m, 4H), 2.63-2.70 (m, 2H), 2.94-3.01 (m, 4H), 3.47-3.54 (m, 4H), 7.30-7.35 (m, 1H), 7.39-7.44 (m, 2H), 7.65-7.71 (m, 1H), 8.58-8.61 (m, 1H). MS (M+H)$^+$ m/z 281.

Example 119

(3aS,6aS)-4-(Hexahydro-pyrrolo[3,4-b]pyrrol-1-yl)-6,7-dihydro-5H-benzo[6,7]cyclohepta[1,2-d]pyrimidin-2-amine The title compound was prepared using the procedure outlined in Example 59D substituting (3aS,6aS)-tert-butyl hexahydropyrrolo[3,4-b]pyrrole-5(1H)-carboxylate for t-butyl octahydro-1H-pyrrolo[3,4-b]pyridine-1-carboxylate followed by the procedure outlined in Example 59E. $^1$H NMR (CD$_3$OD) δ 1.83-1.96 (m, 1H), 1.99-2.26 (m, 4H), 2.58-2.72 (m, 3H), 2.74-2.88 (m, 2H), 2.89-2.97 (m, 1H), 3.04-3.17 (m, 2H), 3.63-3.73 (m, 1H), 3.83-3.96 (m, 1H), 7.22-7.28 (m, 1H), 7.33-7.37 (m, 2H), 7.61-7.66 (m, 1H), 7.88-7.91 (m, 1H). MS (M+H)$^+$ m/z 322.

Example 120

(1S,5S)-4-(3,6-Diaza-bicyclo[3.2.0]hept-3-yl)-6,7-dihydro-5H-benzo[6,7]cyclohepta[1,2-d]pyrimidin-2-ylamine The title compound was prepared using the procedure outlined in Example 59D substituting (1R,5S)-tert-butyl 3,6-diazabicyclo[3.2.0]heptane-6-carboxylate for t-butyl octahydro-1H-pyrrolo[3,4-b]pyridine-1-carboxylate followed by the procedure outlined in Example 59E. $^1$H NMR (CD$_3$OD) δ 2.18-2.29 (m, 2H), 2.41-2.50 (m, 2H), 2.67 (t, 2H), 3.33-3.39 (m, 2H), 3.79 (t, 1H), 4.09 (t, 2H), 4.42-4.48 (m, 1H), 7.24-7.29 (m, 1H), 7.35-7.39 (m, 2H), 7.64-7.69 (m, 1H). MS (M+H)$^+$ m/z 308.

Example 121

N$^4$-piperidin-3-yl-6,7-dihydro-5H-benzo[6,7]cyclohepta[1,2-d]pyrimidine-2,4-diamine The title compound was prepared using the procedure outlined in Example 59D substituting tert-butyl 3-aminopiperidine-1-carboxylate for t-butyl octahydro-1H-pyrrolo[3,4-b]pyridine-1-carboxylate followed by the procedure outlined in Example 59E. $^1$H NMR (CD$_3$OD) δ 1.54-1.66 (m, 2H), 1.73-1.84 (m, 1H), 1.94-2.03 (m, 1H), 2.06-2.16 (m, 2H), 2.17-2.26 (m, 2H), 2.46-2.66 (m, 4H), 2.90-3.00 (m, 1H), 3.17-3.27 (m, 1H), 4.13-4.24 (m, 1H), 7.20-7.27 (m, 1H), 7.29-7.36 (m, 2H), 7.49-7.58 (m, 1H). MS (M+H)$^+$ m/z 310.

Example 122

N$^4$-(Octahydro-isoindol-4-yl)-6,7-dihydro-5H-benzo[6,7]cyclohepta[1,2-d]pyrimidine-2,4-diamine The title compound was prepared using the procedure outlined in Example 59D substituting tert-butyl 4-aminohexahydro-1H-isoindole-2(3H)-carboxylate for t-butyl octahydro-1H-pyrrolo[3,4-b]pyridine-1-carboxylate followed by the procedure outlined in Example 59E. $^1$H NMR (CD$_3$OD) δ 1.18-1.34 (m, 1H), 1.37-1.51 (m, 1H), 1.52-1.77 (m, 3H), 1.78-1.93 (m, 1H), 2.02-2.15 (m, 2H), 2.17-2.26 (m, 2H), 2.50-2.59 (m, 2H), 2.78-2.88 (m, 1H), 2.90-3.01 (m, 1H), 3.03-3.13 (m, 1H), 3.20-3.28 (m, 2H), 3.31-3.37 (m, 1H), 4.40-4.54 (m, 1H), 7.21-7.27 (m, 1H), 7.29-7.37 (m, 2H), 7.50-7.59 (m, 1H). MS (M+H)$^+$ m/z 350.

Example 123

Methyl-(4-piperazin-1-yl-6,7-dihydro-5H-benzo[6,7]cyclohepta[1,2-d]pyrimidin-2-yl)-amine

Example 123A

2-(methylamino)-6,7-dihydro-5H-benzo[6,7]cyclohepta[1,2-d]pyrimidin-4-ol

The title compound was prepared using the procedure outlined in Example 59B substituting 1-methylguanidine hydrochloride for guanidine nitrate. $^1$H NMR (CD$_3$OD) δ 2.08-2.17 (m, 2H), 2.31 (t, 2H), 2.59 (t, 2H), 2.91-2.95 (m, 3H), 7.23-7.29 (m, 1H), 7.31-7.37 (m, 2H), 7.60-7.68 (m, 1H). MS (M+H)$^+$ m/z 242.

Example 123B

2-(methylamino)-6,7-dihydro-5H-benzo[6,7]cyclohepta[1,2-d]pyrimidin-4-yl 4-methylbenzenesulfonate The title compound was prepared using the procedure outlined in Example 59C substituting the product from Example 123A for the product from Example 59B. $^1$H NMR (CDCl$_3$) δ 2.09-2.20 (m, 2H), 2.42 (t, 3H), 2.46-2.49 (m, 3H), 2.55 (t, 2H), 2.80-2.88 (m, 3H), 4.94-5.06 (m, 1H), 7.19-7.25 (m, 1H), 7.32-7.40 (m, 4H), 7.58-7.65 (m, 1H), 8.00 (d, 2H). MS (M+H)$^+$ m/z 396.

Example 123C

Methyl-(4-piperazin-1-yl-6,7-dihydro-5H-benzo[6,7]cyclohepta[1,2-d]pyrimidin-2-yl)-amine The title compound was prepared using the procedure outlined in Example 59D, substituting Example 123B for Example 59C, and substituting piperazine for t-butyl octahydro-1H-pyrrolo[3,4-b]pyridine-1-carboxylate. The product was purified by chromatography eluting with NH$_4$OH:MeOH:CHCl$_3$ (0.8:8:92) to provide the title compound. $^1$H NMR (CD$_3$OD) δ 2.18-2.33 (m, 4H), 2.65 (t, 2H), 2.93-2.98 (m, 7H), 3.43 (t, 4H), 7.23-7.28 (m, 1H), 7.32-7.38 (m, 2H), 7.63-7.69 (m, 1H). MS (M+H)$^+$ m/z 310.

Example 124

4-(3-(R)-Methylamino-pyrrolidin-1-yl)-6,7-dihydro-5H-benzo[6,7]cyclohepta[1,2-d]pyrimidine The title compound was prepared using the procedure outlined in Example 59D substituting Example 1E for t-butyl octahydro-1H-pyrrolo[3,4-b]pyridine-1-carboxylate, and substituting the product from Example 118C for the product from Example 59C, followed by the procedure outlined in Example 59E. $^1$H NMR (CD$_3$OD) δ 1.84-1.98 (m, 1H), 2.17-2.27 (m, 1H), 2.28-2.36 (m, 2H), 2.41-2.50 (m, 5H), 2.66 (t, 2H), 3.33-3.40 (m, 1H), 3.52-3.61 (m, 1H), 3.72-3.80 (m, 1H), 3.83-3.93 (m, 2H), 7.27-7.33 (m, 1H), 7.37-7.43 (m, 2H), 7.65-7.71 (m, 1H), 8.40-8.44 (m, 1H). MS (M+H)$^+$ m/z 295.

Example 125

[1-(6,7-Dihydro-5H-benzo[6,7]cyclohepta[1,2-d] pyrimidin-4-yl)-azetidin-3-yl]-amine The title compound was prepared using the procedure outlined in Example 59D substituting Example 2B for t-butyl octahydro-1H-pyrrolo[3,4-b]pyridine-1-carboxylate, and substituting the product from Example 118C for the product from Example 59C, followed by the procedure outlined in Example 59E. $^1$H NMR (CD$_3$OD) δ 2.20-2.36 (m, 4H), 2.36-2.40 (m, 3H), 2.60 (t, 2H), 3.65-3.74 (m, 1H), 4.06 (dd, 2H), 4.47-4.55 (m, 2H), 7.26-7.34 (m, 1H), 7.36-7.43 (m, 2H), 7.62-7.67 (m, 1H), 8.41-8.44 (m, 1H). MS (M+H)$^+$ m/z 281.

Example 126

8,10-Dimethyl-4-piperazin-1-yl-6,7-dihydro-5H-benzo[6,7]cyclohepta[1,2-d]pyrimidin-2-ylamine

Example 126A

Ethyl 1,3-dimethyl-5-oxo-6,7,8,9-tetrahydro-5H-benzo[7]annulene-6-carboxylate

A solution of 5,7-dimethyl-3,4-dihydronaphthalen-1(2H)-one (1 g, 5.74 mmol) in anhydrous CH$_2$Cl$_2$ (20 mL) under nitrogen atmosphere was cooled to 0° C. To this solution was added triethyloxonium tetrafluoroborate (1M in CH$_2$Cl$_2$, 23 mL, 23 mmol), followed with ethyl diazoacetate (1.2 mL, 11.5 mmol). The mixture was stirred at ambient temperature for 16 hrs. The reaction was worked up with saturated sodium bicarbonate, diluted with water and CH$_2$Cl$_2$, and the layers were separated. The organic layer was dried with MgSO$_4$, concentrated and the residue was purified by chromatography on silica gel eluting with 10% EtOAc/Hexanes to provide the title compound. $^1$H NMR (CD$_3$OD) δ 1.29 (t, 3H), 1.97-2.12 (m, 4H), 2.28-2.30 (m, 3H), 2.30-2.31 (m, 3H), 2.59 (t, 2H), 4.28 (q, 2H), 6.86-6.90 (m, 1H), 6.95-6.99 (m, 1H), 13.17-13.22 (m, 1H). MS (M+H)$^+$ m/z 261.

Example 126B 2-amino-8,10-dimethyl-6,7-dihydro-5H-benzo[6,7]cyclohepta[1,2-d]pyrimidin-4-ol The title compound was prepared using the procedure outlined in Example 20B substituting the product from Example 126A for the product from Example 20A. $^1$H NMR (CD$_3$OD) δ 2.06-2.25 (m, 2H), 2.26-2.28 (m, 3H), 2.30-2.32 (m, 3H), 2.58-2.68 (m, 1H), 2.69-2.80 (m, 2H), 2.79-2.92 (m, 1H), 3.11-3.19 (m, 1H), 6.88-6.91 (m, 1H), 7.12-7.16 (m, 1H). MS (M+H)$^+$ m/z 256.

Example 126C 2-amino-8,10-dimethyl-6,7-dihydro-5H-benzo[6,7]cyclohepta[1,2-d]pyrimidin-4-yl 4-methylbenzenesulfonate The title compound was prepared using the procedure outlined in Example 20C, substituting the product from Example 126B for the product from Example 20B. $^1$H NMR (CDCl$_3$) δ 1.95-2.07 (m, 2H), 2.11-2.19 (m, 1H), 2.21-2.23 (m, 3H), 2.29-2.31 (m, 3H), 2.34-2.40 (m, 1H), 2.40-2.43 (m, 3H), 2.49-2.54 (m, 1H), 2.67-2.73 (m, 1H), 5.08-5.13 (m, 2H), 6.90-6.92 (m, 1H), 6.95-6.97 (m, 1H), 7.20 (d, 2H), 7.67 (d, 2H). MS (M+H)$^+$ m/z 410.

Example 126D 8,10-Dimethyl-4-piperazin-1-yl-6,7-dihydro-5H-benzo[6,7]cyclohepta[1,2-d]pyrimidin-2-ylamine The title compound was prepared using the procedure outlined in Example 20D, substituting the product from Example 126C for the product from Example 20C. $^1$H NMR (CD$_3$OD) δ 1.97-2.18 (m, 3H), 2.24-2.36 (m, 2H), 2.26-2.29 (m, 3H), 2.32-2.35 (m, 3H), 2.55-2.66 (m, 2H), 2.68-2.78 (m, 2H), 2.82-2.95 (m, 1H), 3.08-3.21 (m, 4H), 6.89-6.94 (m, 1H), 6.97-7.02 (m, 1H). MS (M+H)$^+$ m/z 324.

Example 127

6-(2-(1H-imidazol-4-yl)ethylamino-6,7-dihydro-5H-benzo[6,7]cyclohepta[1,2-d]pyrimidin-4-yl)octahydro-1H-pyrrolo[3,4-b]pyridine The title compound was prepared using the procedure outlined in Example Example 92B, substituting histamine for pyridin-3-ylmethanamine. The product was purified by preparative HPLC on a Waters Nova-Pak HR C18 6 um 60 Å Prep-Pak cartridge column (25 mm×100 mm) eluting with a gradient of (A) acetonitrile and (B) 0.1% trifluoroacetic acid in water to provide the title compound as the tri-trifluoroacetic acid salt. MS (M+H)$^+$ m/z. 430.

Example 128

(2-Amino-4-piperazin-1-yl-6,7-dihydro-5H-benzo[6,7]cyclohepta[1,2-d]pyrimidin-10-yl)-methyl-carbamic acid methyl ester

Example 128A 3-amino-6,7,8,9-tetrahydro-5H-benzo[7]annulene-5-one

A solution of 3-nitro-6,7,8,9-tetrahydro-5H-benzo[7]annulene-5-one (CAS #7507-93-9, 2 g, 9.75 mmol), palladium (413 mg, 10% on carbon, 0.4 mmol) in methanol (25 ml) under the hydrogen atmosphere (60 PSI) was stirred at room temperature for 16 hrs. The mixture was filtered through a layer of diatomaceous earth, washed with methanol and concentrated under reduced pressure to provide the title compound. $^1$H NMR (CDCl$_3$) δ 1.77-1.84 (m, 4H), 2.67-2.73 (m, 2H), 2.82 (t, J=6.10 Hz, 2H), 6.75 (dd, J=8.14, 2.71 Hz, 1H), 6.99 (d, J=8.48 Hz, 1H), 7.05 (d, J=2.71 Hz, 1H). MS (M+H)$^+$ m/z 175.

Example 128B

Benzyl 9-oxo-6,7,8,9-tetrahydro-5H-benzo[7]annulene-2-ylcarbamate

A solution of Example 128A (1.63 g, 9.30 mmol) and K$_2$CO$_3$ (2.57 g, 18.60 mmol) in MeOH (10 ml) under nitrogen atmosphere was cooled to 0° C. The mixture was treated with benzyl chloroformate (1.726 ml, 12.09 mmol), raised to room temperature and stirred for 16 hours. The mixture was diluted with CH$_2$Cl$_2$, washed with water, dried and concentrated under reduced pressure. The residue was purified by chromatography on silica gel eluting with 15% EtOAc/hexanes to provide the title product. $^1$H NMR (CDCl$_3$) δ 1.75-1.90 (m, 4H), 2.67-2.75 (m, 2H), 2.84-2.92 (m, 2H), 4.70 (d, J=5.76 Hz, 2H), 6.72 (s, 1H), 7.16 (d, J=8.14 Hz, 1H), 7.36-7.39 (m, 5H), 7.49 (d, J=2.71 Hz, 1H), 7.70 (d, J=7.12 Hz, 1H). MS (M+NH$_4$)$^+$ m/z 327.

Example 128C

Methyl 3-(methoxycarbonyl(methyl)amino)-5-oxo-6,7,8,9-tetrahydro-5H-benzo[7]annulene-6-carboxylate The title compound was prepared using the procedure outlined in Example 20A, substituting the product from Example 128B for 7,8,9,10-tetrahydro-6H-benzocycloocten-5-one. $^1$H NMR (CDCl$_3$) δ 2.03-2.20 (m, 4H), 2.62 (t, J=6.78 Hz, 2H), 3.29-3.32 (m, 3H), 3.71 (s, 3H), 3.83 (s, 3H), 7.16-7.24 (m, 2H), 7.48 (s, 1H), 12.58 (s, 1H). MS (M+NH$_4$)$^+$ m/z 323.

Example 128D 2-amino-10-[(methoxycarbonyl)(methyl)amino]-6,7-dihydro-5H-benzo[6,7]cyclohepta[1,2-d]pyrimidin-4-ol The title compound was prepared using the procedure outlined in Example 20B, substituting the product from Example 128C for the product from Example 20A. $^1$H NMR (DMSO-d6) δ 1.96-2.05 (m, 2H), 2.16 (t, J=6.95 Hz, 2H), 2.47 (t, 2H), 3.21 (s, 3H), 3.60 (s, 3H), 6.39 (s, 2H), 7.24 (d, J=3.05 Hz, 2H), 7.43 (d, J=1.70 Hz, 1H). MS (M+H)$^+$ m/z 315.

Example 128E 2-amino-10-[(methoxycarbonyl)(methyl)amino]-6,7-dihydro-5H-benzo[6,7]cyclohepta[1,2-d]pyrimidin-4-yl 4-methylbenzenesulfonate The title compound was prepared using the procedure outlined in Example 20C, substituting the product from Example 128D for the product from Example 20B. $^1$H NMR (CDCl$_3$) δ 2.15 (q, J=7.01 Hz, 2H), 2.43 (t, J=6.94 Hz, 2H), 2.48 (s, 3H), 2.53 (t, J=6.94 Hz, 2H), 3.32 (s, 3H), 3.71 (s, 3H), 4.99 (s, 2H), 7.18-7.25 (m, 2H), 7.38 (d, J=7.93 Hz, 2H), 7.51 (d, J=2.38 Hz, 1H), 7.99 (d, J=8.33 Hz, 2H). MS (M+H)$^+$ m/z 469.

Example 128F (2-Amino-4-piperazin-1-yl-6,7-dihydro-5H-benzo[6,7]cyclohepta[1,2-d]pyrimidin-10-yl)-methyl-carbamic acid methyl ester The title compound was prepared using the procedure outlined in Example 20D, substituting the product from Example 128E for the product from Example 20C. $^1$H NMR (CD$_3$OD) δ 2.19-2.27 (m, 2H), 2.28-2.37 (m, 2H), 2.65 (t, J=6.61 Hz, 2H), 2.92-2.98 (m, 4H), 3.38-3.43 (m, 4H), 3.69 (s, 3H), 7.28 (d, J=1.36 Hz, 2H), 7.53 (s, 1H). MS (M+H)$^+$ m/z 383.

Example 129

10-N-Methyl-4-piperazin-1-yl-6,7-dihydro-5H-benzo[6,7]cyclohepta[1,2-d]pyrimidine-2,10-diamine A solution of the product from Example 128 (5 mg, 0.013 mmol) in CH$_2$Cl$_2$ (2 ml) was treated with iodotrimethylsilane (5.50 µl, 0.039 mmol) and sealed in a vial. The mixture was heated at 60° C. for 16 hours. The mixture was concentrated under reduced pressure and the residue was purified by chromatography on silica gel eluting with NH$_4$OH:MeOH:CH$_2$Cl$_2$ (0.6:6:94) to provide the title compound. $^1$H NMR (CD$_3$OD) δ 2.15 (q, J=6.61 Hz, 2H), 2.30 (t, J=6.74 Hz, 2H), 2.52 (t, J=6.74 Hz, 2H), 2.80 (s, 3H), 2.92-2.98 (m, 4H), 3.36-3.42 (m, 4H), 6.67 (dd, J=8.13, 2.58 Hz, 1H), 6.92 (d, J=2.38 Hz, 1H), 7.03 (d, J=8.33 Hz, 1H). MS (M+H)$^+$ m/z 325.

Example 130

(2-Amino-4-octahydro-pyrrolo[3,4-b]pyridin-6-yl-6,7-dihydro-5H-benzo[6,7]cyclohepta[1,2-d]pyrimidin-10-yl)-methyl-carbamic acid methyl ester The title compound was prepared using the procedure outlined in Example 20D, substituting the product from Example 128E for the product from Example 20C, and substituting t-butyl octahydro-1H-pyrrolo[3,4-b]pyridine-1-carboxylate (CAS #159877-36-8) for piperazine, followed by the procedure outlined in Example 59E. $^1$H NMR (CD$_3$OD) δ 1.47-1.56 (m, 1H), 1.63-1.75 (m, 1H), 1.76-1.85 (m, 2H), 2.10-2.26 (m, 3H), 2.32-2.43 (m, 1H), 2.56-2.72 (m, 4H), 2.93-3.01 (m, 1H), 3.34-3.40 (m, 1H), 3.52-3.58 (m, 1H), 3.59-3.65 (m, 1H), 3.69 (s, 3H), 3.82-3.91 (m, 2H), 7.27 (s, 2H), 7.53 (s, 1H). MS (M+H)$^+$ m/z 423.

Example 131

10-N-methyl-4-[(4aR,7aR)-octahydro-6H-pyrrolo[3,4-b]pyridin-6-yl]-6,7-dihydro-5H-benzo[6,7]cyclohepta[1,2-d]pyrimidine-2,10-diamine The title compound was prepared using the procedure outlined in Example 129, substituting the product from Example 130 for the product from Example 128. $^1$H NMR (CD$_3$OD) δ 1.51-1.59 (m, 1H), 1.66 (s, 1H), 1.76-1.85 (m, 2H), 2.07-2.20 (m, 3H), 2.38-2.46 (m, 1H), 2.47-2.56 (m, 2H), 2.64 (d, J=2.71 Hz, 1H), 2.66-2.75 (m, 1H), 2.81 (s, 3H), 2.95-3.04 (m, 1H), 3.41 (t, J=4.07 Hz, 1H), 3.54-3.68 (m, 2H), 3.82-3.94 (m, 2H), 6.68 (dd, J=8.14, 2.37 Hz, 1H), 6.92 (d, J=2.71 Hz, 1H), 7.04 (d, J=8.14 Hz, 1H). MS (M+H)$^+$ m/z 365.

Example 132

N-(2-Amino-4-piperazin-1-yl-6,7-dihydro-H-benzo[6,7]cyclohepta[1,2-d]pyrimidin-11-yl)-acetamide

Example 132A 6,7,8,9-tetrahydro-5H-benzo[7]annulene-1-amine

A solution of 1-nitro-6,7,8,9-tetrahydro-5H-benzo[7]annulene-5-one (CAS #251554-42-4, 2.5 g, 12 mmol), palladium (413 mg, 10% on carbon, 0.4 mmol) in acetic acid (25 ml) under the hydrogen atmosphere (60 PSI) was heated at 60° C. and stirred at for 16 hours. The mixture was filtered through a layer of diatomaceous earth, washed with methanol and concentrated under reduced pressure to provide the title compound. $^1$H NMR (CDCl$_3$) δ 1.50-1.69 (m, 4H), 1.75-1.86 (m, 2H), 2.71-2.86 (m, 4H), 5.46 (s, 2H), 7.03-7.12 (m, 3H). MS (M+H)$^+$ m/z 162.

Example 132B

N-(6,7,8,9-tetrahydro-5H-benzo[7]annulene-1-yl) acetamide

A solution of the product from Example 132A (1.6 g, 9.92 mmol) in ethanol (30 ml) was added a solution of acetic anhydride (1.872 ml, 19.85 mmol) in EtOH (30 mL) at 0° C. The mixture was stirred at room temperature for 16 hours. The mixture was concentrated under reduced pressure and the residue was taken up in EtOAc (100 mL) and the organic solution was washed with H$_2$O, dried and concentrated. The residue was purified by chromatography on silica gel eluting with 15% EtOAc/hexanes to provide the title product. $^1$H NMR (CDCl$_3$) δ 1.54-1.71 (m, 6H), 1.77-1.89 (m, 2H), 2.20 (s, 3H), 2.72-2.76 (m, J=5.55 Hz, 1H), 2.78-2.85 (m, J=10.71 Hz, 2H), 6.97-7.11 (m, 2H), 7.22 (d, 1H). MS (M+H)$^+$ m/z 204.

Example 132C

N-(9-oxo-6,7,8,9-tetrahydro-5H-benzo[7]annulene-1-yl)acetamide

A solution of the product from Example 132B (1 g, 4.92 mmol) in acetone (150 ml) was added 15% MgSO$_4$ (15 mL). To the solution was added KMnO$_4$ (1.944 g, 12.30 mmol) and stirred at ambient temperature for 2 hours. Then heated at slightly reflux for 40 hours. The mixture was filtered through diatomaceous earth, and washed with CH$_2$Cl$_2$. The organic was separated, diluted with CH$_2$Cl$_2$, washed with saturated Na$_2$S$_2$O$_3$, dried and concentrated. The residue was purified by chromatography on silica gel column eluting with 20% EtOAc/hexanes to provide the title product. $^1$H NMR (DMSO-d6) δ 1.68-1.74 (m, 4H), 1.94 (s, 3H), 2.55-2.59 (m, 2H), 2.70 (t, J=6.04 Hz, 2H), 6.98 (d, J=7.34 Hz, 1H), 7.22 (d, J=7.34 Hz, 1H), 7.32 (t, J=7.70 Hz, 1H), 9.90 (s, 1H). MS (M+H)$^+$ m/z 218.

Example 132D (Z)-methyl 1-acetamido-9-hydroxy-6,7-dihydro-5H-benzo[7]annulene-8-carboxylate The title compound was prepared using the procedure outlined in Example 20A, substituting the product from Example 132C for 7,8,9,10-tetrahydro-6H-benzocycloocten-5-one. $^1$H NMR (CDCl$_3$) δ 1.94-2.09 (m, 2H), 2.16 (s, 3H), 2.59 (t, J=6.61 Hz, 2H), 2.76-2.97 (m, 2H), 3.86 (s, 3H), 6.96 (d, J=7.80 Hz, 1H), 7.33 (t, 1H), 8.20 (d, J=8.48 Hz, 1H), 8.94 (s, 1H), 13.29 (s, 1H). MS (M+H)$^+$ m/z 276.

Example 132E

N-(2-amino-4-hydroxy-6,7-dihydro-5H-benzo[6,7]cyclohepta[1,2-d]pyrimidin-11-yl)acetamide The title compound was prepared using the procedure outlined in Example 20B, substituting the product from Example 132D for the product from Example 20A. MS (M+H)$^+$ m/z 285.

Example 132F 11-(acetylamino)-2-amino-6,7-dihydro-5H-benzo[6,7]cyclohepta[1,2-d]pyrimidin-4-yl 4-methylbenzenesulfonate The title compound was prepared using the procedure outlined in Example 20C, substituting the product from Example 132E for the product from Example 20B. $^1$H NMR (CDCl$_3$) δ 1.86-2.00 (m, 1H), 2.02-2.09 (m, 2H), 2.09 (s, 3H), 2.22-2.35 (m, 1H), 2.49 (s, 3H), 2.56-2.68 (m, 1H), 2.73-2.84 (m, 1H), 5.00 (s, 2H), 6.98 (d, J=6.78 Hz, 1H), 7.35 (t, 1H), 7.40 (d, J=7.80 Hz, 2H), 7.97-8.05 (m, 2H), 8.24 (d, J=8.14 Hz, 1H). MS (M+H)$^+$ m/z 439.

Example 132G

N-(2-Amino-4-piperazin-1-yl-6,7-dihydro-5H-benzo[6,7]cyclohepta[1,2-d]pyrimidin-11-yl)-acetamide The title compound was prepared using the procedure outlined in Example 20D, substituting the product from Example 132F for the product from Example 20C. $^1$H NMR (CD$_3$OD) δ 1.97-2.06 (m, 2H), 2.08 (s, 3H), 2.17-2.27 (m, 1H), 2.42-2.51 (m, 1H), 2.53-2.62 (m, J=13.68, 6.15 Hz, 1H), 2.65-2.75 (m, 1H), 2.84-2.95 (m, 2H), 2.95-3.05 (m, 2H), 3.32-3.37 (m, 2H), 3.39-3.50 (m, 2H), 7.06 (d, J=7.54 Hz, 1H), 7.32 (t, 1H), 7.96 (d, J=7.93 Hz, 1H). MS (M+H)$^+$ m/z 353.

Example 133

4-(Octahydro-pyrrolo[3,4-b]pyridin-6-yl)-6,7-dihydro-5-benzo[6,7]cyclohepta[1,2-d]pyrimidine-2-carboxylic acid methyl ester

Example 133A tert-Butyl 6-(2-(methoxycarbonyl)-6,7-dihydro-5H-benzo[6,7]cyclohepta[1,2-d]pyrimidin-4-yl)octahydro-1H-pyrrolo[3,4-b]pyridine-1-carboxylate The title compound was prepared using the procedure outlined in Example 108A, substituting Example 92A for Example 102A. $^1$H NMR (CDCl$_3$) δ 1.31-1.53 (m, 2H), 1.49 (s, 9H), 1.68-1.87 (m, 2H), 2.18-2.38 (m, 4H), 2.51-2.64 (m, 1H), 2.64-2.77 (m, 2H), 2.78-2.92 (m, 1H), 3.52 (d, J=11.5 Hz, 1H), 3.65-3.84 (m, 2H), 3.92-4.10 (m, 2H), 3.99 (s, 3H), 4.79 (s, 1H), 7.20-7.25 (m, 1H), 7.33-7.43 (m, 2H), 7.83-7.90 (m, 1H); MS (M+H)$^+$ m/z 479.

Example 133B 4-(Octahydro-pyrrolo[3,4-b]pyridin-6-yl)-6,7-dihydro-5H-benzo[6,7]cyclohepta[1,2-d]pyrimidine-2-carboxylic acid methyl ester The title compound was prepared using the procedure outlined in Example 30B, substituting Example 133A for Example 30A. ¹H NMR (CDCl₃) δ 1.48-1.58 (m, 1H), 1.64-1.89 (m, 3H), 2.23-2.43 (m, 4H), 2.53-2.77 (m, 4H), 3.04 (dt, J=11.5, 3.4, 3.1 Hz, 1H), 3.43 (t, J=3.9 Hz, 1H), 3.58 (dd, J=11.5, 1.0 Hz, 1H), 3.65 (dd, J=10.2, 8.1 Hz, 1H), 3.92-4.05 (m, 2H), 3.98 (s, 3H), 7.20-7.24 (m, 1H), 7.32-7.42 (m, 2H), 7.83-7.89 (m, 1H); MS (M+H)⁺ m/z 379.

Example 134

4-(Octahydro-pyrrolo[3,4-b]pyridin-6-yl)-6,7-dihydro-5H-benzo[6,7]cyclohepta[1,2-d]pyrimidine-2-carboxylic acid

Example 134A 4-(1-(tert-Butoxycarbonyl)octahydro-pyrrolo[3,4-b]pyridin-6-yl)-6,7-dihydro-5H-benzo[6,7]cyclohepta[1,2-d]pyrimidine-2-carboxylic acid Example 133A (27.3 mg, 0.057 mmol) was dissolved in MeOH (1 mL), treated with 1 M NaOH (0.5 mL), stirred overnight, diluted with water (5 mL), acidified with a 0.43 M solution of citric acid in water and extracted with CH2Cl2 (2×25 mL). The combined CH2Cl2 layers were dried (MgSO₄), filtered and concentrated to provide the title compound. ¹H NMR (CDCl₃) δ 1.35-1.55 (m, 2H), 1.49 (s, 9H), 1.69-1.89 (m, 2H), 2.20-2.45 (m, 4H), 2.52-2.64 (m, 1H), 2.68-2.92 (m, 3H), 3.56 (d, J=11.1 Hz, 1H), 3.69-3.87 (m, 2H), 4.02 (dd, J=11.3, 5.8 Hz, 1H), 4.02-4.11 (m, 1H), 4.83 (s, 1H), 7.26-7.32 (m, 1H), 7.39-7.47 (m, 2H), 7.80-7.87 (m, 1H); MS (M+H)⁺ m/z 465.

Example 134B 4-(Octahydro-pyrrolo[3,4-b]pyridin-6-yl)-6,7-dihydro-5H-benzo[6,7]cyclohepta[1,2-d]pyrimidine-2-carboxylic acid Example 134A was treated with TFA (2 mL), heated at 60° C. for 2 minutes, concentrated and dried under vacuum to provide the title compound as the mono TFA salt. ¹H NMR (CD₃OD) δ 1.83-2.03 (m, 4H), 2.25-2.48 (m, 3H), 2.61-2.73 (m, 1H), 2.73-2.85 (m, 2H), 2.85-2.97 (m, 1H), 3.05-3.18 (m, 1H), 3.35-3.45 (m, 1H), 3.93-4.07 (m, 3H), 4.11 (d, J=13.9 Hz, 1H), 4.27 (dd, J=13.9, 5.1 Hz, 1H), 7.39-7.45 (m, 1H), 7.46-7.59 (m, 2H), 7.72-7.78 (m, 1H); MS (M+H)⁺ m/z 365.

Determination of Biological Activity

There are many methods available to show the effectiveness of compounds as histamine $H_4$ receptor ligands. Histamine $H_4$ receptors from mammalian species have been cloned. Methods to clone, express, and assess the potency and functional activity of such cloned genes are well known to those skilled in the art of molecular biology. Examples of methods of cloning and expressing histamine $H_4$ receptors, and of assessing the potency and functional activity are described in Nguyen, et al. Molecular Pharmacology (2001) vol. 59 pp. 427-433; Zhu, et al. Molecular Pharmacology (2001) vol. 59 pp. 434-441; Coge, et al., Biochemical and Biophysical Research Communications (2001) vol. 284, pp. 301-309; Liu, et al. Molecular Pharmacology (2001) vol. 59 pp. 420-426; Liu, et al. Journal of Pharmacology and Experimental Therapeutics (2001) v. 299, pp. 121-130; and Thurmond, et al. Journal of Pharmacology and Experimental Therapeutics (2004) v. 309, pp. 404-413. In the present case, to determine the potency and effectiveness of representative compounds of this invention as histamine-$H_4$ receptor ligands ($H_4$ receptor ligands), the following tests were conducted according to previously described methods (see Esbenshade, et al., Biochemical Pharmacology (2004), vol. 68, pp. 933-945, and in Krueger, et al., Journal of Pharmacology and Experimental Therapeutics (2005) v. 314, pp. 271-281): histamine $H_4$ receptors were cloned and stably expressed in HEK-293 (human embryonic kidney) cells coexpressing a Gαqi5. Before testing, cells are loaded with a $Ca^{+2}$ sensitive fluorescent dye, in this case Fluo-4. In the case of partial agonist or agonist ligands, addition of compound to the cells leads to the increase in intracellular $Ca^{+2}$ which is detected by FLIPR (Fluorescence Imaging Plate Reader; Molecular Devices, Sunnyvale, Calif.) technology. In a similar manner, compounds that are antagonists or inverse agonists, block the increase in fluorescence induced by the full histamine $H_4$ agonist histamine, and partial agonists reduce the amount of fluorescence induced by the full histamine $H_4$ agonist histamine. The fluorescence intensities measured before addition of the test compound are subtracted from the fluorescence intensities at later time points. Peak response values determined at each concentration of ligand are expressed as a percentage of the response obtained with the full agonist histamine. Concentration versus response data are analyzed to obtain compound potency as $K_b$ values for antagonists and inverse agonists and as $EC_{50}$ values for partial agonists.

TABLE 1

In vitro histamine $H_4$ potency of compounds in FLIPR

| Example # | Potency (nM) |
|---|---|
| 1 | 18 |
| 2 | 44 |
| 3 | 9.3 |
| 4 | 398 |
| 5 | 9.8 |
| 6 | 6.6 |
| 7 | 15 |
| 8 | 33 |
| 9 | 32 |
| 10 | 10 |
| 11 | 7.8 |
| 12 | 7.4 |
| 13 | 7.2 |
| 14 | 331 |
| 15 | 209 |
| 16 | 10 |
| 17 | 912 |
| 18 | 25704 |
| 19 | 603 |
| 20 | 32 |
| 21 | 5623 |
| 22 | 66 |
| 23 | 56 |
| 24 | 148 |
| 25 | 646 |
| 26 | 115 |
| 27 | 16596 |
| 28 | 15849 |
| 29 | 39 |
| 30 | 166 |
| 31 | 27 |
| 32 | 8.7 |
| 33 | 13 |
| 34 | 4.2 |
| 35 | 891 |
| 36 | 39 |
| 37 | 537 |
| 38 | 5754 |
| 39 | 22 |
| 40 | 34 |
| 41 | 50 |
| 42 | 13 |

TABLE 1-continued

In vitro histamine H₄ potency of compounds in FLIPR

| Example # | Potency (nM) |
|---|---|
| 43 | 513 |
| 44 | 24 |
| 45 | 69 |
| 46 | 100 |
| 47 | 912 |
| 48 | 43 |
| 49 | 39 |
| 50 | 56 |
| 51 | 41 |
| 52 | 56 |
| 53 | 100 |
| 54 | 32 |
| 55 | 123 |
| 56 | 115 |
| 57 | 562 |
| 58 | 182 |
| 59 | 44 |
| 60 | 724 |
| 61 | 8.7 |
| 62 | 389 |
| 63 | 269 |
| 64 | 1549 |
| 65 | 13 |
| 66 | 17 |
| 67 | 69 |
| 68 | 15 |
| 69 | 3162 |
| 70 | 37 |
| 71 | 263 |
| 72 | 1097 |
| 73 | 468 |
| 74 | 219 |
| 75 | 4898 |
| 76 | 55 |
| 77 | 9333 |
| 78 | 891 |
| 79 | 89 |
| 80 | 178 |
| 81 | 4169 |
| 82 | 2042 |
| 83 | 2951 |
| 84 | 3388 |
| 85 | 85 |
| 86 | 891 |
| 87 | 174 |
| 88 | 209 |
| 89 | 89 |
| 90 | 25119 |
| 91 | 550 |
| 92 | 2570 |
| 93 | 135 |
| 94 | 9.1 |
| 95 | 1413 |
| 96 | 19 |
| 97 | 29 |
| 98 | 52 |
| 99 | 25 |
| 100 | 120 |
| 101 | 269 |
| 102 | 45 |
| 103 | 351 |
| 104 | 141 |
| 105 | 83 |
| 106 | 140 |
| 107 | 11 |
| 108 | 53 |
| 109 | 87 |
| 110 | 54 |
| 111 | 1413 |
| 112 | 2455 |
| 113 | 4266 |
| 114 | 17 |
| 115 | 32 |
| 116 | 15 |
| 117 | 12 |
| 118 | 138 |
| 119 | 269 |
| 120 | 603 |
| 121 | 407 |
| 122 | 1288 |
| 123 | 1622 |
| 124 | 1413 |
| 125 | 631 |
| 126 | 2754 |
| 127 | 933 |
| 128 | 562 |
| 129 | 1096 |
| 130 | 164 |
| 131 | 113 |
| 132 | 1096 |
| 133 | 14454 |
| 134 | 11885 |

Generally, representative compounds of the invention demonstrated potencies in the above FLIPR assay from about 4 nM to about 26000 nM. Preferred compounds of the invention have potencies at histamine-H₄ receptors from about 4 nM to about 200 nM. More preferred compounds of the invention have potencies at histamine H₄ receptors from about 4 nM to about 40 nM.

The potency of compounds of the invention in displacing ³H-histamine in competition binding assays is assessed by methods described in Esbenshade, et al., Biochemical Pharmacology (2004), vol. 68, pp. 933-945. In this assay, membranes were prepared from HEK-293 cells transiently transfected with the pCINeo expression vector harboring the histamine H₄ receptor by homogenization of the cells on ice in TE buffer (50 mM Tris-HCl buffer, pH 7.4, containing 5 mM EDTA), 1 mM benzamidine, 2 µg/ml aprotinin, 1 µg/ml leupeptin, and 1 µg/ml pepstatin. The homogenate was centrifuged at 40,000 g for 20 minutes at 4° C. This step was repeated, and the resulting pellet was resuspended in TE buffer. Aliquots were frozen at −70° C. until needed. On the day of assay, membranes were thawed and diluted with TE buffer. Competition radioligand binding assays were performed with increasing concentrations of test compound in the presence of [³H]-histamine incubated at 25° C. for 1 hour in a total volume of 0.5 ml of 50 mM Tris, 5 mM EDTA, pH 7.4. All binding reactions were terminated by filtration under vacuum onto polyethylenimine (0.3%) presoaked Unifilters (PerkinElmer Life Sciences) or Whatman GF/B filters (Whatman, Clifton, N.J.) followed by three brief washes with 4 ml of ice-cold TE buffer. Bound radiolabel was determined by liquid scintillation counting. For all of the radioligand competition binding assays, IC₅₀ values and Hill slopes were determined by Hill transformation of the data and K$_i$ values were determined by the Cheng-Prusoff equation. The following table of representative histamine H₄ receptor ligands is provided, along with potency values:

| Compound Name (Example number) | Potency (nM) |
|---|---|
| 4-((3R)-3-Amino-pyrrolidin-1-yl)-6,7-dihydro-5H-benzo[6,7]cyclohepta[1,2-d]pyrimidin-2-ylamine (Example 16) | 4 |
| 4-Piperazin-1-yl-6,7-dihydro-5H-benzo[6,7]cyclohepta[1,2-d]pyrimidin-2-ylamine (Example 7) | 8 |

| Compound Name (Example number) | Potency (nM) |
|---|---|
| 4-(3-Methylamino-azetidin-1-yl)-6,7-dihydro-5H-benzo[6,7]cyclohepta[1,2-d]pyrimidin-2-ylamine (Example 3) | 4 |
| 4-(3-(R)-Methylamino-pyrrolidin-1-yl)-6,7-dihydro-5H-benzo[6,7]cyclohepta[1,2-d]pyrimidin-2-ylamine (Example 6) | 5 |

Generally, representative compounds of the invention demonstrate potencies from about 4 nM to about 26000 nM. Preferred compounds of the invention have potencies at histamine-$H_4$ receptors from about 4 nM to about 200 nM. More preferred compounds of the invention have potencies at histamine $H_4$ receptors from about 4 nM to about 40 nM.

In addition to the utility of in vitro methods for characterizing the potency of compounds at the $H_4$ receptor, there are animal disease models of available which demonstrate the utility of compounds. There are a number of methods to test the activity of compounds in different pain models that are well known to those skilled in the art. A description of the formalin test in rats, as neuropathic pain models in rats, and general descriptions of methods of testing and descriptions of pain models are found in the book 'Drug Discovery and Evaluation, $2^{nd}$ edition' (H. Gerhard Vogel, editor; Springer-Verlag, New York, 2002; pp. 702-706).

One example of human disease relates to a novel utility for $H_4$ antagonists, the treatment of pain. The utility of histamine $H_4$ receptor ligands to treat pain has not been reported, whether inflammatory pain, non-inflammatory pain, or neuropathic pain. This invention discloses the novel utility of the compounds of the invention to treat pain, including multiple types of pain, including inflammatory pain, non-inflammatory pain, and neuropathic pain. Neuropathic pain is distinct from other types of pain (e.g. inflammatory pain), and can develop in response to previous or ongoing tissue injury, nerve injury, or diabetes, but persists long after signs of the original injury or damage have disappeared. Neuropathic pain is not well treated currently and therefore there is a strong need for methods to treat this particular type of pain. The topic of neuropathic pain has been reviewed in the scientific literature, for example, Smith, et al. Drug Development Research (2001) vol. 54(3), pp. 140-153; Collins and Chessell Expert Opinion on Emerging Drugs (2005) vol. 10(1), pp. 95-108; Vinik and Mehrabyan Medical Clinics of North America (2004), vol. 88(4), pp. 947-999; Dray, Urban, and Dickenson Trends in Pharmacological Sciences (1994) vol. 15(6) pp. 190-7; Dworkin Clinical Journal of Pain (2002) vol. 18(6) pp. 343-9. There do exist a number of animal models of neuropathic pain that can be used to assess the ability of the compounds of the invention to treat neuropathic pain, as discussed herein.

Animal models of neuropathic pain are predictive of efficacy of treatment of neuropathic pain in humans. These models are used to assess the efficacy of compounds of the invention in treating neuropathic pain. Examples of models well known to those skilled in the art include the Chung model (Kim and Chung, Pain (1992) vol. 50 pp. 355-363) and the Bennett model (Bennett and Xie, Pain (1988) vol. 30 pp. 87-107).

Determination of Analgesic Effect Against Neuropathic Pain

Animals were prepared for testing, by use of a surgical procedure that induces neuropathic pain in one paw. Male Sprague Dawley rats were purchased from Charles River (Portage, Mich.). Prior to surgery, animals were housed in groups and maintained in a temperature-regulated environment. Following nerve ligation surgery, animals were housed in groups, and had access to food and water ad libitum.

The L5 and L6 spinal nerves of anesthetized rats were tightly ligated in a manner described previously (see Kim and Chung, Pain (1992) vol. 50 pp. 355-363). An incision was made on the dorsal portion of the hip and the muscle was blunt-dissected to reveal the spinal processes. The L6 transverse process was removed, and the left side L5 and L6 spinal nerves were tightly ligated with 5.0 braided silk suture. The wound was cleaned, the membrane sewn with 4.0 dissolvable Vicryl suture and the skin closed with wound clips. The paw affected by the surgical procedure (the left paw) develops an allodynic response, a hypersensitivity to mechanical and other stimuli; neuropathic pain is assessed as an increased sensitivity in the surgically affected (left) allodynic paw compared to the control paw on the right side, and measured by comparing the response of the (left side) allodynic paw to the response of the unaffected right side control paw.

For the assessment of neuropathic pain, mechanical allodynia in the affected paw of animals that had undergone spinal nerve ligation was evaluated using testing with von Frey filaments. As described previously by S. R. Chaplan, et al ("Quantitative assessment of tactile allodynia in the rat paw" J. Neurosci. Meth. (1994) vol. 53 pp. 55-63), two weeks following surgery rats were acclimated to a testing box constructed of plexiglass with a wire mesh floor which allowed access to the plantar surface of the animal's hindpaws. Using an Up-Down method (Dixon, Annu. Rev. Pharmacol. Toxicol. (1980) vol. 20, pp. 441-462; Chaplan et al. "Quantitative assessment of tactile allodynia in the rat paw" J. Neuroscience Methods (1994) vol. 53 pp. 55-63), von Frey filaments of increasing stiffness were applied to the plantar surface of the hindpaws and the withdrawal response of the animals was observed; for the surgically affected paw with neuropathic pain (the left side paw) the baseline level of allodynia has a withdrawal threshold of ≤4 g of pressure. By comparison, for the control paw without allodynia (in this case the right side paw), the typical withdrawal pressure is around 15 g. Representative compounds of the invention, administered intraperitoneally 30 minutes before testing, are able to reduce the symptoms of neuropathic pain and induce a dose-dependent increase in the withdrawal threshold for allodynic (left side) limb, up to a maximum effect of 15 g. The efficacy of the compound in reducing neuropathic pain at different doses is determined by comparing response in the surgery-affected paw versus the response in the control paw. This is expressed as the MPE (maximum percent effect), or 100 times the withdrawal threshold of the allodynic (left side) divided by the withdrawal threshold of the control (right side).

The following table of representative histamine $H_4$ receptor ligands is provided, along with potency values:

| Compound Name (Example number) | Dose injected, (micromole/kg, intraperitoneally (i.p.)) | MPE (%) |
|---|---|---|
| 4-((3R)-3-Amino-pyrrolidin-1-yl)-6,7-dihydro-5H-benzo[6,7]cyclohepta[1,2-d]pyrimidin-2-ylamine (Example 16) | 100 | 47 |

-continued

| Compound Name (Example number) | Dose injected, (micromole/kg, intraperitoneally (i.p.)) | MPE (%) |
|---|---|---|
| 4-Piperazin-1-yl-6,7-dihydro-5H-benzo[6,7]cyclohepta[1,2-d]pyrimidin-2-ylamine (Example 7) | 100 | 30 |
| 4-(3-Methylamino-azetidin-1-yl)-6,7-dihydro-5H-benzo[6,7]cyclohepta[1,2-d]pyrimidin-2-ylamine (Example 3) | 100 | 36 |
| 4-(3-Methylamino-azetidin-1-yl)-6,7-dihydro-5H-benzo[6,7]cyclohepta[1,2-d]pyrimidin-2-ylamine (Example 3) | 300 | 78 |

Representative compounds are active in this model, with preferred compounds of the invention active in the model at doses of ranging about 30-500 micromoles/kg of body weight.

Determination of Analgesic Effect Against Inflammatory Pain

To assess the effectiveness of representative compounds of the invention against acute model inflammatory pain, animals were tested in an acute model of carrageenan-induced thermal hyperalgesia (see for example, Honore, et al. *Behavioural Brain Research* 167 (2006) 355-364; Porreca, et al. Journal of Pharmacology and Experimental Therapeutics (2006) vol. 318 pp. 195-205). Carrageenan was injected into the test paw of the animal, and after 90 minutes, the test drug was administered by intraperitoneal dosing; the effect on thermal hyperalgesia was assessed in a hotbox assay which done 30 minutes after the intraperitoneal dosing of the test drug, and the MPE (maximal percent effect) reported by comparison to the control paw (not injected with carrageenan), according to 100 times the withdrawal latency of the carrageenan injected paw (in seconds) divided by the withdrawal latency of the control (not injected with carrageenan) paw. At 100 micromole/kg injected intraperitoneally, 4-((3R)-3-Amino-pyrrolidin-1-yl)-6,7-dihydro-5H-benzo[6,7]cyclohepta[1,2-d]pyrimidin-2-ylamine (compound of Example 16) showed a 68% MPE. At 100 micromole/kg injected intraperitoneally, 4-Piperazin-1-yl-6,7-dihydro-5H-benzo[6,7]cyclohepta[1,2-d]pyrimidin-2-ylamine (compound of Example 7) showed a 23% MPE. At 100 micromole/kg injected intraperitoneally, 4-(3-Methylamino-azetidin-1-yl)-6,7-dihydro-5H-benzo[6,7]cyclohepta[1,2-d]pyrimidin-2-ylamine (compound of Example 3) showed a 41% MPE.

Representative compounds are active in this model, with preferred compounds of the invention active in the model at doses of about 100 micromoles/kg of body weight.

Determination of Analgesic Effect Against Pain in a Surgical Skin Incision Model This is a surgical skin incision model (Joshi, et al. Pain 123 (2006) 75-82). Animals (rats) were prepared for testing by subjecting them in a surgical procedure carried out under sterile conditions, where the plantaris muscle was elevated and incised longitudinally with the origin and insertion of the muscle remaining intact. The skin was then closed with two mattress sutures (e.g. 5-0 nylon sutures). After surgery, animals were allowed to recover on a warming plate and housed individually in cages with soft bedding. After this surgery, the animals develop a hypersensitivity called allodynia; allodynia is pain due to a stimulus that does not normally provoke pain. Animals were tested for mechanical allodynia using von Frey hair mechanical stimulation 2, 24, and 48 h after surgery as described for the Chung model. At 30 micromole/kg injected intraperitoneally, 4-(3-Methylamino-azetidin-1-yl)-6,7-dihydro-5H-benzo[6,7]cyclohepta[1,2-d]pyrimidin-2-ylamine (compound of Example 3) showed a 21% MPE. At 100 micromole/kg injected intraperitoneally, 4-(3-Methylamino-azetidin-1-yl)-6,7-dihydro-5H-benzo[6,7]cyclohepta[1,2-d]pyrimidin-2-ylamine (compound of Example 3) showed a 69% MPE.

Representative compounds are active in this model, with preferred compounds of the invention active in the model at doses of ranging about 30-500 micromoles/kg of body weight.

Compounds of the invention are histamine $H_4$ receptor ligands that modulate function of the histamine $H_4$ receptor by altering the activity of the receptor. These compounds may be antagonists that block the action of receptor activation induced by histamine $H_4$ receptor agonists such as histamine; they may be histamine $H_4$ receptor inverse agonists that inhibit the basal activity of the receptor and block the action of receptor activation induced by histamine $H_4$ receptor agonists such as histamine, and they may be partial agonists that partially block the action of receptor activation induced by histamine $H_4$ receptor agonists such as histamine and prevent full activation of histamine $H_4$ receptors.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A compound of formula (I):

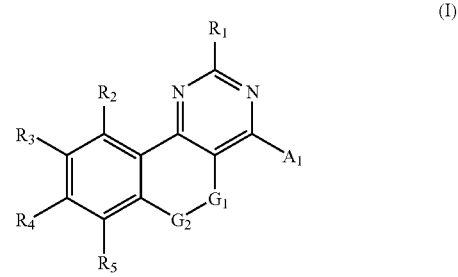

or a pharmaceutically acceptable, salt, ester, or amide thereof, wherein:

$G_1$ and $G_2$ make —$CH_2CH_2CH_2$—, wherein each carbon of —$CH_2CH_2CH_2$— may be optionally substituted with one or more groups selected from the group consisting of alkyl, fluoroalkyl, cyanoalkyl, cycloalkyl, fluorocycloalkyl, cycloalkoxyalkyl, alkylcycloalkyl, alkylfluorocycloalkyl, fluorine, acyl, acyloxy, alkenyl, alkoxy, alkoxyalkoxy, alkoxyalkyl, alkoxycarbonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, alkylthio, and oxo;

R₁ is selected from the group consisting of NH₂, —NH(acyl), —NH(alkyl), —N(alkyl)₂, —NH(C=O)aryl, —NH(C=O)CH₃, —NH-alkylene(NR₈R₉), —NH(C=O)-alkylene(NR₈R₉), —NR₈(C=O)NR₈R₉, —NH-alkylene-heteroaryl, —NHOH, —NHOCH₃, —O-alkylene(NR₈R₉), piperazine, fluoroalkyl, cyanoalkyl, cycloalkyl, fluorocycloalkyl, hydroxyalkyl, cyano, alkoxycarbonyl, carboxy, —(C=O)—(NR₈R₉), —(C=O)—NH-alkylene(NR₈R₉), and alkoxy;

R₂, R₃, R₄, and R₅ are each independently selected from the group consisting of hydrogen, alkyl, fluoroalkyl, cyanoalkyl, cycloalkyl, fluorocycloalkyl, cycloalkoxyalkyl, alkylcycloalkyl, alkylfluorocycloalkyl, aryl, heteroaryl, heterocycle, O-aryl, O-heteroaryl, S-aryl, —CONR₈R₉, —NR₈COalkyl, —NR₈(C=O)Oalkyl, acyl, acyloxy, alkenyl, alkoxy, alkoxyalkoxy, alkoxyalkyl, alkoxycarbonyl, alkoxyimino, alkoxysulfonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, alkylthio, —NR₈R₉, -carbonyl(NR₈R₉), —SO₂(NR₈R₉), and —N(R₈)SO₂(R₉);

R₆ is selected from the group consisting of hydrogen, alkyl, fluoroalkyl, cyanoalkyl, hydroxyalkyl, alkoxyalkyl, cycloalkyl, fluorocycloalkyl, cycloalkoxyalkyl, alkylcycloalkyl, and alkylfluorocycloalkyl;

R₇ is selected from the group consisting of fluoroalkyl, hydroxyalkyl, alkoxyalkyl, fluorocycloalkyl, and alkylfluorocycloalkyl;

R₈ and R₉ each are each independently selected from the group consisting of hydrogen, alkyl, fluoroalkyl, cycloalkyl, cyanoalkyl, fluorocycloalkyl, cycloalkoxyalkyl, alkylcycloalkyl, alkylfluorocycloalkyl, aryl, heteroaryl, heterocycle, acyl, alkoxyalkyl, alkoxycarbonyl, alkylcarbonyl, alkylsulfonyl, amido, formyl, hydroxy, and hydroxyalkyl;

A₁ is a group of structure A₂ selected from the group consisting of:

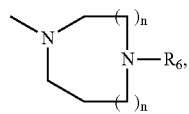  A

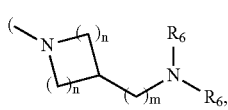  B

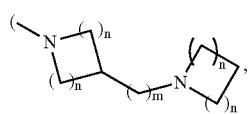  C

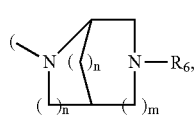  D

-continued

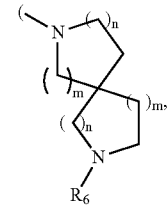  E

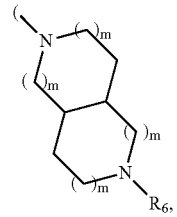  F

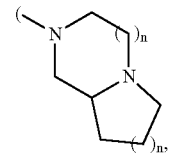  G

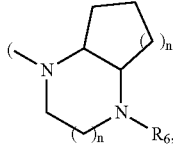  H

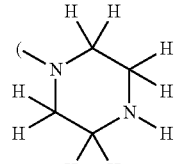  I

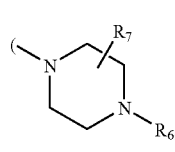  J

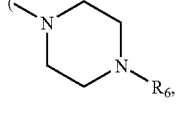  K

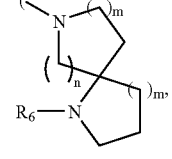  L

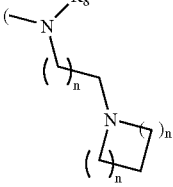  M

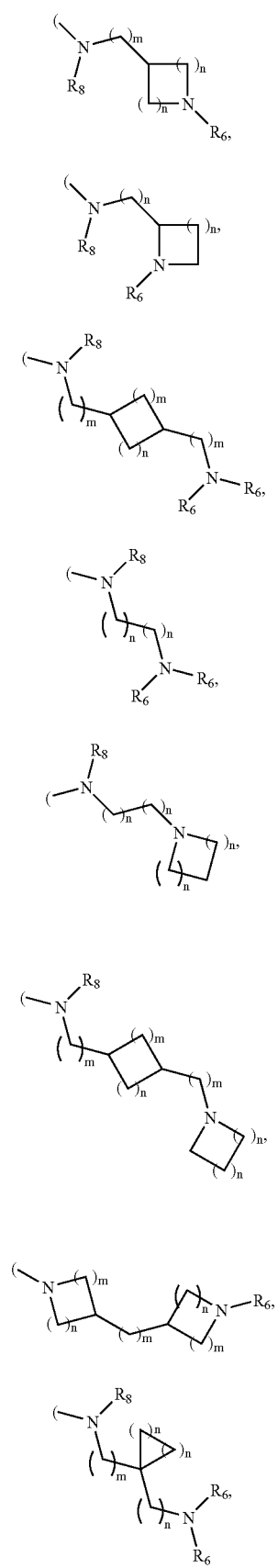
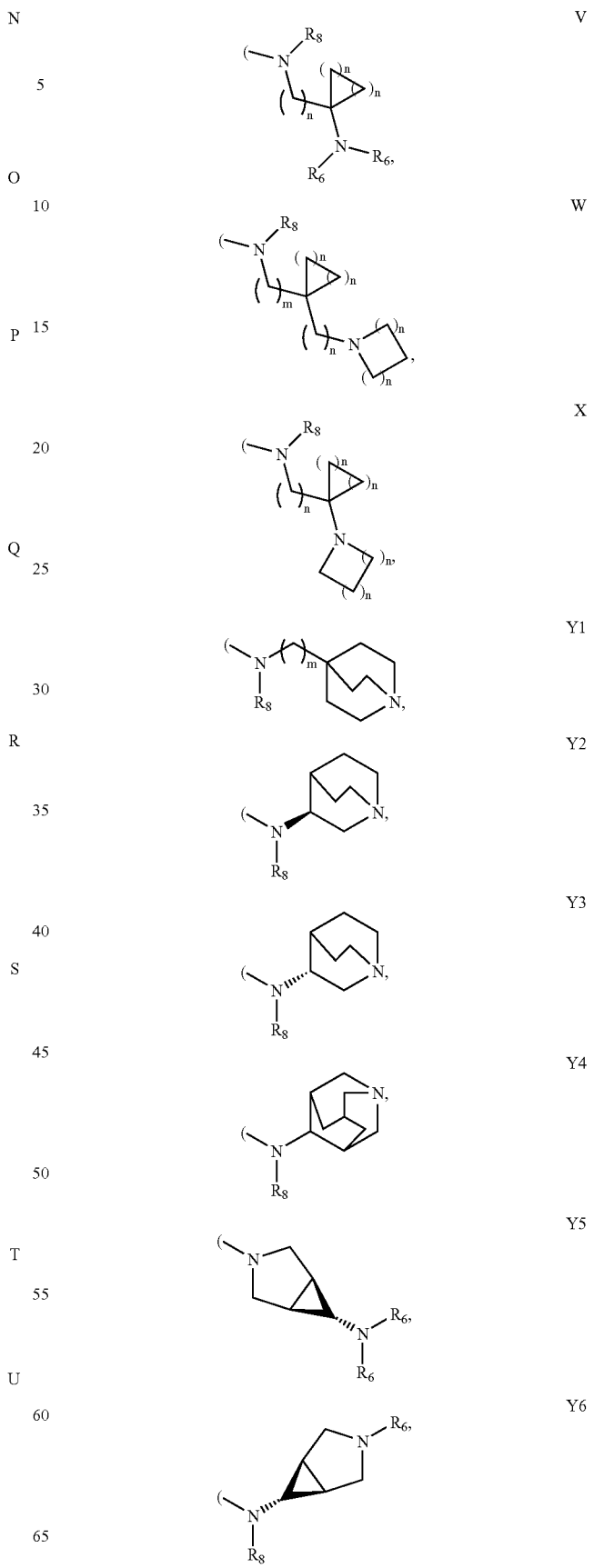

-continued

Y7 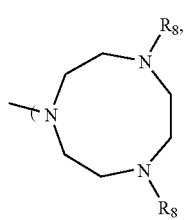

Y8 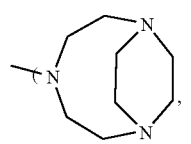

Y9 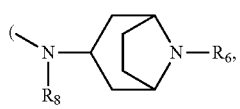

Y10 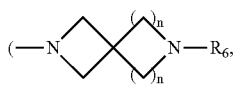

Y11 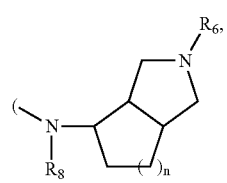

Y12 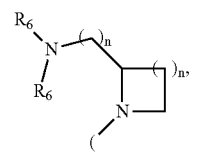

Y13 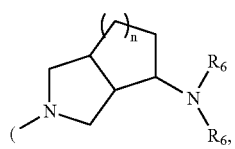

Y14 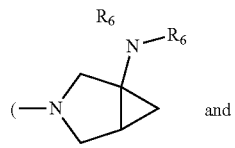

Y15 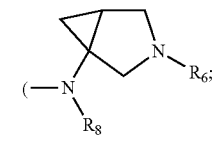

n is 1, 2, or 3;
m is 0, 1, or 2;
wherein each carbon atom of groups A₁ may be optionally substituted with one or more groups selected from the group consisting of alkyl, fluoroalkyl, cyanoalkyl, cycloalkyl, fluorocycloalkyl, cycloalkoxyalkyl, alkylcycloalkyl, alkylfluorocycloalkyl, fluorine, acyl, acyloxy, alkenyl, alkoxy, alkoxyalkoxy, alkoxyalkyl, alkoxycarbonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, and alkylthio;
provided that when R₁ is NH₂, NHalkyl, or alkyl, then A₁ is not a group of structure K.

2. The compound of claim 1, wherein R₁ is selected from the group consisting of —NHOH, —NHOCH₃, fluoroalkyl, cyanoalkyl, cycloalkyl, fluorocycloalkyl, hydroxyalkyl, cyano, and alkoxy.

3. The compound of claim 1, wherein A₁ is a group selected from A₂ of structure A, B, C, D, E, F, G, H, I, J, L, M, N, O, P, Q, R, S, T, U, V, W, X, Y1, Y2, Y3, Y4, Y5, Y6, Y7, Y8, Y9, Y10, Y11, Y12, Y13, Y14, or Y15.

4. The compound of claim 1, wherein R₁ is NH₂, —NHCH₃, —NH(C=O)CH₃, —NH(C=O)phenyl, —NH(C=O)NHCH₃, —NH(C=O)CH₂NH₂, —NH(C=O)CH₂NHCH₃, —NH(C=O)CH₂N(CH₃)₂, —NH(C=O)CH₂CH₂CH₂NH₂, —NHCH₂(pyridin-3-yl), —NHCH₂(imidazol-4-yl), —NHCH₂CH₂N(CH₃)₂, piperazin-1-yl, —(C=O)OCH₃, or —(C=O)OH.

5. The compound of claim 1, wherein R₂, R₃, R₄, and R₅ each are independently hydrogen, fluorine, chlorine, methyl, methoxy, iodine, pyridin-3-yl, phenyl, —(C=O)OCH₃, cyano, —NCH₃(C=O)OCH₃, —NHCH₃, or —NH(C=O)CH₃.

6. The compound of claim 1, wherein A₁ is a group of the formula:

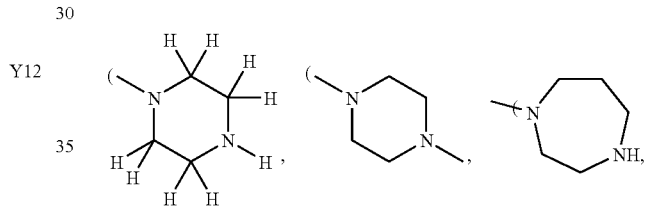

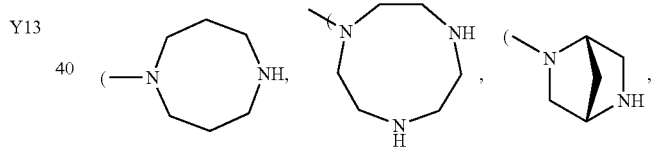

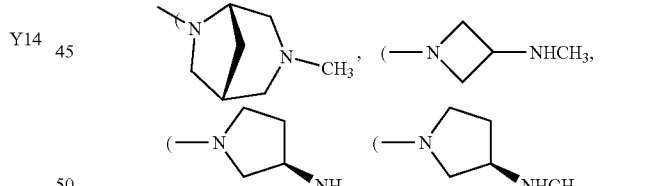

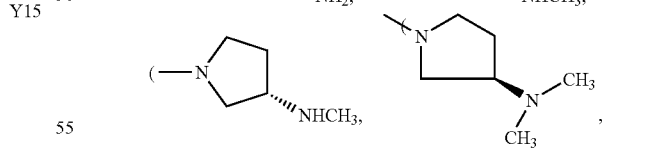

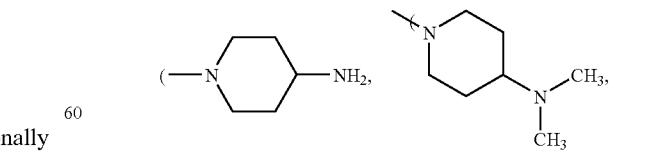

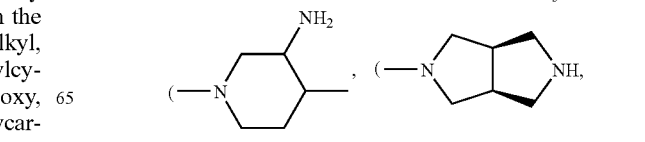

-continued

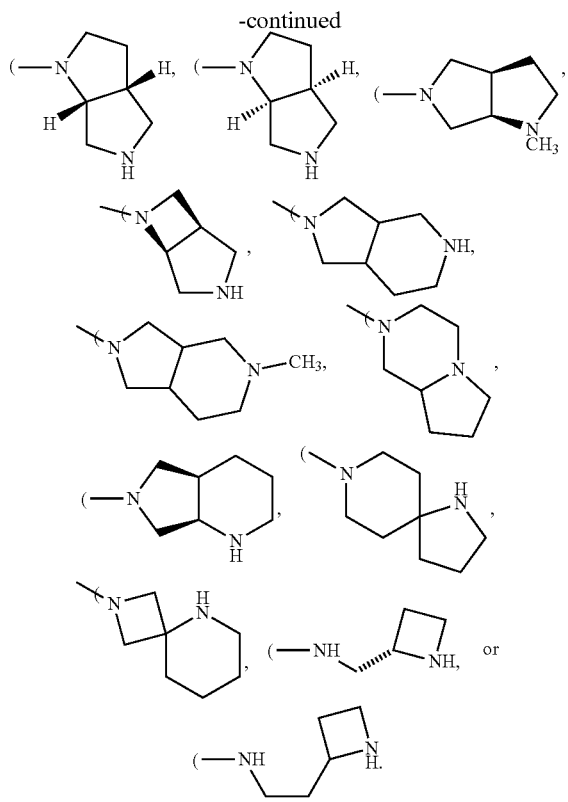

7. The compound of claim 6, wherein $A_1$ is

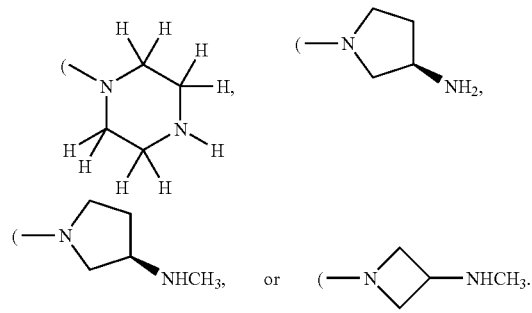

8. The compound of claim 1, wherein the compound is:
4-(3-Methylamino-azetidin-1-yl)-6,7-dihydro-5H-benzo[6,7]cyclohepta[1,2-d]pyrimidin-2-ylamine;
4-(3-(R)-Methylamino-pyrrolidin-1-yl)-6,7-dihydro-5H-benzo[6,7]cyclohepta[1,2-d]pyrimidin-2-ylamine;
10-Fluoro-4-(3-(R)-methylamino-pyrrolidin-1-yl)-6,7-dihydro-5H-benzo[6,7]cyclohepta[1,2-d]pyrimidin-2-ylamine;
10-Fluoro-4-(3-methylamino-azetidin-1-yl)-6,7-dihydro-5H-benzo[6,7]cyclohepta[1,2-d]pyrimidin-2-ylamine;
4-[(3S)-3-Methylamino-pyrrolidin-1-yl]-6,7-dihydro-5H-benzo[6,7]cyclohepta[1,2-d]pyrimidin-2-ylamine;
4-((3aR,6aR)-1-Methyl-hexahydro-pyrrolo[3,4-b]pyrrol-5-yl)-6,7-dihydro-5H-benzo[6,7]cyclohepta[1,2-d]pyrimidin-2-ylamine;
4-((3R)-3-Amino-pyrrolidin-1-yl)-6,7-dihydro-5H-benzo[6,7]cyclohepta[1,2-d]pyrimidin-2-ylamine;
4-((1S,4S)-2,5-Diaza-bicyclo[2.2.1]hept-2-yl)-6,7-dihydro-5H-benzo[6,7]cyclohepta[1,2-d]pyrimidin-2-ylamine;
4-(3-Piperidin-1-yl-pyrrolidin-1-yl)-6,7-dihydro-5H-benzo[6,7]cyclohepta[1,2-d]pyrimidin-2-ylamine;
4-((3aR,6aR)-Hexahydro-pyrrolo[3,4-b]pyrrol-1-yl)-6,7-dihydro-5H-benzo[6,7]cyclohepta[1,2-d]pyrimidin-2-ylamine;
4-(Hexahydro-pyrrolo[3,4-c]pyrrol-2-yl)-6,7-dihydro-5H-benzo[6,7]cyclohepta[1,2-d]pyrimidin-2-ylamine;
4-octahydro-6H-pyrrolo[3,4-b]pyridin-6-yl-6,7-dihydro-5H-benzo[6,7]cyclohepta[1,2-d]pyrimidin-2-amine;
4-(2,8-diazaspiro[4.5]dec-8-yl)-6,7-dihydro-5H-benzo[6,7]cyclohepta[1,2-d]pyrimidin-2-amine;
4-(1,5-diazocan-1-yl)-6,7-dihydro-5H-benzo[6,7]cyclohepta[1,2-d]pyrimidin-2-amine;
4-(4-aminopiperidin-1-yl)-6,7-dihydro-5H-benzo[6,7]cyclohepta[1,2-d]pyrimidin-2-amine;
$N^4$-(2-azetidin-2-ylethyl)-6,7-dihydro-5H-benzo[6,7]cyclohepta[1,2-d]pyrimidine-2,4-diamine;
$N^4$-[(2R)-azetidin-2-ylmethyl]-6,7-dihydro-5H-benzo[6,7]cyclohepta[1,2-d]pyrimidine-2,4-diamine;
$N^4$-(1-methylpiperidin-4-yl)-6,7-dihydro-5H-benzo[6,7]cyclohepta[1,2-d]pyrimidine-2,4-diamine;
$N^4$-[(1R,5S)-8-methyl-8-azabicyclo[3.2.1]oct-3-yl]-6,7-dihydro-5H-benzo[6,7]cyclohepta[1,2-d]pyrimidine-2,4-diamine;
4-(5-methyl-1,4-diazepan-1-yl)-6,7-dihydro-5H-benzo[6,7]cyclohepta[1,2-d]pyrimidin-2-amine;
4-(1,9-Diaza-spiro[5.5]undec-9-yl)-6,7-dihydro-5H-benzo[6,7]cyclohepta[1,2-d]pyrimidin-2-ylamine;
4-((R)-3-Dimethylamino-pyrrolidin-1-yl)-6,7-dihydro-5H-benzo[6,7]cyclohepta[1,2-d]pyrimidin-2-ylamine;
4-(2,6-Diaza-spiro[3.5]non-2-yl)-6,7-dihydro-5H-benzo[6,7]cyclohepta[1,2-d]pyrimidin-2-ylamine;
4-(2,5-Diaza-spiro[3.5]non-2-yl)-6,7-dihydro-5H-benzo[6,7]cyclohepta[1,2-d]pyrimidin-2-ylamine;
4-(Octahydro-pyrrolo[3,4-c]pyridin-2-yl)-6,7-dihydro-5H-benzo[6,7]cyclohepta[1,2-d]pyrimidin-2-ylamine;
4-(Octahydro-pyrrolo[1,2-a]pyrazin-2-yl)-6,7-dihydro-5H-benzo[6,7]cyclohepta[1,2-d]pyrimidin-2-ylamine;
4-(3,6-Diaza-bicyclo[3.2.1]oct-6-yl)-6,7-dihydro-5H-benzo[6,7]cyclohepta[1,2-d]pyrimidin-2-ylamine;
4-(2,6-Diaza-bicyclo[3.2.1]oct-2-yl)-6,7-dihydro-5H-benzo[6,7]cyclohepta[1,2-d]pyrimidin-2-ylamine;
N-(4-Piperazin-1-yl-6,7-dihydro-5H-benzo[6,7]cyclohepta[1,2-d]pyrimidin-2-yl)-acetamide;
N-(4-Piperazin-1-yl-6,7-dihydro-5H-benzo[6,7]cyclohepta[1,2-d]pyrimidin-2-yl)-benzamide;
4-(5-Methyl-octahydro-pyrrolo[3,4-c]pyridin-2-yl)-6,7-dihydro-5H-benzo[6,7]cyclohepta[1,2-d]pyrimidin-2-ylamine;
4-(3-Methyl-3,6-diaza-bicyclo[3.2.1]oct-6-yl)-6,7-dihydro-5H-benzo[6,7]cyclohepta[1,2-d]pyrimidin-2-ylamine;
2-Dimethylamino-N-(4-piperazin-1-yl-6,7-dihydro-5H-benzo[6,7]cyclohepta[1,2-d]pyrimidin-2-yl)-acetamide;
2-Methylamino-N-(4-piperazin-1-yl-6,7-dihydro-5H-benzo[6,7]cyclohepta[1,2-d]pyrimidin-2-yl)-acetamide;
2-Amino-N-(4-piperazin-1-yl-6,7-dihydro-5H-benzo[6,7]cyclohepta[1,2-d]pyrimidin-2-yl)-acetamide;
1-Methyl-3-(4-piperazin-1-yl-6,7-dihydro-5H-benzo[6,7]cyclohepta[1,2-d]pyrimidin-2-yl)-urea;
4-Amino-N-(4-piperazin-1-yl-6,7-dihydro-5H-benzo[6,7]cyclohepta[1,2-d]pyrimidin-2-yl)-butyramide;
6-(2-pyridin-3-ylmethylamino-6,7-dihydro-5H-benzo[6,7]cyclohepta[1,2-d]pyrimidin-4-yl)octahydro-1H-pyrrolo[3,4-b]pyridine;

3-Amino-N-(4-piperazin-1-yl-6,7-dihydro-5H-benzo[6,7]cyclohepta[1,2-d]pyrimidin-2-yl)-propionamide;

4-[1,4,7]Triazonan-1-yl-6,7-dihydro-5H-benzo[6,7]cyclohepta[1,2-d]pyrimidin-2-ylamine;

N,N-Dimethyl-N'-(4-piperazin-1-yl-6,7-dihydro-5H-benzo[6,7]cyclohepta[1,2-d]pyrimidin-2-yl)-ethane-1,2-diamine;

2,4-Di-piperazin-1-yl-6,7-dihydro-5H-benzo[6,7]cyclohepta[1,2-d]pyrimidine;

$N^4$-(3-Piperidin-1-yl-propyl)-6,7-dihydro-5H-benzo[6,7]cyclohepta[1,2-d]pyrimidine-2,4-diamine;

4-(4-Dimethylamino-piperidin-1-yl)-6,7-dihydro-5H-benzo[6,7]cyclohepta[1,2-d]pyrimidin-2-ylamine;

10-fluoro-4-octahydro-6H-pyrrolo[3,4-b]pyridin-6-yl-6,7-dihydro-5H-benzo[6,7]cyclohepta[1,2-d]pyrimidin-2-amine;

4-[1,4]Diazepan-1-yl-6,7-dihydro-5H-benzo[6,7]cyclohepta[1,2-d]pyrimidin-2-ylamine;

(1R,5S)-4-(3,6-Diaza-bicyclo[3.2.0]hept-6-yl)-6,7-dihydro-5H-benzo[6,7]cyclohepta[1,2-d]pyrimidin-2-ylamine;

(3aS,6aS)-4-(Hexahydro-pyrrolo[3,4-b]pyrrol-1-yl)-6,7-dihydro-5H-benzo[6,7]cyclohepta[1,2-d]pyrimidin-2-ylamine;

(1S,5S)-4-(3,6-Diaza-bicyclo[3.2.0]hept-3-yl)-6,7-dihydro-5H-benzo[6,7]cyclohepta[1,2-d]pyrimidin-2-ylamine;

$N^4$-Piperidin-3-yl-6,7-dihydro-5H-benzo[6,7]cyclohepta[1,2-d]pyrimidine-2,4-diamine;

$N^4$-(Octahydro-isoindol-4-yl)-6,7-dihydro-5H-benzo[6,7]cyclohepta[1,2-d]pyrimidine-2,4-diamine;

6-(2-(1H-imidazol-4-yl)ethylamino-6,7-dihydro-5H-benzo[6,7]cyclohepta[1,2-d]pyrimidin-4-yl)octahydro-1H-pyrrolo[3,4-b]pyridine;

(2-Amino-4-octahydro-pyrrolo[3,4-b]pyridin-6-yl-6,7-dihydro-5H-benzo[6,7]cyclohepta[1,2-d]pyrimidin-10-yl)-methyl-carbamic acid methyl ester;

10-N-methyl-4-[(4aR,7aR)-octahydro-6H-pyrrolo[3,4-b]pyridin-6-yl]-6,7-dihydro-5H-benzo[6,7]cyclohepta[1,2-d]pyrimidine-2,10-diamine;

4-(Octahydro-pyrrolo[3,4-b]pyridin-6-yl)-6,7-dihydro-5H-benzo[6,7]cyclohepta[1,2-d]pyrimidine-2-carboxylic acid methyl ester; or 4-(Octahydro-pyrrolo[3,4-b]pyridin-6-yl)-6,7-dihydro-5H-benzo[6,7]cyclohepta[1,2-d]pyrimidine-2-carboxylic acid.

9. The compound of claim 1, wherein the compound is 4-(3-methylamino-azetidin-1-yl)-6,7-dihydro-5H-benzo[6,7]cyclohepta[1,2-d]pyrimidin-2-ylamine, 4-(3-(R)-methylamino-pyrrolidin-1-yl)-6,7-dihydro-5H-benzo[6,7]cyclohepta[1,2-d]pyrimidin-2-ylamine, or 4-((3R)-3-amino-pyrrolidin-1-yl)-6,7-dihydro-5H-benzo[6,7]cyclohepta[1,2-d]pyrimidin-2-ylamine.

10. A pharmaceutical composition comprising a compound of claim 1 and a pharmaceutically acceptable carrier.

11. A method of treating pain in a mammal, said method comprising administering to a subject having or susceptible to said pain with a therapeutically effective amount of a compound of claim 1.

12. The method of claim 11, wherein the pain is inflammatory pain, cancer pain, osteoarthritic pain, post-surgical pain, non-inflammatory pain, neuropathic pain, peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, post-mastectomy pain, trigeminal neuralgia, central neuropathic pain syndromes, central poststroke pain, multiple sclerosis pain, Parkinson disease pain, spinal cord injury pain, or a combination thereof.

13. The method of claim 11, wherein the pain is neuropathic pain.

14. The method of claim 11, wherein the pain is cancer pain, visceral pain, osteoarthritis pain, or post-surgical pain, or a combination thereof.

15. A method of treating pain comprising administering a compound of claim 1, or a salt, ester, or amide thereof, in combination with a histamine H, antagonist; a histamine $H_2$ antagonist, a histamine $H_3$ antagonist; a modulator of TNF-α, an anti-inflammatory corticocosteroids; a 5-lipoxygenase inhibitor; a leukotriene antagonist; a LTB4 antagonist; a non-steroidal anti-inflammatory drug; a COX-2 inhibitor; a β-adrenergic receptor agonist; an anti-nociceptive opiate agonist, an anti-nociceptive alpha adrenergic agonist, a TRPV1 antagonist, a nicotinic acetylcholine receptor agonist, a CB-1 agonist; a CB-2 agonist; a P2X7 antagonist; a metabotropic glutamate receptor antagonist; or an adrenergic agonist, or a combination thereof.

* * * * *

UNITED STATES PATENT AND TRADEMARK OFFICE
CERTIFICATE OF CORRECTION

PATENT NO. : 8,735,411 B2
APPLICATION NO. : 11/863559
DATED : May 27, 2014
INVENTOR(S) : Altenbach et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1285 days.

Signed and Sealed this
Twenty-eighth Day of July, 2015

Michelle K. Lee
*Director of the United States Patent and Trademark Office*